US009826764B2

(12) United States Patent
Li et al.

(10) Patent No.: US 9,826,764 B2
(45) Date of Patent: Nov. 28, 2017

(54) PRODUCTION OF FOOD AND BEVERAGE PRODUCTS FROM BARLEY GRAIN

(71) Applicants: Zhongyi Li, Kaleen (AU); Matthew Kennedy Morell, Aranda (AU); Stephen Alan Jobling, Nicholls (AU)

(72) Inventors: Zhongyi Li, Kaleen (AU); Matthew Kennedy Morell, Aranda (AU); Stephen Alan Jobling, Nicholls (AU)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 113 days.

(21) Appl. No.: 13/958,472

(22) Filed: Aug. 2, 2013

(65) Prior Publication Data

US 2014/0205709 A1 Jul. 24, 2014

Related U.S. Application Data

(63) Continuation of application No. PCT/AU2012/000098, filed on Feb. 3, 2012.

(60) Provisional application No. 61/439,163, filed on Feb. 3, 2011.

(30) Foreign Application Priority Data

Feb. 3, 2012 (WO) ............... PCT/AU2012/000098

(51) Int. Cl.
| | |
|---|---|
| *A23L 5/00* | (2016.01) |
| *A23L 7/10* | (2016.01) |
| *A23L 1/10* | (2006.01) |
| *A01H 1/04* | (2006.01) |
| *A01H 5/10* | (2006.01) |
| *C12N 9/10* | (2006.01) |
| *C12N 15/82* | (2006.01) |

(52) U.S. Cl.
CPC ............ *A23L 1/1025* (2013.01); *A01H 1/04* (2013.01); *A01H 5/10* (2013.01); *A23L 7/197* (2016.08); *C12N 9/1051* (2013.01); *C12N 15/8245* (2013.01); *C12Y 204/01021* (2013.01)

(58) Field of Classification Search
None
See application file for complete search history.

(56) References Cited

U.S. PATENT DOCUMENTS

| | | | |
|---|---|---|---|
| 3,690,896 A | 9/1972 | Maxwell et al. | |
| 4,770,710 A | 9/1988 | Friedman et al. | |
| 5,051,271 A | 9/1991 | Iyengar et al. | |
| 5,792,920 A | 8/1998 | Bridges et al. | |
| 6,013,861 A | 1/2000 | Bird et al. | |
| 6,083,547 A | 7/2000 | Katta et al. | |
| 6,303,174 B1 | 10/2001 | McNaught et al. | |
| 6,307,125 B1 | 10/2001 | Block et al. | |
| 6,376,749 B1 | 4/2002 | Broglie et al. | |
| 6,483,009 B1 | 11/2002 | Poulsen et al. | |
| 6,635,756 B1* | 10/2003 | Jobling ............... C08B 30/048 536/102 |
| 6,730,825 B1 | 5/2004 | Goldsbrough et al. | |
| 6,734,339 B2 | 5/2004 | Block et al. | |
| 6,897,354 B1 | 5/2005 | Yamamori et al. | |
| 6,903,255 B2 | 6/2005 | Yamamori et al. | |
| 6,916,976 B1 | 7/2005 | Li et al. | |
| 7,001,771 B1 | 2/2006 | Morell et al. | |
| 7,009,092 B1 | 3/2006 | Jane et al. | |
| 7,041,484 B1 | 5/2006 | Baga et al. | |
| 7,521,593 B2 | 4/2009 | Regina et al. | |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,790,955 B2 | 9/2010 | Li et al. | |
| 7,812,221 B2 | 10/2010 | Regina et al. | |
| 7,888,499 B2 | 2/2011 | Morell et al. | |
| 7,919,132 B2 | 4/2011 | Regina et al. | |
| 7,993,686 B2 | 8/2011 | Bird et al. | |
| 8,115,087 B2 | 2/2012 | Regina et al. | |
| 8,178,759 B2 | 5/2012 | Morell et al. | |
| 8,188,336 B2 | 5/2012 | Li et al. | |
| 8,501,262 B2 | 8/2013 | Bird et al. | |
| 2003/0035857 A1 | 2/2003 | Sroka et al. | |
| 2003/0213013 A1 | 11/2003 | Caimi et al. | |
| 2004/0060083 A1* | 3/2004 | Regina et al. ............ 800/284 |
| 2004/0204579 A1 | 10/2004 | Block et al. | |
| 2005/0164178 A1 | 7/2005 | Morell et al. | |

(Continued)

FOREIGN PATENT DOCUMENTS

| | | |
|---|---|---|
| GB | 2 360 521 | 3/2000 |
| WO | WO 97/22703 | 6/1997 |

(Continued)

OTHER PUBLICATIONS

Bird et al, 2008, British J. of Nutrition, 99:1032-1040.*
Holmes et al., Henderson's Dictionary of Biological Terms, 9th Ed., Van Nostrand Reinhold Co., New York, p. 218 (1979).
Jansson et al., Cloning, Characterization and Modification of Genes Encoding Starch Branching Enzymes in Barley. Starch: Structure and Functionality. Royal Society of Chemistry, London, pp. 196-203 (1997).
Jarvi and Eslick, Shrunken. Endosperm Mutants in Barley. Crop Science 15:363-366 (1975).
Klesgen, et al., Molecular Analysis of the Waxy Locus of *Zea mays*, Mol. Gen. Genet. 203: 237-244 (1986).

(Continued)

*Primary Examiner* — Jason Deveau Rosen
(74) *Attorney, Agent, or Firm* — John P. White; Cooper & Dunham LLP

(57) ABSTRACT

The present invention provides a process for producing a food ingredient or beverage ingredient. The present invention also provides a process for producing food product or beverage product. The present invention also provides a process for providing starch, amylose, amylopectin, β-glucan, fructan, non-starch polysaccharide, dietary fiber or resistant starch to improve one or more indicators of health in a mammal.

21 Claims, 8 Drawing Sheets

(56) References Cited

U.S. PATENT DOCUMENTS

| | | | |
|---|---|---|---|
| 2006/0010517 | A1 | 1/2006 | Li et al. |
| 2007/0300319 | A1 | 12/2007 | Li et al. |
| 2011/0010807 | A1 | 1/2011 | Morell et al. |
| 2011/0059225 | A1 | 3/2011 | Li et al. |
| 2011/0212916 | A1 | 9/2011 | Bird et al. |
| 2011/0281818 | A1 | 11/2011 | Jenkins et al. |
| 2012/0074247 | A1 | 3/2012 | Regina et al. |
| 2012/0114770 | A1 | 5/2012 | Regina et al. |
| 2012/0266267 | A1 | 10/2012 | Li et al. |
| 2013/0115362 | A1 | 5/2013 | Regina et al. |
| 2013/0156924 | A1 | 6/2013 | Morell et al. |

FOREIGN PATENT DOCUMENTS

| | | | |
|---|---|---|---|
| WO | WO 99/14314 | | 3/1999 |
| WO | WO 99/66050 | | 12/1999 |
| WO | WO 9966050 | A1 * | 12/1999 |
| WO | WO 00/015810 | | 3/2000 |
| WO | WO 00/66745 | | 9/2000 |
| WO | WO 01/32886 | | 5/2001 |
| WO | WO 01/62934 | | 8/2001 |
| WO | WO 02/37955 | | 5/2002 |
| WO | WO 02/101059 | | 12/2002 |
| WO | WO 03/023024 | | 3/2003 |
| WO | WO 03/094600 | | 11/2003 |
| WO | WO 2005/001098 | | 1/2005 |
| WO | WO 2005/040381 | | 5/2005 |
| WO | WO 2006/069422 | | 7/2006 |
| WO | WO 2010/006373 | | 1/2010 |
| WO | WO 2011/011833 | | 2/2011 |
| WO | WO 2012/058730 | | 5/2012 |
| WO | WO 2012/103594 | | 8/2012 |

OTHER PUBLICATIONS

Knight, et al., Molecular Cloning of Starch Synthase 1 from Maize (w64) Endosperm and Expression in *Escherichia coli*. Plant J. 14 (5) : 613-622 (1998).

Kull et al., Genetic Engineering of Potato Starch Composition: Inhibition of Amylose Biosynthesis in Tubers from Transgentic Potato Lines by the Expression of Antisense Sequences of the Gene for Granule-bound Starch Synthase. 3. Genet. Breed. 49: 69-76 (1995).

Li et al., Cloning and Characterization of a Gene Encoding Wheat Starch Synthase I. Theor. AEEI. Genet. 98: 1208-1216.

Li et al., The Localization and Expression of the Class II Starch Synthases of Wheat. Plant Physiology 120:1147-1155.

Li et al., Triticum aestivum Starch Synthase IIA mRNA, Complete cds. EMBL Abstract Accession No. AF155217 (1999).

Li et al., The structural organisation of the gene encoding class II starch synthase of wheat and barley and the evolution of the genes encoding starch synthases in plants. Funct Integr Genomics 3:76-85 (2003).

Liu et al., Stable Inheritance of the Antisense Waxy Gene in Transgenic Rice with Reduced Amylose Level and Improved Quality. Transgenic Research, 12:71-82, (2003).

Lorberth et al., Inhibition of a starch-granule—bound protein leads to modified starch and repression of cold sweetening. Nature Biotechnology, 16(1):473-477 (1998).

Mazzolini et al., Assaying synthetic ribozymes in plants: high-level expression of a functional hammerhead structure fails to inhibit target gene activity in transiently transformed protoplasts. Plant Mol. Biol. 20: 715-731 (1992).

Miao, Hongmei et al., Evaluation and Characterization of an Endosperm-Specific stella Promoter in Wheat II Chinese Science Bulletin. vol. 49, No. 6, pp. 579-585 (2004).

Mizuno et al., Alteration of the Structural Properties of Starch Components by the Lack of an Isoform of Starch Branching Enzyme in Rice Seeds. J. Biol. Where. 268 (25): 15084=19091.

Morell et al., The Biochemistry and Molecular Biology of Starch Synthesis in Cereals. Aust. J. Plant. Physiol. 22: 647-660.

Myers et al., Recent Progress toward Understanding Biosynthesis of the Amylopection Crystal. Plant Physiology 122: 989-997.

Nakamura Y., Towards a Better Understanding of the Metabolic System for Amylopectin Biosynthesis in Plants: Rice Endosperm as s Model Tissue. Plant Cell Physiology 43 (7): 718-725 (2002).

Nishi et al., Biochemical and Genetic Analysis of the Effects of Amylose-Extender Mutation in Rice Endosperm. Plant Physiology 127:459-472 (2001).

Okagaki R. J., Nucleotide Sequence of a Long cDNA from the Rice Waxy Gene. Plant Molecular Biology 19: 513-516 (1992).

Puchta, Gene Replacement by Homologous Recombination in Plants. Plant Mol. Biol. 48: 173-182 (2002).

Rahman et al., GenBank Accession #AF076680 (May 1999) Aegilops tauschii starch branching enzyme-I (SBE-1) gene, complete cds.

Rahman, S. et al., The Major Proteins of Wheat Endosperm Starch Granules. Aust. J. Plant Physiol. 22:793-803 (1995).

Rahman, S. et al., A Complex Arrangement of Genes at a Starch Branching Enzyme I Locus in the D-genome Donor of wheat. Genome 40: 465-474 (1997).

Rahman, S. et al., Characterisation of a Gene Encoding Wheat Endosperm Starch Branching Enzyme-I. Theor, Appl. Genet. 98: 156-163 (1999).

Rahman, S. et al., Comparison of Starch-Branching Enzyme Genes Reveals Evolutionary Relationships Among Isoforms vol. 125, pp. 1314-1324 (2001).

Regina A., High-amylose wheat generated by RNA interference improves indices of large-bowel health in rats. PNAS, vol. 103, pp. 3546-3551 (2006).

Safford, et al., Consequences of Antisense RNA Inhibition of Starch Branching Enzyme Activity on Properties of Potato Starch. Carbohydrate Polymers 35: 155-168 (1998).

Sathish et al., Cloning and Anti-Sense Rna Constructs of a Starch Branching Enzyme Gene From Barley Endosperm. Photosynthesis: from Light to Biosphere vol. V. P. Mathis (ed.) pp. 313-316 (1995).

Schondelmaier et al., Genetical Studies in the Mode of Inheritance and Localization of the amol (High Amylose) Gene in Barley. Plant Breeding 109: 274-280 (1992).

Schulman et al., Structural analysis of starch from normal and shx (shrunken endosperm) barley (*Hordeum vuigare* L.). Carbohydrate Research, 275:361-369 (1995).

Schulman and Kammiovirta, Purification of Barley Starch by Protein Extraction. Starch, 43(10):387-389 (1991).

Schwall, et al., Production of Very-High-Amylose Potato Starch by inhibition of SBE A and B. Nature Biotechnology 18: 551-554 (2000).

Sestili et al., Increasing the amylose content of durum wheat through silencing of the SBEIIa genes. Bmc Plant Biol. 10:144.

Shannon and Garwood, in Starch: Chemistry and Technology. Whistler et al., eds, Academic Press, Orlando, FL, 25-86 (1984).

Sidebottom et al., Characterization of the Difference of Starch Branching Enzyme Activities in Normal and Low- Amylopectin Maize during Kernel Development. Journal of Cereal Science 27: 279-287 (1998).

Slade et al., Development of High Amylase Wheat Through Tilling. BMC Plant Biology, 12:69-100 (2012).

Sun et al., Identification of Four Starch-Branching Enzymes in Barley Endosperm: Partial Purification of forms I, IIa and IIb. New Phytol. 137:215-222 (1997).

Sun et al., The Two Genes Encoding Starch-Branching Enzymes IIa and IIb Are Differentially Expressed in Barley. Plant Physiology 118:37-49 (1998).

Sundberg et al., Glycaemic Responses and Hyopcholesteralaemic Effects of High-Amylose Barley Diets on Broiler Chicks. J. Sci. Food Agric. 76:457-463 (1998).

Takaoka, M. et al., Structural characterization of high molecular weight starch granule-bound proteins in wheat (*Triticum aestivum* L.). J. Agric. Food Chem. 45: 2929-2934.

Terada at al., Efficient Gene Targeting by Homologous Recombination in Rice. Nature Biotech. 20: 1030-1034 2002

Tester, R.F. The effects of ambient temperature during the Grain-filling period on the composition and properties of starch and four barley genotypes. Journal of Cereal Science 13:113-127 (1991).

(56) References Cited

OTHER PUBLICATIONS

Tester, T.F. Influence of growth conditions on barley starch properties. Biological Macromolecules 21:37-45 (1997).
Tetlow et al., Recent developments in understanding the regulation of starch metabolism in higher plants. Journal of Experimental Botany 55(406):2131-2145 (2004).
Thomas et al., Size Constraints for Targeting Post-Transcriptional Gene Silencing and for RNA-directed Methylation in Nicotiana benthamiana Using a Potato Virus X Vector. Plant J. 25 : 417-425 (2001).
USDA, ARS, National Genetic Resources Program. Germplasm Resources Information Network (GRIN) [Online Database] National Germplasm Resources Laboratory, Beltsville, Maryland (www.ars'grin.gov/npgs/), GRIN System [Accession No. GSHO 2476, Jun. 23, 1997).
Van der Leij et al., Sequence of the Structural Gene for Granule-Bound Starch Synthase of Potato (*Solanum Tuberosum* L.) and Evidence for a Single Point Deletion in the amf allele. Mel. Gen. Genet. 228: 240-248 (1991).
Vrinten and Nakamura, Wheat Granule-Bound Starch Synthase I and II Are Encoded by Separate Genes That Arc Expressed in Different Tissues. Plant Physiology 122:255-263 (2000).
Walker and Meritt, Genetic Control of Abnormal Starch Granules and High Amylose Content in a Mutant of Glacier Barley. Nature 221:482-484 (1969).
Walter et al., GenBank Accession #AAB17085 (Oct. 1996) Starch Synthase.
Walter et al., GenBank Accession #U66377 (Oct. 1996) *Triticum aestivum* soluble starch synthase mRNA; partial cds.
Wasserman et al., Microstructure, Thermal properties and susceptibility of the high amylose wheat starch to enzymatic hydrolysis: a new material for resistant starch (SRIII) production. Polish Journal of Food and Nutrition Sciences vol. 13-54, No. 2, pp. 151-156 (2004).
Wei et al., C-Type Starch from High-Amylose Rice Resistant Starch Granules Modified by Antisense RNA Inhibition of Starch Branching Enzyme. Journal of Agricultural and Food Chemistry, 58: 7383-7388 (2010).
Yamamori and Endo, Variation of Starch Granule Proteins and Chromosome Mapping of Their Coding Genes in Common Wheat. Theor. Appl. Genet. 93: 275-181 (1996).
Yamamori et al., Genetic Elimination of a Starch Granule Protein, SGP-1, of Wheat Generates an Altered Starch with Apparent High Amylose. TAG Theoretical and Applied Genetics 101: 21-29 (2000).
Yamamori, Selection of a Wheat Lacking a Putative Enzyme for Starch Synthesis, Sg:P=1. Proc. 9th in Wheat Gen. Symp. 4:300-302 (1998).
Yoshimoto et al., Molecular Structure and Some Physiochemical Properties of High-Amylose Barley Starches. Cereal Chem, 77(3):279-285 (2000).
Zobel et al., Starch Gelatinization: An X-ray Diffraction Study. Cereal Chem, 65(6):443-446 (1988).
Zobel, H.F., Starch Crystal Transformations and Their Industrial Importance. Starch, 40(1): 1-7 (1988).
Zwar and Chandler, α-Amylose production and leave protein synthesis in a gibberellin-responsive dwarf mutant of 'Himalaya' barley (*Hordeum vulgare* L.). Planta, 197:39-48.
International Report on Patentability, dated Aug. 6, 2013 in connection with ECT International Patent Application No. PCT/AU2012/000098.
International Search Report, dated May 14, 2012 in connection with PCT International Patent Application No. PCT/AU2012/000098.
Fujita et al., Characterization of SSIIIa-Deficient Mutants of Rice: the Function of SSIIIa and Pleiotropic Effects by SSIIIa Deficiency in the Rice Endosperm. Plant Physiology, 144: 2009-2023.
Li et al., The barley amol locus is tightly linked to the starch synthase IIIa gene and negatively regulates expression of granule-bound starch synthetic genes. journal of Experimental Botany 62: 5217-5231 (2011).

Morell et al., Barley sex6 Mutants Lack Starch Synthase IIa Activity and Contain a Starch with Novel Properties. the Plant Journal 34:173-185 (2003).
Newman et al., Comparative Nutritive Value of Glacier and High Amylose Glacier Barleys. Journal of Animal Science, 47:448-456.
Zhang et al., Overlapping functions of the starch syntheses SSII and SSIII in amylopectin biosynthesis in Arabidopsis. Bmc Plant Biology 8:96 (2008).
File History of U.S. Pat. No. 7,812,221, Regina et al., issued Oct. 12, 2010 (U.S. Appl. No. 10/881,808, filed Jun. 20, 2004).
File History of U.S. Patent Application Publication No. 2011-0070352, Regina et al., published Mar. 24, 2011 (U.S. Appl. No. 12/881,040, filed Sep. 13, 2010).
File History of U.S. Pat. No. 7,700,139, Bird et al., issued Apr. 20, 2010 (U.S. Appl. No. 11/324,063, filed Dec. 30, 2005.
File History of U.S. Patent Application Publication No. 2006-0286186, Bird et al.., published Dec. 21, 2006 (U.S. Appl. No. 11/417,330, filed May 2, 2006).
File History of U.S. Patent Application Publication No. U.S. 2011-0212916, Bird et al., published Sep. 1, 2011 (U.S. U.S. Appl. No. 12/799,013, filed Apr. 16, 2010).
File History of U.S. Pat. No. 7,790,955, Li et al., issued Sep. 7, 2010 (U.S. Appl. No. 10/577,564, filed Apr. 27, 2006.
File History of U.S. Patent Application Publication No. 2011-0059225, Li et al., published Mar. 10, 2011 (U.S. Appl. No. 12/806,167, filed Aug. 6, 2010).
File History of U.S. Pat. No. 7,888,499, Morell et al., issued Feb. 15, 2011 (U.S. Appl. No. 10/416,439, filed Dec. 5, 3003).
File History of U.S. Pat. No. 7,001,771, Morell et al., issued Feb. 21, 2006 (U.S. Appl. No. 10/018,418, filed May 9, 2002).
File History of U.S. Pat. No. 7,700,826, Morell et al., issued Apr. 20, 2010 (U.S. Appl. No. 11/231,599, filed Sep. 21, 2005).
File History of U.S. Pat. No. 7,521,593, Regina et al., issued Apr. 21, 2009 (U.S. Appl. No. 10/434,893, filed May 9,.
File History of U.S. Pat. No. 7,919,132, Regina et al., issued Apr. 5, 2011 (U.S. Appl. No. 12/384,823, filed Apr. 9, 2009).
File History of U.S. Pat. No. 7, 667, 114, Morell et al., issued Feb. 23, 2010 (U.S. Serial No. 10/204,34'7, filed Feb. 20, 2002).
File History of U.S. Pat. No. 2011-0010807, Morell et al., published Jan. 13, 2011 (U.S. Appl. No. 12/707,437, filed Feb. 17, 2010).
File History of U.S. Pat. No. 2010-0330253, Morell et al., published Dec. 20, 2010 (U.S. Appl. No. 12/800,143, filed May 10, 2010).
File History of U.S. Pat. No. 2012-0074247, Regina et al., published Mar. 29, 2012 ((U.S. Appl. No. 13/243,220).
File History of U.S. Pat. No. 2013-0156924, Morell et el., published Jun. 20, 2013.
File History of U.S. Pat. No. 2012-0129805, Li et al., published May 24, 2012.
Abel et al., GenBank Accession #Y10416 (Jan. 1997) S. Tuberosum mRNA for Soluble Starch Synthase.
Abel, G.J.W. et al., Cloning and functional analysis of a cDNA encoding a novel 139 kDa Starch Synthase from Potato (*Solanum tuberosurn* L.). Plant J. 10(6): 981-991 (1996).
Ainsworth, C. et al., Expression, organization and structure of the genes encoding the waxy protein (granule-bound starch synthase) in wheat. Plant Mol. Biol. 22:67-82 (1993).
Anchikhoroya, Methods for crying out port experiements with granulated fertilizers. Doklady Vsesoyuznoi Akademii Sel'skokhozyaistvennykh Nauk V.I. Lenina (1971), Vol 8, pp. 20-22). (Abstract in English).
Baba, T. et al., Identification, cDNA cloning and gene expression of soluble starch synthase in rice (*Oryza stativa* L.) Immature Seeds. Plant Physiol. 103:565-573 (1993).
Banks et al., Studies on Starches of High Amylose Content. Starch 26: 289-300 (1974).
Batey and Curtin, Measurement of Amylose/Amylopectin Ratio by High-Performance Liquid Chromatography. Starch 48: 338-344 (1996).
Bhullar et al., GenBank Accession #CAB40374 (Apr. 1999) Starch synthase isoform SS III [Vigna unguiculata].
Blauth et al., Identification of Mutator Insertional. Mutants of Starch-Branching Enzyme 2a in Corn. Plant Physiology 125:1396-1405 (2001).

(56) References Cited

OTHER PUBLICATIONS

Block et al., GenBank Accession #1148227 (Jun. 1996) Triticum aestivum soluble starch synthase mRNA, partial cds.
Boyer and Preiss, Evidence for Independent Genetic Control of the Multiple Forms of Maize Endosperm Branching Enzymes and Starch Synthases. Plant Physiology 67: 1141-1145 (1981).
Buleon et al., Starch Granules: Structure and Biosynthesis. International Journal of Biological Macromolecules 23: 85-112.
Calvert et al., High Amylose Glacier Barley in Swine Diets. Nutritional Reports International. 23:29-36 (1981).
Clarke et al., Gene expression in a starch synthase IIa mutant of barley: changes in the level of gene transcription and grain composition. Functional Integrated Genomics (2008) 8:211-221 (Only the Abstract Provided).
Craig et al., Mutations in the Gene Encoding Starch Synthase II Profoundly Alter Amylopectin Structure in Pea Embryos. The Plant Cell 10:413-426 (1998).
Denser; K. et al., Identification of Multiple Isoforms of Soluble and Granule Bound Starch Synthase in Developing Wheat Endosperm. Planta 196: 256-265 (1995).
D'Huist et al., GenBank Accession #AAC17969 (Nov. 2001) Granule-bound starch synthase 1 precursor [Chlamydomonas reinhardtii].
et al., Characterization of cUNAs encoding two isoforms of granule-bound synthase which show differential expression in developing storage organs of pea and potato. Plant J. 2 (2): 193-202 (1992).
Edwards et al., Biochemical and Molecular Characterization of a Novel Starch Synthase from Potato Tubers. Plant J. 8 (2): 283- 294 (1995).
Flipse et al., Introduction of Sense and Antisense cDNAfor Branching Enzyme in the Amylose-Free Potato Mutant Leads to Physico-Chemical Changes in the Starch. Plant a 198: 340-347 (1996).
Fujita et al., Grain and Starch Characteristics of the Double Recessive Lines for Amylose-free and High Amylose Gene in Barley. Breeding Science 49: 217-219 (1999).
Fujita et al., Antisense Inhibition of Isoamylase Alters the Structure of Amylopectin and the Physiochemical Properties of Starch in Rice Endosperm. Plant Cell Physiol. 44(6):607-618.
Gao and Chibbar, Isolation, Characterization, and Expression Analysis of Starch Synthase IIa cDNA from wheat (*Triticum aestivum* L. ). Genome 43:768-775 (2000).
Gao et al., GenBank Accession #AAC14014 (Apr. 1998) Starch synthase Dull 1 [*Zea mays*].
Gao et al., GenBank Accession #AAC14015 (Apr. 1998) Starch synthase Dull 1 [*Zea mays*].
Gao et al., Characterization of dull I, a Maize Gene Coding fora Novel Starch Synthase. Plant Cell 10:399-412 (1998).
Gao et al., Triticum aestivum mRNA for Starch Synthase IIa-2 (wSs2a-2). Embl Abstract Accession No. AJ269503, Jul. 6, 2000.
Gao et al., GenBank Accession #AJ26502 (Apr. 2002) Triticum aestivum mRNA for starch synthase IIa-1 (wSs2a-1 gene).
Gao et al., GenBank Accession #CAB86618 (Apr. 2002) Starch synthase IIa-1 [*Triticum aestivum*].
Gillespie, K., Type 1 diabetes: pathogenesis and prevention. CMAJ0 vol. 175, pp. 165-170 (2006).
Goering and DeHass, A Comparison of the Properties of Large- and Small-Granule Starch Isolated from Several Isogenic Lines of Barley. Cereal Chemistry 51:573-578 (1974).
Hare et al., Isolation and Characterization of the zSSIIA and zSSITb Starch Synthase cDNA Clones from Maize Endosperm. Plant Mel. Biol. 37:639-649 (1998).
Andersson et al. (1999) Chemical Composition and Microstructure of Two Naked Waxy Barleys. Journal of Cereal Science, 30, 183-191.
Ball and Morell (2003) From Bacterial Glycogen to Starch: Understanding the Biogenesis of the Plant Starch Granule. Annu. Rev. Plant Biol. 54:207-33.
Ball et al. (1996) From Glycogen to Amylopectin: A Model for the Biogenesis of the Plant Starch Granule. Cell, vol. 86, 349-352.

Bird et al. (2004) A Novel Barley Cultivar (Himalaya 292) with a Specific Gene Mutation in Starch Synthase IIa Raises Large Bowel Starch and Short-Chain Fatty Acids in Rats. The Journal of Nutrition. 134:831-835.
Bird et al. (2004) A novel high-amylose barley cultivar (*Hordeum vulgare* var. *Himalaya* 292) lowers plasma cholesterol and alters indices of large-bowel fermentation in pigs. British Journal of Nutrition, 92, 607-615.
Boyer and Preiss (1978) Multiple Forms of $(1 \rightarrow 4)$-α-D-Glucan, $(1 \rightarrow 4)$-α-D-Glucan-6-Glycosyl Transferase From Developing *Zea mays* L. Kernels. Carbohydrate Research, 61:321-334.
Cao et al. (1999) Identification of the Soluble Starch Synthase Activities of Maize Endosperm. Plant Physiology, vol. 120, pp. 205-215.
Cao et al. (2000) Purification and Characterization of Soluble Starch Synthases from Maize Endosperm. Archives of Biochemistry and Biophysics, vol. 373, No. 1, pp. 135-146.
Devalle et al. (2005) Soluble starch synthase I: A major determinant for the synthesis of amylopectin in *Arabidopsis thaliana* leaves. The Plant Journal, 43, 398-412.
Denyer et al. (1996) The Major Form of ADP-Glucose Pyrophosphorylase in Maize Endosperm Is Extra-Plastidial. Plant Physiol. 112: 779-785.
Fujita et al. (2006) Function and Characterization of Starch Synthase I Using Mutants in Rice. Plant Physiology, vol. 140, pp. 1070-1084.
Hedman and Boyer (1982) Gene Dosage at the amylose-extender Locus of Maize: Effects on the Levels of Starch Branching Enzymes. Biochemical Genetics, 20: 483-492.
Hirose and Terao (2004) A comprehensive expression analysis of the starch synthase gene family in rice (*Oryza sativa* L.). Planta, 220: 9-16.
James et al. (2003) Starch synthesis in the cereal endosperm. Current Opinion in Plant Biology, 6: 215-222.
Jane et al. (1999) Effects of Amylopectin Branch Chain Length and Amylose Content on the Gelatinization and Pasting Properties of Starch. Cereal Chem. 76(5):629-637.
Kim et al. (2003) Physicochemical Properties and End-use Quality of Wheat Starch as a Function of Waxy Protein Alleles. Journal of Cereal Science, 37: 195-204.
Kossman and Lloyd (2010) Understanding and Influencing Starch Biochemistry. Critical Reviews in Plant Sciences, 19:3, 171-226.
Li et al. (2000) The Structure and Expression of the Wheat Starch Synthase III Gene. Motifs in the Expressed Gene Define the Lineage of the Starch Synthase III Gene Family. Plant Physiology, 123: 613-624.
Maddelein et al. (1994) Toward an Understanding of the Biogenesis of the Starch Granule. the Journal of Biological Chemistry, vol. 269, No. 40, pp. 25150-25157.
Mizuno et al. (1992) Starch Branching Enzymes from Immature Rice Seeds. J. Biochem. 112, 643-65.
Morell et al. (2001) Wheat starch biosynthesis. Euphytica, 119: 55-58.
Morell et al. (2003) Advances in the Understanding of Starch Synthesis in Wheat and Barley. J. Appl. Glycosci., 50, 217-224.
Morell et al. (2006) Control of starch biosynthesis in vascular plants and algae. In: Plaxton WC, McManus MT (eds).vol. 22, Blackwell, Oxford, pp. 258-289.
Ohdan et al. (2005) Expression profiling of genes involved in starch synthesis in sink and source organs of rice. Journal of Experimental Botany, vol. 56, No. 422, pp. 3229-3244.
Rahman et al. (2000) Genetic Alteration of Starch Functionality in Wheat. Journal of Cereal Science, 31: 91-110.
Topping et al. (2003) Resistant Starch and Health—*Himalaya* 292, a Novel Barley Cultivar to Deliver Benefits to Consumers. Starch/Starke, 55:539-545.
Yamamori and Quynh (2000) Differential effects of Wx-Al, -Bl and -D1 protein deficiencies on apparent amylase content and starch pasting properties in common wheat. Theor Appl Genet,.
Yasui et al. (1996) Amylose and Lipid Contents, Amylopectin Structure, and Gelatinisation Properties of Waxy Wheat (*Triticum aestivum*) Starch. Journal of Cereal Science 24: 131-137.

(56) References Cited

OTHER PUBLICATIONS

Zhang et al. (2005) Mutations Affecting Starch Synthase III in Arabidopsis Alter Leaf Starch Structure and Increase the Rate of Starch Synthesis. Plant Physiology, vol. 138, pp. 663-674.

* cited by examiner (A)

(B)

```
                              10         20         30         40         50         60
                              ....|....|....|....|....|....|....|....|....|....|....|....|
Himalaya         ............................................................
Himalaya292      MEMSLWPRSPLCPRGRQPLVVVVCPAGLAQPFWWNGRFTRSRTVRGMVASSDSPNRKSRR
HAG              ............................................................
Glacier          ............................................................

70         80         90        100        110        120
                              ....|....|....|....|....|....|....|....|....|....|....|....|
Himalaya         ............................................................
Himalaya292      LVSPQVKVISSRGYTTRLIVEPSTENTEHNNGDEEILDTYNALLHTEAAEWTDTREAFTA
HAG              ............................................................
Glacier          ............................................................

130        140        150        160        170        180
                              ....|....|....|....|....|....|....|....|....|....|....|....|
Himalaya         ............................................................
Himalaya292      EADSSQNASSSSIIRELDAADEDILAVDLTVNALSSVTKREVDAADKARVEDVFELDLP
HAG              ............................................................
Glacier          ............................................................

190        200        210        220        230        240
                              ....|....|....|....|....|....|....|....|....|....|....|....|
Himalaya         ............................................................
Himalaya292      ATTLRSVIVDVIDDNGTVQETLRSVIVDVTDDVADKARVEEDIFELDFSGNVSSSAATVE
HAG              ............................................................
Glacier          ............................................................

250        260        270        280        290        300
                              ....|....|....|....|....|....|....|....|....|....|....|....|
Himalaya         ............................................................
Himalaya292      LDAVDEVGPVQDTFRASLSGNVSNSAATVQEVDAVDEAGNDQDIFKADLSGNIFSSSTVE
HAG              ............................................................
Glacier          ............................................................
```

FIGURE 3

```
                    310       320       330       340       350       360
                 ....|....|....|....|....|....|....|....|....|....|....|....|
Himalaya         VGVVDEAGSTKDRFEMDSSGNVSTSATMNDAIDEAVADQIAVEADLSGNASSWATYRELD
Himalaya292      ............................................................
HAG              ............................................................
Glacier          ............................................................

370       380       390       400       410       420
                 ....|....|....|....|....|....|....|....|....|....|....|....|
Himalaya         DMVDENRSEEETFVMDLVGEATDEEENYQQQYPVPSSFSMMDKAIAKTGVSLNPEPRLTS
Himalaya292      ............................................................
HAG              .V..........................................................
Glacier          .V..........................................................

430       440       450       460       470       480
                 ....|....|....|....|....|....|....|....|....|....|....|....|
Himalaya         VQEQGKVNFSDKQDLSIADLPGONQSIVGSCKQDKSIADVAGPPQSIFGSSKQHRPIVAP
Himalaya292      ............................................................
HAG              ............................................................
Glacier          ............................................................

490       500       510       520       530       540
                 ....|....|....|....|....|....|....|....|....|....|....|....|
Himalaya         RKQNHSIVSDPKQKQSIVGFRSQDLSAVDLPKQNIPIVGTSSEGQTKQVPVVDRQDALYV
Himalaya292      ............................................................
HAG              ............................................................
Glacier          ............................................................

550       560       570       580       590       600
                 ....|....|....|....|....|....|....|....|....|....|....|....|
Himalaya         NGLELKEGDHRSEKTDEDALHVKFNIDNVLQKHLADRTQAVETTIWKEVDEEHLYMTEHQ
Himalaya292      ............................................................
HAG              ........V...................................................
Glacier          ........V...................................................
```

FIGURE 3 (CONTINUED)

```
                    610       620       630       640       650       660
                    ....|....|....|....|....|....|....|....|....|....|....|....|
Himalaya            IGSTEGHMVLNEDELSITEIGMGSGDKIQHALSEEELSWSEDEVQLNKDDCQYKVDETSA
Himalaya292
HAG
Glacier 670       680       690       700       710       720
                    ....|....|....|....|....|....|....|....|....|....|....|....|
Himalaya            SFTVEQDIQGPPQDVVDLPQALRAMLQELADNNYSMRNKLFVFPEVVKADSVIDLYLNRDL
Himalaya292
HAG
Glacier 730       740       750       760       770       780
                    ....|....|....|....|....|....|....|....|....|....|....|....|
Himalaya            TALANEPDVVIKGAFNGWKWKLFSERLHKSDLGVWWSCKLHIPKEAYRLDFVFPNGRTV
Himalaya292
HAG
Glacier 790       800       810       820       830       840
                    ....|....|....|....|....|....|....|....|....|....|....|....|
Himalaya            YENNGNNDFCIGIEGTMNEDLFEDFLVAEKQRELEKLAMEEAERRTQTDEQRRRKEARAA
Himalaya292
HAG
Glacier 850       860       870       880       890       900
                    ....|....|....|....|....|....|....|....|....|....|....|....|
Himalaya            DEAVRAQAKAEIEIKKNKLHSMLSLARTCDDNLWYIEASTDTRGDTIRLYYANRNSRPLAH
Himalaya292
HAG
Glacier
```

FIGURE 3 (CONTINUED)

```
              1210       1220       1230       1240       1250       1260
              ....|....|....|....|....|....|....|....|....|....|....|....|
Himalaya      LYQSFSWSGTEIKVWVGQVENLTVIFLEPQNGMFGVGCVYGRNDRRFGFFCHSALEFIL
Himalaya292   ............................................................
HAG           ............................................................
Glacier       ............................................................

1270       1280       1290       1300       1310       1320
              ....|....|....|....|....|....|....|....|....|....|....|....|
Himalaya      QNGLSPHIIHCHDWSSAPVAWLYKEHYSQSRMASTRVVPTIHNLEPGAHYIGKAMTYCDK
Himalaya292   ............................................................
HAG           ............................................................
Glacier       ............................................................

1330       1340       1350       1360       1370       1380
              ....|....|....|....|....|....|....|....|....|....|....|....|
Himalaya      ATTVSPTYSREVAGHGAIAPHREKFYGILNGIDPDIWDPYTDNFIPVPYTYENVVEGKSA
Himalaya292   ............................................................
HAG           ............................................................
Glacier       ............................................................

1390       1400       1410       1420       1430       1440
              ....|....|....|....|....|....|....|....|....|....|....|....|
Himalaya      AKRALQQKFGLQQTDVPVVGIITRLTAQKGIHLIKAHIHQTLESNGQVVLLGSAPDHRIQ
Himalaya292   ............................................................
HAG           ............................................................
Glacier       ............................................................

1450       1460       1470       1480       1490       1500
              ....|....|....|....|....|....|....|....|....|....|....|....|
Himalaya      GDFCRLADALHGVYHGRVKLVLTYDEPLSHLIYAGSDFILVPSIFEPCGLTQLVAMRYGS
Himalaya292   ............................................................
HAG           ...........................................R................
Glacier       ............................................................
```

FIGURE 3 (CONTINUED)

```
                    1510       1520       1530       1540       1550       1560
                ....|....|....|....|....|....|....|....|....|....|....|....|
Himalaya        IPIVRKTGGLHDTVPDVDNDKERARSLGLEPNGFSPDGADSNGVDYALNRAIAAWFDARD
Himalaya292     ............................................................
HAG             ............................................................
Glacier         ............................................................

1570       1580       1590
                ....|....|....|....|....|....|..
Himalaya        WFHSLCKRVMEQDWSWNRPALDYIELYHAARKF
Himalaya292     ................................
HAG             ................................
Glacier         ................................
```

FIGURE 3 (CONTINUED)

PRODUCTION OF FOOD AND BEVERAGE PRODUCTS FROM BARLEY GRAIN

CROSS-REFERENCE TO RELATED APPLICATIONS

This application is a continuation of PCT International Application No. PCT/AU2012/000098, filed Feb. 3, 2012, claiming benefit of U.S. Provisional Patent Application No. 61/439,163, filed Feb. 3, 2011, the contents of each of which are hereby incorporated by reference in its entirety.

REFERENCE TO SEQUENCE LISTING

This application incorporates-by-reference nucleotide and/or amino acid sequences which are present in the file named "140404_0687_82522_A_Substitute_Sequence_Listing_REB.txt," which is 133 kilobytes in size, and which was created Apr. 4, 2014 in the IBM-PC machine format, having an operating system compatibility with MS-Windows, which is contained in the text file filed Apr. 4, 2014 as part of this application.

FIELD

The present specification describes variant barley grain comprising a reduced level or activity of SSIII and exhibiting desirable starch and non-starch components in relatively high yield.

BACKGROUND

Barley is widely used for food production. Wildtype barley seed contains approximately 50 to 60% of starch, contained in its endosperm, that has approximately 25% amylose and 75% amylopectin. Amylose is a mostly linear $\alpha$-(1-4) linked glucosyl chain with a few $\alpha$-(1-6) linked glucan chains and has a molecular weight of $10^4$ to $10^5$ daltons. Amylopectin is a highly branched glucan in which $\alpha$-(1-4) linked glucosyl chains with mostly 3 to 60 glucosyl units are connected by $\alpha$-(1,6)-linkages, so that approximately 5-6% of the glucosyl linkages are $\alpha$-(1,6)-linkages, and has a molecular weight of $10^5$ to $10^6$ daltons.

A suite of enzymes are involved in cereal starch biosynthesis including ADP-glucose pyrophosphorylases (EC 2.7.7.27), starch synthases (EC 2.4.1.21), starch branching enzymes (EC 2.4, 1.18) and starch debranching enzymes (EC 3.2.1.41 and 3.2.1.68). The first committed step of starch synthesis is synthesis of ADP-glucose from Glucose-1-P and ATP, catalyzed by the enzyme ADP-glucose pyrophosphorylase. The ADP-glucose is then used as substrate for the synthesis of starch by starch synthases which transfer glucose to the non-reducing end of pre-existing $\alpha$-(1-4) linked glucosyl chain of starch. The branched glucan chains of starch, linked with $\alpha$-(1-6) linkages, are formed by starch branching enzymes through the cleavage of a region of the $\alpha$-(1-4) linkage glucan and subsequent transfer of the short glucan to a position on the $\alpha$-(1-4) linkage glucan of starch. Excess $\alpha$-(1-6) linked glucan chains are removed by debranching enzymes to maintain starch in a defined structure.

Ten starch synthase genes have been identified in the rice genome and are grouped into five distinct classes: granule-bound starch synthase (GBSS), starch synthase I (SSI), starch synthase II (SSII), starch synthase III (SSIII) and starch synthase IV (SSIV). There are two GBSS isoforms (GBSSI and GBSSII), one SSI isoform, three SSII isoforms (SSIIa [SSII-3], SSIIb [SSII-2], and SSIIc [SSII-1]), two SSIII isoforms (SSIIIa [SSIII-2] and SSIIIb [SSIII-1]), and two SSIV isoforms (SSIVa [SSIV-1] and SSIVb [SSIV-2]) in rice. Proteins corresponding to SSI, SSIIa and GBSSI have been detected within starch granules, whereas SSIIIa protein has been only detected in the soluble phase of amyloplastids. The precise role of these starch synthases individually and cooperatively in determining the final structure of the starch granule largely remains undefined although the potential roles of some starch synthases have been characterized in different organs and different species.

Mutants in starch synthases have been useful in determining the roles in some cereal species. GBSSI plays a crucial role in the biosynthesis of amylose, (Nelson et al., *Biochem. Biophys. Res. Comm.*, 9: 297-300, 1962) but it may also contribute to the synthesis of the long chains of amylopectin (Maddelein et al., *J. Bio. Chem.*, 269: 25150-25157, 1994).

A barley SSIIa mutant has been shown to have a high amylose phenotype with reduced starch content and reduced seed weight due to the reduction of starch biosynthesis. The mutant barley lines M292 and M342 which were homozygous for a null mutation in the gene encoding SSIIa were obtained following mutagenesis of grains of the barley variety 'Himalaya' with sodium azide. Mutant seeds were initially selected from progeny grain of the mutagenized population on the basis of a shrunken grain phenotype. The mutant lines were further characterized by their altered starch properties, reduced SSIIa protein level and activity, and genetically by the presence of a premature stop codon in the protein coding region of the gene encoding SSIIa which caused loss of the SSIIa enzyme in the endosperm (Morell et al., *Plant Journal* 34: 173-185, 2003) incorporated herein in its entirety by reference). The SSIIa mutant grain also had substantially reduced starch content and this was associated with a moderate reduction in yield when the barley plants were grown in the field. It was not known if the yield could be improved, or how, while still maintaining the high amylose phenotype.

There is a need for barley grain with improved agronomic performance and methods of producing same.

SUMMARY

In one embodiment barley grain is described comprising: (a) starch, (b) a first genetic variation which is: (i) an induced mutation in an endogenous gene encoding a starch synthase III (SSIII), or (ii) a transgene which encodes an RNA molecule which reduces expression of an endogenous gene encoding an SSIII, and (c) a reduced level or activity of SSIII protein relative to the level or activity in barley grain lacking the first genetic variation.

In some embodiments, the barley grain comprises an allele of SSIIIa other than a allele comprising the nucleic acid sequence of SEQ ID NO: 3.

In an illustrative embodiment, the grain further comprises a second genetic variation in a gene encoding a protein involved in starch synthesis, starch catabolism, starch phosphorylation or non-starch carbohydrate synthesis. In some embodiments, the second genetic variation is (i) a mutation in a gene encoding a starch synthase (SSII), preferably a starch synthase IIa (SSIIa), or (ii) a transgene which encodes an RNA molecule which inhibits expression of a gene encoding an SSII, preferably an SSIIa.

In some embodiments, the grain comprises (i) an allele of SSIIIa other than an allele comprising the nucleic acid sequence of SEQ ID NO: 3 and (ii) an allele of SSIIa other than an allele comprising the nucleic acid sequence of SEQ ID NO: 33. In another version of this embodiment, the grain lacks the allele of SSIIIa comprising the nucleic acid sequence of SEQ ID NO: 3 and lacks the allele of SSIIa comprising the nucleic acid sequence of SEQ ID NO: 33.

In another embodiments, the description enables barley grain comprising: (a) starch, (b) a first genetic variation which is (i) a mutation in a gene encoding an SSIII, or (ii) a transgene which encodes an RNA molecule which inhibits expression of a gene encoding an SSIII, and (c) a reduced level or activity of SSIII protein relative to the level or activity in barley grain lacking the first genetic variation, (d) a second genetic variation which is (i) a mutation in a gene encoding an SSII, or (ii) a transgene which encodes a nucleic acid molecule which inhibits expression of a gene encoding an SSII, (e) a reduced level or activity of SSII protein relative to the level or activity in barley grain lacking the second genetic variation, and wherein the grain comprises an allele of SSIIIa other than an allele comprising the nucleic acid sequence of SEQ ID NO: 3.

In exemplary embodiments, the SSIII is SSIIIa. In further illustrative embodiments, the SSII is SSIIa.

In further illustrative embodiments the starch content of the grain is at least 43% (w/w), at least 45% (w/w), at least 47% (w/w), at least 50% (w/w), or 41-65% (w/w).

In still further illustrative embodiments, the amylose content of the grain is at least 40%, at least 50% or at least 60% as a proportion of the total starch in the grain.

In further embodiments, the β-glucan content of the grain is 5-9% (w/w), or greater than 9% (w/w).

In still further embodiments, the fructan content of the grain as described herein is 2-11%, 3-11%, or 4-11% (w/w). Illustratively, the fructan comprises a degree of polymerization from about 3 to about 12.

In yet further embodiments, the grain comprises an elevated protein content relative to wild-type barley, or relative to HAG.

In some embodiments, the grain is homozygous for the sex6-292 allele of SSIIa.

As described herein, in some embodiments the SSM gene encodes an SSIII protein comprising an amino acid sequence having at least 98% sequence identity to SEQ ID NO: 4.

The grain of the present invention is, in some embodiments, wholegrain or cracked, ground, polished, milled, kibbled, rolled or pearled grain. In particular embodiments, the grain is processed and is unable to germinate.

The present invention extends of course to barley plants that produce or are capable of producing the grain are hereinabove described and as herein described. In some embodiments, the barley plants produce or are capable of producing barley grain comprising: (a) starch, (b) a first genetic variation which is (i) an induced mutation in an endogenous gene encoding a starch synthase (SSIII), or (ii) a transgene which encodes an RNA molecule which reduces expression of an endogenous gene encoding an SSIII, and (c) a reduced level or activity of SSIII protein relative to the level or activity in barley grain lacking the first genetic variation.

In some embodiments, the plant or part therefrom comprises an allele of SSIIIa other than a allele comprising the nucleic acid sequence of SEQ ID NO: 3.

In some embodiments, the barley plants are a population of at least 1000 plants growing in a field.

The description encompasses barley wholemeal or flour produced from the grain as herein above described.

In another aspect the description provides a process for producing a food ingredient or beverage ingredient, wherein the process comprises: (i) obtaining or producing barley grain as described hereinabove or as described herein; and (ii) processing the grain to produce the ingredient.

In some embodiments, the ingredient is isolated wholemeal, flour, starch, bran, β-glucan, fructan, non-starch polysaccharides, a baking ingredient, a baking mix, a thickening agent, or cracked, ground, polished, milled, kibbled, rolled or pearled grain, or any combination thereof.

In further embodiments, the description provides for a process for producing a food or animal feed or beverage product, wherein the process comprises: (i) obtaining or producing an ingredient produced according to a process as described herein above or herein and (ii) Mixing the ingredient with another food ingredient or beverage ingredient to produce the product.

In some embodiments of the process, the ingredient is used as a bulking agent, a dietary fibre, a texturizing agent, a preservative, a sweetener, a thickening agent, a probiotic agent or any combination of these, in the food or beverage product. In other embodiments, the process further comprises assessing the level or type of starch or starch synthase activity, starch content, amylose, amylopectin, β-glucan, fructan, non-starch polysaccharides, dietary fibre, resistant starch in the barley grain or the ingredient or the product produced therefrom.

In some embodiments of the process the food product is a breakfast cereal, biscuit, muffin, muesli bar, noodle, bread, cake, chip, pancake, tortilla, buns, pastry, cracker, pizza, croissants, bagels, pretzels, pasta, soup, sauce, confectionary, and other farinaceous goods.

In yet another aspect the description enables a barley plant capable of producing grain as herein described, wherein the process comprises: (i) introducing into a barley plant a nucleic acid which down-regulates the level or activity of an SSIII in the plant, or introducing into a barley plant a mutation in an endogenous gene encoding SSIII in the plant, and (ii) selecting a barley plant from step (i) which is capable of producing said grain. In some embodiments of the process the SSIII gene of the barley plant encodes a protein having at least 98% sequence identity to SEQ ID NO: 4.

In an illustrative embodiment, the process further comprises assessing the level, activity and/or type of starch, starch content, the level or activity of SSIIIa and/or a non-SSIII starch synthase such as SSI and/or GBSSI, amylose, amylopectin, β-glucan, fructan, non-starch polysaccharide, dietary fibre or resistant starch in the barley grain or a product therefrom, or analysing the plant with one or more genetic markers.

In some embodiments of the process, the level or activity of SSIII protein is less than 25%, less than 10%, less than 5%, or is essentially lacking relative to that of a control plant or the plant prior to the introduction of the nucleic acid or mutation.

In another aspect, the description enables a process for producing the herein described barley grain, the process comprising the steps of growing a barley plant and harvesting the grain. In some useful embodiments, the process comprises processing the grain to produce grain that is cracked, ground, polished, milled, kibbled, rolled or pearled.

Food production is an aspect of the present invention. The present invention provides barley grain as described herein or an ingredient produced according to the processes described herein, wholemeal or flour therefrom, when used or for use in the production of a product to increase the level of starch, amylose, amylopectin, resistant starch, dietary fibre, protein, lipid, water soluble carbohydrate, β-glucan, fructan or non-starch carbohydrate in said product or to decrease the glycemic index (GI) of said product.

Accordingly, the present description provides for the use of a grain as described herein or an ingredient produced according to a process described herein such as flour, wholemeal, starch, β-glucan or fructan isolated from a plant, grain, wholemeal or flour in the production of a food product.

In one embodiment, the present invention provides a food product comprising a food ingredient at a level of at least 10% on a dry weight basis, wherein the food ingredient is a barley grain according to any one of the herein described embodiments or an ingredient produced according to the process embodiments described herein such as wholemeal or flour.

Illustratively, the product is selected from the group consisting of bread, buns, breakfast cereal, cake, biscuit, pastry, crackers, muffins, pizza, croissants, bagels, pretzels, pasta, noodles, soup, sauce, confectionary and other farinaceous goods. Illustratively, the barley grain used to produce the above products comprises the sex6-292 allele. Accordingly, the present invention provides a process for preparing a food or beverage, comprising mixing the barley grain or ingredient such as barley wholemeal or flour with another food or beverage ingredient.

The invention also encompasses methods of improving the health of a subject. In some embodiments, the invention provides a process for providing starch, amylose, amylopectin, β-glucan, fructan, non-starch polysaccharide, dietary fibre or resistant starch to improve one or more indicators of health in a mammal, wherein the process comprises administering, to the mammal, a composition comprising barley grain as herein described, or wholemeal or flour therefrom or the food product or ingredient as described herein. In some embodiments, the grain, flour, starch, amylose, amylopectin, β-glucan, fructan, non-starch polysaccharide, dietary fibre or resistant starch is in the form of a food product, a beverage or a pharmaceutical composition.

Illustratively, the one or more indicators of health is an increased number of beneficial intestinal bacteria, reduced number of aberrant crypt foci, increased mineral absorption, reduced level of insulin, reduced glycaemic index, reduced glycaemic load, reduced blood glucose, reduced blood pressure, reduced body weight, reduced blood cholesterol level, increased HDL cholesterol level, increased bone density, increased calcium levels, more frequent bowel movement, or improved blood serum cardiovascular profile.

Thus, in some embodiments the invention provides a process/method for ameliorating one or more symptoms of a condition associated with low levels of dietary starch, amylose, amylopectin, β-glucan, fructan, non-starch polysaccharide, dietary fibre or resistant starch in a subject, said process comprising administering orally to the subject grain as herein described or a processed product or ingredient comprising starch, starch content, amylose, amylopectin, β-glucan, fructan, non-starch polysaccharide, dietary fibre or resistant starch obtained therefrom for a time and under conditions sufficient to ameliorate one or more symptoms. In some embodiments, the condition is selected from the group consisting of diabetes, obesity, heart disease, hypertension, constipation, osteoporosis and cancer.

In another aspect, the present invention provides a process for analyzing a barley plant or a part thereof, comprising the steps of: (i) analysing DNA, RNA, protein, starch granules, starch or grain obtained from the barley plant or part thereof, and (ii) determining from step (i) whether the barley plant or part thereof comprises an allele of SSIIIa which comprises the nucleic acid sequence of SEQ ID NO: 3 or which comprises a nucleic acid sequence other than SEQ ID NO: 3.

In some embodiments of the process, a plant or part therefrom is selected which has SEQ ID NO: 3. In some other embodiments of the process, a plant or part therefrom is selected which an allele other than SEQ ID NO: 3.

In some embodiments of the process, the barley plant or part thereof is a member of a population of barley plants or parts thereof. Illustratively, the process will find broad application in breeding programs.

The above summary is not and should not be seen in any way as an exhaustive recitation of all embodiments of the present invention.

BRIEF DESCRIPTION OF THE TABLES

Figure 1:
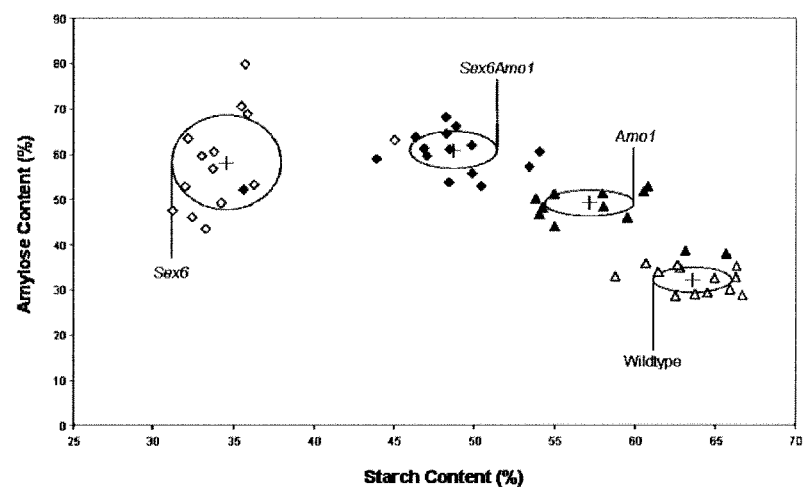
FIG. 1 is a graphical representation illustrating the relationship between amylose content and starch content is shown for 53 homozygous BC3F6 lines. Lines containing the wildtype ssIIa gene (triangular symbols) contained the three markers from the mutant amo1 locus (solid triangles) or were wildtype for all three amo1 markers (open triangles). The lines with the sex6 mutant genotype (diamond symbols) contained the wild type amo1 markers (open diamonds), or mutant amo1 markers (solid diamonds).

Table 1 provides a statistical analysis of genotypes and phenotypes of BC3F6 lines of barley.

Table 2 provides a summary of grain constituents of barley genotypes on a per seed basis.

Table 3 describes the intron and exon structure of barley ssIIIa gene and SNPs among barley ssIIIa genes from HAG, Glacier, Himalaya292 and Himalaya.

Table 4 provides the results of an analysis of RS content and GI level of barley wholemeal.

Table 5 provides the results of an analysis of RS content and GI level of bread produced using 100% barley wholemeal.

Table 6 provides the results of an analysis of the effects of genotype on RS contents of bread produced with 30% or 100% barley flour.

Table 7 provides the results of an analysis of RS content and GI level of breads produced with 30% barley flour.

Table 8 provides the results of an analysis of the effects of genotype on RS content (mg RS per g starch) of bread produced with 100% barley flour.

Table 9 provides the results of an analysis of the effects of genotype on RS content (mg RS per g starch) of breads produced with 30% barley flour.

Table 10 provides the results of an analysis of the effects of genotype on GI level of the 10 g breads produced with 30% or 100% barley flour.

Table 11 provides a description of the SEQ ID NOs provided herein.

Table 12 provides an amino acid sub-classification.

Table 13 provides exemplary amino acid substitutions.

DETAILED DESCRIPTION

The description includes a mutational approach to produce barley grain having, or that has been subject during development to, a reduced level or activity of an endogenous SSIII protein or an SSIII gene.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Thus, for example, reference to grain comprising 45% amylose includes grains having 45% amylose or any greater percentage value of amylose.

As used herein the singular forms "a", "an" and "the" include plural aspects unless the context clearly dictates otherwise. Thus, for example, reference to "a mutation" includes a single mutation, as well as two or more mutations; reference to "an agent" includes one agent, as well as two or more agents (i.e. to at least one); and so forth.

Accordingly, in one aspect the present invention is directed to barley grain comprising: (a) starch; (b) a reduced level or activity of SSIIIa protein; and (c) a genetic variation which is (i) an induced mutation in a gene encoding SSIIIa, or (ii) a transgene which encodes an RNA molecule which reduces expression of a gene encoding SSIIIa, wherein the genetic variation causes said reduced level or activity of SSIIIa protein. SSIIIa activity is typically in the developing endosperm.

In another embodiment, the present invention is directed to barley grain comprising (a) starch; (b) a reduced level or activity of SSIII protein; and (c) a genetic variation which is (i) an induced mutation in a gene encoding SSIII, or (ii) a transgene which encodes an RNA molecule which reduces expression of a gene encoding SSIII, wherein the genetic variation causes said reduced level or activity of SSIII protein, and further comprising a mutation in a gene encoding a protein involved in starch synthesis, starch catabolism, starch phosphorylation or non-starch carbohydrate synthesis. In an illustrative non-limiting embodiment, SSIII is SSIIIa.

In an illustrative embodiment, the further mutation or second genetic variation encodes a nucleic acid encoding a protein which is an ADP-glucose pyrophosphorylase, a starch synthase, a starch branching enzyme, a starch debranching enzyme, or an amylase or a combination of two or more of these. Debranching enzymes include an isoamylase and a pullulanase. Starch phosphorylation enzymes include a glucose-water dikinase (GWD) and a phosphoglucan water dikinase (PWD). Starch branching enzymes include SBEI, SBEII, SBEII, and starch synthase enzymes including an array of isoforms including GBSSI, GBSSII, SSI, SSIIa, SSIIb, SSIIc, SSIIIa, SSIIIb SSIVa, SSIVb and CSL.

In some embodiments, the barley grain does not comprise an allele of SSIIIa comprising the nucleic acid sequence of SEQ ID NO: 3. This allele encompasses the SSIIIa-38 mutation, also referred to as the amo1-38 mutation and comprises a leucine to arginine substitution at a position corresponding to amino acid 1480 of SEQ ID NO:4. In some embodiments, the barley grain does not comprise the combination of an allele of SSIIIa comprising the nucleic acid sequence of SEQ ID NO: 3 (SSIIIA-38, amo1-38) and an allele of SSIIa comprising the nucleic acid sequence of SEQ ID NO: 33 (SSIIa-292, sex6-292).

In another embodiment, the present invention provides barley grain comprising starch and: (a) a genetic variation which is (i) an induced mutation in a gene encoding SSIII; or (ii) a transgene which encodes an RNA molecule which inhibits expression of a gene encoding SSIII, wherein the genetic variation leads to said reduced level or activity of SSIII protein; and (b) a genetic variation which is (i) a mutation in a gene encoding SSII, or (ii) a transgene which encodes an RNA molecule which inhibits expression of a gene encoding SSII, wherein the genetic variation leads to said reduced level or activity of SSII protein. As above, the grain does not comprise a combination of an allele of SSIII comprising the nucleic acid sequence of SEQ ID NO: 3 (SSIIIA-38, amo1-38) and an allele of SSIIa comprising the nucleic acid sequence of SEQ ID NO: 33 (SSIIa-292, sex6-292). In some embodiments, the SSIII and the SSII mutations are homozygous null mutations. In some of these embodiments, the SSII mutation is an SSIIa mutation. In other embodiments, the SSIIa mutation is the sex6-292 mutation.

In another embodiment, the invention provides barley grain comprising: (a) starch, (b) a reduced level or activity of SSIIIa protein, (c) a genetic variation which is (i) a mutation in a gene encoding SSIIIa, or (ii) a transgene which encodes an RNA molecule which inhibits expression of a gene encoding SSIIIa, wherein the genetic variation leads to said reduced level or activity of SSIIIa protein, and (d) a genetic variation which is (i) a mutation in a gene encoding SSIIa, or (ii) a transgene which encodes a nucleic acid molecule which inhibits expression of a gene encoding SSIIa, wherein the genetic variation leads to said reduced level or activity of SSIIa protein, and wherein the grain does not comprise a combination of an allele of SSIIIa comprising the nucleic acid sequence of SEQ ID NO: 3 (SSIIIA-38). In some embodiments, the SSIIIa and the SSIIa mutations are homozygous null mutation. In some of these embodiments, the SSIIa mutation is the sex6-292 mutation.

In some embodiments, the genetic variation reducing the level or activity of SSIII produces an increased level of GBSSI protein in the grain.

In some embodiments, the genetic variation reducing the level or activity of SSIII produces (leads to) an increased level of starch synthase enzyme such as SSI protein in the grain. In some embodiments, the level of GBSSI and SSI is increased. The term "reduced" includes, in some embodiments, substantially no protein or protein with substantially no starch synthase activity.

In some embodiments, the barley grain has a starch content of at least 41% (w/w).

In other embodiments, the barley grain comprises a starch content of at least 43% (w/w), at least 45% (w/w), at least 47% (w/w), at least 50% (w/w), or comprises a starch content of 41-65% (w/w).

In some embodiments, the barley grain comprises an amylose content of at least 40%, at least 50% or at least 60% as a proportion of the total starch in the grain. In some embodiments, amylose content is determined or expressed on a per caryopsis basis relative to controls.

In other embodiments, the barley grain comprises a β-glucan content of 5-9% (w/w), or greater than 9% (w/w).

In some embodiments, the barley grain comprises a fructan content of 2-11%, 3-11%, or 4-11% (w/w).

In other embodiments, the fructan comprises a degree of polymerization from about 3 to about 12.

In other embodiments, the barley grain comprises an elevated protein content relative to wild-type barley, or relative to HAG.

In many embodiments, the barley grain is homozygous for the sex6-292 allele of SSIIa.

The grain may be in any useful form such as, without limitation, wholegrain or cracked, ground, polished, milled, kibbled, rolled or pearled grain.

The present invention extends to a barley plant capable of producing the grains as described herein having a reduced level or activity of SSIII and also to barley wholemeal or flour produced from the grains.

Grains comprising a reduced level or activity of SSIII as described herein are obtained or produced and processed to produce a food or beverage product.

In some embodiments, the invention is directed to a method of producing a food ingredient or beverage ingredient, wherein the method comprises: (i) obtaining or producing barley grain as described herein; and (ii) processing the grain to produce the ingredient.

In some embodiments, the ingredient comprises a nucleic acid molecule comprising a genetic variation which is (i) an induced mutation in a gene encoding SSIII, or (ii) a transgene which encodes an RNA molecule which reduces expression of a gene encoding SSIII, wherein the genetic variation causes said reduced level or activity of SSIII protein.

In another embodiment, the invention is directed to a method of producing a food or beverage product, wherein the method comprises: (i) obtaining or producing the ingredient produced according to the above method; and (ii) mixing the ingredient with another food ingredient or beverage ingredient to produce the product.

The ingredient may be conveniently selected from wholemeal, flour, starch, bran, β-glucan, fructan, non-starch polysaccharides, or cracked, ground, polished, milled, kibbled, rolled or pearled grain.

In another illustrative embodiment, the product is selected from the group consisting of bread, buns, breakfast cereal, cake, biscuit, pastry, crackers, muffins, pizza, croissants, bagels, pretzels, pasta, noodles, baking ingredients, baking mixes, soup, sauce, thickening agent, confectionary, tortillas, granola bars, snacks and other farinaceous goods. The product may be a beverage such as a high energy drink or smoothie.

The food or beverage product may conveniently be selected from flour, wholemeal, bran, fructan, starch, β-glucan, a low calorie additive, a bulking agent, a dietary fibre, a texturizing agent, a preservative, a probiotic agent or the like or any combination of these.

In some embodiments, the methods further comprise assessing the level or type of starch, starch content, the level or activity of GBSSI, SSI or SSIIIa or other starch-related enzymes or isoforms thereof, amylose, amylopectin, β-glucan, fructan, non-starch polysaccharides, dietary fibre, resistant starch in the barley grain or the ingredient or product therefrom.

In some embodiments, the invention provides a method of producing a barley plant capable of producing grain which has a reduced level or activity of SSIII protein and starch wherein the method comprises: (i) introducing into said plant, a nucleic acid which down-regulates the level or activity of endogenous starch synthase III (SSIII) in the plant relative to a control plant, or a mutation in an endogenous gene encoding SSIII in the plant, and (ii) selecting the barley plant which produces said grain.

In some embodiments, the nucleic acid molecule comprises a gene-silencing chimeric gene, an antisense, ribozyme, co-suppression, dsRNA molecule, hairpin RNA or other exogenous nucleic acid molecule that down-regulates endogenous SSIIIa and/or b expression.

In some embodiments, the method further comprises assessing the level, activity and/or type of starch, starch content, the level or activity of GBSSI, SSI, or SSIIIa or other starch related enzymes, amylose, amylopectin, β-glucan, fructan, non-starch polysaccharide, dietary fibre or resistant starch in the barley grain or a product therefrom, or analyzing the plant with one or more genetic markers including those using the presently disclosed sequences of barley SSIIIa.

In some embodiments, the reduced level or activity of SSIIIa protein in the grain is less than 25%, less than 10%, less than 5%, or essentially lacking relative to that of a control plant or the plant prior to the introduction of the genetic variation. In some embodiments, the method of producing the barley grain comprises the steps of growing a barley plant and harvesting the grain.

In another embodiment, the present invention provides for the use of a grain or flour isolated from a plant or grain as described herein in the production of a food product to increase the level of one or two or more of starch, amylose, amylopectin, β-glucan, fructan, non-starch polysaccharide, dietary fibre or resistant starch in the food product.

In another embodiment, the invention provides a method for preparing a food or beverage, comprising mixing the barley grain or a product obtained therefrom by the presently disclosed methods with another food or beverage ingredient. Thus the method comprises: (i) obtaining or producing barley grain comprising a reduced level or activity of SSIIIa protein; and (ii) processing the grain to produce the product.

The invention further provides a method for providing one or more starch, amylose, amylopectin, β-glucan, fructan, non-starch polysaccharide, dietary fibre or resistant starch to improve one or more indicators of health in a mammal, wherein the method comprises administering, to the mammal, a composition comprising barley grain, wholemeal or flour therefrom or a food or beverage obtained therefrom comprising a reduced level or activity of SSIIIa protein or the food product as described herein.

In some embodiments, the grain, flour, starch, amylose, amylopectin, β-glucan, fructan, non-starch polysaccharide, dietary fibre or resistant starch is in the form of a food product, a beverage or a pharmaceutical composition. In some embodiments, the one or more indicators of health is an increased number of beneficial intestinal bacteria, reduced number of aberrant crypt foci, increased mineral absorption, reduced level of insulin, reduced glycaemic index, reduced glycaemic load, reduced blood glucose, reduced blood pressure, reduced body weight, reduced blood cholesterol level, increased HDL cholesterol level, increased bone density, increased calcium levels, more frequent bowel movement, or improved blood serum cardiovascular profile.

In a related embodiment, the invention provides a method for ameliorating one or more symptoms of a condition associated with low levels of one or more dietary starch, starch content, amylose, amylopectin, β-glucan, fructan, non-starch polysaccharide, dietary fibre or resistant starch in a subject, said method comprising administering orally to the subject grain as described herein or a processed product comprising one or more of starch, amylose, amylopectin, β-glucan, fructan, non-starch polysaccharide, dietary fibre or resistant starch obtained therefrom for a time and under conditions sufficient to ameliorate one or more symptoms.

In some embodiments of the method the condition is selected from the group consisting of diabetes, obesity, heart disease, hypertension, constipation, osteoporosis and cancer.

In another in another aspect the present invention provides isolated nucleic acid molecules comprising sequences encoding barley SSIII such as SEQ ID NOs: 2 and 3 or their complements or oligonucleotide fragments thereof for use inter alia in the product of the subject barley grains. In another embodiment, the invention provides isolated barley SSIII proteins having at least about 98% sequence identity to SEQ ID NO: 4 and/or variants thereof and barley grain or products therefrom or ingredients comprising same.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of sequence identifiers is provided in Table 11. A sequence listing is provided after the claims.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated (non coding) sequences).

The term "5' non-coding region" is used herein in its broadest context to include all nucleotide sequences which are derived from the upstream region of an expressible gene, other than those sequences which encode amino acid residues which comprise the polypeptide product of the gene, wherein 5' non-coding region confers or activates or otherwise facilitates, at least in part, expression of the gene.

Genes and other genetic material (e.g. mRNA, nucleic acid constructs etc) are represented herein in italics while their proteinaceous expression products are represented in non-italicized form. Thus, for example starch synthase III (SSIII) polypeptide is the expression product of SSIII nucleic acid sequences.

Representative examples of the nucleic acid and amino acid sequences of SSIII and SSIII molecules are provided in the sequence listing further described in Table 11. In an illustrative embodiment, the SSIII gene is a SSIIIa gene. In some embodiments, barley SSIIIa shares at least about 70% amino acid sequence identity with SSIIIb.

Bibliographic details of the publications referred to by author in this specification are collected at the end of the description.

The citation of any reference herein should not be construed as an admission that such reference is available as "Prior Art" to the instant application.

Any subject who could benefit from the present methods or compositions is encompassed. The term "subject" includes, without limitation, humans and non-human primates, livestock animals such as cattle, pigs or chickens, or young animals such as calves or piglets, companion animals such as dogs or cats, horses, laboratory test animals, captive wild animals, reptiles and amphibians, fish, and birds. A subject, regardless of whether it is a human or non-human organism may be referred to as a patient, individual, subject, animal, host or recipient. In a particular embodiment the subject is a human.

The present invention is predicated in part upon the provision of barley starch synthase III (SSIII) genetic and/or proteinaceous mutants which by themselves, or combined with other mutants, provide agronomic advantages.

As used herein, the terms "modifying", "altering", "increasing", "increased", "reducing", "reduced", "inhibited", "mutant", "variant" or the like are considered relative terms, i.e. in comparison with the wild-type or unaltered or control state. In some embodiments, a wild-type plant is an appropriate "control plant" however in many situations the control plant must be determined by the skilled addressee using their ordinary skill in the art and the information disclosed herein.

In an illustrative example, a reduced level or activity of SSIII protein or SSII protein expressed from a gene having a genetic variation as described herein is reduced relative to the level or activity of the protein in a barley plant or grain lacking the genetic variation. Illustrative controls include grain from Himalaya and Glacier.

The terms "wild-type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild-type" form of the gene.

The "level of a protein" refers to the amount of a particular protein, for example SSIII, which may be measured by any means known in the art such as, for example, by Western blot analysis, spectrophotometric, enzymatic or immunological means.

The "level of an enzyme activity" refers to the amount of a particular enzyme measured, for example, in an enzyme assay, an incorporation assay or a zymogram.

The "activity of SSIII protein" refers to the amount of a particular enzyme measured in an enzyme assay. SSIII protein refers to all isolated or non-isolated naturally occurring forms of SSIII and variants thereof. In some embodiments. SSIIIa proteins comprise an amino acid sequence that comprises at least 98% sequence identity to the SSIIIa amino acid sequence of a barley variety such as Himalaya, Himalaya292 or Glacier. In other embodiments, an SIIIa protein comprises an amino acid sequence having at least 98% sequence identity to SEQ ID NO: 4. Illustrative SSIIIa proteins comprise up to 15 amino acid residue substitutions, insertions or deletions or combinations thereof relative to SEQ ID NO: 4. Thus variants of SEQ ID NO: 4 or SSIIIa proteins encompass amino acid sequences which differ from SEQ ID NO: 4 by 1, 2, 3, 4, 5, 6, 7, 8, 9, 10, 11, 12, 13, 14, or 15 amino acid residues, or suitably as few as 10, 9, 8, 7, 6, 5, 4, 3, 2 or 1 amino acid residue(s).

SSIIIa genes/alleles encode SSIIIa proteins including a protein comprising at least 98% sequence identity to SEQ ID NO: 4. In some embodiments, an SSIIIa gene of the present invention is expressed as a SSIIIa protein having reduced or no starch synthase activity, or a reduced ability to repress starch synthase expression. In some embodiments, an SSIIIa gene of the barley grain comprising a herein described genetic variant expresses an RNA that is not translated or is only translated at a reduced level relative to SSIIIa nucleic acids encoding a protein having a sequence of SEQ ID NO: 4. In other embodiments, an SSIIIa gene of the barley grain comprising a genetic variant and is not transcribed or is only transcribed at a reduced level relative to SSIIIa genes encoding a protein having a sequence of SEQ ID NO: 4. The activity of isoforms of starch synthases are typically assayed by activity immunostaining or detection after native gel electrophoresis. Thus, for example, starch synthase activity is tested by incubated gels with amylopectin and staining for derived glucans with iodine. A reduction in SSIII activity may alternatively be determined by contacting gel resolved enzymes with ADP-glucose and measuring the incorporation of ADP by standard methods. In other embodiments, an SSIIIa protein with reduced or partial activity has a reduced activity as a repressor of GBSSI expression or the expression of other starch synthases such as SSI. SSIIa/SBEII genes and activity can be determined indirectly via measuring the activity of a non-SSIII starch synthase.

It would be appreciated that the level of activity of an enzyme might be altered in a mutant if a more or less active protein is produced, but not the expression level (amount) of the protein itself. Conversely, the amount of protein might be altered but the activity (per unit protein) remain the same. Reductions in both amount and activity are also possible such as, for example, when the expression of a gene encoding the enzyme is reduced transcriptionally or post-transcriptionally.

In certain embodiments, the reduction in the level of protein or activity of SSIII is by at least 40% or by at least 60% compared to the level of protein or activity in the grain of unmodified barley, or by at least 75%, at least 90% or at least 95% or at least 99%.

Figure 3:
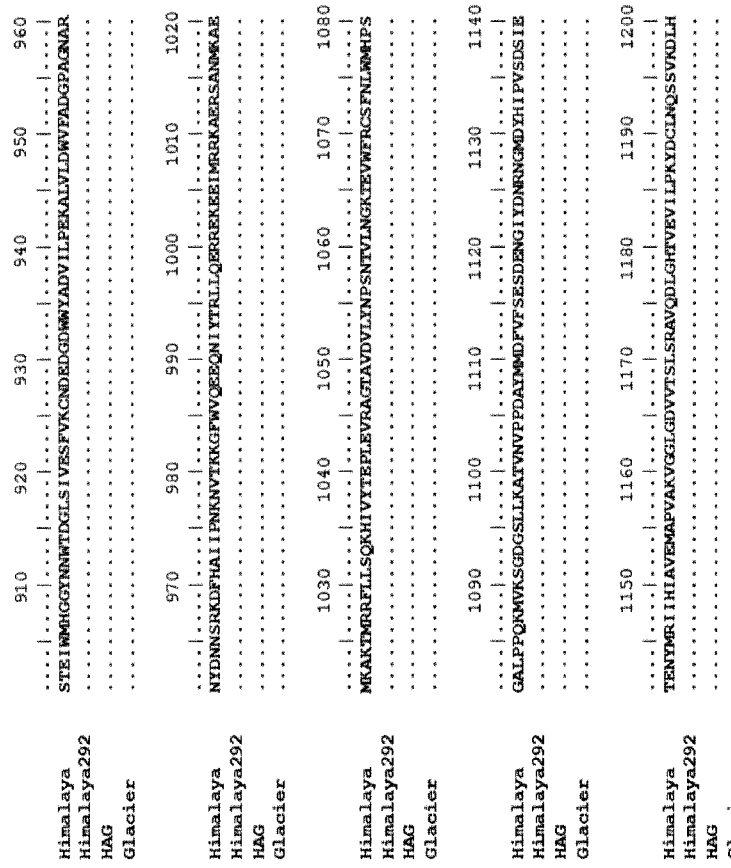
FIG. 3 is a comparison of amino acid sequences of barley ssIIIa gene from Himalaya (SEQ ID NO:4). Himalava292 (SEQ ID NO:4). HAG (SEQ ID NO:71), and Glacier (SEQ ID NO:72) showing the amo mutation at L1480R in HAG.

In some embodiments, a reduction in activity is measured relative to the activity of SSIIIa proteins comprising the amino acid sequence set out in SEQ ID NO: 4 that has the activity or the same amino acid sequence (see FIG. 3) of SSIIIa of Himalaya, Himalaya292 or Glacier barley varieties. In some embodiments, a reduced activity of SSIIIa protein includes partial activity such as 5-75% of the wild-type (unmodified) activity of SSIIIa protein. In some embodiments, the reduced activity is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% of SSIIIa protein activity.

The reduction in the level of the protein or enzyme activity or gene expression may occur at any stage in the development of the leaf, seed or grain, particularly during the daytime when photosynthesis is occurring, or during the grain filling stage while starch is being synthesized in the developing endosperm, or at all stages of grain development through to maturity. The term "wild-type" as used herein has its normal meaning in the field of genetics and includes barley cultivars or genotypes which are not modified as taught herein. Some preferred "wild-type" barley varieties are described herein, such as, for example, the cultivar Himalaya.

In some embodiments, the modified phenotype is achieved by full or partial inhibition of the expression of an SSIIIa gene. Techniques well known in the art such as SDS-PAGE and immunoblotting are carried out on hydrolysed and unhydrolysed grains and fractions thereof to identify the plants or grain where modifications have occurred to starch related enzymes These methods include analysis of plants by methods described herein or further by methods such as such as microarray analysis, electrophoresis, chromatography (including paper chromatography, thin layer chromatography, gas chromatography, gas-liquid chromatography and high-performance liquid chromatography) techniques. Separated components are typically identified by comparison of separation profiles with standards of known identity, or by analytical techniques such as mass spectrometry and nuclear magnetic resonance spectroscopy. For example, reference may be made to Example 9, Robinson, *The Organic Constituents of Higher Plants*, Cordus Press, North Amherst, USA, 1980; Adams et al., *Anal. Biochem.*, 266: 77-84, 1999; Veronese et al., *Enz. Microbial Tech.*, 24: 263-269, 1999; Hendrix et al., *J. Insect Physiol.*, 47: 423-432, 2001; Thompson et al., *Carbohydrate Res.*, 331: 149-161, 2001; and references cited therein. Carbohydrates can be assayed using standard protocols known to persons skilled in the art.

Alteration in SSIIIa level or activity may be achieved by the introduction of one or more genetic variations into the barley plant. That is, the genetic variations lead, directly or indirectly, to the alteration in enzyme activity or level in the plant part during growth or development and consequently to the enzyme, starch and non-starch modifications described herein. The genetic variation may be a heterologous polynucleotide which is introduced into the plant or a progenitor cell, for example by transformation or mutagenesis. The genetic variation and further genetic variation may subsequently be introduced into different genetic backgrounds by crossing, as known in the art of plant breeding.

In some embodiments, the level or functional activity of SSIIIa is down regulated to a level less than about 80%, less than 70%, less than 60%, less than 50%, less than 40%, less than 30%, less than 20% or less than 15%, and suitably less than about 10%, less than 9%, less than 8%, less than 7%, less than 6%, less than 5%, less than 4%, less than 3%, less than 2% or less than 1% relative to a corresponding control plant.

In other embodiments, the level or activity of non-SSIIIa starch synthase is upregulated to a level more than about 80%, more than 70%, more than 60%, more than 50%, more than 40%, more than 30%, more than 20% or more than 15%, and suitably more than about 10%, more than 9%, more than 8%, more than 7%, more than 6%, more than 5%, more than 4%, more than 3%, more than 2% or more than 1% relative to a corresponding control plant.

In some embodiments, the level of downregulation of SSIIIa is modulated to achieve elevated levels of starch or non-starch components of agronomic interest as described herein and elsewhere. The amount of reduced SSIIIa level or activity required may depend upon other factors such as the variety genetic background and environmental factors. However, it is considered that any optimisation, which may be required in such an event is achievable using routine methods including those described herein. In some embodiments, the variant is a homozygous null mutation.

Reduced SSIIIa level or activity may be accomplished in tissues throughout the plant, for example using a constitutive promoter to drive expression of a (transgene) to down regulate SSIIIa. Preferably, it may be accomplished in sink tissues, more preferably in developing endosperm, using a tissue-specific or developmentally regulated promoter. "Sink cell" and "sink tissue" as used herein, refer to cells, tissues or organs which comprise a net inflow of organic carbon that has entered the cells in a form other than fixation of carbon dioxide i.e. as sugars or other carbohydrates. In plants, sink tissues include all non-photosynthetic tissues, as well as photosynthetic tissues with a net inflow of organic carbon fixed by other photosynthetic cells or otherwise obtained from the surrounding medium or environment by means other than direct fixation of carbon dioxide.

Genes

In some embodiments, the present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

The "starch synthase 111 gene" "SSIII" or the like as used herein refers to a nucleotide sequence encoding starch synthase (SSIII) in barley, which can readily be distinguished from other starch synthases or other proteins by those skilled in the art. SSIII proteins are described herein as including proteins having an amino acid sequence of at least 98% sequence identity to SEQ ID NO: 4. In a preferred embodiment, a barley SSIIIa gene refers to a nucleic acid molecule or its complement, which may be present in or isolated from barley or derived therefrom, comprising nucleotides having a sequence having at least 80% identity to the cDNA sequence shown in SEQ ID NO: 2 or the genomic sequence of SEQ ID NO: 1. In a preferred embodiment, the SS/1/gene is an SSIIIa gene, or the SSII protein is an SSIIa protein, each of which may be applied to any or all of the aspects of the invention disclosed herein. The nucleotide sequence of cDNA of the SSIIIa gene from wildtype Himalaya is set out in SEQ ID NO: 2.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome. Table 3 describes the intron/exon structure of barley SSIIIa gene and SNPs from various varieties (HAG, Glacier, Himalaya292 and Himalaya).

As used herein, a "chimeric gene" refers to any gene that is not a native gene in its native location. Typically a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. These include gene sequences found in that cell so long as the introduced gene contains some modification (e.g. a mutation, the presence of a selectable marker gene, etc.) relative to the naturally-occurring gene. Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Polynucleotides

The present invention including the description, tables and sequence listing, refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement.

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence.

The present invention contemplates the use of oligonucleotides. As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length. Various oligonucleotides are described herein (see Table 11).

Polynucleotides used as a probe are typically conjugated with a detectable label such as a radioisotope, hapten, an enzyme, biotin, a fluorescent molecule or a chemiluminescent molecule. Oligonucleotides based on barley SSIIIa sequences are useful in methods of detecting an allele of an SSIIIa. Such methods, for example, employ nucleic acid hybridization and in many instances include oligonucleotide primer extension by a suitable polymerase (as used in PCR).

A variant of an oligonucleotide of the invention includes molecules of varying sizes of, and/or are capable of hybridizing, for example, to the cereal genome close to that of, the specific oligonucleotide molecules defined herein. For example, variants may comprise additional nucleotides (such as 1, 2, 3, 4, or more), or less nucleotides as long as they still hybridize to the target region. Furthermore, a few nucleotides may be substituted without negatively influencing the ability of the oligonucleotide to hybridize to the target region. In addition, variants may readily be designed which hybridize close to, for example to within 50 nucleotides, the region of the plant genome where the specific oligonucleotides defined herein hybridize. Probes, oligonucleotides and the like are based upon the herein described sequences or corrected versions thereof or variants thereof or functional homologs from other cereal plants.

The terms "polynucleotide variant" and "variant" and the like refer to polynucleotides or their complementary forms displaying substantial sequence identity with a reference polynucleotide sequence. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridizing agents. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

By "corresponds to" or "corresponding to" is meant a polynucleotide (a) having a nucleotide sequence that is substantially identical or complementary to all or most of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a minimum number of nucleotides or amino acid residues or over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The °/0 identity of a polynucleotide can be determined by GAP (Needleman and Wünsch, *J. Mol. Biol.* 48: 444-453, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, at least 500 or at least 600 nucleotides in each case. Reference also may be made to the BLAST family of programs as for example disclosed by Altschul et al., *Nucleic Acids Res.* 25: 3389, 1997. A detailed discussion of sequence analysis can be found in Unit 19.3 of Ausubel et al., "*Current Protocols in Molecular Biology*", John Wiley & Sons Inc, 1994-1998, Chapter 15.

Nucleotide or amino acid sequences are indicated as "essentially similar" when such sequences have a sequence identity of at least 80%, particularly at least 85%, quite particularly at least 90%, especially at least 95%, more especially are identical. It is clear that when RNA sequences are described as essentially similar to, correspond to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO., such as SEQ ID NO: 1, 2, 32 or 33.

Preferably, a polynucleotide of the invention which encodes a polypeptide with SSIIIa activity is greater than 800, preferably greater than 900, and even more preferably greater than 1,000 or 2000 nucleotides in length.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

The present invention refers to the stringency of hybridization conditions to define the extent of complementarity of two polynucleotides. "Stringency" as used herein, refers to the temperature and ionic strength conditions, and presence or absence of certain organic solvents, during hybridization and washing. The higher the stringency, the higher will be the degree of complementarity between a target nucleotide sequence and the labelled polynucleotide sequence (probe). "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Ausubel et al., (eds.), *Current Protocols in Molecular Biology*, John Wiley & Sons, NY, 6.3.1-6.3.6., 1989. Aqueous and non-aqueous methods are described in that reference and either can be used. Specific hybridization conditions referred to herein are as follows: 1) low stringency hybridization conditions are for hybridization in 6× sodium chloride/sodium citrate (SSC) at 45° C., followed by two washes in 0.2×SSC, 0.1% SDS at 50-55° C.; 2) medium stringency hybridization conditions are for hybridization in 6×SSC at about 45° C., followed by one or more washes in 0.2×SSC, 0.1% SDS at 60° C.; 3) high stringency hybridization conditions are for hybridization in 6×SSC at 45° C., followed by one or more washes in 0.2×SSC, 0.1% SDS at 65° C.; and 4) very high stringency hybridization conditions are for hybridization in 0.5 M sodium phosphate buffer, 7% SDS at 65° C., followed by one or more washes at 0.2×SSC, 1% SDS at 65° C.

Polypeptides

The terms "polypeptide" and "protein" are generally used interchangeably. The terms "proteins" and "polypeptides" as used herein also include variants, mutants, modifications, analogs and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 90% free from other components with which it is naturally associated. By "recombinant polypeptide" is meant a polypeptide made using recombinant techniques, i.e., through the expression of a recombinant polynucleotide in a cell, preferably a plant cell and more preferably a cereal plant cell.

Illustrative proteins having SSIIIa activity (unmodified) or partial (reduced) SSIIIa activity are set out in the sequence listing and described in Table 11. Accordingly, the present invention proposes without limitation the modification of SSIIIa polypeptides having the amino acid sequences set forth in SEQ ID NO: 4 and naturally occurring variants, corrected versions thereof and variants as described herein such as variants having at least about 80% sequence identity or at least 98% sequence identity. The invention extends however to SSIIIa proteins having substantially no activity such as substantially no starch synthase activity or no SSIIIa activity in the endosperm including the developing endosperm, or starch granule or soluble fraction.

With regard to a defined polypeptide, it will be appreciated that % identity figures higher than those provided above will encompass particular embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO: 4.

In some embodiments, the length of a reference sequence aligned for comparison purposes is at least 30%, usually at least 40%, more usually at least 50%, 60%, and even more usually at least 70%, 80%, 90%, 1001 of the length of the reference sequence. The comparison of sequences and determination of percent identity or percent similarity between sequences can be accomplished using a mathematical algorithm. In some embodiments, the comparison is along the full length protein, preferably using the BLASTP program with default parameters. In certain embodiments, the percent identity or similarity between amino acid sequences is determined using the Needleman and Wünsch, 1970 (supra) algorithm which has been incorporated into the GAP program in the GCG software package (available at www.gcg.com), using either a Blossum 62 matrix or a PA 250 matrix, and a gap weight of 16, 14, 12, 10, 8, 6, or 4 and a length weight of 1, 2, 3, 4, 5, or 6. In specific embodiments, the percent identity between nucleotide sequences is determined using the GAP program in the GCG software package (available at www.gcg.com), using a NWSgapdna.CNP matrix and a gap weight of 40, 50, 60, 70, or 80 and a length weight of 1, 2, 3, 4, 5, or 6. An non-limiting set of parameters (and the one that should be used unless otherwise specified) includes a Blossom 62 scoring matrix with a gap penalty of 12, a gap extend penalty of 4, and a frameshift gap penalty of 5.

In some embodiments, the percent identity or similarity between amino acid or nucleotide sequences can be determined using the algorithm of Meyers and Miller, *Cabins*, 4: 11-17, 1989 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al., *J. Mol. Biol*, 215: 403-10, 1990). BLAST nucleotide searches can be performed with the NBLAST program, score=100, wordlength=12 to obtain nucleotide sequences homologous to 53010 nucleic acid molecules of the invention. BLAST protein searches can be performed with the XBLAST program, score=50, wordlength=3 to obtain amino acid sequences homologous to 53010 protein molecules of the invention. To obtain gapped alignments for comparison purposes, Gapped BLAST can be utilized as described in Altschul et al., 1997 (supra). When utilizing BLAST and Gapped BLAST programs, the default parameters of the respective programs (e.g., XBLAST and NBLAST) can be used.

As used herein a "biologically active" fragment of a polypeptide is a portion of a polypeptide of the invention, less than full length, which maintains a defined activity of the full-length polypeptide. In a particularly preferred embodiment, the biologically active fragment is able to elongate long B chains connecting amylopectin structures. Biologically active fragments can be any size as long as they maintain the defined activity, but are preferably at least 200 or at least 250 amino acid residues long.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics. In some embodiments, the subject genetic variations encompass mutations that are non-conservative substitutions in conserved regions of SSIIIa conserved regions of SSIII such as the amino acid motifs set out in SEQ ID NOs: 34 to 41. These motifs are further described in International Publication No. WO/2000/066745 incorporated herein by reference in its entirety.

The sequence motifs from the WO2000/066745 (wheat SSIII) are present at the following positions in the barley SSIIIa sequence: (a) 1159-1169; (b) 1178-1188; (c) 1272-1287; (d) 1347-1362; (e) 1395-1410; (f) 1425-1434; (g) 1474-1500; and (h) 1507-1514 (al) inclusive).

The Himalaya (wildtype) barley sequence has one amino acid substitution in each of e, g and h compared to the wheat SSIIIa sequence. Those substitutions are conservative amino acid changes. The mutant sequence in amo1-38 is at position 1480 within motif (g), and is non-conservative. Accordingly, particular mutants are non-conservative changes in these motifs. Mutant (variant) sequences can be produced using any technique known in the art. Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 13 under the heading of "exemplary substitutions".

Polypeptides of the present invention can be produced in a variety of ways, including production and recovery of natural polypeptides, production and recovery of recombinant polypeptides, and chemical synthesis of the polypeptides.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, including a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promote" refers to a promoter that directs expression of an operably linked transcribed sequence in many or all tissues of a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of the plant, such as, for example, endosperm, embryo, leaves, fruit, tubers or root. In one embodiment, a promoter is expressed in all photosynthetic tissue, which may correspond to all aerial parts of the plant, for example a promoter that is involved in expressing a gene required for photosynthesis such as rubisco small subunit promoters. The term may also refer to expression at specific developmental stages in an organ, such as in early or late embryogenesis or different stages of maturity; or to expression that is inducible by certain environmental conditions or treatments. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the endosperm, cytosol, vacuole, or apoplastic space may be achieved by the inclusion in the structure of the gene product of appropriate signals for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in a plant. Typically, the promoter is expressed at a level 10-fold higher in the specific tissue or organ than in other tissues or organs. An illustrative tissue specific promoter is the promoter for high molecular weight (HMW) glutenin gene, Bx17 (see FIG. 2) which is expressed preferentially in the developing endosperm of cereal plants. Further endosperm specific promoters include the high molecular weight glutenin promoter, the wheat SSI promoter, and the wheat BEII promoter. Other endosperm-specific promoters may readily be obtained from genes which encode starch biosynthetic enzymes or storage proteins in the developing grain.

The promoters contemplated by the present invention may be native to the host plant to be transformed or may be derived from an alternative source, where the region is functional in the host plant. Other sources include the Agrobacterium T-DNA genes, such as the promoters of genes for the biosynthesis of nopaline, octapine, mannopine, or other opine promoters; promoters from plants, such as ubiquitin promoters such as the Ubi promoter from the maize ubi-1 gene, Christensen et al., (1996) (see, e.g., U.S. Pat. No. 4,962,028) or actin promoters; tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, *J. Mol. Appl. Genet.*, 1: 499-511, 1983; Salomon et al., *EMBO J.*, 3: 141-146, 1984; Garfinkel et al., *Cell*, 27: 143-153, 1983; Barker et al., *Plant Mol. Biol.*, 2: 235-350, 1983; including various promoters isolated from plants and viruses such as the cauliflower mosaic virus promoter (CaMV 35S, 19S). Many tissue specific promoter regions are known. Other transcriptional initiation regions which preferentially provide for transcription in certain tissues or under certain growth conditions, include those from genes encoding napin, seed ACP, zein, or other seed storage proteins. Fruit specific promoters are also known, one such promoter is the E8 promoter, described by Deikman et al., *EMBO* 1, 2: 3315-3320, 1998 and DellaPenna et al., *Plant Cell*, 1: 53-63, 1989. Non-limiting methods for assessing promoter activity are disclosed by Medberry et al., *Plant Cell*, 4: 185-192, 1992; Medberry et al., *Plant J.* 3: 619-626, 1993, Sambrook et al., *Molecular Cloning: A Laboratory Manual* (2nd ed.). Cold Spring Harbour Laboratory, Cold Spring Harbour, N.Y., 1989, and McPherson et al. (U.S. Pat. No. 5,164,316).

Alternatively or additionally, the promoter may be an inducible promoter or a developmentally regulated promoter which is capable of driving expression of the introduced polynucleotide at an appropriate developmental stage of the plant. Other cis-acting sequences which may be employed include transcriptional and/or translational enhancers. Enhancer regions are well known to persons skilled in the art, and can include an ATG translational initiation codon and adjacent sequences. The initiation codon must be in phase with the reading frame of the coding sequence relating to the foreign or exogenous polynucleotide to ensure translation of the entire sequence. The translation control signals and initiation codons can be of a variety of origins, both natural and synthetic. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention typically comprises a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from the nopaline synthase (nos) gene of *Agrobacterium tumefaciens* (Bevan et al., *Nucl. Acid Res.*, 11: 369, 1983) and the terminator for the 17 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the small subunit of the ribulose-1,5-bisphosphate carboxylase (ss-RUBISCO) gene, although other 3' elements known to those of skill in the art can also be employed. Alternatively, 3' non-translated regulatory sequences can be obtained de novo as, for example, described by An, *Methods in Enzymology*, 153: 292, 1987, which is incorporated herein by reference.

As the DNA sequence inserted between the transcription initiation site and the start of the coding sequence, i.e., the untranslated 5' leader sequence (5'UTR), can influence gene expression, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi, *Nucl. Acid Res.* 15: 6643, 1987.

Additionally, targeting sequences may be employed to target the enzyme encoded by the foreign or exogenous polynucleotide to an intracellular compartment, for example to the chloroplast, within plant cells or to the extracellular environment. For example, a nucleic acid sequence encoding a transit or signal peptide sequence may be operably linked to a sequence that encodes a chosen enzyme of the subject invention such that when translated, the transit or signal peptide can transport the enzyme to a particular intracellular or extracellular destination, and can then be optionally post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct of the invention can further comprise a plastid transit peptide-encoding nucleic acid sequence operably linked between a promoter region and the foreign or exogenous polynucleotide.

Vectors

The present invention includes use of vectors for manipulation or transfer of genetic constructs. By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (npt) gene conferring resistance to kanamycin, paromomycin, G418 and the like as, for example, described by Potrykus et al., *Mol. Gen. Genet.* 199: 183, 1985; a glutathione-S-transferase gene from rat liver conferring resistance to glutathione derived herbicides as, for example, described in EP-A 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP-A 275957, a gene encoding a 5-enolshikimate-3-phosphate synthase (EPSPS) conferring tolerance to N-phosphonomethylglycine as, for example, described by Hinchee et al., *Biotech.* 6: 915, 1988, a bar gene conferring resistance against bialaphos as, for example, described in WO 91/02071; a nitrilase gene such as bxn from *Klebsiella ozaenae* which confers resistance to bromoxynil (Stalker et al., *Science,* 242: 419, 1988); a dihydrofolate reductase (DHFR) gene conferring resistance to methotrexate (Thillet et al., *J. Biol, Chem.* 263: 12500, 1988); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., *Biochem. Biophys. Res. Comm.* 126: 1259-68, 1985), which may be employed in calcium-sensitive bioluminescence detection; a green fluorescent protein gene (Niedz et al., *Plant Cell Reports,* 14: 403, 1995); a luciferase (luc) gene (Ow et al., *Science,* 234: 856, 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Methods of Modifying Gene Expression

In an illustrative embodiment, the level of an SSIIIa protein may be modulated by decreasing the level of expression of a gene encoding the protein in the plant. A plurality of transformants may be selected and screened for those with a favourable level and/or specificity of transgene expression arising from influences of endogenous sequences in the vicinity of the transgene integration site. A favourable level and pattern of transgene expression as disclosed herein is one which results in a substantial decrease in SSIIIa protein of SSIIIa activity or an increase in other starch synthase levels such as GBSSI and/or SSI levels. This may be detected by simple testing of grain from the transformants. Testing may conveniently be performed based upon enzyme activity, e.g. zymogram analysis Alternatively, a population of mutagenized grain or a population of plants from a breeding program may be screened for individual lines with altered phenotypes.

Reducing gene expression may be achieved through introduction and transcription of a "gene-silencing chimeric gene" introduced into the plant cell. The gene-silencing chimeric gene may be introduced stably into the plant cell's genome, preferably nuclear genome, or it may be introduced transiently, for example on a viral vector. As used herein "gene-silencing effect" refers to the reduction of expression of a target nucleic acid in a plant cell, which can be achieved by introduction of a silencing RNA. Such reduction may be the result of reduction of transcription, including via methylation of chromatin remodeling, or post-transcriptional modification of the RNA molecules, including via RNA degradation, or both. Gene-silencing includes an abolishing of the expression of the target nucleic acid or gene and a partial effect in either extent or duration. It is sufficient that the level of expression of the target nucleic acid in the presence of the silencing RNA is lower that in the absence thereof. The level of expression may be reduced by at least about 40%, or at least about 50%, or at least about 60%, or at least about 70%, or at least about 80%, or at least about 90%, or at least about 95%, or at least about 99%.

Antisense RNA Molecules

Antisense techniques may be used to reduce gene expression according to the invention. The term "antisense RNA" shall be taken to mean an RNA molecule that is complementary to at least a portion of a specific mRNA molecule and capable of reducing expression of the gene encoding the mRNA. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, Hartmann and Endres, *Manual of Antisense Methodology*, Kluwer, 1999). The use of antisense techniques in plants has been reviewed by Bourque, *Plant Sci.* 105: 125-149, 1995 and Senior, *Biotech. Genet. Engin. Revs.* 15: 79-119, 1998. Bourque, 1995 (supra) lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior, 1998 (supra) states that antisense methods are now a very well established technique for manipulating gene expression.

As used herein, the term "an antisense polynucleotide which hybridizes under physiological conditions" means that the polynucleotide (which is fully or partially single stranded) is at least capable of forming a double stranded polynucleotide with an RNA product of the gene to be inhibited, typically the mRNA encoding a protein such as those provided herein, under normal conditions in a cell. Antisense molecules may include sequences that correspond to the structural genes or for sequences that effect control over the gene expression or splicing event. For example, the antisense sequence may correspond to the coding region of SSIIIa gene, or the 5'-untranslated region (UTR) or the 3'-UTR or combination of these. It may be complementary in part to intron sequences, which may be spliced out during or after transcription, but is preferably complementary only to exon sequences of the target gene. In view of the generally greater divergence of the UTRs, targeting these regions provides greater specificity of gene inhibition.

The length of the antisense sequence should be at least 19 contiguous nucleotides, preferably at least 25 or 30 or 50 nucleotides, and more preferably at least 100, 200, 500 or 1000 nucleotides, to a maximum of the full length of the gene to be inhibited. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Genetic constructs to express an antisense RNA may be readily made by joining a promoter sequence to a region of the target gene in an "antisense" orientation, which as used herein refers to the reverse orientation relative to the orientation of transcription and translation (if it occurs) of the sequence in the target gene in the plant cell. Accordingly, also provided by this invention is a nucleic acid molecule such as a chimeric DNA coding for an antisense RNA of the invention, including cells, tissues, organs, plants, grain and the like comprising the nucleic acid molecule. Illustrative gene constructs are described in the Examples.

Ribozymes

The term "ribozyme" as used herein refers to an RNA molecule which specifically recognizes a distinct substrate RNA and catalyzes its cleavage. Typically, the ribozyme contains a region of nucleotides which are complementary to a region of the target RNA, enabling the ribozyme to specifically hybridize to the target RNA under physiological conditions, for example in the cell in which the ribozyme acts, and an enzymatic region referred to herein as the "catalytic domain". The types of ribozymes that are particularly useful in this invention are the hammerhead ribozyme (Haseloff and Gerlach, *Nature* 334: 585-591, 1988; Perriman or al. Gene, 113: 157-163, 1992) and the hairpin ribozyme (Shippy et al., *Mol. Biotech.* 12: 117-129, 1999). DNA encoding the ribozymes can be synthesized using methods well known in the art and may be incorporated into a genetic construct or expression vector for expression in the cell of interest. Accordingly, also provided by this invention is a nucleic acid molecule such as a chimeric DNA coding for a ribozyme of the invention, including cells, tissues, organs, plants, grain and the like comprising the nucleic acid molecule. Typically, the DNA encoding the ribozyme is inserted into an expression cassette under control of a promoter and a transcription termination signal that function in the cell. Specific ribozyme cleavage sites within any potential RNA target may be identified by scanning the target molecule for ribozyme cleavage sites which include the trinucleotide sequences GUA. GUU and GUC. Once identified, short RNA sequences of between about 5 and 20 ribonucleotides corresponding to the region of the target gene 5' and 3' of the cleavage site may be evaluated for predicted structural features such as secondary structure that may render the oligonucleotide sequence less suitable. When employed, ribozymes may be selected from the group consisting of hammerhead ribozymes, hairpin ribozymes, axehead ribozymes, newt satellite ribozymes, Tetrahymena ribozymes and RNAse P ribozymes, and are designed according to methods known in the art based on the sequence of the target gene (for instance, see U.S. Pat. No. 5,741,679). The suitability of candidate targets may also be evaluated by testing their accessibility to hybridization with complementary oligonucleotides, using ribonuclease protection assays.

As with antisense polynucleotides described herein, ribozymes of the invention should be capable of hybridizing to a target nucleic acid molecule (for example an mRNA encoding a polypeptide provided as SEQ ID NO: 4) or a naturally occurring variant thereof under "physiological conditions", namely those conditions within a cell, especially conditions in a plant cell such as a wheat or barley cell.

RNA Interference/Duplex RNA

As used herein, "artificially introduced dsRNA molecule" refers to the introduction of dsRNA molecule, which may e.g. occur endogenously by transcription from a chimeric gene encoding such dsRNA molecule, however does not refer to the conversion of a single stranded RNA molecule into a dsRNA inside the eukaryotic cell or plant cell. RNA interference (RNAi) is particularly useful for specifically reducing the expression of a gene or inhibiting the production of a particular protein. Although not wishing to be limited by theory, Waterhouse et al., *Proc. Natl. Acad. Sci. U.S.A.* 95: 13959-13964, 1998 have provided a model for the mechanism by which dsRNA can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are transcribed to produce a hairpin RNA in which the sense and anti-sense sequences hybridize to form the dsRNA region with an intervening sequence or spacer region forming a loop structure, so the hairpin RNA comprises a stem-loop structure. The design and production of suitable dsRNA molecules for the present invention is well within the capacity of a person skilled in the art, particularly considering Waterhouse et al., 1998 (supra), Smith et al., *Nature,* 407: 319-320, 2000, WO 99/53050, WO 99/49029, and WO 01/34815. Accordingly, also provided by this invention is a nucleic acid molecule such as a chimeric DNA coding for a duplex RNA such as a hairpin RNA of the invention, including cells, tissues, organs, plants, grain and the like comprising the nucleic acid molecule.

In one example, a DNA is introduced that directs the synthesis of an at least partly double stranded RNA product(s) with homology to the target gene to be inactivated. The DNA therefore comprises both sense and anti-sense sequences that, when transcribed into RNA, can hybridize to form the double-stranded RNA region.

In a preferred embodiment, the sense and antisense sequences are separated by a spacer region that comprises an intron which, when transcribed into RNA, is spliced out. This arrangement has been shown to result in a higher efficiency of gene silencing (Smith et al., 2000 (supra)). The double-stranded region may comprise one or two RNA molecules, transcribed from either one DNA region or two.

The dsRNA may be classified as long hpRNA, having long, sense and antisense regions which can be largely complementary, but need not be entirely complementary (typically forming a basepaired region larger than about 100 bp, preferably ranging between 200-1000 bp). hpRNA can also be smaller with the double-stranded portion ranging in size from about 30 to about 50 bp, or from 30 to about 100 bp (see WO 04/073390, herein incorporated by reference). The presence of the double stranded RNA region is thought to trigger a response from an endogenous plant system that processes the double stranded RNA to oligonucleotides of 21-24 nucleotides long, and also uses these oligonucleotides for sequence-specific cleavage of the homologous RNA transcript from the target plant gene, efficiently reducing or eliminating the activity of the target gene.

The length of the sense and antisense sequences that hybridize should each be at least 19 contiguous nucleotides, preferably at least 27 or 30 or 50 nucleotides, and more preferably at least 100, 200, or 500 nucleotides, up to the full-length sequence corresponding to the entire gene transcript. The lengths are most preferably 100-2000 nucleotides. The degree of identity of the sense and antisense sequences to the targeted transcript should be at least 85%, preferably at least 90% and more preferably 95-100%. The longer the sequence, the less stringent the requirement is for overall sequence identity. The RNA molecule may of course comprise unrelated sequences which may function to stabilize the molecule. The RNA molecule may be a hybrid between different sequences targeting different target RNAs, allowing reduction in expression of more than one target gene, or it may be one sequence which corresponds to a family of related target genes such as a multigene family. The sequences used in the dsRNA preferably correspond to exon sequences of the target gene and may correspond to 5' and/or 3' untranslated sequences or protein coding sequences or any combination thereof.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors. Typically, the RNA molecule is expressed under the control of a RNA polymerase II or RNA polymerase III promoter. Examples of the latter include tRNA or snRNA promoters.

Other silencing RNA may be "unpolyadenylated RNA" comprising at least 20 consecutive nucleotides having at least 95% sequence identity to the complement of a nucleotide sequence of an RNA transcript of the target gene, such as described in WO 01/12824 or U.S. Pat. No. 6,423,885 (both documents herein incorporated by reference). Yet another type of silencing RNA is an RNA molecule as described in WO 03/076619 (herein incorporated by reference) comprising at least 20 consecutive nucleotides having at least 95% sequence identity to the sequence of the target nucleic acid or the complement thereof, and further comprising a largely-double stranded region as described in WO 03/076619.

MicroRNA regulation is a specialized branch of the RNA silencing pathway that evolved towards gene regulation, diverging from conventional RNAi/PTGS. MicroRNAs are a specific class of small RNAs that are encoded in gene-like elements organized in a characteristic partial inverted repeat.

When transcribed, microRNA genes give rise to partially basepaired stemlooped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, *Funct Integr Genomics,* 5: 129-135, 2005; Pasquinelli et al., *Curr Opin Genet Develop* 15: 200-205, 2005; Almeida and Allshire, *Trends Cell Biol.* 15: 251-258, 2005, herein incorporated by reference).

Cosuppression

Another molecular biological approach that may be used for specifically reducing gene expression is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter.

Methods of Introducing Nucleic Acids into Plant Cells/Transformation

A number of techniques are available for the introduction of nucleic acid molecules into a plant host cell, well known to workers in the art. The term "transformation" means alteration of the genotype of an organism, for example a bacterium or a plant, by the introduction of a foreign or exogenous nucleic acid. By "transformant" is meant an organism so altered. As used herein the term "transgenic" refers to a genetically modified plant in which the endogenous genome is supplemented or modified by the integration, or stable maintenance in a replicable non-integrated form, of an introduced foreign or exogenous gene or sequence. By "transgene" is meant a foreign or exogenous gene or sequence that is introduced into the genome of a plant. The nucleic acid molecule may be stably integrated into the genome of the plant, or it may be replicated as an extrachromosomal element. By "genome" is meant the total inherited genetic complement of the cell, plant or plant part, and includes chromosomal DNA, plastid DNA, mitochondrial DNA and extrachromosomal DNA molecules. The term "regeneration" as used herein in relation to plant materials means growing a whole, differentiated plant from a plant cell, a group of plant cells, a plant part such as, for example, from an embryo, scutellum, protoplast, callus, or other tissue, but not including growth of a plant from a seed.

The particular choice of a transformation technology will be determined by its efficiency to transform certain plant species as well as the experience and preference of the person practicing the invention with a particular methodology of choice. It will be apparent to the skilled person that the particular choice of a transformation system to introduce a nucleic acid construct into plant cells is not essential to or a limitation of the invention, provided it achieves an acceptable level of nucleic acid transfer. Guidance in the practical implementation of transformation systems for plant improvement is provided by Birch, *Ann Rev Plant Physiol Plant Mol Biol.* 48: 297-326, 1997.

Introduction and expression of foreign or exogenous polynucleotides may be performed using the T-DNA of the tumor-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilizing *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbors a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond, *Biotechnology,* 1: 262, 1983 and Hoekema et al., *Nature,* 303: 179, 1983. Such a binary system is preferred inter alia because it does not require integration into the Ti plasmid in *Agrobacterium*.

Methods involving the use of *Agrobacterium* include, but are not limited to: (a) co-cultivation of *Agrobacterium* with cultured isolated protoplasts; (b) transformation of plant cells or tissues with *Agrobacterium*; (c) transformation of seeds, apices or meristems with *Agrobacterium*, or (d) inoculation in planta such as the floral-dip method as described by Bechtold et al., *C. R. Acad. Sci. Paris,* 316: 1194, 1993 or in wheat (as described in WO 00/63398, herein incorporated by reference). This approach is based on the infiltration of a suspension of *Agrobacterium* cells. Alternatively, the chimeric construct may be introduced using root-inducing (Ri) plasmids of *Agrobacterium* as vectors.

Methods for transformation of cereal plants such as wheat and barley for introducing genetic variation into the plant by introduction of an exogenous nucleic acid and for regeneration of plants from protoplasts or immature plant embryos are well known in the art, see for example, Wan and Lemaux, *Plant Physiol,* 104: 37-48, 1994, Tingay et al., *Plant Journal* 11: 1369-1376, 1997, Canadian Patent Application No. 2,092,588, Australian Patent Application No 61781/94, Australian Patent No 667939, U.S. Pat. No. 6,100,447, International Patent Application PCT/US97/10621, U.S. Pat. No. 5,589,617, U.S. Pat. No. 6,541,257. Preferably, transgenic plants are produced by *Agrobacterium tumefaciens* mediated transformation procedures. Vectors carrying the desired nucleic acid construct may be introduced into regenerable cereal cells of tissue cultured plants or explants. The regenerable cells are preferably from the scutellum of immature embryos, mature embryos, callus derived from these, or the meristematic tissue. Immature embryos are preferably those from inflorescences about 10-15 days after anthesis.

The genetic construct can also be introduced into plant cells by electroporation as, for example, described by Fromm et al., *Proc. Natl. Acad, Sci. U.S.A.* 82: 5824, 1985 and Shimamoto et al., *Nature*, 338: 274-276, 1989. In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus.

Another method for introducing the nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al., *Nature,* 327: 70, 1987.

Alternatively, the nucleic acid construct can be introduced into a plant cell by contacting the plant cell using mechanical or chemical means. For example, a nucleic acid can be mechanically transferred by microinjection directly into plant cells by use of micropipettes. Alternatively, a nucleic acid may be transferred into the plant cell by using polyethylene glycol which forms a precipitation complex with genetic material that is taken up by the cell.

Mutagenesis

The plants of the invention can be produced and identified after mutagenesis. This may provide a plant which is non-transgenic, which is desirable in some markets.

Mutants can be either naturally occurring (that is to say, isolated from a natural source) or synthetic (for example, by performing mutagenesis on the nucleic acid) or induced. Generally, a progenitor plant cell, tissue, seed or plant may be subjected to mutagenesis to produce single or multiple mutations, such as nucleotide substitutions, deletions, additions and/or codon modification. In the context of this application, an "induced mutation" is an artificially induced genetic variation which may be the result of chemical, radiation or biologically-based mutagenesis, for example transposon or T-DNA insertion. In some embodiments, mutations are null mutations such as nonsense mutations, frameshift mutations, insertional mutations or splice-site variants which completely inactivate the gene. Nucleotide insertional derivatives include 5' and 3' terminal fusions as well as intra-sequence insertions of single or multiple nucleotides. Insertional nucleotide sequence variants are those in which one or more nucleotides are introduced into the nucleotide sequence, which may be obtained by random insertion with suitable screening of the resulting products. Deletional variants are characterized by the removal of one or more nucleotides from the sequence. Preferably, a mutant gene has only a single insertion or deletion of a sequence of nucleotides relative to the wild-type gene. Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or only one nucleotide. Such a substitution may be "silent" in that the substitution does not change the amino acid defined by the codon. Alternatively, conservative substituents are designed to alter one amino acid for another similar acting amino acid.

Typical conservative substitutions are those made in accordance with Table 13 "Exemplary substitutions".

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions.

In some embodiments, the barley grain comprises non-conservative substitution deletion of at least part of a SSII gene or a frameshift or splice site variation in such gene.

In some embodiments, one or more mutants are within a conserved region of SSIIIa encoding conserved motifs comprising the amino acid sequences set out in SEQ ID NOs: 34 to 41. In some embodiments, one or more mutations are within the region of SSIIIa encoding the catalytic domain of SSIIIa. Mutagenesis can be achieved by chemical or radiation means, for example EMS or sodium azide (Zwar and Chandler, *Planta* 197: 39-48, 1995).

Chemical mutagenesis tends to favour nucleotide substitutions rather than deletions. Heavy ion beam (HIB) irradiation is known as an effective technique for mutation breeding to produce new plant cultivars, see for example Hayashi et al., 2007 and Kazama et al., *Plant Biotechnology* 25: 113-117, 2008. Ion beam irradiation has two physical factors, the dose (gy) and LET (linear energy transfer, keV/um) for biological effects that determine the amount of DNA damage and the size of DNA deletion, and these can be adjusted according to the desired extent of mutagenesis. HIB generates a collection of mutants, many of them comprising deletions, that may be screened for mutations in SSIIIa. Useful mutants which are identified may be back-crossed with non-mutated plants as recurrent parents in order to remove and therefore reduce the effect of unlinked mutations in the mutagenised genome.

Biological agents useful in producing site-specific mutants include enzymes that include double stranded breaks in DNA that stimulate endogenous repair mechanisms. These include endonucleases, zinc finger nucleases, transposases and site-specific recombinases. Zinc finger nucleases (ZFNs), for example, facilitate site-specific cleavage within a genome allowing endogenous or other end-joining repair mechanisms to introduce deletions or insertions to repair the gap. Zinc finger nuclease technology is reviewed in Le Provost et al., *Trends in Biotechnology* 28(3): 134-141, 2009, See also Durai et al., *Nucleic Acids Research* 33(18): 5978-5990, 2005 and Liu et al., *Biotechnology and Bioengineering,* 106: 97-105, 2010.

Isolation of mutants may be achieved by screening mutagenized plants or seed. For example, a mutagenized population of barley plants may be screened for low SSIIIa activity in grain starch, mutation of the SSIIIa or by a PCR or heteroduplex based assay, or loss of the SSIII protein by ELISA or loss or gain of enzyme activity or level by starch gel electrophoresis and straining. Alternatively, the mutation may be identified using techniques such as "tilling" in a population mutagenized with an agent such as EMS (Slade and Knauf, *Transgenic Res.* 14: 109-115, 2005) or by deep sequencing of mutagenized pools. Such mutations may then be introduced into desirable genetic backgrounds by crossing the mutant with a plant of the desired genetic background and performing a suitable number of backcrosses to cross out the originally undesired parent background.

The mutation may have been introduced into the plant directly by mutagenesis or indirectly by crossing of two parental plants, one of which comprised the introduced mutation. The modified plants may be transgenic or non-transgenic. Using mutagenesis, a non-transgenic plant having reduced SSIIIa level or activity or essentially no SSIIIa of may be produced. The invention also extends to the grain or other plant parts produced from the plants and any propagating material of the plants that can be used to produce the plants with the desired characteristics, such as cultured tissue or cells. The invention clearly extends to methods of producing or identifying such plants or the grain produced by such plants.

Plants of the invention can be produced using the process known as TILLING (Targeting induced Local Lesions IN Genomes). In a first step, introduced mutations such as novel single base pair changes are induced in a population of plants by treating cells, seeds, pollen or other plant parts with a chemical mutagen or radiation, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel1, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique. TILLING is further described in Slade and Knauf, 2005 (supra), and Henikoff et al., *Plant Physiol.* 135: 630-636, 2004, herein incorporated by reference.

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., *Plant J.* 37: 778-786, 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Genetic Linkage and Analysis

As used herein, the term "genetically linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait barley grain. Such markers are well known to those skilled in the art and include molecular markers linked to genes determining traits such disease resistance, the presence or absence of a null yield, plant morphology, grain quality, other dormancy traits such as grain colour, gibberellic acid content in the seed, plant height, flour colour and the like.

Marker assisted selection is a well recognized method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants.

Any molecular biological technique known in the art which is capable of detecting alleles of an SSIIIa based upon the sequences disclosed herein or other gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, *Current Genomics*, 1: 301-311, 2000; Langridge et al., *Aust Agric Res* 52: 1043-1077, 2001). The invention also includes the use of molecular marker techniques to detect polymorphisms linked to alleles of (for example) an SSII gene which confers altered fructan accumulation. Such methods include the detection or analysis of restriction fragment length polymorphisms (RFLP). RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., 2001 (supra).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (McPherson and Moller (Ed), BIOS Scientific Publishers Ltd, Oxford, 2000). PCR can be performed on cDNA obtained from reverse transcribing mRNA isolated from plant cells expressing an SSIII gene or on genomic DNA isolated from a plant.

A primer is an oligonucleotide sequence that is capable of hybridizing in a sequence specific fashion to the target sequence and being extended during the PCR. Ampicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook or et al. (supra). Sequencing can be carried out by any suitable method, for example, dideoxy sequencing, chemical sequencing or variations thereof. Direct sequencing has the advantage of determining variation in any base pair of a particular sequence.

Many of the above methods are suitable for analyzing DNA and/or RNA to determine whether the barley plant or a part thereof comprises an allele of SSIII which comprise the sequence of SEQ ID NO: 3 or which comprise a nucleic acid other than SEQ ID NO: 3. In some embodiments, a process comprises analysing SSIIIa RNA of a barley plant or grain at a position corresponding to nucleobase 4439 of SEQ ID NO: 2 or characterising SSIIIa gene of a barley plant or grain at a position corresponding to nucleobase 8610 of SEQ ID NO: 1 or characterising the SSIIIa protein of a barley plant or grain at a position corresponding to amino acid 1480 of SEQ ID NO: 4. In accordance with this aspect of the invention the detection of a nucleobase other than threonine at a position corresponding to nucleobase 4439 of SEQ ID NO: 2 or a position corresponding to nucleobase 8610 of SEQ ID NO: 1 or an amino acid other than leucine at a position corresponding to amino acid 1480 of SEQ ID NO: 4 indicates the presence of an amo-1 allele/the presence of SEQ ID NO:3.

Plants

The present invention extends to barley plants that produce or are capable of producing the grain as hereinabove described and as herein described. For example, in some embodiments, the barley plants produce or are capable of producing barley grain comprising: (a) starch, (b) a first genetic variation which is (i) an induced mutation in an endogenous gene encoding a starch synthase III (SSIII), or (ii) a transgene which encodes an RNA molecule which reduces expression of an endogenous gene encoding an SSIII, and (c) a reduced level or activity of SSIII protein relative to the level or activity in barley grain lacking the first genetic variation.

In some embodiments, the plant or part therefrom comprises an allele of SSIIIa other than a allele comprising the nucleic acid sequence of SEQ ID NO: 3.

In some embodiments, the barley plants are a population of at least 1000 plants growing in a field.

In some embodiments, the plant is capable of producing grain which further comprises a second genetic variation in a gene encoding a protein involved in starch synthesis, starch catabolism, starch phosphorylation or non-starch carbohydrate synthesis. Illustrative proteins are described in the summary. In some embodiments, the second genetic variation is (i) a mutation in a gene encoding a starch synthase (SSII), in some embodiments a starch synthase IIa (SSIIa), or (ii) a transgene which encodes an RNA molecule which inhibits expression of a gene encoding an SSII, illustratively an SSIIa.

In some embodiments, the plant is capable of producing grain which comprises (i) an allele of SSIIIa other than an allele comprising the nucleic acid sequence of SEQ ID NO: 3 and (ii) an allele of SSIIa other than an allele comprising the nucleic acid sequence of SEQ ID NO: 33. In another version of this embodiment, the plant produces grain which lacks the allele of SSIIIa comprising the nucleic acid sequence of SEQ ID NO: 3 and lacks the allele of SSIIa comprising the nucleic acid sequence of SEQ ID NO: 33.

In another embodiments, the description enables a plant capable of producing barley grain comprising: (a) starch, (b) a first genetic variation which is (i) a mutation in a gene encoding an SSIII, or (ii) a transgene which encodes an RNA molecule which inhibits expression of a gene encoding an SSIII, and (c) a reduced level or activity of SSIII protein relative to the level or activity in barley grain lacking the first genetic variation, (d) a second genetic variation which is (i) a mutation in a gene encoding an SSII, or (ii) a transgene which encodes a nucleic acid molecule which inhibits expression of a gene encoding an SSII, (e) a reduced level or activity of SSII protein relative to the level or activity in barley grain lacking the second genetic variation, and wherein the grain comprises an allele of SSIIIa other than an allele comprising the nucleic acid sequence of SEQ ID NO: 3.

In exemplary embodiments, the SSIII is SSIIIa. In further illustrative embodiments, the SSII is SSIIa. In further illustrative embodiments the starch content of the grain is at least 43% (w/w), at least 45% (w/w), at least 47% (w/w), at least 50% (w/w), or 41-65% (w/w). In still further illustrative embodiments, the amylose content of the grain is at least 40%, at least 50% or at least 60% as a proportion of the total starch in the grain. In further embodiments, the β-glucan content of the grain is 5-9% (w/w), or greater than 9% (w/w). In still further embodiments, the fructan content of the grain as described herein is 2-11%, 3-11%, or 4-11% (w/w). Illustratively, the fructan comprises a degree of polymerization from about 3 to about 12. In yet further embodiments, the grain comprises an elevated protein content relative to wild-type barley, or relative to HAG. In some embodiments, the plant is capable of producing grain which is homozygous for the sex6-292 allele of SSIIa. As described herein, in some embodiments the SSIII gene encodes an SSIII protein comprising an amino acid sequence having at least 98% sequence identity to SEQ ID NO: 4.

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, endosperm, and seed coat), plant tissue (for example, vascular tissue, ground tissue, starch granules, starch, grain and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, pollen, tumor tissue, such as crown galls, and various forms of aggregations of plant cells in culture, such as calli. Exemplary plant tissues in or from seeds are endosperm, scutellum, aleurone layer and embryo. The invention accordingly includes plants and plant parts and products comprising these, particularly grain.

As used herein, the term "grain" refers to mature seed of a plant, such as is typically harvested commercially in the field. Thus, the term includes harvested seed and seed on a plant that is ready for harvesting. Mature cereal grain such as wheat or barley commonly has a moisture content of less than about 18-20%.

A "transgenic plant" as used herein refers to a plant that contains a gene construct not found in a wild-type plant of the same species, variety or cultivar.

That is transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence, Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "corresponding non-transgenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant, "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilization of the primary transgenic plant or by crossing such plants with another plant of the same species. This would generally be to modulate the production of at least one protein/enzyme defined herein in the desired plant or plant organ. Transgenic plant parts include all parts and cells of said plants comprising the transgene such as, for example, cultured tissues, callus and protoplasts.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers to amplify a specific DNA, the presence of which will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of the grain of the plant, or related phenotype such as altered starch related enzymatic activity.

As used herein, "germination" refers to the emergence of the root tip from the seed coat after imbibition. "Germination rate" refers to the percentage of seeds in a population which have germinated over a period of time, for example 7 or 10 days, after imbibition. A population of seeds can be assessed daily over several days to determine the germination percentage over time. With regard to seeds of the present invention, as used herein the term "germination rate which is substantially the same" means that the germination rate of the transgenic seeds is at least 90%, that of isogenic wild-type seeds.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Food Production

Accordingly, the invention provides barley plants and grain, and products obtained therefrom, that are useful for food or animal feed production. The description provides a process for producing a food ingredient or beverage ingredient, wherein the process comprises (i) obtaining or producing barley grain as described hereinabove or as described herein; and (ii) processing the grain to produce the ingredient.

Accordingly, in one embodiment, barley grain comprises: (a) starch, (b) a first genetic variation which is (i) an induced mutation in an endogenous gene encoding a starch synthase III (SSIII), or (ii) a transgene which encodes an RNA molecule which reduces expression of an endogenous gene encoding an SSIII, and (c) a reduced level or activity of SSIII protein relative to the level or activity in barley grain lacking the first genetic variation.

In some embodiments, the barley grain comprises an allele of SSIIIa other than a allele comprising the nucleic acid sequence of SEQ ID NO: 3.

In some embodiments, the grain further comprises a second genetic variation in a gene encoding a protein involved in starch synthesis, starch catabolism, starch phosphorylation or non-starch carbohydrate synthesis. In some embodiments, the second genetic variation is (i) a mutation in a gene encoding a starch synthase (SSII), in some embodiments a starch synthase IIa (SSIIa), or (ii) a transgene which encodes an RNA molecule which inhibits expression of a gene encoding an SSII, preferably an SSIIa.

In some embodiments, the grain comprises (i) an allele of SSIIIa other than an allele comprising the nucleic acid sequence of SEQ ID NO: 3 and (ii) an allele of SSIIa other than an allele comprising the nucleic acid sequence of SEQ ID NO: 33. In another version of this embodiment, the grain lacks the allele of SSIIIa comprising the nucleic acid sequence of SEQ ID NO: 3 and lacks the allele of SSIIa comprising the nucleic acid sequence of SEQ ID NO: 33.

In another embodiments, the barley grain comprises: (a) starch, (b) a first genetic variation which is (i) a mutation in a gene encoding an SSIII, or (ii) a transgene which encodes an RNA molecule which inhibits expression of a gene encoding an SSIII, and (c) a reduced level or activity of SSIII protein relative to the level or activity in barley grain lacking the first genetic variation, (d) a second genetic variation which is (i) a mutation in a gene encoding an SSII, or (ii) a transgene which encodes a nucleic acid molecule which inhibits expression of a gene encoding an SSII, (e) a reduced level or activity of SSII protein relative to the level or activity in barley grain lacking the second genetic variation, and wherein the grain comprises an allele of SSIIIa other than an allele comprising the nucleic acid sequence of SEQ ID NO: 3.

In exemplary embodiments, the SSIII is SSIIIa. In further illustrative embodiments, the SSII is SSIIa. In further illustrative embodiments the starch content of the grain is at least 43% (w/w), at least 45% (w/w), at least 47% (w/w), at least 50% (w/w), or 41-65% (w/w). In still further illustrative embodiments, the amylose content of the grain is at least 40%, at least 50% or at least 60% as a proportion of the total starch in the grain. In further embodiments, the β-glucan content of the grain is 5-9% (w/w), or greater than 9% (w/w). In still further embodiments, the fructan content of the grain as described herein is 2-11%, 3-11%, or 4-11% (w/w). Illustratively, the fructan comprises a degree of polymerization from about 3 to about 12. In yet further embodiments, the grain comprises an elevated protein content relative to wild-type barley, or relative to HAG. In some embodiments, the grain is homozygous for the sex6-292 allele of SSIIa. As described herein, in some embodiments the SSIII gene encodes an SSIII protein comprising an amino acid sequence having at least 98% sequence identity to SEQ ID NO: 4.

The grain of the present invention is, in some embodiments, wholegrain or cracked, ground, polished, milled, kibbled, rolled or pearled gain. In particular embodiments, the grain is processed and is unable to germinate. In some embodiments, the ingredient is isolated wholemeal, flour, starch, bran, β-glucan, fructan, non-starch polysaccharides, a baking ingredient, a baking mix, a thickening agent, or cracked, ground, polished, milled, kibbled, rolled or pearled grain, or any combination thereof.

In further aspects of this embodiment, the description provides for a process for producing a food or animal feed or beverage product, wherein the process comprises: (i) obtaining or producing an ingredient produced according to a process as described herein above or herein; and (ii) mixing the ingredient with another food ingredient or beverage ingredient to produce the product.

In some embodiments of the process, the ingredient is used as a bulking agent, a dietary fibre, a texturizing agent, a preservative, a sweetener, a thickening agent, a probiotic agent or any combination of these, in the food or beverage product. In other embodiments, the process further comprises assessing the level or type of starch or starch synthase activity, starch content, amylose, amylopectin, β-glucan, fructan, non-starch polysaccharides, dietary fibre, resistant starch in the barley grain or the ingredient or the product produced therefrom. In some embodiments of the process the food product is a breakfast cereal, biscuit, muffin, muesli bar, noodle, bread, cake, chip, pancake, tortilla, buns, pastry, cracker, pizza, croissants, bagels, pretzels, pasta, soup, sauce, confectionary, and other farinaceous goods.

In some embodiments, the grain has increased levels of starch and non-starch components compared to corresponding wild-type grains or HAG grains. The plant from which the grain is obtained has a reduced level of SSIIIa activity typically in the endosperm during development. The plant of the present invention is useful for food production and in particular for commercial food production. Such food production might include the making of flour, dough or other products that might be an ingredient in commercial food production. In an embodiment which is desirable for use in food production, the seed or grain of the plant has a starch or non-starch content that is increased relative to the wild-type plant. The grain may have a modified level or activity of degradative enzymes, particularly of one or more amylases such as α-amylase or β-amylase, which is reduced by the presence of a transgene or an introduced mutation which reduces expression of a gene encoding such a degradative enzyme in the grain. Flour or dough from such grain has desirable properties for baking or other food production. Amylose content may be increased as described in WO03/94600 by suppressing SBEIIa gene expression or as described in WO04/06751 by suppressing GWD gene expression.

The desired genetic background of the plant will include considerations of agronomic yield and other characteristics. Such characteristics might include whether it is desired to have a winter or spring types, agronomic performance (yield), disease resistance and abiotic stress resistance. Other varieties will be suited for other growing regions. It is preferred that the plant variety of the invention provide a yield not less than 80% of the corresponding wild-type variety in at least some growing regions, more preferably not less than 85% and even more preferably not less than 90%. The yield can readily be measured in controlled field trials.

In further embodiments, the starch content of the grain is at least about 42%, at least about 43%, at least about 45%, at least about 47%, at least about 50%, or at least about 55%

(w/w), up to 65%, and more preferably not decreased relative to the wild-type. Wild-type barley grain grown commercially usually has a starch content in the range 55-65%, depending somewhat on the cultivar grown. Alternatively, the seed or grain of the invention has a starch content of at least 90% relative to that of grain from a wild-type plant, and preferably at least 95%. Other desirable characteristics include the capacity to mill the grain, in particular the grain hardness. Another aspect that might make a plant of higher value is the degree of fructan or starch extraction from the grain, the higher extraction rates being more useful, or the protein content, the ration of amylose to amylopectin, or the content of other non-starch polysaccharides such as β-glucan which also contribute to the dietary fibre content of the grain products. Grain shape is also another feature that can impact on the commercial usefulness of a plant, thus grain shape can have an impact on the ease or otherwise with which the grain can be milled.

Starch is readily isolated from grain of the invention using standard methods, for example the method of Schulman and Kammiovirta, Starch, 43: 387-389, 1991. On an industrial scale, wet or dry milling can be used. Starch granule size is important in the starch processing industry where there is separation of the larger A granules from the smaller B granules.

Food Products

The invention also encompasses foods, beverages or pharmaceutical preparations produced with products, preferably those comprising increased resistant starch, dietary fibre, amylose, β-glucan, fructan, or other components obtained from the plants or grain of the invention. Such food production might include the making of processed grain, wholemeal, flour, dough or other products that might be an ingredient in commercial food production. The grain of the invention or products derived therefrom containing resistant starch, dietary fibre, amylose, β-glucan or fructan may be used in a variety of food applications for human consumption. As used herein, "humans" refers to Homo sapiens. The grain can be used readily in food processing procedures and therefore the invention includes milled, ground, kibbled, pearled or rolled grain or products obtained from the processed or whole grain of the plants of the invention, including flour. These products may be then used in various food products, for example farinaceous products such as breakfast cereals, breads, cakes, biscuits and the like or food additives such as thickeners or binding agents or to make drinks, noodles, pasta or quick soups. The grain or products derived from the grain of the invention are particularly desired in breakfast cereals or as extruded products. The starch or other components may be incorporated into fat or oil products such as margarine or shortening, salad dressing, egg products such as mayonnaise, dairy products such as icecream, yogurt or cheese, cereal products such as wheat flour, fruit juices, other foods or food materials, or the starch or other components may be processed into beverages or foods such as bread, cake, biscuits, breakfast cereals, pasta, noodles or sauces. Fructan is also useful as a low calorie sweetening product.

In bread, the ingredients may be in the form of flour or wholemeal may substitute for 10% (w/w) or more of unaltered flour or wholemeal, preferably substituting at least 30% and even more preferably at least 50% of the unaltered flour or wholemeal. The formulation might therefore be, for example, flour 90 parts, fat 2 parts, salt 2 parts, improver 1 part, yeast 2.5 parts. The production of the bread may be by a rapid dough technique or other techniques as is known by those skilled in the art.

Alternatively, the product of the invention may be incorporated into a farinaceous based pasta product. The amount of ingredient of the invention employed in the pasta composition may be in the range of 5-20% (w/w) based on the total weight of farinaceous material more particularly in the range of 10 to 20%. Suitable other farinaceous materials will readily be chosen by a person skilled in the art. Other material may also be added to the composition for example dry or liquid eggs (yolks, whites, or both) or high protein substances such as milk protein or fish protein. Vitamins, minerals, calcium salts, amino acids, buffering agents such as disodium hydrogen phosphate, seasoning, gum, gluten or glyceryl monostearate may also be added.

Other parts of the plants of the invention that are edible may be used as foods for human consumption or as feed for animal use. For example, leaves, stems, or extracts or parts of these comprising cells of the invention from any of these may be used for human or animal consumption. Increased resistant starch, dietary fibre, amylose, β-glucan or fructan content of the plants of the invention and parts thereof may provide advantages for use of these materials as animal feed such as, for example, as feed for pigs, cattle, horses, poultry such as chickens and other animals.

Methods

The products or compounds of the present invention can be formulated in pharmaceutic compositions which are prepared according to conventional pharmaceutical compounding techniques. See, for example, Remington's Pharmaceutical Sciences, $18^{th}$ Ed., Mack Publishing, Company, Easton, Pa., U.S.A. 1990). The composition may contain the active agent or pharmaceutically acceptable derivative active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques.

The active agent is preferably administered in a therapeutically effective amount. The actual amount administered and the rate and time-course of administration will depend on the nature and severity of the condition being treated. Prescription of treatment, e.g. decisions on dosage, timing, etc. is within the responsibility of general practitioners or specialists and typically takes account of the disorder to be treated, the condition of the individual patient, the site of delivery, the method of administration and other factors known to practitioners. Examples of techniques and protocols can be found in Remington's Pharmaceutical Sciences, (supra).

The food or beverage or pharmaceutical preparation may be packaged ready for sale or in bulk form. The invention also provides methods of preparing the food, beverage or pharmaceutical preparation of the invention, and recipes or instructions for preparing such foods or beverages. The methods may comprise the steps of harvesting the plant or plant part, separating grain from other plant parts, crushing, extracting, milling, cooking, canning, packaging or other processing steps known in the art. The methods or recipes or instructions may include the steps of processing the plant product of the invention and/or admixing it with other food ingredients, such as heating or baking the mixture or the product to, for example, at least 100° C. The method may include the step of packaging the product so that it is ready for sale.

Industrial Use

The plant products, preferably grain, may be used in production of industrial products such as, for example, ethanol.

The present invention is further described by the following non-limiting Examples.

Example 1: Materials and Methods

Plant Material

Barley (*Hordeum vulgare*) lines used in Examples 2-5 were from a back crossed population starting with a cross between parental varieties Himalaya292 (M292, Morell et al., (2003)) which contained the sex6 (SSIIa) mutation designated herein as the SSIIa-292 allele, and the variety High Amylose Glacier (HAG, also named AC38 or Glacier Pentlandfield) (Banks or al 1971) containing the amo1 mutation. These parental varieties are available in the art. The Himalaya292 and HAG varieties, for example, are available from CSIRO or from the Australian Winter Cereals Collection, Tamworth, NSW. Crossing of barley plants was carried out in the greenhouse by standard methods. The back cross populations were generated through 3 back crosses from Himalaya292 (male) to HAG (female), and then 3 generations of single seed descent (SSD). The seeds from the third back cross were named as BC3F1 and from the 3$^{rd}$ SSD were named as BC3F4. To increase the quantity of seeds for each line, 2 or 3 further generations were grown. These were designated as the BC3F6 or BC3F7 generations and used for this study.

Seventy-one BC3F6 barley lines were grown at CSIRO Plant Industry, Canberra in pots under otherwise natural conditions in 2005. To confirm the selected seed compositions and parameters, a subset of the BC3F7 barley lines which were selected by seed weight, amylose content, and the presence of SSIIa and amo1 mutations were grown either at CSIRO Plant Industry, Canberra in a glasshouse, with natural light and at the temperatures 18° C. (night) and 24° C. (day), or in the field at Yanco, New South Wales, Australia in 2007.

Barley spikes were labelled as at anthesis 2 days after the awns first appeared through the top of the flag leaf containing the enclosed spike. Developing seeds were harvested at 15 days post anthesis (DPA) and after removal of the embryo the developing endosperm was extruded through the cut surface and stored at −80° C.

Other varieties as described herein were obtained commercially or from the Australian Winter Cereals Collection, Tamworth, NSW, Australia.

Genotyping of the BC3F6 Population by PCR Amplification

Young barley leaves from the BC3F6 generation of the back crossed population were collected and freeze-dried (FTS systems, Stone Ridge, N.Y.). Genomic DNA was isolated with a fast DNA® kit according to the supplier's instructions (Q-BIOgene, CA., USA).

For genotyping for the presence or absence of the SSIIa mutation (SSIIa-292 allele) in plants derived from crosses with mutant Himalaya292, primers SSIIaF (5'-CCTG-GAACACTTCAGACTGTACG-3 (SEQ ID NO: 10)) starting at nucleotide 1616 and SSIIaR (5'-AGCATCACCA-GCTGCACGTCCT-3' (SEQ ID NO: 11)) starting at nucleotide 2044 of the SSIIa cDNA (GenBank Accession no: AY133249) were used for the PCR amplification of a 451 bp product spanning the SSIIa mutation site at nucleotide 1829 of Himalaya292, as described by Morell et al., (2003). The microsatellite PCR marker EBmac0501 was used in initial experiments for the detection of the amo1 mutation as it located at 68.0 cM on chromosome 1H and was closely linked to the amo1 locus also at 68.0 cM. Primers HHac0501F (5' CACGACGTTGTAAAACGA-CACTTAAGTGCCATGCAAAG 3' (SEQ ID NO: 12) and HHac0501R (5' AGGGACAAAAATGGCTAAG 3' (SEQ ID NO: 13)) (GrainGenes Database) were used for the amplification of a PCR fragment from the amo1 locus.

For each PCR reaction of 20 μl, 50 ng genomic DNA, 1.5 mM MgCl$_2$, 0.125 mM each dNTP, 10 pmol primers, 0.5 M glycine betaine, 1 μl DMSO and 1.5 U of Hotstar Taq polymerase (QIAGEN) were used. The PCR reactions were conducted using a HYBAID PCR Express machine (Integrated Sciences) with 1 cycle of 95° C. for 5 minutes, 35 cycles of 94° C. for 45 seconds, 58° C. for 30 seconds, and 72° C. for 1 minute, 1 cycle of 72° C. for 10 minutes and 1 cycle of 25° C. for 1 minute. The PCR products for the detection of the SSIIa mutation were digested with the restriction enzyme NlaIV at 37° C. overnight. Both digested (for SSIIa mutation) and non-digested (for amo1 mutation) PCR fragments were separated on 2% agarose gels and visualized with gel documentary (UVitec) after GelRed (Biotium) staining.

For genotyping of barley lines from the back crossed barley population between Himalaya292×HAG, primers SSIIaF and SSIIaR were used as described above for the detection of the SSIIa mutation from parental line Himalaya292, and the microsatellite marker EBmac0501 was used for the detection of the amo1 locus from parental line HAG. For the SSIIa mutation, three types of PCR fragment patterns were evident after digestion of the PCR product with NlaIV followed by gel electrophoresis, that differentiated the mutated and wildtype SSIIa alleles. A single DNA fragment of 347 bp indicated the presence of the mutated SSIIa gene (i.e. from Himalaya292), a single 236 bp DNA fragment indicated the presence of the wildtype SSIIa gene (i.e. from Himalaya, Glacier and HAG), and the presence of both the 347 bp and 236 bp fragments indicated the heterozygous genotype lines. For the amo1 mutation from HAG, the EBmac0501 microsatellite marker also gave three PCR fragmentation patterns for the BC3F6 population. A 167 bp fragment was detected from the wool mutant, a 141 bp fragment was detected from Himalaya292 (wild-type for amo1) lines, and both 167 bp and 141 bp fragments were detected in the heterozygous lines. Using the 3130×1 Genetic Analyser, the Bmac0090 microsatellite marker gave three PCR fragmentation patterns for the BC3F6 population. A 234 bp fragment was detected from HAG (amo1 mutation), a 236 bp fragment was detected from Himalaya292

(wild-type for amo1), and both 236 bp and 234 bp fragments were detected in the heterozygous lines.

For the SSIIIa gene, the PCR products were digested with the restriction enzyme EcoRI and separated on 2% agarose gels as above. Two types of PCR fragment patterns were evident that differentiated the SSIIIa genes in HAG (mutant SSIIIa) and Himalaya292 (wild-type SSIIIa). A 464 bp DNA fragment only indicated the occurrence of the SSIIIa gene from Himalaya292, while both 303 bp and 161 bp DNA fragments indicated the presence of the SSIIIa gene from HAG. Three fragments (464 bp, 303 bp and 161 bp) were detected in the heterozygous lines.

Grain Characteristics

Grain was harvested from plants at maturity unless otherwise stated, and average seed weight was determined by weighing 100 seeds with 3 replicates. The seed weight for selected lines was also determined as average seed weight of 500 seeds for 3 replicates for BC3F7 field grown materials at Yanco, NSW. Seed moisture content of grain was measured by standard nuclear magnetic resonance (NMR) methods using an Oxford 4000 NMR Magnet (Oxford analytical instruments Limited). Grain texture was measured using the Single-Kernel Characterization system 4100 (Perten Instruments Inc. Springfield, Ill. 62707 USA) using the RACI Cereal Chemistry Official testing method 12-01. Seed plumpness was grouped as three categories: shrunken, semi-plumped and plumped as known in the art.

Microscopic Examination of Barley Seed Cross Sections and Scanning Electronic Microscopy Transverse sections approximately 1 mm thick of the middle part of the barley seeds were produced by cutting sections with razor blades, and photographed. They were also coated with gold particles and examined with a JSM-6400 Scanning Electron Microscope (SEM) operating at 15 KV.

Milling of Grain

Grain was ground to wholemeal that would pass through a 0.5 mm sieve, using a cyclonic mill (Cyclotec 1093, Tecator, Sweden). The wholemeal was then used for the analysis below.

β-Glucan and Pentosan Analysis

β-glucan content was assayed as described in Megazyme Method (AACC32.23), using 20 mg of wholemeal for each of three replicate samples. Pentosan content was measured using the method from Bell, (1985) using 20 mg of wholemeal for each of three replicate samples.

Total Starch Content and Starch Extraction

Barley grains were first ground to wholemeal using a Cyclone mill machine (Cyclote 1093, Tecator, Sweden). Total starch content was assayed using an AACC method 76.13 using 20 mg of wholemeal for each of three replicate samples (Konik-Rose et al., 2007). Starch was isolated from wholemeal by a protease extraction method (Morrison et al., 1984) followed by water washing and removal of the tailings. Starch was then washed with acetone and air dried at room temperature (Konik-Rose et al., 2007).

Analysis of Starch Composition and Characteristics

Amylose and amylopectin contents in the starch of the grain, or the ratio of amylose to amylopectin, was determined by Sepharose CL-2B gel filtration as follows (Gel filtration method). Approximately 10 mg of total starch was dissolved in 3.0 ml of 1M NaOH and fractionated on the basis of molecular weight by chromatography on a Sepharose CL-2B column (Regina et al., 2006). The amount of starch in each of the fractions from the column was measured using the Starch Assay Kit (Sigma) according to the suppliers instructions. The total amount of amylopectin (first peak, higher molecular weight) and amylose (second peak, lower molecular weight) was calculated and the ratio or contents determined.

Alternatively, amylose content was measured using a small scale (2 mg starch) iodine adsorption method (Morrison and Laignelet, 1983) with some modifications as described by Konik-Rose et al., 2007.

Chain Length Distribution

Amylopectin chain length distribution was measured, after debranching of the starch samples, by the method of O'Shea et al., 1998 using a P/ACE 5510 capillary electrophoresis system (Beckman Coulter, NSW Australia) with argon laser-induced fluorescence (LIF) detection. Molar difference plots were generated by subtracting the normalized chain length distribution for modified starch from the normalized distribution for starch from an isogenic non modified control.

The gelatinization temperature profiles of starch samples were measured using a Pyris 1 differential scanning calorimeter (Perkin Elmer, Norwalk Conn., USA). The viscosity of starch solutions was measured on a Rapid-Visco-Analyser (RVA, Newport Scientific Pty Ltd, Warriewood, Sydney), using conditions as reported by Batey et al., 1997. The parameters that were measured included peak viscosity (the maximum hot paste viscosity), holding strength, final viscosity and pasting temperature. Pasting properties were measured using the Rapid Visco Analyser as follows. Starch (3.0 g) was added to distilled water (25.0 ml) in the DSC pan and the RVA run profile was: 2 mins at 50° C., heat for 6 mins to 95° C., hold at 95° C. for 4 mins, cool for 4 mins to 50° C., hold at 50° C. for 4 mins. The measured parameters were: Peak viscosity at 95° C., Holding strength at end of 95° C. holding period, Breakdown=Peak Viscosity−Holding strength, Final viscosity at end of 50° C. holding period, Setback=Final Viscosity−Holding strength. The software Thermocline for Windows version 2.2 (Newport Scientific Pty Ltd, NSW Australia) was used for collection and analysis of data.

The swelling volume of flour or starch was determined according to the method of Konik-Rose et al., 2001. The uptake of water was measured by weighing the sample prior to and after mixing the flour or starch sample in water at defined temperatures (for example, 90° C.) and following collection of the gelatinized material.

Starch Granule Morphology, Birefringence and Granule Size Distribution

Granule morphology was examined by SEM (JSM-6400) and light microscopy with polarized light. The shapes and birefringence of the starch granules were examined as described by Yamamori et al., (2000). Granule size distribution (by volume) of the starch slurries was determined using a laser diffraction particle size analyser (Mastersizer 2000, Malvern Instruments, Malvern, England). The percentage of small B-type starch granules was determined using a cut-off diameter of 7 μm.

Lipid Analysis

Total lipid content was assayed by NMR using an Oxford 4000 NMR Magnet, Oxford Analytical Instruments Limited, UK. For each sample, 1 g of seeds was dried at 38.8° C. for 64 hours. The dried seeds were then measured using NMR and compared against a pure barley oil extracted from cv. Himalaya or M292 grain.

Protein Content, Lipid Content, Moisture Content and Ash Content

Protein content was determined by measurement of nitrogen content using Mass Spectrometer Method using a Europa 20-20 isotope ratio mass spectrometer with an automated nitrogen and carbon analyzer preparation system. Three to 8 mg of barley wholemeal was used. A nitrogen to protein conversion factor of 6.25 was used for the calculation of the protein content in barley seeds (Mosse 1990). Lipid content, moisture content and ash content were measured using the AOAC 983.23 method, AACC Method 44-19 and AACC Method 08-01 (AOA Chemists, 1990).

Total Dietary Fibre Assay

The gravimetric method of Prosky et al. (1985; AOAC 985.29) was used to determine total dietary fibre (TDF) of the wholemeal. Duplicate samples were assayed.

Non Starch Polysaccharide Assay

Total neutral non-starch polysaccharides (NSP) were measured by a modification of the gas chromatographic procedure of Theander et al., (1995). The modification involved a 2-hour hydrolysis with 1 M sulphuric acid followed by centrifugation to remove insoluble NSP and a further hydrolysis of the supernatant using 2 M trifluoroacetic acid for soluble NSP.

Resistant Starch Assay

An in vitro procedure was used to determine resistant starch (RS) content. The method has two sections: firstly, starch in each sample was hydrolysed under simulated physiological conditions; secondly, by-products were removed through washing and the residual starch determined after homogenization and drying of the sample. Starch quantitated at the end of the digestion treatment represented the resistant starch content of the sample. Typically, triplicate samples of whole meal along with appropriate standards were mixed with artificial saliva and the resultant bolus incubated with pancreatic and gastric enzymes at physiological pH and temperature. The amount of residual starch in the digesta was determined using conventional enzymatic techniques and spectrophotometry and the resistant starch content of the sample expressed as a percentage of sample weight or total starch content.

On day 1, an amount of sample representing up to 500 mg of carbohydrate was weighed into a 125 ml Erlenmeyer flask. A carbonate buffer was prepared by dissolving 121 mg of NaHCO$_3$ and 157 mg of KCl in approximately 90 ml purified water, adding 159 µL of 1 M CaCl$_2$.6H$_2$O solution and 41 µL of 0.49 M MgCl$_2$.6H$_2$O, adjusting the pH to 7 to 7.1 with 0.32 M HCl, and adjusting the volume to 100 ml. This buffer was stored at 4° C. for up to five days. An artificial saliva solution containing 250 units of α-amylase (Sigma A-3176 Type VI-B from porcine pancreas) per ml of the carbonate buffer was prepared. An amount of the artificial saliva solution, approximately equal to the weight of food, was added to the flask. About 15-20 sec after adding the saliva, 5 ml of pepsin solution in HCl (1 mg/ml pepsin (Sigma) in 0.02 M HCl, pH 2.0, made up on day of use) was added to each flask. The mixing of the amylase and then pepsin mimicked a human chewing the sample before swallowing it. The mixture was incubated at 37° C. for 30 min with shaking at 85 rpm. The mixture was then neutralised with 5 ml of 0.02M NaOH. 25 ml of acetate buffer (0.2 M, pH 6) and 5 ml of pancreatin enzyme mixture containing 2 mg/ml pancreatin (Sigma, porcine pancreas at 4×USP activity) and 28 U of amyloglucosidase (AMG, Sigma) from *Aspergillus niger* in acetate buffer, pH6, were added per flask. Each flask was capped with aluminium foil and incubated at 37° C. for 16 hours in a reciprocating water bath set to 85 rpm.

On day 2, the contents of each flask was transferred quantitatively to a 50 ml polypropylene tube and centrifuged at 2000×g for 10 min at room temperature. The supernatants were discarded and each pellet washed three times with 20 ml of water, gently vortexing the tube with each wash to break up the pellet, followed by centrifugation. 50 uL of the last water wash was tested with Glucose Trinder reagent for the absence of free glucose. Each pellet was then resuspended in approximately 6 ml of purified water and homogenised three times for 10 seconds using an Ultra Turrax TP18/10 with an S25N-8G dispersing tool. The contents were quantitatively transferred to a 25 ml volumetric flask and made to volume. The contents were mixed thoroughly and returned to the polypropylene tube. A 5 ml sample of each suspension was transferred to a 25 ml culture tube and immediately shell frozen in liquid nitrogen and freeze dried.

On day 3, total starch in each sample was measured using reagents supplied in the Megazyme Total Starch Procedure kit. Starch standards (Regular Maize Starch, Sigma S-5296) and an assay reagent blank were prepared. Samples, controls and reagent blanks were wet with 0.4 ml of 80% ethanol to aid dispersion, followed by vortexing. Immediately, 2 ml of DMSO was added and solutions mixed by vortexing. The tubes were placed in a boiling water bath for 5 min, and 3 ml of thermostable α-amylase (100 U/ml) in MOPS buffer (pH 7, containing 5 mM CaCl$_2$ and 0.02% sodium azide added immediately. Solutions were incubated in the boiling water bath for a further 12 min, with vortex mixing at 3 min intervals. Tubes were then placed in a 50° C. water bath and 4 ml of sodium acetate buffer (200 mM, pH 4.5, containing 0.02% sodium azide) and 0.1 ml of amyloglucosidase at 300 U/ml added. The mixtures were incubated at 50° C. for 30 min with gentle mixing at 10 min intervals. The volumes were made up to 25 ml in a volumetric flask and mixed well. Aliquots were centrifuged at 2000×g for 10 min. The amount of glucose in 50 µL of supernatant was determined with 1.0 ml of Glucose Trinder reagent and measuring the absorbance at 505 nm after incubation of the tubes at room temperature in the dark for a minimum of 18 min and a maximum of 45 min.

Quantification of Water-Soluble Carbohydrate Contents

Total water soluble carbohydrates (WSC) were extracted from wholemeal following the method of Lunn and Hatch, (1995) with the following modifications. Wholemeal is defined herein as the product obtained by milling mature grain, without subsequent fractionation (e.g. sieving) to remove the bran. Therefore wholemeal contains all of the components in the grain.

Barley wholemeal (100 mg) was extracted three times with 10 ml each time of 80% ethanol (v/v) in a boiling water bath for 10 minutes. The supernatants from each extraction were pooled, freeze dried and re-suspended in 2 ml milliQ water. The quantities of sucrose, glucose, fructose, maltose and fructo-oligosaccharides (fructans) were analysed by high performance anion exchange chromatography (HPAEC) as described in Ruuska et al., (2006).

To determine maltose levels, total sugars extracted from barley whole meal were assayed essentially as described by Bernfeld, (1955), using maltose standard solutions for comparison, as follows. Total sugars were diluted 10 to 100-fold. Maltose standards (10 tubes) were prepared as 0.3 to 5 micromoles per ml. One ml of each dilution of maltose (in total sugars or maltose dilutions) was mixed with 1 ml of dinitrosalicylic acid colour reagent. The sugar solution was then incubated at 100° C. for 5 minutes and cooled to room temperature. Ten ml reagent grade water was added to each tube and mixed well. The samples were measured at $A_{540}$ with a spectrophotometer. Maltose was also determined by HPAEC as described above.

Analysis of Starch Granule Bound Proteins and SSIIIa Enzymatic Activity

Starch granule bound proteins were isolated and separated on SDS-PAGE gel as described (Rahman et al., 1995). The proteins were then stained by silver staining (Li et al., 1999a). The protein gels were scanned (Epson Perfection PHOTO; Epson America Inc., CA, USA).

For zymogram analysis, developing endosperms at 15 dpa were isolated and ground in a mortar and a pestle with 3 volumes of extraction buffer (20 mm Tris-HCl, pH 7.5, 5 mM DTT, and 1 mM Pefabloc) at 4° C. The homogenate was then centrifuged at 10,000 g for 20 min at 4° C. and samples of the supernatants (containing 20 µg proteins) were used for analysis of SSIIIa activity and SSI activity by zymogram analysis (Abel et al., 1996).

Enzyme Assays

Total starch synthase activity in samples such as developing endosperm of cereals are measured by extraction of proteins and assay by the methods described in Libessart et al. 1995 or Cao et al., 1999. The assays use $^{14}C$ labeled ADPG substrate and measure incorporation of the monomer into starch polymers. Individual isoforms of starch synthase in extracts were separated by gel electrophoresis and assayed in-gel (zymogram) as follows. Extracts from samples such as developing seeds were prepared using 50 mM potassium phosphate buffer, pH7.5, 5 mM EDTA, 20% glycerol, 10 µM Pefabloc and 0.05 mM dithiothreitol (DTT). After grinding the seeds to a pulp in the buffer or homogenizing the sample, the mixtures were centrifuged at 14,000 g for 15 min at 4° C. and the supernatants drawn off. The protein concentration in the supernatants was measured using Coomassie Protein Reagent. Extracts were stored at −80° C. if the protein extracts were to be run on native gels later on. For denaturing gel electrophoresis, 100 µl of extract was mixed with SDS and β-mercaptoethanol and the mixtures are incubated in boiling water for 4 min to denature the proteins. Electrophoresis was carried out in standard denaturing polyacrylamide gels using 8% polyacrylamide separating gels overlaid with 4.5% polyacrylamide stacking gels. After electrophoresis, the proteins were renatured by soaking the gels in 40 mM Tris-HCl buffers for a minimum of 2 hr, changing the buffer every 30 min and using at least 100 ml of buffer for each buffer change. For non-denaturing gels, the denaturing step with SDS and β-mercaptoethanol was omitted and SDS omitted from the gels. A starch synthase assay buffer including Tris-glycine (25 mM Tris, 0.19 M glycine), 0.133 M ammonium sulphate, 10 mM $MgCl_2$, 670 µg/ml BSA and 1 mM ADPG substrate was used to detect starch synthase bands, followed by staining with 2% KI, 0.2% $I_2$ iodine solution to detect the starch product.

Alternatively, starch synthase or other starch biosynthetic enzymes are detected in samples using specific antibodies (ELISA).

Statistical Analyses of the Relationship Between Genotypes and Seed Components or Starch Properties Statistical analyses were performed using Genstat version 9. Analysis of variance was performed for grain weight, total starch content, amylose content, amylopectin content, protein content, lipid content, β-glucan content, pentosan content, WSC content, starch granule size and amylopectin chain length distribution to obtain the least significant difference (LSD, $P<0.05$), looking at variation between the genotypes.

Example 2: Genotyping Plants

A population of barley lines segregating for the presence or absence of mutations at the SSIIa and amo1 loci was generated by performing three backcrosses from a SSIIa-292 donor line (Himalaya292) into an amo1 recurrent parent (High Amylose Glacier, HAG) as described in Example 1 (Plant Material). Three generations of single seed descent were performed from the BC3F2 lines in order to generate sufficient fixed genotypes to investigate the relative impact of the sex6 and amo1 loci, alone and in combination, on starch synthesis, grain composition and morphology. The ability to accurately assign the progeny lines to genotypes was central to this study. Because the genetic change underpinning the sex6 phenotype had previously been demonstrated to be a lesion in the SSIIa gene (Morell et al., 2003), the status of all lines at the sex6 locus could be unambiguously defined. However, the amo1 mutation was defined by phenotype alone given that the causal gene had not previously been defined. In order to assign lines to the four possible genotype classes (wild type, SSIIa mutant, amo1 mutant, SSIIa-amo1 double mutant), markers linked to amo1 were required.

Given that the causal gene at the amo1 locus had not been identified, the closest linked markers available were sought. SSR markers identified from barley mapping populations within approximately 10 cM of the amo1 locus were examined for polymorphism in this population and the two parental varieties. Of the 12 markers tested (see Example 4), EBmac0501 located at 58.0 cM, and Bmac0090 located at 58.0 cM gave clear polymorphisms between the Himalaya292 and amo1 parents. Therefore, all of the barley BC3F6 lines were initially genotyped using the marker for the causal mutation in the SSIIa gene as described in Example 1 and the microsatellite marker EBmac0501 which was tightly linked and therefore useful as a surrogate marker of amo1-38 or wild-type status.

Among the 71 BC3F6 lines genotyped, 13 lines were homozygous for both SSIIa-292 and amo1-AC38 alleles (SSIIa-292/amo1-AC38) and were therefore considered as SSIIa-amo1 double mutants, 13 lines were homozygous for the SSIIa-292 and wild type amo1-alleles (SSIIa-292/amo1-wt) and therefore designated as SSIIa single mutants, 9 lines were homozygous for wild type SSIIa and mutant amo1-AC38 alleles (SSIIa-wt/amo1-AC38) and were therefore designated as amo1 single mutants, while 13 lines were wild type for both SSIIa and amo1 (SSIIa-wt/amo1-wt) and designated as wild type. Other lines were heterozygous for either the SSIIa mutation or for the EBmac0501 marker. In each of these lines, there was no recombination seen between either of the markers EBmac0501 or Bmac0090 and the amo1 alleles (mutant and wild-type). A further 5 lines were identified that were homozygous at the sex6 locus and homozygous for the 3 amo1 markers but had recombined between these three markers. The remaining 18 lines were heterozygous at one of the 4 markers used and were excluded from the phenotypic analysis. These genotypes are summarized in Table 1.

The parental varieties were also different in the hulled or hulless phenotypes-HAG is a hulled variety of barley while Himalaya292 was hulless. The SSIIa-amo1 double mutants were segregating for this characteristic, and therefore they could be classed in two subgroups-hulled or hulless. Therefore, the four genotypes of barley lines distinguished as described above were categorized into five groups, namely: wildtype lines. SSIIa single mutants, amo1 single mutants, hulless double mutants and hulled double mutants, Four lines were used from each of the five groups for the analysis of starch granule distribution, WSC, CE and seed morphology. One line from each genotype was used for endosperm structure and starch granule morphology. Eleven wildtype lines, 9 lines of amo1 mutants, 13 lines of SSIIa mutants, 4 lines of hulless double mutants and 6 lines of hulled double mutants were used for the analysis of grain composition, amylose content and seed weight as follows.

Example 3: Phenotyping Plants

Grain Weight

Average seed weight (average of 100 seed weight) was measured for homozygous lines from the BC3F6 population. Average seed weight was 52.7±5.0 mg for 11 wildtype lines, 52.8±2.8 mg for 9 amo1 lines, 38.7±2.5 mg for 13 SSIIa mutant lines, and 47.6±4.5 mg for the 6 hulled double mutant lines and 44.7±1.0 mg for the 4 hulless double mutant lines. There were no statistically significant differences between seed weights of the amo1 mutant lines and the wildtype lines ($P<0.05$), showing that the amo1 mutation did not affect seed weight. However, there were statistically significant differences ($P<0.05$) between each of the SSIIa single mutants and double mutant (hulled and hulless) and each of the three other genotypes. Similar observations on the seed weights of the 4 genotypes were also obtained for BC3F7 populations in separate glasshouse and field trials of the lines in 2007. One surprising and unexpected result was that the reduced seed weight caused by the presence of the SSIIa mutation, known to be due to the reduced amylopectin synthesis in the absence of SSIIa activity, was partly offset by the combination with the amo1 mutation.

Grain Morphology

Intact grains from four representative lines for each genotype were examined by stereoscopic microscope on both dorsal and crease sides. The SSIIa single mutant lines produced shrunken seeds while the wildtype and amo1 single mutant lines produced plump well filled seeds. The double mutant seeds, both hulled and hulless, were observed to have an intermediate phenotype, plumper than SSIIa mutant seeds, yet not as well filled as amo1 and wildtype seeds (semi-plump phenotype). These observations were consistent with the grain weight data.

To further illustrate the nature of plumpness of the seeds from these genotypes, transverse sections of the middle part of seeds across the largest diameter were examined. Transverse sections from wildtype and amo1 mutant lines showed fully filled endosperms while SSIIa mutant lines showed incompletely filled (shrunken) seeds with a considerable reduction in endosperm packing density. The SSIIa-amo1 double mutant lines showed an intermediate phenotype with an endosperm that was more filled than the SSIIa mutant endosperm and yet less filled than wildtype or amo1 mutant lines.

Grain Composition and Starch Analysis

The analysis of starch and grain composition of BC3F6 population was conducted using all homozygous lines for both SSIIa and three markers for amo1 locus lacking recombinations at the amo1 locus. These lines included all wildtype lines, lines containing the amo1 locus alone, lines containing the mutant SSIIa locus alone, and lines containing both the SSIIa and amo1 mutations. For the analysis of starch granule distribution, water soluble carbohydrates (WSC), starch chain length distribution and grain morphology, a subset of 4 lines per genotype was used.

Total Starch Content.

Total starch content was measured as described in Example 1 on BC3F6 seed for the four genotypes. Starch content averaged 64.3±2.4% for wildtype lines, 57.2±2.8% for amo1 mutant lines, 34.9±4.0% for SSIIa mutant lines, 50.8±2.8% for hulless double mutant lines and 47.6±2.3% for hulled double mutant lines. Compared to the wildtype lines, amo1 mutants, hulless double mutants, hulled double mutants and SSIIa mutant lines contained 7.1%, 13.5%, 16.7% and 29.4% respectively less total starch. These values were statistically different among the five groups ($P<0.05$) except that the values for the hulless and hulled groups were not significantly different. Consistent relationships between the grain weights of the five groups were also obtained ($P<0.05$) for BC3F7 grain from separate glasshouse and field trials in 2007. These data showed that the increased grain weights observed for the SSIIa-amo1 double mutant seeds compared to the SSIIa single mutant seeds were due to increased starch content.

Amylose Content

Amylose content was measured for all lines from the four genotypes by an iodine method and calculated as a percentage of the starch extracted from the grain (w/w). Amylose content ranged from 32.0±3.2% for wildtype grain, 49.5±27% for amo1 mutant grain, 57.6±10.0% for SSIIa mutant grain, 62.2±4.1% for hulless double mutant grain and 59.8±2.3% for hulled double mutant grain. Statistical analysis showed that the SSIIa mutant grain and double mutant grain contained significantly higher amylose contents in the seed than those from amo1 mutants and wildtype lines. However, the amylose contents of SSIIa mutant and double mutants were not significantly different ($P<0.05$), showing that the SSIIa mutation was increasing the proportion of amylose in the total starch of the grain but addition of the amo1 mutation did not further significantly increase the proportion of amylose. These differences in amylose content between genotypes were consistent in BC3F7 lines grown in 2007.

FIG. 1 shows the relationship between amylose content and starch content for the 53 homozygous BC3F6 lines. For lines containing the wildtype SSIIa gene (triangular symbols) a clear separation into two phenotypic groupings could be made. The grouping with elevated amylose consistently contained the three markers from the amo1 locus (solid triangles) while the group with lower amylose content were wildtype for all three amo1 markers (open triangles). The lines with the SSIIa genotype (non-functional SSIIa lines) also revealed the presence of two phenotypic groupings, separated in this case not by amylose content but by starch content. The lower starch content group contained the SSIIa mutant allele and the wild type amo1 locus (open diamonds), while the higher starch content group contained both the SSIIa and amo1 mutant loci (solid diamonds). Five lines exhibiting recombinations between the amo1 markers (3 with wild type alleles at SSIIa, 2 with the mutant SSIIa allele) were included in the phenotypic analysis. Alignment of the phenotypic and genotypic data for the 5 recombinant lines provided evidence suggesting that, of the three markers, the SSIIIa SNP (single nucleotide polymorphism) marker was more tightly linked to the amo1 locus than either of the EBmac 0501 or Bmac0090 markers.

Starch Chain Length Distribution

To examine the effects of the genotypes on starch chain length distribution, starch was isolated from grain from four lines from each group of the BC3F6 cross population and analysed by Fluorophore Assisted Carbohydrate Electrophoresis (FACE). The percentage of chains were pooled into bins consisting of DP 6-8, DP 9-14, DP 15-24, DP 35-34, DP 35-44, and DP>45. There were no statistically significant differences ($P<0.05$) among the bins for SSIIa mutants, hulless double mutants and hulled double mutants. However, there was a major difference ($P<0.05$) between groups containing the wild type SSIIa allele compared to groups containing the mutant SSIIa allele, Those genotypes with the SSIIa mutant allele contained an increased proportion of chains of DP6-8, with greater than 10% of chains of this size, and also an increased proportion of chains of DP 9-14. They also exhibited a decreased proportion of chains with DP15-24. The wildtype lines had less than 5% DP6-8 chain lengths. The amo1 mutants contained a statistically significantly decreased amount of DP 9-14 and an increased amount of DP 15-24 relative to the wild-type chain length distribution.

Starch Granule Size Distribution

To investigate the effects of SSIIa and amo1 mutant genotypes on starch granule size in endosperm starch, the starch granule size distribution was examined for four selected lines from each group of the BC3F6 backcross population. The results showed that B starch granule (defined as <7 μm diameter) contents in the wildtype, amo1 mutants, SSIIa mutants, hulless double mutants and hulled double mutants were 20.2±6.4%, 30.7±3.6%, 17.5±1.8%, 19.7±3.6% and 18.3±7.2% of total starch in each line, respectively. The amo1 mutant seeds contained significantly more B starch granules than seeds from the other four groups.

The mean granule sizes of the distribution peaks larger than 10 μm in diameter (A starch granules) were also evaluated. The mean size of A starch granules was 18.9±0.5 μm for wildtype lines, 10.9±0.3 μm for amo1 mutants, 16.4±2.6 μm for SSIIa mutants, 18.7±0 μm for hulless double mutants and 17.5±0.60 μm for hulled double mutants. Statistical analysis showed that amo1 mutant seeds contained significantly smaller A starch granules than seeds from each of other four groups of barley (P<0.05). There were no statistically significant differences (P<0.05) among the A granules in seeds of wildtype, SSIIa mutants, hulless double mutants and hulled double mutants, as for the B granules.

Starch Granule Morphology

Purified barley starches from lines from the five groups were stained with iodine and examined under normal light microscopy. Consistent with their amylose content, starch granules from all genotypes gave a purple color after staining with iodine. Under polarized light microscopy, more than 90% of the starch granules from wildtype seeds and amo1 seeds showed the "maltose cross" birefringence signature of crystalline starch granules. However, less than 10% of the starch granules from SSIIa mutant or double mutant seeds exhibited such birefringence.

When observed under SEM, grain from the wildtype lines exhibited normal spherical starch granules, while the amo1 mutant genotype gave smaller spherical A starch granules that matched the results from the analysis described above. Starches from the SSIIa and double mutant seeds showed predominantly smaller deformed starch granules. Of the two mutants giving deformed starch granules, the SSIIa mutant line produced tubular, elongated A granules (26 μm×12 μm) while the hulless double mutant seeds exhibited more pronounced tubular elongations of the A granules (28 μm×21 μm).

The location of starch granules in the endosperm matrix was examined in transverse sections of the barley seeds. Wildtype lines contained multiple flat spherical starch A granules surrounding multiple small B starch granules while the amo1 mutant line contained multiple loosely packed starch granules surrounding smaller B starch granules. Starch granules could not be clearly identified for the SSIIa mutant seeds in transverse sections. Hulless double mutant lines contained lenticular shaped starch A granules tightly packed in the endosperm cells.

Previous analysis of the SSIIa mutation in Himalaya292 showed that the mutation was associated with pleotropic effects on grain composition (Clarke et al., 2008) which were thought to result from redirection of carbohydrate in the grain as a result of alterations in total starch synthesis (Moreli et al., 2003). Therefore, an analysis of the major carbohydrate, protein and lipid fractions of the grain for each of the 4 genotype groups was conducted.

Beta-Glucan Content

Beta-glucan content in grain was measured for all lines from the BC3F6 population. β-glucan content was 6.0±0.5% (ranging from 5.3% to 7.0%) for wildtype lines, 8.2±0.5% (ranging from 7.6% to 8.4%) for amo1 mutant lines, 7.6±1.4% (ranging from 5.9% to 11.3%) for SSIIa mutants, 7.1±0.4% for hulless double mutants and 6.5±0.8% (ranging from 5.5% to 7.7%) for hulled double mutants. Statistical analysis showed that amo1 mutant, SSIIa mutant and hulless double mutant seeds contained significantly more β-glucan than seeds from wildtype lines and hulled double mutant lines (P<0.05), but there was no statistically significant difference among amo1 mutants, SSIIa mutants and hulless double mutants, or between wildtype and hulled double mutants seeds in β-glucan content, respectively.

The statistical analysis for these selected F7 lines from five groups grown under glasshouse or field conditions showed that for each trial, seed from amo1 mutant lines contained more β-glucan than seed from double mutant lines. There were no significant differences in β-glucan content between SSIIa mutant or double mutant seeds.

Pentosan Content

Pentosan content in grain was measured for lines from the five groups. Pentosen content was 4.9±0.6% for wildtype lines, 4.9±1.1% for amo1 mutant lines, 7.3±1.4% for SSIIa mutants, 5.0±0.3% for hulless double mutants and 6.5±1.0% for hulled double mutants. Statistical analysis showed that both SSIIa mutant lines and hulled double mutants significantly contained more pentosan in grain than that from wildtype lines, amo1 mutant and hulless double mutant lines (P<0.05), but, there was no significant difference between SSIIa mutant lines and hulled double mutants or among wildtype lines, amo1 mutant and hulless double mutants in pentosan content, respectively.

Water Soluble Carbohydrates

To determine the effect of the mutations singly or in combination on water soluble carbohydrate contents in barley grain, four lines were analysed from each group. Compared to the water soluble carbohydrate composition in wildtype seeds, amo1 seeds did not contain significantly different levels of total WSC, free glucose, sucrose or maltose, or fructan. However, SSIIa mutant and double mutant seeds contained significantly greater amounts of each of these carbohydrates (P<0.05). The seeds of the SSIIa single mutants contained significantly more fructose, sucrose and total WSC.

Protein Content

Protein content was measured in grains of the five groups. Protein content was 10.3±0.8% for wildtype seeds, 10.4±1.1% for amo1 mutant seeds, 12.6±0.9% for SSIIa mutant seeds, 14.6±0.6% for hulless double mutant seeds and 13.8±1.4% for hulled double mutant seeds. Both hulless and hulled double mutant seeds contained significantly more protein than SSIIa mutant seeds, wildtype seeds or amo1 mutant seeds, but there were no significant differences between hulless and hulled double mutant seeds or between amo1 mutants and wildtype seeds in protein content.

Lipid Content

Lipid content was measured for grains of the five groups. Total lipid content was 2.9±0.2% for wildtype seeds, 3.5±0.3% for amo1 mutant seeds, 6.4±0.9% for SSIIa mutant seeds, 4.9±0.3% for hulless double mutant seeds and 5.0±0.3% for hulled double mutant seeds. SSIIa mutant seeds contained significantly more lipid than hulless and hulled double mutant seeds, wildtype seeds and amo1 mutant seeds, but there were no significant differences between hulless and hulled double mutant seeds or between amo1 mutant and wildtype seeds.

Contents of Starch and Other Grain Components on a Per Caryopsis Basis

Expressing grain composition data on a percentage basis can be misleading when the major grain constituent, starch, differs in content significantly between genotypes, leading to apparent increases in grain constituents that do not reflect underlying synthesis rates. In order to examine the absolute levels of synthesis of the various grain components in each of the genotypes. Table 2 presents the composition data on a per caryopsis basis. This analysis confirmed that, as expected, modification in starch synthesis levels was the major driver of grain weight differences between these genotypes. However, analysis of the data on this basis indicated that there were major changes in grain starch synthesis among the genotypes. Each of the mutant genotypes had decreased grain amylopectin synthesis, with the SSIIa mutant genotype having a severe suppression of amylopectin synthesis. In contrast, the amo1 mutant genotypes (amo1 mutants and SSIIa-amo1 double mutants) had significant increases in amylose synthesis compared to the amo1 wild-type genotype, while the SSIIa genotype (SSIIa mutants) had a small decrease in amylose synthesis. The data however demonstrated that the major cause of a restoration of starch content in the SSIIa-amo1 double mutant genotype relative to the SSIIa single mutant genotype was due to an increase in both amylose (79% increase) and amylopectin content (61% increase).

Analysis of the levels of other grain constituents on a per caryopsis basis suggested that protein content was increased by at least 5% in the SSIIa-amo1 double mutant genotype relative to the other genotypes, lipid content was specifically increased in both the SSIIa and SSIIa-amo1 mutant genotypes, β-glucan and pentosan synthesis levels remained unaltered in all genotypes with the potential exception of β-glucan synthesis in the amo1 genotype, and water soluble carbohydrates levels were inversely proportional to starch contents.

Discussion

The interaction between recessive mutations at the SSIIa and amo1 loci was examined. These mutations both resulted in an elevated amylose phenotype relative to wildtype, with amylose contents typically 60-70% in the starch of SSIIa mutant grains and 35-45% in amo1 mutant grains. Determination of the 4 possible genotypes for the SSIIa (SSIIa-wt and SSIIa-292) and amo1 (amo1-wt and amo1-AC38) loci was an important aspect of this study. The mutant and wildtype alleles of the SSIIa locus were able to be unambiguously distinguished using a marker based on the causal mutation in the starch synthase IIa gene. Initially, a closely linked marker (Bmac0501, consensus map location 58.0 cM) was used to assay for the presence of the chromosome region containing the amo1 locus.

The impact of combining these mutations on amylose content was examined. The data showed that there was no statistically significant difference in the proportion of amylose (as a weight percentage of the total starch content) when the SSIIa mutant and amo1 mutant loci were combined relative to lines carrying the SSIIa mutant locus alone. However, the combination of the SSIIa and amo1 mutations did have unexpected consequences on starch synthesis and grain weight, increasing starch content and seed weight relative to the SSIIa mutation alone by virtue of increasing both amylose and amylopectin contents per grain.

Barley SSIIa mutants contained starch with a high percentage of amylose. The data showed that SSIIa single mutant grain on average contained only 40% as much starch as the wildtype grain on a per grain basis. The high amylose phenotype of SSIIa mutant seed was thus due to a preferential reduction of amylopectin, which was decreased by 75%, compared to amylose which was only decreased by 25%. In the case of the SSIIa-amo1 double mutant grain, there was also a decrease in amylopectin synthesis compared to wildtype (31% reduction) but an increase in amylose content (increased by 37%) per seed. These results were intriguing, suggesting that the amo1-wt (wild-type) gene product not only participated in amylopectin synthesis but also repressed amylose synthesis.

The impact of the amo1 mutant allele on starch chain length distribution was subtle. In a wildtype background, the presence of the amo1 mutant allele caused a slight decrease in short chain lengths (DP 9-14) and an increase in the DP 15-24 fraction. In SSIIa mutant backgrounds, the impact of the amo1 mutant locus on chain length distribution was negligible. In contrast, the SSIIa mutant allele had a major affect on amylopectin structure and thus chain length distribution, increasing the proportion of short chains (DP 6-8 and DP 9-14) and decreasing chains with DP15-25.

The combination of the SSIIa and amo1 mutant alleles provided an unexpected phenotype in which starch content and seed weight were partially restored compared to the properties of lines containing only the SSIIa mutant allele.

Example 4: Genetic Markers Linked to the Barley Amo1 Locus

In order to identify genetic markers linked closely to the amo1 locus, 12 SSR (Simple Sequence Repeat) markers (Ramsay et al., 2000) located between 56.00 cM and 64.60 cM on the short arm of chromosome of barley were selected. These SSR markers were EBmac0405, Bmag0105, Bmac0063, HVM20, Bmac0090, EBmac0560a, EBmac0501, Bmac0044, Bmac0032, Bmag0113, Bmag0211, and Bmag0350. The primers for these SSR markers were synthesized according to the sequences listed in the GrainGenes Database. These markers were tested in PCR reactions using DNA from each of two parental barley varieties, High Amylose Glacier (HAG) and Himalaya292 and the amplification products compared between the parents by gel electrophoresis.

For each PCR reaction (20 μl), 50 ng genomic DNA, 1.5 mM MgCl$_2$, 0.125 mM each dNTP, 10 pmol primers, 0.5 M glycine betaine, 1 μl DMSO and 1.5 U of Hotstar Taq polymerase (QIAGEN, Australia) were used. The PCR conditions for the amplifications for the SSR markers were: 1 cycle of 95° C. for 4 minutes, 15 cycles of 94° C. for 30 seconds, 65° C. to 50° C. with decreasing 1° C. each cycle for 30 seconds, and 72° C. for 1 minute 20 seconds, 30 cycles of 94° C. for 15 seconds, 50° C. for 15 seconds, and 72° C. for 45 seconds, and 1 cycle of 25° C. for 1 minute. The PCR reactions were assembled in identical fashion except for the primer pairs. The PCR products were separated by electrophoresis on 2% agarose gels and visualized with gel documentary (UVitec) after GelRed (Biotium)

staining, or by using a 3130×1 Genetic Analyser (Applied Biosystems) according to the manufacturer's instructions.

When the 12 SSR markers were tested, 3 of 12 markers, namely Bmac0032 located at 64.6 cM, EBmac0501 located at 58.0 cM and Bmac0090, gave different sized PCR products amplified from DNA from the HAG and Himalaya292 parental plants. That is, these markers showed polymorphism between the two parental varieties. These SSR markers were then used for the genotyping of 71 BC3F6 lines. All of the lines genotyped with the Bmac0032 marker gave the same sized fragments as HAG, which showed that all of the lines had recombined between the Bmac0032 and amo1 loci and the SSR marker Bmac0032 was not tightly linked with the amo1 locus. In contrast, of the 71 BC3F6 lines genotyped with the EBmac0501 marker, 56 were homozygous for one or the other of the fragment patterns. Of the 56 homozygous lines, 25 displayed the EBmac0501 marker from HAG and 31 exhibited the EBmac0501 marker from Himalaya292. These results showed that the EBmac0501 marker did not have a high frequency of genetic recombination with amo1 locus. Therefore, the SSR marker EBmac0501 was a tightly linked microsatellite marker for the amo1 locus.

Markers Based on the SSIIa Gene of Barley

SSI, SSIIa and SSIII are thought to be primarily involved in amylopectin synthesis involved in the extension of specific subsets of available non-reducing ends within the starch molecule. Studies of *Arabidopsis* and rice SSI null mutants showed that SSI is involved in biosynthesis of the small outer chains of the amylopectin cluster (8-12 dp) in leaf starch of *Arabidopsis* and in the endosperm starch of rice (L I et al., *J. of Exp. Botany*, 62(14), 5217-5213, 2011 and reference referred to herein). Starch from barley and wheat SSIIa mutants had an increase in chains of DP3-8, indicating that the SSIIa enzyme played a role in extending shorter glucan chains of DP3-8 to longer glucan chains of DP12-35 (Yamamori et al., *Theoretical and Applied Genetics*, 101: 21-29, 2000; Morrell et al., *The Plant Journal*, 34: 173-185, 2003; Konik et al., *Theoretical and Applied Genetics*, 115: 1053-1065, 2007). Loss of SSIIIa in maize and rice conferred an increased amylase phenotype, with a reduction in the proportion of very long chains (DP>50 in maize or DP >30 in rice), and slightly reduced gelatinization temperature Jane et al., *Cereal Chemistry*, 76: 629-637, 1999; Fujita et al., *Plant Physiol.*, 144: 2009-2023, 2007). *Arabidopsis* mutants, defective for SSIV, appear to have fewer, larger starch granules within the plastid and a role in priming starch granule formation has been postulated for the SSIV protein (Roldan et al., *The Plant Journal*, 49: 492-504, 2007).

Based on the data described above, it was thought that the amo1 locus might be near to the SSIIIa gene of barley. To test this possibility and to develop a DNA marker based on the SSIIIa gene in barley, portions of the SSIIIa gene were first isolated from the two parental varieties. DNAs from HAG and Himalaya292 were used for the amplification of PCR fragments using primers based on the wheat SSIIIa genomic DNA sequence (Li et al., 2000). The oligonucleotide primers SSIIIaF (5'-GGAGGTCTCGGGGATGT-3' (SEQ ID NO: 14)) locating in exon 7 and SSIIIaR (5'-GCTCCAGGAAGTAAACGGTCAGG-3 (SEQ ID NO: 15)) locating in exon 8 of the wheat SSIIIa gene were used for the PCR amplification of a 464 bp product. For each PCR reaction (20 μl), 50 ng genomic DNA, 1.5 mM $MgCl_2$, 0.125 mM each dNTP, 10 pmol primers, 0.5 M glycine betaine, 1 μl DMSO and 1.5 U of Hotstar Taq polymerase were used. The PCR reactions were conducted using 1 cycle of 95° C. for 5 minutes, 35 cycles of 94° C. for 45 seconds, 58° C. for 30 seconds, and 72° C. for 1 minute, I cycle of 72° C. for 10 minutes and 1 cycle of 25° C. for 1 minute. A 464 bp fragment was produced in each amplification. The PCR fragments were treated with 0.5 units of Shrimp Alkaline Phosphatase (USB Corporation, USA), 2.5 units of Exonuclease 1 and 1×PCR buffer (QIAGEN, Australia) according to the protocol from USB Corporation and sequenced using the automated ABL system with dye terminators as described by the manufacturers.

The 464 bp fragments had a sequence difference which provided an NlaIV restriction site in one fragment but not the other. Therefore, treatment of the PCR products with this enzyme followed by electrophoresis on 2% agarose gels provided a convenient way to distinguish the SSIIIa genes from the two parental varieties. The production of only the 464 bp DNA fragment indicated the presence of the SSIIIa gene from Himalaya292 (i.e. wild-type SSIIIa gene), and the production of both 303 bp and 161 bp DNA fragments indicated the presence of the SSIIIa gene from HAG.

The DNA marker for the SSIIIa gene which was polymorphic between the HAG and Himalaya292 parental lines (Example 4) was also used to genotype the homozygous lines. This analysis showed the presence of the SSIIIa gene from HAG in 26 lines, and the SSIIIa gene from Himalaya292 in 30 lines. Among the 56 lines genotyped with the EBmac0501 and SSIIIa gene markers, 5 lines showed recombinant genotypes. When the genotypes and phenotypes including the plumpness of seeds and the starch contents were correlated, 4 lines genotyped with EBmac0501 and 1 line genotyped with the SSIIIa gene marker initially gave recombinant phenotypes (PCT/AU2010/000968), suggesting that there was some recombination between the SSIIIa marker and the amo1 locus and that the amo1 gene and SSIIIa genes were genetically distinct even if closely linked in barley. However, repeated tests showed that the presumed recombinant between the SSIIIa marker and the amo1 gene had been mis-classified, and indeed there were no recombinants between the SSIIIa marker and the amo1 gene in the segregating barley population.

The SSIIIa gene sequences and SSIIIa activities in the barley varieties and mutants were therefore examined more closely, in particular between HAG and its wild-type parent Glacier, as described in the following Examples.

Example 5: Detection of SSIIIa Activity by Zymogram Analysis

The presence of SSIIIa activity in endosperms from the barley varieties Himalaya and Glacier, the mutants Himalaya292 and HAG and from selected lines from each of the 4 BC3F6 genotypes was examined by zymogram analysis, which detects enzymatic activity, as described in Example 1 and summarized as follows. Developing endosperms at 15 DPA were isolated and ground in a mortar and a pestle with 3 volumes of extraction buffer (20 mM Tris-HCl, pH 7.5, 5 mM DTT, and 1 mM Pefabloc SC (Roche)) at 4° C. Each homogenate was then centrifuged at 10,000 g for 20 min at 4° C. and aliquots of the supernatants, each containing 20 μg of extracted protein, were used for analysis of SSIIIa activity by zymogram analysis according to Abel et al., 1996).

Two starch synthase activities were detected on the zymogram gels, a faster migrating band which was starch synthase I (SSI) and a slower migrating band which was SSIIa, possibly a combination of SSIIIa and SSIIIb. The zymograms did not show any consistent change in the SSIIIa band among lines from the 4 BC3F6 genotypes. In particular, the amo1 mutant endosperms contained an active SSIII protein. However, surprisingly, three out of 5 SSIIa-amo1 double mutants showed a substantially higher level of SSI activity compared to the amo1 and SSIIa single mutants. Wildtype lines had consistently low SSI activity.

Example 6: The Amo1 Locus Negatively Regulates the Expression of GBSSI, SSI and SSIIa/SBEII Proteins in the Endosperm To understand the cause of the observed increase in amylose content on a per caryopsis basis (Example 3, Table 1), the level of granule bound starch synthase I (GBSSI) protein in the starch granules in barley grains from each of the 4 genotypes was analysed. GBSSI is the major starch synthase enzyme involved in amylose synthesis in cereal grains including barley and is primarily localized in starch granules within the endosperm. Starch granules from amo1 mutants contained significantly higher levels on a weight basis of GBSSI, SSI, SSIIa, SBEIIa and SBEIIb proteins compared to wild-type starch granules. Starch granules from SSIIa-amo1 double mutants also contained more GBSSI protein than granules from SSIIa single mutants, but had similar amounts of GBSSI protein compared to wildtype granules. However, starch granules from SSIIa-amo1 double mutant granules did not detectably contain any SSI protein or any SSIIa/SBEIIa/SBEIIb proteins, consistent with an altered localization of these proteins from the granules to the soluble fraction in the developing endosperms. Starch granules from SSIIa single mutants contained significantly less GBSSI protein than the other 3 genotypes as well as no detectable SSI protein or SSIIa/SBEIIa/SBEIIb proteins.

Discussion

The description in Examples 2-6 illustration the impact on amylose content of combining recessive mutations at the SSIIa and amo1 loci. Both of these mutations alone yielded increased amylose content in barley grains and reduced starch content. By combining them, it would have been reasonable to expect a more severe phenotype such as a further increase in amylose content and a further reduction in starch content. Unexpectedly however, combining the amo1 mutation with the SSIIa mutation significantly restored starch synthesis in the endosperm of SSIIa mutants through parallel increases in both amylose and amylopectin content, and without further raising the proportion of amylose in the starch.

The Examples also provided a further description of the effects of the SSIIa and amo1 mutations on starch synthesis. The effect of the SSIIa mutation was to predominantly decrease amylopectin synthesis, yielding a 75% reduction on a per caryopsis basis (Table 1), while amylose synthesis was decreased by 28%. Given that amylose synthesis requires the granular matrix to be present, the impact on amylose synthesis of the loss of starch synthase IIa through the SSIIa mutation might be a secondary consequence of the major decrease in amylopectin synthesis in this mutant. It was evident that the high amylose content of the grain starch of SSIIa mutants was a consequence of the greater inhibition of amylopectin synthesis than amylose synthesis. In contrast, the data presented in Table 1 suggested that the amo1 mutation promoted a shift from amylopectin synthesis to amylose synthesis, resulting in the elevated amylose phenotype of the amo1 mutant. When combined with the SSIIa mutation, the impact of amo1 was to increase the synthesis of both amylose and amylopectin, resulting in the significant restoration of starch synthesis and therefore grain weight in the SSIIa-amo1 double mutant, but no further increase in amylose content on a percentage basis was observed. However, the amylose content on a per seed basis was significantly increased in the SSIIa-amo1 double mutant compared to the SSIIa mutant alone (Table 1). Therefore, the amo1 mutation in both amo1 mutant endosperms and SSIIa-amo1 mutant endosperms promoted the synthesis of more amylose than in wildtype endosperms. This result suggested that the function of the gene at the amo1 locus is to negatively regulate amylose synthesis.

As GBSSI is essential for the biosynthesis of amylose in the endosperm (Nelson & Rines, 1962) and also contributes to the synthesis of the long chains of amylopectin (Maddelein et al., 1994; Denyer et al., 1996), the expression level of GBSSI in the starch granules in the endosperm was tested. This showed that the levels of expressed GBSSI protein in both amo1 mutant grains and SSIIa-amo1 double mutant grains were significantly increased compared to the wildtype grains and SSIIa single mutant grains, respectively. This suggested that the function of the gene at the amo1 locus was to negatively regulate expression of GBSSI, which has a primarily role in synthesizing amylose.

The data that the SSIIIa gene mapped close to the amo1 locus in barley suggested that the ssIIIa gene was a candidate for the gene containing the amo1 mutation. This conclusion was strengthened by further mapping data presented above and the sequencing data in Example 7. The SSIIIa gene was very tightly linked to the amo1 locus and we did not see any recombination between this gene and amo1 in more than 190 lines. Secondly, sequencing of the entire SSIIIa gene (Example 7) showed that there was a non-conservative difference in the amino acid sequence of the SSIIIa protein in the amo1 mutant compared to either the reference Himalaya or parent Glacier proteins and this substitution (from leucine to arginine) was in conserved motif 7 within the catalytic domain of SSIIIa proteins (Li et al., 2000). Activity of SSIIIa as assayed by zymograms was similar, however, in amo1 and wild type endosperms, so either the amo1 variant of SSIIIa retained its starch synthase activity or the band of activity observed in the zymograms was from the co-migrating isoform SSIIIb. It is proposed without limitation that the SSIIIa gene in HAG comprises the amo1 mutation, and that SSIIIa is a negative regulator of GBSSI in barley although SSIIIa is expressed in developing endosperm.

The role of starch synthase IIa in the elongation of amylopectin chains of DP15-24 has been previously demonstrated in barley (Morell et al., 2003) and extensively reviewed elsewhere for other species (Konik-Rose et al., 2007). As described herein the amo-1 mutation had only a subtle effect on chain length distribution, with minor but statistically significant effects in the chain length ranges DP9-14 (and DP15 to 24). The chain length distributions of the SSIIa and SSIIa-amo1 mutant amylopectins did not show statistically significant differences across the entire distribution.

The analysis of mutations affecting starch biosynthesis in a wide range of systems (including *Chlamydomonas*, rice, maize, pea, barley, *Arabidopsis*) has been highly informative in defining the key genes involved in the synthetic process and understanding their respective roles. However, it has frequently been noted that when combinations of mutations are generated, the effects of the mutations are not additive, suggesting interactions between genes and gene products are important.

Example 7: Cloning and Sequencing of Barley SSIIIa Genomic DNA and cDNA

Whilst the zymogram evidence showed that complete inactivation of the SSIIIa enzymatic activity was not responsible for the amo1 phenotype, the zymogram data did not exclude the possibility of a more subtle effect in the protein such as a change in kinetic properties of the enzyme, perhaps caused by a change in the amino acid sequence of the SSIIIa protein in the amo1 mutants. In order to investigate whether other polymorphisms in the SSIIIa gene could cause the amo1 phenotype, the cDNA sequences from wildtype barley Himalaya, and genomic DNA sequences from wildtype barley (Himalaya), SSIIa mutant (Himalaya292), amo1 mutant (HAG) and wildtype barley (Glacier, a parent line for HAG) were obtained by PCR cloning and sequenced as follows.

In order to obtain genomic SSIIIa DNA sequences, genomic DNA preparations isolated from barley varieties Himalaya, Himalaya292, Glacier and HAG were used for the PCR amplification of fragments using 3 pairs of primers. These primers were based on the cDNA and genomic DNA sequences of two wheat SSIIIa genes (Li et al., 2000), GenBank Accession Nos: AF258608 and AF258609). The three pairs of primers were ZLSSIIIa-P1F (5'ATGGAGAT-GTCTCTCTGGCCA 3' (SEQ ID NO: 16), locating at nucleotide 29 of wheat SSIIIa cDNA) and ZLSSIIIa-PER (5' TCTGCATACCACCAATCGCCGT 3' (SEQ ID NO: 17), locating at nucleotide 3806 of wheat SSIIIa genomic DNA); ZLSSIIIa-P2F (5'ATCGTGACCTAACAGCT TTGGCG 3' (SEQ ID NO: 18), locating at nucleotide 3189 of wheat SSIIIa genomic DNA) and ZLSSIIIa-P2R (5' GACA-GAAGAACCCAAATCTGCGGTC 3' (SEQ ID NO: 19) locating at nucleotide 7189 of wheat SSIIIa genomic DNA); ZLSSIIIa-P3F (5' GGAGGTCTCGGGGATGTTGTTAC 3' (SEQ ID NO: 20), locating at nucleotide 6038 of wheat SSIIIa genomic DNA) and ZLSSIIIa-P3R (5' CCACAAAT-GTAAATA TCATTGATGTAT 3' (SEQ ID NO: 21), locating at nucleotide 9524 of wheat SSIIIa genomic DNA).

For obtaining SSIIIa cDNA sequences, total RNA was extracted from the developing endosperm (15 days post anthesis, (dpa)) of the barley varieties. The procedures for the RNA extraction were as detailed in Clarke and Rahman, 2005. First strand cDNA was synthesized and used for PCR amplification of SSIIIa cDNAs. Primers used for amplification of full length of cDNA sequence were ZLSSIIIa-P1F and ZLSSIIIa-P4R (5'-ACGTCACTGCGGTTCT-TATCTCG-3 (SEQ ID NO: 22), located at nucleotide 9403, after the translation stop codon of the genomic DNA sequence of wheat SSIIIa.

For each PCR reaction (20 µl), 50 ng cDNA or genomic DNA, 1.5 mM MgCl$_2$, 0.125 mM each dNTP, 10 pmol primers, 0.5 M glycine betaine, 1 µl DMSO and 1.5 U of Advantage 2 Taq polymerase mix (Clontech) were used. The PCR reactions were conducted using a HYBAID PCR Express (Integrated Sciences) with 1 cycle of 95° C. for 5 minutes, 35 cycles of 94° C. for 45 seconds, 59° C. for 30 seconds, and 72° C. for 3 minute, 1 cycle of 72° C. for 10 minutes and 1 cycle of 25° C. for 1 minute. The PCR fragments were cloned into a pCR2.1 TOPO cloning vector (Invitrogen). DNA sequencing was performed at JCMRS, ANU, Australia using an automated ABI system with dye terminators as described by the manufacturers. DNA sequences were analysed using the GCG suite of programs (Devereaux et al., 1984) to detect single-nucleotide polymorphisms (SNPs) in genomic DNAs of the SSIIIa genes from Himalaya292, Himalaya, Glacier and HAG.

The SSIIIa genomic DNA sequences from Himalaya, Himalaya292, HAG and Glacier lines beginning at the translation initiation codon (ATG) in each case were each 9550 nucleotides long and contained 16 exons and 15 introns (Table 3). The SSIIIa cDNA sequence from Himalaya was 5088 nucleotides long, with a protein coding region from nucleotides 1 to 4770 which encoded a polypeptide with 1593 amino acid residues (SEQ ID NO: 4). Comparison between the SSIIIa genomic nucleotide sequences from Himalaya292 (and its parent Himalaya) and HAG (and its parent Glacier) showed that there were 8 single nucleotide polymorphisms (SNPs) for HAG (and 7 SNPs for Glacier) (Table 3). All of these were nucleotide substitutions, not deletions or insertions. Among them, 4 SNP variations for HAG (and 3 SNPs for Glacier) were in exons (Table 3). Three SNPs were in exon 3 (for HAG and Glacier) and one was in exon 14 of SSIIIa only from HAG. Two SNP variations at nucleotide 1084 (for HAG and Glacier) and 4439 (for HAG only) of the cDNA sequences produced a change in the amino acid sequence of the encoded protein. One change was conservative, changing a hydrophobic amino acid methionine (present in SSIIIa in Himalaya and Himalaya292) to another hydrophobic amino acid valine (in HAG and Glacier) at amino acid position 362 of the protein, whereas the other was a non-conservative change from a hydrophobic amino acid leucine (in Himalaya, Himalaya292 and Glacier) to a basic amino acid arginine (HAG) at position 1480 of the protein (Table 3). This last amino acid variation present only in the amo1 mutant HAG but not its parental variety Glacier was a good candidate for the genetic variation that caused the amo1 phenotype.

In the 5 lines that exhibited a broken linkage between the amo1 locus and either the EBmac0501 or Bmac0090 marker, all showed a linkage association between the SSIIIa marker and amo1 locus (Table 1) indicating that the SSIIIa gene was the closest marker to the amo1 locus of these markers. We therefore attempted to identify lines containing a recombination between the SSIIIa marker used and the gene underpinning the amo1 phenotype, by genotyping progeny from each of the 18 heterozygous lines comprising the SSIIa mutation and which were not used for the genotypic grouping analysis described above. Grains harvested from those plants were morphologically phenotyped and all 190 grains analysed showed no linkage breakdown between the SSIIIa gene and the amo1 locus, confirming that the SSIIIa gene was very tightly linked to the casual gene for the amo1 phenotype and a strong candidate as the gene causing the amo1 phenotype. Further studies such as down-regulation of the expression of the SSIIIa gene and complementation of the amo1 mutation by over-expression of a wild type SSIIIa gene were aimed at confirming this and are described in Examples 8-10 as follows.

A CAPS marker (Cleaved Amplified Polymorphic Sequence) was designed based on one SNP at nucleotide 6323 of the barley SSIIIa genomic DNA between two parental lines. This polymorphism created an EcoRI site in the SSIIIa gene from HAG, but not from Himalaya292. Primers SSIIIa-P5F (5' GGAGGTCTCGGGGATGT 3', (SEQ ID NO: 14)) located at nucleotide 7442 bp and SSIIIa-P5R (5' GGTTCCAGGAAGTAAACGGTCAGG 3 (SEQ ID NO: 23)) located at nucleotide 7893 of the barley SSIIIa genomic DNA were used for the PCR amplification of the CAPS marker for SSIIIa gene, a 464 bp product which was then digested with EcoRI.

Example 8: Reducing SSIIIa and SSIIIb Gene Expression in Barley with Transgenes Encoding Inhibitors of Gene Expression Two starch synthase III enzymes (SSIIIa, also known as SSIII-2, and SSIIIb also known as SSIII-1) are expressed in the developing wild-type barley endosperm from the SSIIIa and SSIIIb genes, respectively. In order to confirm the specific roles of these isoforms on starch synthesis and particularly on their role in negatively regulating amylose content in the grain, hairpin RNA constructs were made targeting these two genes.

Barley SSIIIa and SSIIIb share approximately 70% amino acid sequence identity. The wheat SSIIIa sequence is approximately 90% identical to the barley SSIIIa protein.

Constructs to Inhibit SSIIIa and SSIIIb Gene Expression in Barley.

A plasmid vector (pBx17IRcasNOT) was first constructed as a backbone vector for making constructs for the specific suppression of gene expression in barley endosperm by hairpin RNA technology i.e. using duplex RNA. The vector contained the following elements in order: an endosperm-specific promoter which included a 1895 bp sequence from a gene encoding the high molecular weight (HMW) glutenin Bx17 subunit in wheat (Reddy and Appels, 1992), a forward oriented cassette of attR-ccdB of 1447 bp in length (Gateway cloning technology GibcoBRL/Life Technologies) with a BamHI restriction enzyme site at the 5' end and an EcoRI site at the 3' end, a rice starch branching enzyme I intron 4 which was a 467 bp sequence corresponding to nucleotide 6202 to nucleotide 6668 of Genbank Accession No. D10838 in reverse orientation to the promoter, a rice branching enzyme I intron 9 which was a 495 bp sequence from nucleotide 9112 to nucleotide 9606 of the sequence D10838 in forward orientation, a reverse cassette of attR-ccdB (1435 bp) with a SpeI site at its 5' end and a KpnI site at its 3' end, and lastly a nos 3' polyadenylation sequence of 267 bp long (Chamberlain et al., 1994). The promoter was known to be expressed strongly in a tissue specific manner in wheat and barley endosperm in developing seeds.

To make the hairpin RNA construct targeting expression of the barley SSIIIa gene, a targeting sequence of 399 bp was amplified by PCR from a wheat SSIIIa cDNA (GenBank Accession No: AF258608 from nucleotide 4514 to nucleotide 4912) using the primers SSIIIa-F 5'-AAAAGGATCCG-GTACCGTTCTA ACCTATGATGAGCCTCT-3' (SEQ ID NO: 24), containing BamHI and KpnI sites towards its 5' end, and SSIIIa-R 5'-AAAAGAATTCACTAGT-GAATTTTCGAGCG GCATGGTAC-3' (SEQ ID NO: 25), containing EcoRI and SpeI sites towards its 5' end. A wheat sequence could be used in the inhibitory construct because of the degree of similarity of the wheat and barley genes. PCR amplification was carried out under standard conditions using Hotstar polymerase (Qiagen, Australia) on a Hybaid PCR Express thermal cycler (Hybaid, UK). The thermal profile was 4 min at 94° C. followed by 35 cycles of 30 sec at 94° C., 30 sec at 58° C. and 1 min at 72° C. Two copies of the resultant PCR fragment were inserted into the backbone vector pBx17IRcasNOT, one copy in reverse orientation into the SpeI and KpnI sites and a second copy in the forward orientation into the BamHI and EcoRI sites i.e. to form an inverted repeat structure. The resultant plasmid was designated as pwSSIIIaRNAi. This construct is shown schematically in FIG. 2. The HindIII/NotI fragment from pwSSIIIaRNAi was then cloned into an *Agrobacterium* Ti binary expression vector, pWBVec8, which contains a hygromycin resistance gene driven by a cauliflower mosaic virus (CaMV) 35S promoter (Wang et al. 1998). The resultant construct designated pwSSIIIaRNAi-vec8 was suitable for transformation of plant cells using *Agrobacterium*. The binary vector containing the pwSSIIIaRNAi-vec8 sequence was introduced into *Agrobacterium tumefaciens* strain AGL1 by electroporation and transformants containing the binary vector selected and grown using LB broth supplemented with 50 μg/ml each of rifampicin and spectinomycin as a growth medium.

Figure 2:
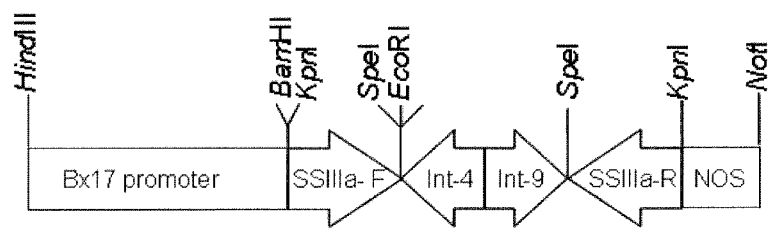
FIG. 2 is a schematic representation of the gene constructs encoding hairpin RNA for suppression of gene expression targeting (A) barley SSIIIa or (B) barley SSIIIb. See Example 8 for details of the constructs.
Figure 2:
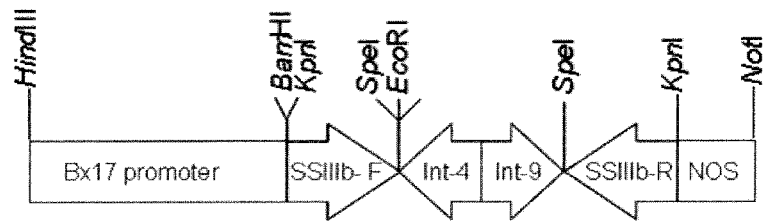

To make the hairpin RNA construct targeting expression of the barley SSIIIb gene, the targeting sequence of 428 bp was amplified by PCR from a wheat SSIIIb cDNA (GenBank Accession No: EU333946.2 from nucleotide 3414 to nucleotide 3841) using the primers SSIIIb-F 5'-AAAAGGATCCGGTACCGGT GAATTTGATGGTC-CCGTGTAG-3' (SEQ ID NO: 26), containing BamHI and KpnI sites towards its 5 end, and SSIIIb-R 5'-AAAAGAAT-TCACTAGTCAGTTCTTGC GCGTGGATGGTAC-3' (SEQ ID NO: 27), containing EcoRI and SpeI sites towards its 5' end. PCR amplification and cloning into the backbone vector were analogous to the SSIIIa construct (above) to form the plasmid designated pwSSIIIbRNAi (FIG. 2). The HindIII/NotI fragment from the pwSSIIIbRNAi construct was then cloned into vector pWBVec8 to form the construct designated pwSSIIIbRNAi-vec8. This binary vector was introduced into *Agrobacterium tumefaciens* strain AGL1 and transformants grown as for the SSIIIa construct, above.

Transformation of Barley with the Gene Constructs

*Agrobacterium*-mediated transformation of barley (cv. Golden Promise) was carried out using the method of Tingay et al., 1997, modified by the addition of 1.25 mg $CuSO_4.5H_2O$ into the plant tissue culture media. Regenerated hygromycin-resistant plants were acclimatised for one week inside a moist growth chamber and then planted individually in 8 cm pots with soil supplemented with 1 g/kg Osmocote (Scotts, Australia). The plants were then grown in a glasshouse with a temperature regime of 24° C. (day) and 18° C. (night).

Analysis for the Presence of Transgenes in the Plants

Genomic DNA was extracted from leaves of the plants after about one month of growth using a FastDNA Kit (Q-BIOgene) according to the manufacturer's instructions. Initial screening to confirm that plants are transformed with the hygromycin gene of the constructs was done using primers ZLhph253 5'-CGACGTCTGTCGAGAAGTTT CTG-3' (SEQ ID NO: 28) and ZLhph915 5'-CTCCA-GAAGAAGATGTTGGCGAC-3' (SEQ ID NO: 29). The plants were further verified as transformants and the presence of the hairpin RNA encoding genes detected using gene-specific primers that amplified a fragment containing a portion of the HMW glutenin Bx17 promoter and the forward wSSIIIa or the forward wSSIIIb fragment. The PCR primers for this were Bx17-3' 5'-CAACCATGTCCTGAAC-CTTCACC-3' (SEQ ID NO: 30), and SSIIIa-R 5'-AAAAGAATTCACTAGTGAATTTTCGAGCG-GCATGGTAC-3' (SEQ ID NO: 25) for pwSSIIIaRNAi transgenic plants, and Bx17-3' and SSIIIb-R 5'-AAAAGAATTCACTAGTCAGTTCTTGCGCGTG-GATGGTAC-3' (SEQ ID NO: 19) for the pwSSIIIbRNAi transgenic plants. PCR reactions were carried out using Go Taq Flexi DNA Polymerase (Promega) and amplification products were resolved in 1% agarose in 1×TBE buffer using 1 Kb Plus DNA Ladder (Invitrogen) as molecular weight standards. A 550 bp fragment specific to the pwSSIIIaRNAi construct and a 570 bp fragment specific to pwSSIIIbRNAi construct was amplified from the transgenic plants, including in each case about 150 bp from the Bx17 promoter region and about 400 bp of the SSIIIa or SSIIIb fragments.

Southern blot hybridisation analysis to determine the copy number of the introduced transgenes is carried out as described by Lagudah et al., 1991 with the modification that 6 M ammonium acetate is used to precipitate protein contaminants prior to the final precipitation of the DNA with isopropanol. A total of 10 µg DNA per sample is digested with the restriction enzymes HindIII or NotI and resolved in 1.3% agarose, using the Bx17 promoter digested with BamHI/HindIII as molecular weight and positive control. Hybridisation and wash conditions are as previously described (Rahman et al., 1997) using 25% formamide in the hybridization solution.

Analysis of the Expression Level of SSIIIa and SSIIIb Genes in the Transformants For detection of the expression levels of endogenous barley SSIIIa and SSIIIb genes or transgenes encoding SSIIIa or SSIIIb, the RNA products were detected by quantitative RT-PCR. Proteins such as SSIIIa and SSIIIb are detected by Western blot methods or zymogram analysis. Total RNA from 15 dpa barley grains was extracted using Trizol Reagent (Invitrogen) according to the manufacturer's instructions. Long and short RNAs were fractionated using a Nucleospin miRNA extraction kit (Macherey-Nagel) and quantified using the Nanodrop 1000 kit (Thermo Scientific). A total of 5 µg long RNA template was used to synthesise cDNA using the SuperScript III reverse transcriptase kit (Invitrogen). Quantitative real time PCR (qRT-PCR) was done in a Rotor-Gene 6000 (Corbett) using 100 ng cDNA template and primers for the wSSIIIaRNAi or wSSIIIbRNAi fragments. Real-time PCR amplification was conducted using Platinum Taq DNA polymerase (Invitrogen) and Sybr Green I (Invitrogen) reporter dye. Quantitation was normalised using a tubulin reference gene which was constitutively expressed (Toyota et al., 2006) and data validation and melt curve analysis was done using Rotor-Gene Series Real Time Rotary Analyzer Software (Corbett).

Among about 84 regenerated plants for each construct, five confirmed transgenic barley plants transformed with pwSSIIIaRNAi-vec8 and 10 plants transformed with pwSSIIIbRNAi-vec8 were selected and analysed by RT-PCR for expression levels of the endogenous SSIII genes. Each of the transformed plants exhibited reductions in the levels of the SSIIIa or SSIIIb genes, respectively, with some plants exhibiting less than 50% of the wild-type levels: for SSIIIa (pwSSIIIaRNAi-vec8) transformed lines 3, 4, 19, 9 and 21, and for SSIIb (pwSSIIIbRNAi-vec8) lines 23, 30, 40, 5, 20, 26, 36, 76, 9, 53 showed reductions of at least 50%.

Analysis of Starch Granule Bound Proteins and SSIIIa Enzymatic

Developing and mature grains are obtained from each transformed plant and assayed for SSIII proteins by zymogram analysis, and for total starch content, amylose content, starch chain length distribution, β-glucan content, pentosan content and other parameters as described above.

Example 9: Constructs to Express Barley SSIII Genes

In order to confirm and compare the functionality of the cloned SSIIIa sequences, expression constructs were made to express the sequences in barley or in heterologous plant species such as rice or *Arabidopsis*. These constructs also allowed complementation analysis of the amo1 mutation in barley, to provide further evidence that the amo1 mutation was in the barley SSIIIa gene. A cDNA including the full length SSIIIa protein coding sequence from barley, isolated as described in Example 7, was inserted into an expression vector as an EcoRI fragment in the sense orientation between the Bx17 promoter and nos3' polyadenylation sequence/transcription terminator. The NotI fragment containing the Bx17-SSIIIa-N08 expression cassette was then excised from this vector and inserted into the NotI site of the pWBVec8 derivative vector pVec8SJ to create pSJ101. pVec8SJ differed from pWBVec8 in that the orientation of the hygromycin selectable marker cassette was reversed by cutting with ClaI and religation. In pVec8SJ, the NotI and HindIII sites for insertion of expression cassettes were therefore closer to the right border and the gene of interest would therefore be transferred before the selectable marker gene which conferred hygromycin resistance.

Barley transformation and analysis of the plants, including for the presence of the trangenes were performed as described in Examples 1 and 8. The presence of transgenes in the transformants was confirmed using gene-specific primers that amplified a fragment containing a portion of the HMW glutenin Bx17 promoter and a part of the SSIIIa coding region. The PCR primers for this were Bx17-3' 5'-CAACCATGTCCTGAACCTTCACC-3' (SEQ ID NO: 30), and ZLSSIIIa-IR_RM 5'-GCTTGGITCAACAAT-GAGTCTTGTCG-3' (SEQ ID NO: 31)

Regenerated $T_0$ barley plants from the transformation process were planted in soil and screened by PCR. Among 52 $T_0$ transgenic lines containing the hygromycin resistance gene from pSJ101, 27 contained the exogenopus SSIIIa gene. Immature seeds (15 dpa) were collected from the lines containing gene of interest and stored at −80° C.

Total RNAs were isolated from the immature seeds and used in real-time PCR amplifications. Six transgenic barley lines (lines 19, 6, 17, 2, 13 and 16) were selected which were transformed with pSJ101, and shown to have SSIIIa transcript levels at least 2-fold higher than in the wild-type immature seeds at the same stage. The enzymatic activities for SSIIIa in the 15 dpa immature seeds are examined using the zymogram assay.

The transformed plants were grown in soil and, when flowering, are crossed with an SSIIa mutant (line 871), double mutants (HH4 or HH29) and an amo1 mutant (HH130) for transgenic plants containing pwSSIIIaRNAi-vec8 and pwSSIIIbRNAi-vec8, or with an amo1 mutant (HH130) or double mutant (HH4 or HH29) for transgenic plants transformed with pSJ101.

Example 10: Complementation of SSIII Mutants of Plants Other than Barley

Functionality of the SSIII sequences can also be tested in heterologous species, including in SSII/mutants in species such as *Arabidopsis thaliana*. Two mutant *Arabidopsis* lines each containing a T-DNA insertion (SALK_065732 and SALK_102605) were ordered from the *Arabidopsis* Biological Resource Center (ABRC stock center). The T-DNA insertions were in exon 13 of SSIII for mutant line SALK_065732, located at nucleotide 34865 of the sequence of Genbank Accession No. AC007296.2 and in the exon 9 of SSIII for SALK_102605, located at nucleotide 35724 of AC007296.2. Transcripts for the 5' part of the endogenous SSIIIa gene could be detected in these mutant *Arabidopsis* lines, but not for the 3' part of the gene. There was no SSIII protein expression detected in either mutant. Detailed analyses of both mutants were published in Zhang et al., 2005.

Construction of Expression Constructs for Dicot Plants

The CaMV 35S promoter was cloned into the *Agrobacterium* vector pORE02 (Coutu et al., 2007) as described by Wood et al., 2009. The promoter, multiple cloning sites and nos3' polyA regions were excised as an SphI-ZraI fragment and ligated into pVec8SJ vector cut with EcoRI, Klenow blunted-SphI. This deleted the hygromycin selectable marker cassette from the vector. The duplicated region of the 35S promoter was then removed by cutting with ScaI and self ligation and the hygromycin marker was inserted from pJP3303 (obtained from James Petrie, CSIRO, Canberra, Australia) as a KpnI, T4 DNA polymerase blunt-SphI fragment between the NcoI, Klenow blunt-SphI sites to create the plasmid vector designated as pVec8SJ35SHYG.

The full length SSIIIa cDNA from the barley variety High Amylose Glacier (HAG) was cloned in analogous fashion as described for the Himalaya SSIIIa cDNA (Example 7) and both cDNAs were excised from the TOPO vectors as NotI-SacI fragments and ligated into the pVec8SJ35SHYG plasmid cut with the same enzymes to create plasmids pSJ119 and pSJ120.

Plants of *Arabidopsis* lines SALK-065732 and SALK-10260 were each separately transformed with constructs pSJ119 and pSJ120 by the dipping method as described by Clough and Bent, (1998). $T_0$ seeds were harvested from the four transformation combinations, SALK-065732/pSJ119, SALK-065732/pSJ120, SALK-10260/pSJ119 and SALK-10260/pSJ120. To seeds were grown on agar plates containing MS basic medium supplemented with 50 mg/l Hygromycin and 150 mg/l Timentin to select $T_1$ transgenic plants. Fast growing $T_1$ transgenic plants that were resistant to hygromycin were transferred to and grown in soil. PCR amplification analysis confirmed that 7 $T_1$ plants for SALK102605/pSJ119, 10 for SALK102605/pSJ120, 6 for SALK065732/pSJ119 and 6 for SALK065732-pSJ120 were transformed.

The starch properties of the *Arabidopsis* mutant and overexpression transformed lines are compared to determine if the SSIIIa gene can complement the *Arabidopsis* mutation in the SALK lines. It is predicted that overexpression of the barley cv. Himalaya SSIIIa gene (wild-type) will complement the *Arabidopsis* mutation whereas overexpression of the SSIIIa gene isolated from HAG will not complement the mutation or only partially complement the mutation. This procedure therefore can be used to screen for the functionality of isolated SSIIIa genes.

Example 11: Mutagenesis of Barley and Isolation of Mutants

Barley mutagenesis was performed as described by Zwar and Chandler, 1995 using grain from the SSIIa mutant, line 871, which has a mutant SSIIa (SSIIa-292 allele) gene in a barley cv. Tantagara genetic background. Barley grain was washed several times until the water was clean. Approximately 1.5 kg of grain was imbibed at 4° C. overnight without surface-sterilization using about 4 L water in a bucket. Air was bubbled through the water with several air stones and an air pump. Air was bubbled through the mixture for 8 hours and the water changed several times during this period. The barley grains were then treated with 1 mM Na azide (0.13 g) dissolved in 2 liter 0.1 M $KH_2PO_4$ (27.2 g) buffer pH 3.0 for 2 h, with air bubbling as above, then washed extensively for 2 hours by running tap water into the bucket. Treated grains were air dried and were stored at 4° C. before sowing in flats in the greenhouse or in the field within a week.

Line 871 M1 mutagenised seeds (1.5 kg) were grown in the field (Ginninderra Experimental Station, Canberra, Australia) and approximately 2.1 kg of M2 seeds were bulk harvested. Five 871 M2 seeds which showed a plump morphology in comparison with the shrunken phenotype of the parental 871 seeds (named as 871MP M2) were identified by visual inspection. These were sown into soil to produce progeny plants (M2 plants), grown to maturity and seeds harvested (M3 seeds). Three of the 5 plump 871MP M2 seeds produced plumped 871MP M3 seeds, i.e. the altered phenotype was heritable.

Total leaf DNAs were isolated from the young leaves of 20 cm tall 871MP M3 plants. DNA fragments were amplified using 15 pairs of primers which spanned the full length of the genomic DNA sequence of the SSIIIa gene, spanning a region of 9550 bp. The primer pair used were pair 1: ZLwSSIII5'F (5' ATGGAGATGTCTTCCTGGCCA 3') (SEQ ID NO: 16. locating at nucleotide 1 of barley SSIIIa genomic DNA, and ZLBSSIII-2G17R (5'CTFCTGACCT-CATCTAAGCAAGG 3') (SEQ ID NO: 42), locating at nucleotide 818 of barley SSIIIa genomic DNA, pair 2: ZLwSSIIIN-1F (5' CTGGTCTTTGG CTGCCATATAGC 3') (SEQ ID NO: 43) locating at nucleotide 710 of barley SSIIIa genomic DNA, and ZLBSSIIIE3-2R (5' TCTCAAT-GTCTCTTGCACAGTCC 3') (SEQ ID NO: 44), locating at nucleotide 1604 of barley SSIIIa genomic DNA, pair 3: ZLSSIII-IR-FM (5' GCATTIGAGCTGGATTIGCCAGC 3') (SEQ ID NO: 451 locating at nucleotide 1559 of barley SSIIIa genomic DNA, ZLBSSIIIE3-IR (5' TCCTGAC-GAATCCATCTCAAACC 3') (SEQ ID NO: 46). locating at nucleotide 1955 of barley SSIIIa genomic DNA, pair 4: ZLBSSIII-2TLF1 (5' GCAGTIGAT GAAGCTGGGAAT-GATC 3') (SEQ ID NO: 47), locating at nucleotide 1858 of barley SSIIIa genomic DNA, and ZLBSSIII-2R12 (5' TCTCCCTCCTTAAGTTCC AGTCC 3') (SEQ ID NO: 48). locating at nucleotide 2641 of barley SSIIIa genomic DNA, pair 5: ZLBSSIII-2GI9F (5' GGATCTTTCGGCTGTT-GATCTCC 3') (SEQ ID NO: 49 locating at nucleotide 2548 of barley &a genomic DNA, and ZLBSS3E3R7 (5' GCCAT-TGTTCTCATAGACCGTGC 3') (SEQ ID NO: 50) locating at nucleotide 3350 of barley SSIIIa genomic DNA, pair 6: ZLSS3P21 (5' ATCGT GA CCTAACAGCTTTGGCG 3') (SEQ ID NO: SI) locating at nucleotide 3189 of barley SSIIIa genomic DNA, and ZLwSS3P2 (5' TCTGCATAC-CACCA ATCGCCGT 3') (SEQ ID NO: 2. locating at nucleotide 3806 of barley SSIIIa genomic DNA, pair 7: ZLBSSIII-2TLF2 (5' GTTGAGTTGGCCAGAACATGTG 3') (SEQ ID NO: 53) locating at nucleotide 3625 of barley SSIIIa genomic DNA. and ZLBSSIII-2TLR2 (5' GTGC-CATCACTCAACTGATAGAAC 3')(SEQ ID NO: 54), locating at nucleotide xxx of barley SSIIIa genomic DNA, pair 8: ZLSS3P3 (5' AAAGGCACTTGTGTTGGACTGGG 3') (SEQ ID NO: 55), locating at nucleotide 4062 of barley SSIIIa genomic DNA. and ZLBSSIII-2R14 (5' CAGTGAT-GTAAGAACGCAAGCTC 3') (SEQ ID NO: 56), locating at nucleotide 4867 of barley SSIIIa genomic DNA, pair 9: ZLBSSIII-2G17F (5' CTTCTGACCTC ATCTAAGCAAGG 3') (SEQ ID NO: 57) locating at nucleotide 4803 of barley SSIIIa genomic DNA, and ZLB-SSIII-2R9 (5' CTCGACGGCAATATGGATA ATACGC 3') (SEQ ID NO: 58 locating at nucleotide 5857 of barley SSIIIa genomic DNA, pair 10: ZLBSSIII-2F5 (5' TCTC-CGAGTCGGATGAAAATGGG 3') (SEQ ID NO: 59. locating at nucleotide 5785 of barley SSIIIa genomic DNA, and ZLBSSIII-2SNPR4 (5' TAAACCAGTACAAGGCTCT AGCC 3') (SEQ ID NO: 60) locating at nucleotide 6555 of barley SSIIIa genomic DNA, pair 11: ZLBSSIII-2F6 (5' CAAAGTITITCTTGGAGTGGCACAG 3') (SEQ ID NO: 61). locating at nucleotide 6425 of barley SSIIIa genomic DNA, and ZLSS3P16 (5' CAGAAGAACCCAAATCT-GCGGTC 3') (SEQ ID NO: 62' locating at nucleotide 7189 of barley SSIIIa genomic DNA, pair 12: ZLBSSIII-2F15 (5' TAGGATGTTGGCGTCGGATGTG 3') (SEQ ID NO: 63. locating at nucleotide 7171 of barley SSIIIa genomic DNA, and ZLBSSIII-2R15 (5' GTGTACGGATCC CAGA- TATCTGG 3') (SEQ ID NO: 64 locating at nucleotide 7919 of barley SSIIIa genomic DNA, pair 13: ZLSS3P14 (5' CGCCATTGCTCCTCATCGTGAC 3')(SEQ ID NO: 65L locating at nucleotide 7888 of barley SSIIIa genomic DNA, and ZLBSSIII-2R (5' CTCACCCTACCGTG GTAAACACC 3') (SEQ ID NO: 661 locating at nucleotide 8417 of barley SSIIIa genomic DNA. pair 14: ZLBSSIII-2P4F (5' TGGATTTT AGGTGGTTGCTTGG 3') (SEQ ID NO: 67, locating at nucleotide 8358 of barley SSIIIa genomic DNA, and ZLSS3P4 (5' CTCCATGACCCTCTTA-CACAGG 3') (SEQ ID NO: 68L locating at nucleotide 9030 of barley SSIIIa genomic DNA, pair IS: ZLBSSIII-2F7 (5' GCTCTGTCTCTTGGTCTTGAACC 3') (SEQ ID NO: 69), locating at nucleotide 8849 of barley SSIIIa genomic DNA, and ZLSS3P11 (5' CCACAAATGTAAATATCATTGATG-TAT 3') (SEQ ID NO: 70). locating at nucleotide 9550 of barley SSIIIa genomic DNA.

Conditions for PCR amplification of DNA fragments from barley genomic DNA, DNA sequencing and sequence analysis were as described in the Example 7 above. The SSIIIa gene sequences from the mutants are determined and compared to the wild-type and mutant sequence in the amo1 barley.

The zymogram method described above is used on progeny from the mutagenesis to identify mutants having altered mobility of the SSIIIa protein in its grain, or lacking SSIIIa altogether. Two starch synthase activities were seen on zymogram gels for wild-type barley endosperm extracts, a faster migrating activity band which was starch synthase I (SSI) and a slower migrating activity band which was SSIIIa. The zymogram method also allowed detection of grains having increased levels of SSI, as for the amo1 mutant grain. The visual inspection method described above followed by zymogram analysis on selected grains allows the screening of large numbers (>100,000) of grains from mutagenized populations.

Sodium azide mutagenesis induces mainly single nucleotide substitutions in the genomic DNA of G bases to A bases. In some cases, the changes form a premature stop codon in the protein coding sequences, resulting in mutants with little or no SSIII activity. Although DNA based screening methods or TILLING methods can also be used to detect mutants in a population mutagenized with sodium azide, in most cases the single nucleotide polymorphisms that are identified will not have formed premature stop codons. Moreover, each set of PCR reactions in such methods would screen fragments of the SSIIIa genes of about 800 nucleotides, not the whole 9550 nucleotides of the barley SSIIIa genomic DNA, so multiple reactions would need to be set up to cover the whole gene. In contrast, zymogram-based screening will detect stop codons formed by mutation in any part of the amino acid sequence of SSIIIa cDNA and therefore single assays can be performed for each mutant line.

Mutants are analysed for total starch content, amylose content, starch chain length distribution, β-glucan content and other parameters as described in Example 1. A range of mutants is obtained, from ones with only partial loss of SSIIIa activity through to complete loss (null mutants).

Example 12: Combination of SSIIIA Mutations and Other Starch Genetic Variations The barley amo1 mutant variety HAG was crossed with barley plants transformed with a hairpin RNA construct targeting the SBEIIa gene or the SBEIIb gene, or both transgenes, in order to combine the SSIIIa mutation from HAG with the transgene(s). Transformants containing the transgenes that suppressed SBEIIa gene expression, in particular, yielded a dramatic increase in amylose content (WO03/94600). The combination of the SSIIIa mutation with the transgene did not increase the grain amylose content on a per caryopsis basis relative to the grain having the transgene(s) but not the SSIIIa mutation.

In similar fashion, the barley SSIIIa mutants are crossed with barley plants containing a transgene expressing a hairpin RNA targeting the glucose, water di-kinase (GWD) gene (WO2009/067551). Suppression of GWD gene expression in the endosperm caused reduced grain starch phosphorylation, increased grain α-amylase and increased plant production characteristics such as increased grain yield and increased seedling vigour. Plants and grain containing both of these genetic variations are generated.

Example 13: Field Trials of SSIIA-Amo1 Double Mutants

To evaluate the yield performance of the SSIIa-SSIIIa double mutants when growing in the field, 3 hulless double mutant lines, 2 hulled double mutant lines, 4 hulless SSIIa mutants, 1 hulled SSIIa mutant line, 1 hulless wildtype barley line (cultivar Torrens) and 2 hulled wildtype barley lines (cultivars Tantangara, Sloop) were grown at Narrandera and Moree, NSW, Australia. Each of the barley lines was grown under both irrigated and non-irrigated (dryland) conditions at both sites. Two plots for each line were grown under each condition at both sites in a randomized pattern. Barley seeds (120 g) were sown in each plot (19 m$^2$).

The grain weight obtained after harvesting each plot in December 2008 was measured. At Narrandera, under irrigation, the double mutant, SSIIa mutant hulless wildtype lines produced 2.23±0.16 kg, 1.14±0.57 kg and 1.65±0.79 kg of grain, respectively, per plot. Under dryland conditions, the double mutant, SSIIa mutant and hulless wildtype lines produced 0.55±0.34 kg, 0.11±0.12 kg and 0.41±0.16 kg of grain, respectively, per plot.

At Moree, under irrigation, the double mutant, SSIIa mutant and hulless wildtype lines produced 1.62±0.72 kg, 0.54±0.40 kg and 2.11±0.08 kg of grain, respectively. Under dryland conditions, the double mutant, SSIIa mutant and hulless wildtype lines produced 0.88±0.33 kg, 0.38±0.27 kg and 1.14±0.34 kg of barley grains, respectively.

Therefore, under both irrigated and non-irrigated conditions at both sites, hulless double mutant and hulless wildtype lines produced similar yields of grain. The grain yields were significantly greater than the yield from hulless SSIIa mutants.

Grain Yield of Hulled Barley Lines:

At Narrandera, under irrigation, the double mutant, SSIIa mutant and hulled wildtype lines produced 2.77±0.37 kg, 2.09±0.76 kg and 4.39±2.59 kg of grain, respectively, per plot. Under dryland conditions, the double mutant, SSIIa mutant and hulled wildtype line produced 0.60±0.06 kg, 0.35±0.14 kg and 0.59±0.46 kg of grain, respectively.

At Moree, under irrigation condition, the double mutants, SSIIa mutants and hulled wildtype lines produced 2.15±0.81 kg, 1.24±0.12 kg and 2.73±0.96 kg of grain, respectively, per plot. Under dryland conditions, the double mutants, SSIIa mutants and hulled wildtype lines produced 1.19±0.40 kg, 0.76±0.60 kg and 2.13±0.23 kg of grain, respectively, per plot.

Therefore, under both irrigated and non-irrigated conditions at both sites, hulled wildtype lines yielded more grain than hulled double mutant and hulled SSIIa mutant lines, and hulled double mutants produced more grain than hulled SSIIa mutants. These experiments showed the benefit of combining the SSIIa and SSIIIa mutations to increase field-grown grain yield relative to the SSIIa mutation alone.

Example 14: Production of Food Products and Ingredients

Grain was harvested from eleven barley lines grown in the field at Yanco, NSW, Australia in 2008, and milled to produce flour. The lines were 3 hulless double mutants, 2 hulled double mutants, 3 SSIIa mutants including Himalaya292, 2 wildtype (cultivars Tantangara and Himalaya) and 1 amo1 mutant (HAG). The grain harvested from these lines was milled using a Quadrumat Jnr. mill (Brabender Quadrumat Jnr. Mill, Cyrulla's Instruments, Sydney, NSW Australia) to produce flour that was then sieved to 300 μm diameter. No tempering regime was applied before Quadrumat milling.

Two types of small-scale (10 g) breads were baked for each of 11 barley lines. Small-scale loaves were baked for these test purposes, but the method can be readily scaled up to commercial quantities. One type of bread was made with 100% barley flour as an ingredient, milled as described above, while the other type of bread was made with a blend of 30% flour and 70% commercial wheat flour as the flour ingredient. Flour (13.02 g) and the other ingredients were mixed into a dough, to peak dough development time in a 35-g mixograph. The recipe used, based on the 13.02 g of flour in each case was: flour 100%, salt 2%, dry yeast 1.5%, vegetable oil 2%, and improver 1.5%. The water addition level was based on the micro Z-arm water absorption values that were adjusted for the full formula. The moulding and panning were done in two-stage proofing steps at 40° C. and 85% room humidity. Baking was done in a Rotel oven for 14 min at 190° C.

After baking, the 10 g bread loaves were stored at −80° C. for three weeks for the batch of 100% barley breads, or for 1 week for the batch of 30% barley breads, and then analysed for RS content as described in Example 1, and GI levels. For the RS content, the in vitro procedure determined resistant starch content. Duplicated samples from the 10 g bread loaves, along with appropriate standards, were mixed with artificial saliva, and the resultant bolus was incubated with pancreatic and gastric enzymes at physiological pH and temperature. The amount of residual starch in the digesta was determined using conventional enzymatic and spectrophotometric techniques, and the resistant starch content of the sample was expressed as a percentage of sample weight.

RS Content of Barley Wholemeals

RS content and GI levels were first determined for the wholemeal milled from each of the groups of barley genotypes. The RS contents were 0.9%, 3.5±0.3%, 3.4±0.1%, 1.9% and 0.5±0.1% for the amo1 mutant, hulless double mutant, hulled double mutant, SSIIa mutant and wildtype wholemeal, respectively. Unexpectedly, both the hulless and hulled double mutant wholemeal contained approximately 3.5-, 2.3- and 10-fold higher RS content than the amo1 mutant, SSIIa mutant and wildtype wholemeal, respectively (Table 4). Importantly, wholemeals from both hulless and hulled double mutants contained significantly more RS than wholemeal from the SSIIa mutant. There were no statistically significant differences in RS content between hulless double mutant and hulled double mutant wholemeal, or between amo1 mutant and wildtype wholemeal. Although GI levels differed among wholemeals from 5 groups of barley, they were not statistically significantly different.

RS Content of Breads Containing 100% Barley Flour

The RS contents for breads that contained 100% barley wholemeal were determined and are given in Table 5. The analyses showed that the RS contents in breads made with 100% barley wholemeal as the flour ingredient were 2.2±0.3%, 5.5±0.1%, 5.6±0.3%, 2.1±0.4% and 0.8±0.3% for amo1 mutant, hulless double mutant, hulled double mutant, SSIIa mutant and wildtype grain (Table 6). The statistical analysis indicated that breads made from wholemeal from both hulless and hulled double mutant barley yielded significantly higher RS contents than that from SSIIa mutants, amo1 mutant and normal barley lines (Table 6). There were no significant differences in RS content from breads containing 100% flour of hulless and hulled double mutants. The breads from hulless and hulled double mutants produced 2.5-fold, 2.5-fold and 6.7-fold higher RS content than bread made from SSIIa mutant, amo1 mutant and normal barley, respectively (Table 6).

RS Content of Breads Containing 30% Barley Flour

The RS contents of breads that contained 30% barley flour were determined and are given in Table 7. RS contents of breads made from amo1 mutant, hulless double mutant, hulled double mutant, SSIIa mutant and wildtype wholemeal were 1.9±0.3%, 3.1±0.2%, 3.0±0.1%, 2.0±0.3%, 0.9±0.1%, respectively. Breads from both hulless and hulled double mutant barley yielded significantly higher RS contents than bread from SSIIa mutant, amo1 mutant and normal barley grain (Table 6). There were no significantly differences in RS content between breads containing 30% flour of hulless and hulled double mutants. The breads from hulless and hulled double mutants produced 1.6-, 1.6- and 3.3-fold higher RS content than bread from SSIIa mutants, amo1 mutant and normal barley lines, respectively (Table 6).

The calculation of RS content as mg RS per gram of starch was performed to analyse the nature of the increase of RS in breads made from the double mutants. These data were analysed to see whether the increase of RS content was due to the increase of total starch or due to the changes of starch structure. The results showed that bread produced with 100% barley flour from amo1 mutant, hulless double mutant, hulled double mutant, SSIIa mutant and wildtype grain had 41.7, 105.1±2.8, 106.9±3.3, 75.0±8.1 and 16.3±4.5 mg RS per g of starch of breads (FIG. 4.6). Both hulless double mutants and hulled double mutant breads yielded approximately 2.5-, 1.4- and 6.5-fold higher RS than breads from amo1 mutant, SSIIa mutant and wildtype grain. The statistical analysis showed that although breads from all 4 groups of barley contained more RS than that from the wildtype lines, the RS content (mg RS per g of starch) of breads from both double mutants were statistically significantly higher than that from amo1 mutants, SSIIa mutants ($P<0.05$). Bread from SSIIa mutant grain contained statistically significantly more RS than that from amo1 mutants.

GI Level of 100% Barley Breads

The GI level of breads that contained 100% barley wholemeal from all barley lines were determined and are given in Table 5. GI levels of breads from amo1 mutant, hulless double mutant, hulled double mutant, SSIIa mutant and wildtype grain were 68.5±2.1, 63.5±4.5, 60.8±4.1, 63.9±10.3, 80.3±2.9, respectively (Table 10). The statistical analysis indicated that breads from both hulless and hulled double mutant, and SSIIa mutant grain produced significantly lower values of GI than that from amo1 mutant and normal barley lines (Table 10). There were no significant differences for GI values for breads containing 100% flour of hulless and hulled double mutant, and SSIIa mutant grain. The breads from hulless and hulled double mutant, and SSIIa mutant grain yielded approximately 80% of GI level as that from amo1 mutant and normal barley lines, respectively (Table 10).

GI Level of 30% Barley Breads

The GI level of breads that contained 30% barley flour from all barley lines were determined and are given in Table 7. GI levels of breads from amo1 mutants, hulless double mutants, hulled double mutants, SSIIa mutants and wildtype lines were 84.5±3.5, 83.2±2.1, 83.5±0.8, 82.3±3.9, 87.8±4.5, respectively (Table 10). The GI values for breads made from the 5 groups of barley were not statistically significantly different.

Conclusions

Wholemeal from both hulless and hulled double mutant barley grain contained significantly higher RS contents than wholemeal from amo1 mutant, SSIIa mutant and wildtype grain. Wholemeal from both double mutants contained approximately 3.5-, 1.8- and 7.0-fold higher RS content comparing to wholemeal from amo1 mutants, SSIIa mutants and wildtype lines. In a similar pattern, bread made from the double mutant barley grain contained significantly higher RS content than bread made from SSIIa mutants, amo1 mutant and wildtype barley. The increase of RS content was not only due to the increase of amount of high amylose starch, but also the changes of starch structure as the increase of RS content was observed per g of starch.

Breads from both double mutant and SSIIa mutant grain yielded significantly lower GI values than that from both amo1 mutant and wildtype grain. The GI values of breads containing SSIIa-amo1 double mutant grain and SSIIa mutant grain were approximately 7% and 20% lower than of breads containing amo1 mutant and wildtype grain when the breads were made from 100% barley flour.

Many modifications will be apparent to those skilled in the art without departing from the scope of the present invention.

The disclosure of every patent, patent application, and publication cited herein is hereby incorporated herein by reference in its entirety.

TABLE 1

Genotypes and phenotypes of BC3F6 lines of barley

| Genotype | Line No. | Seed Weight (mg) | Starch Content (%) | Amylose Content (%) | Sex6 Locus Genotype | EBmac0501 Genotype | Bmac0090 Genotype | SSIIIa Genotype | Phenotype Assignment |
|---|---|---|---|---|---|---|---|---|---|
| Wild type | HH18 | 60.10 | 62.49 | 28.56 | Wt* | Wt | Wt | wt | Wildtype |
| Wild type | HH21 | 49.33 | 62.77 | 34.80 | Wt | Wt | Wt | wt | Wildtype |
| Wild type | HH28 | 55.85 | 62.61 | 35.50 | Wt | Wt | Wt | wt | Wildtype |
| Wild type | HH60 | 48.19 | 66.25 | 32.73 | Wt | Wt | Wt | wt | Wildtype |
| Wild type | HH61 | 44.34 | 61.42 | 33.96 | Wt | Wt | Wt | wt | Wildtype |
| Wild type | HH71 | 44.43 | 58.75 | 33.02 | Wt | Wt | Wt | wt | Wildtype |
| Wild type | HH73 | 56.13 | 64.93 | 32.59 | Wt | Wt | Wt | wt | Wildtype |
| Wild type | HH93 | 57.20 | 66.66 | 28.82 | Wt | Wt | Wt | wt | Wildtype |
| Wild type | HH94 | 57.80 | 66.3 | 35.20 | Wt | Wt | Wt | wt | Wildtype |
| Wild type | HH103 | 51.82 | 65.9 | 30.07 | Wt | Wt | Wt | wt | Wildtype |
| Wild type | HH109 | 49.59 | 64.5 | 29.31 | Wt | Wt | Wt | wt | Wildtype |
| Wild type | HH110 | 48.72 | 63.72 | 29.04 | Wt | Wt | Wt | wt | Wildtype |
| Wild type | HH126 | 53.88 | 60.64 | 35.93 | Wt | Wt | Wt | wt | Wildtype |
| amo1 | HH17 | 55.52 | 53.81 | 50.15 | Wt | amo1 | amo1 | amo1 | amo1 |
| amo1 | HH30 | 53.59 | 58.01 | 48.40 | Wt | amo1 | amo1 | amo1 | amo1 |
| amo1 | HH56 | 45.99 | 54.97 | 51.23 | Wt | amo1 | amo1 | amo1 | amo1 |
| amo1 | HH63 | 51.60 | 54.24 | 48.26 | Wt | amo1 | amo1 | amo1 | amo1 |
| amo1 | HH79 | 53.47 | 57.96 | 51.32 | Wt | amo1 | amo1 | amo1 | amo1 |
| amo1 | HH81 | 54.38 | 60.5 | 51.75 | Wt | amo1 | amo1 | amo1 | amo1 |
| amo1 | HH82 | 54.80 | 60.79 | 52.86 | Wt | amo1 | amo1 | amo1 | amo1 |
| amo1 | HH125 | 53.22 | 55 | 44.00 | Wt | amo1 | amo1 | amo1 | amo1 |
| amo1 | HH130 | 52.56 | 59.5 | 46.00 | Wt | amo1 | amo1 | amo1 | amo1 |
| SSIIa M | HH2 | 33.68 | 36.27 | 53.30 | SSIIa M | Wt | Wt | wt | SSIIa M |
| SSIIa M | HH35 | 34.85 | 35.48 | 70.63 | SSIIa M | Wt | Wt | wt | SSIIa M |
| SSIIa M | HH39 | 36.98 | 35.86 | 68.90 | SSIIa M | Wt | Wt | wt | SSIIa M |
| SSIIa M | HH42 | 36.07 | 33.02 | 59.66 | SSIIa M | Wt | Wt | wt | SSIIa M |
| SSIIa M | HH43 | 33.22 | 33.27 | 43.51 | SSIIa M | Wt | Wt | wt | SSIIa M |
| SSIIa M | HH48 | 36.35 | 33.71 | 56.77 | SSIIa M | Wt | Wt | wt | SSIIa M |
| SSIIa M | HH50 | 40.88 | 32.42 | 46.09 | SSIIa M | Wt | Wt | wt | SSIIa M |
| SSIIa M | HH51 | 38.72 | 31.22 | 47.56 | SSIIa M | Wt | Wt | wt | SSIIa M |
| SSIIa M | HH69 | 40.14 | 32 | 52.86 | SSIIa M | Wt | Wt | wt | SSIIa M |
| SSIIa M | HH83 | 41.20 | 35.71 | 79.90 | SSIIa M | Wt | Wt | wt | SSIIa M |
| SSIIa M | HH84 | 39.57 | 32.18 | 63.53 | SSIIa M | Wt | Wt | wt | SSIIa M |
| SSIIa M | HH97 | 38.27 | 33.77 | 60.56 | SSIIa M | Wt | Wt | wt | SSIIa M |
| SSIIa M | HH127 | 40.73 | 34.22 | 49.29 | SSIIa M | Wt | Wt | wt | SSIIa M |
| SSIIa-amo1 | HH4 | 43.79 | 53.42 | 57.21 | SSIIa M | amo1 | amo1 | amo1 | SSIIa-amo1 |
| SSIIa-amo1 | HH6 | 46.17 | 54.06 | 60.57 | SSIIa M | amo1 | amo1 | amo1 | SSIIa-amo1 |
| SSIIa-amo1 | HH7 | 44.20 | 48.83 | 66.27 | SSIIa M | amo1 | amo1 | amo1 | SSIIa-amo1 |
| SSIIa-amo1 | HH19 | 52.21 | 43.88 | 59.03 | SSIIa M | amo1 | amo1 | amo1 | SSIIa-amo1 |
| SSIIa-amo1 | HH29 | 44.52 | 48.25 | 64.53 | SSIIa M | amo1 | amo1 | amo1 | SSIIa-amo1 |
| SSIIa-amo1 | HH33 | 49.34 | 49.85 | 55.78 | SSIIa M | amo1 | amo1 | amo1 | SSIIa-amo1 |
| SSIIa-amo1 | HH74 | 43.39 | 46.3 | 63.84 | SSIIa M | amo1 | amo1 | amo1 | SSIIa-amo1 |
| SSIIa-amo1 | HH88 | 54.22 | 48.4 | 53.82 | SSIIa M | amo1 | amo1 | amo1 | SSIIa-amo1 |
| SSIIa-amo1 | HH98 | 48.13 | 48.43 | 61.11 | SSIIa M | amo1 | amo1 | amo1 | SSIIa-amo1 |

TABLE 1-continued

Genotypes and phenotypes of BC3F6 lines of barley

| Genotype | Line No. | Seed Weight (mg) | Starch Content (%) | Amylose Content (%) | Sex6 Locus Genotype | EBmac0501 Genotype | Bmac0090 Genotype | SSIIIa Genotype | Phenotype Assignment |
|---|---|---|---|---|---|---|---|---|---|
| SSIIa-amo1 | HH99 | 47.62 | 49.81 | 61.99 | SSIIa M | amo1 | amo1 | amo1 | SSIIa-amo1 |
| SSIIa-amo1 | HH122 | 49.04 | 47.03 | 59.68 | SSIIa M | amo1 | amo1 | amo1 | SSIIa-amo1 |
| SSIIa-amo1 | HH40 | 39.04 | 46.84 | 61.24 | SSIIa M | amo1 | amo1 | amo1 | SSIIa-amo1 |
| SSIIa-amo1 | HH77 | 35.54 | 48.2 | 68.24 | SSIIa M | amo1 | amo1 | amo1 | SSIIa-amo1 |
| amo1 Recombinant | HH116 | 48.11 | 50.39 | 52.94 | SSIIa M | Wt | amo1 | amo1 | SSIIa-amo1 |
| amo1 Recombinant | HH46 | 39.05 | 35.59 | 52.20 | SSIIa M | amo1 | wt | wt | SSIIa- |
| amo1 Recombinant | HH23 | 56.33 | 54.05 | 46.67 | wt | Wt | wt | amo1 | amo1 |
| amo1 Recombinant | HH24 | 52.62 | 63.11 | 38.69 | wt | amo1 | amo1 | wt | Wild type |
| amo1 Recombinant | HH118 | 49.68 | 65.65 | 38.00 | wt | Wt | amo1 | wt | Wild type |

*wt: wildtype.
SSIIa M: SSIIa mutation.

TABLE 2

Grain constituents of barley genotypes on a per seed basis

| | Starch (mg) | Amylose (mg) | Amylopectin (mg) | Protein |
|---|---|---|---|---|
| Wildtype | 34.1 ± 3.9$^a$ | 10.7 ± 1.5$^b$ | 23.4 ± 2.8$^a$ | 5.4 ± 0.7$^b$ |
| amo1 | 30.2 ± 2.5$^b$ | 15.0 ± 1.7$^a$ | 15.3 ± 1.3$^b$ | 5.5 ± 0.6$^b$ |
| SSIIa M | 13.2 ± 1.7$^d$ | 7.7 ± 2.1$^c$ | 5.5 ± 1.2$^d$ | 4.9 ± 0.4$^c$ |
| SSIIa-amo1 | 22.7 ± 1.9$^c$ | 13.8 ± 1.1$^a$ | 8.9 ± 1.2$^c$ | 6.5 ± 0.5$^a$ |
| LSD P < 0.05) | 2.4 | 1.5 | 1.7 | 0.5 |

| | Lipid (mg) | α-glucan (mg) | Pentosan (mg) | WSC (mg) |
|---|---|---|---|---|
| Wildtype | 1.6 ± 0.2$^c$ | 3.2 ± 0.5$^b$ | 2.6 ± 0.5$^a$ | 1.4 ± 0.2$^b$ |
| amo1 | 1.9 ± 0.2$^b$ | 4.3 ± 0.3$^a$ | 2.6 ± 0.6$^a$ | 2.2 ± 0.1$^b$ |
| SSIIa M | 2.5 ± 0.3$^a$ | 3.0 ± 0.4$^b$ | 2.8 ± 0.4$^a$ | 3.8 ± 1.3$^a$ |
| SSIIa-amo1 | 2.3 ± 0.2$^a$ | 3.1 ± 0.3$^b$ | 2.7 ± 0.5$^a$ | 3.3 ± 0.4$^a$ |
| LSD P < 0.05) | 0.2 | 0.3 | 0.5 | 0.9 |

All data are from the BC3F6 population and expressed on a mg per seed basis
Data represent the mean of samples assayed ±SD.
Data marked with the same letter are not significantly different at p = 0.05

TABLE 3

Intron and exon structure of barley SSIIIa gene and SNPs among barley SSIIIa genes from HAG, Glacier, Himalaya292 and Himalaya

| Nucleotide No. | Exon No. | Intron No. | Size of exon or intron in barley | Nucleotide No. | SNP in HAG, Glacier genomic DNA | SNP in Himalaya-292, Himalaya genomic DNA |
|---|---|---|---|---|---|---|
| 1 to 90 | 1 | | 90 | | | |
| 91 to 1019 | | 1 | 929 | 330 | T | C |
| 1020 to 1083 | 2 | | 64 | | | |
| 1084 to 1171 | | 2 | 88 | | | |
| 1172 to 3829 | 3 | | 2658 | 2101 | G (V)* | A (M) |
| | | | | 2693 | T | C |
| | | | | 3273 | C | T |
| 3830 to 4026 | | 3 | 197 | | | |
| 4027 to 4244 | 4 | | 218 | | | |
| 4245 to 4591 | | 4 | 347 | | | |
| 4592 to 4862 | 5 | | 271 | | | |
| 4863 to 5723 | | 5 | 861 | 5610 | G | A |
| 5724 to 5899 | 6 | | 176 | | | |
| 5900 to 6012 | | 6 | 113 | | | |
| 6013 to 6120 | 7 | | 108 | | | |
| 6121 to 6379 | | 7 | 259 | 6323 | C (EcoRI)# | T |
| 6380 to 6489 | 8 | | 110 | | | |
| 6490 to 7151 | | 8 | 662 | | | |
| 7152 to 7254 | 9 | | 103 | | | |
| 7255 to 7564 | | 9 | 310 | | | |
| 7565 to 7735 | 10 | | 171 | | | |
| 7736 to 7828 | | 10 | 93 | | | |
| 7829 to 7957 | 11 | | 129 | | | |
| 7958 to 8042 | | 11 | 85 | | | |
| 8043 to 8225 | 12 | | 183 | | | |
| 8226 to 8344 | | 12 | 119 | 8338 | A | T |
| 8345 to 8476 | 13 | | 132 | | | |

TABLE 3-continued

Intron and exon structure of barley SSIIIa gene and SNPs among barley SSIIIa genes from HAG, Glacier, Himalaya292 and Himalaya

| Nucleotide No. | Exon No. | Intron No. | Size of exon or intron in barley | Nucleotide No. | SNP in HAG, Glacier genomic DNA | SNP in Himalaya-292, Himalaya genomic DNA |
|---|---|---|---|---|---|---|
| 8477 to 8575 | | 13 | 99 | | | |
| 8576 to 8687 | 14 | | 112 | 8602 | T (L) for Glacier<br>G (R) for HAG | T (L) |
| 8688 to 8777 | | 14 | 90 | | | |
| 8778 to 8906 | 15 | | 129 | | | |
| 8907 to 8986 | | 15 | 80 | | | |
| 8987 to 9498 | 16 | | 128 | | | |

*Letters in the brackets are amino acid residues encoded. V: Valine; M: Methionine; L: Leucine; R: Arginine.
DNA sequences at nucleotide 6323 from HAG and Glacier can be digested by restriction enzyme, EcoRI.

TABLE 4

RS content and GI level of barley wholemeal

| Genotype | Line name | GI | GI average | SD | RS wholemeal (g/100 g) | RS average | SD |
|---|---|---|---|---|---|---|---|
| amo1 mutant | HAG | 64.6 | 64.6$^a$ | | 0.9 | 0.9$^c$ | |
| Hulled double mutant | HH88_F7 | 81.0 | 79.0$^a$ | 2.8 | 3.5 | 3.4$^a$ | 0.1 |
| Hulled double mutant | HH122_F7 | 77.0 | | | 3.3 | | |
| Hulless double mutant | HH4_F7 | 77.3 | 78.0$^a$ | 0.9 | 3.3 | 3.5$^a$ | 0.3 |
| Hulless double mutant | HH29_F7 | 79.1 | | | 3.4 | | |
| Hulless double mutant | HH29_F7- | 77.8 | | | 3.8 | | |
| SSIIa mutant | 292 | 68.2 | 68.2$^a$ | | 1.9 | 1.9$^b$ | |
| wildtype barley | Himalaya | 76.6 | 70.8$^a$ | 9.6 | 0.6 | 0.5$^c$ | 0.1 |
| wildtype barley | Glacier | 76.0 | | | 0.4 | | |
| wildtype barley | Tantangara | 59.7 | | | 0.4 | | |
| LSD (5%) | | | 22.6 | | | 0.7 | |

L.S.D.: it is the least significant difference; differences greater than this are significant (P < 0.05).
$^{a,b}$ and $^c$ based on LSD, mean values with the same letter are not significantly different, and with the different letter are significantly different at significant difference (P < 0.05).

TABLE 5

RS content and GI level of bread produced using 100% barley wholemeal

| Sample ID | Genotype | Line name | RS content (g/100 g) | GI level |
|---|---|---|---|---|
| ZL2.9.1 | amo1 mutant | HAG | 2.39 | 70 |
| ZL2.9.1 | amo1 mutant | HAG | 2.01 | 67 |
| 10.1 | Hulless double mutant | HH29_F7 | 5.46 | 57 |
| 10.1 | Hulless double mutant | HH29_F7 | 5.6 | 62 |
| 6.1 | Hulless double mutant | HH4_F7 | 5.53 | 66 |
| 6.1 | Hulless double mutant | HH4_F7 | 5.32 | 61 |
| 2.1 | Hulless double mutant | HH7_F7 | 5.61 | 70 |
| 2.1 | Hulless double mutant | HH7_F7 | 5.65 | 65 |
| 11.1 | hulled double mutant | HH88_F7 | 5.76 | 66 |
| 11.1 | hulled double mutant | HH88_F7 | 5.96 | 62 |
| 1.1 | hulled double mutant | HH122_F7 | 5.29 | 57 |
| 1.1 | hulled double mutant | HH122_F7 | 5.2 | 58 |
| ZL1.8.1 | SSIIa mutant | 871 | 1.96 | 49 |
| ZL1.8.1 | SSIIa mutant | 871 | 2.08 | 53 |
| ZL1.1.1 | SSIIa mutant | Himalaya292 | 1.49 | 57 |
| ZL1.1.1 | SSIIa mutant | Himalaya292 | 1.58 | 60 |
| 4.1 | SSIIa mutant | HH50_F7 | 2.22 | 74 |
| 4.1 | SSIIa mutant | HH50_F7 | 2.26 | 74 |
| 3.1 | wildtype | Himalaya | 0.65 | 82 |
| 3.1 | wildtype | Himalaya | 0.52 | 82 |
| 9.1 | wildtype | Tantangara | 1.04 | 76 |
| 9.1 | wildtype | Tantangara | 1.05 | 81 |

TABLE 6

Statistical analysis of the effects of genotype on RS contents of bread produced with 30% or 100% barley flour

| Genotype | No Sample | RS content 100% (g/100 g) | SD | RS content 30% (g/100 g) | SD |
|---|---|---|---|---|---|
| amo1 mutant | 2 | 2.2$^b$ | 0.3 | 1.9$^b$ | 0.3 |
| hulless double mutant | 6 | 5.5$^a$ | 0.1 | 3.1$^a$ | 0.2 |
| hulled double mutant | 4 | 5.4$^a$ | 0.4 | 3.0$^a$ | 0.1 |
| SSIIa mutant | 6 | 1.9$^b$ | 0.4 | 1.8$^b$ | 0.3 |
| Wildtype | 4 | 0.7$^c$ | 0.3 | 1.0$^c$ | 0.1 |
| L.S.D. (P < 0.05) | | 0.5 | | 0.3 | |

Note:
RS content 30%: RS content of the breads that contained 30% barley flour.
RS content 100%: RS content of the breads that contained 100% barley flour.
L.S.D.: it is the least significant difference; differences greater than this are significant (P < 0.05).
$^{a,b}$ and $^c$ based on LSD, mean values with the same letter are not significantly different, and with the different letter are significantly different at significant difference (P < 0.05).

TABLE 7

RS content and GI level of breads produced with 30% barley flour

| Sample ID | Genotype | Line name | RS (g/100 g) | GI level |
|---|---|---|---|---|
| ZL1.4.1 | amo1 mutant | HAG | 2.15 | 82 |
| ZL1.4.1 | amo1 mutant | HAG | 1.72 | 87 |
| ZL1.5.1 | Hulless double mutant | HH29_F7 | 3.01 | 83 |
| ZL1.5.1 | Hulless double mutant | HH29_F7 | 3.07 | 82 |
| ZL2.7.1 | Hulless double mutant | HH4_F7 | 3.03 | 83 |
| ZL2.7.1 | Hulless double mutant | HH4_F7 | 3.27 | 83 |
| ZL2.6.1 | Hulless double mutant | HH7_F7 | 3.15 | 84 |
| ZL2.6.1 | Hulless double mutant | HH7_F7 | 3.03 | 84 |
| ZL1.3.1 | Hulled double mutant | HH88_F7 | 3.04 | 83 |
| ZL1.3.1 | Hulled double mutant | HH88_F7 | 3.09 | 86 |
| ZL1.10.1 | Hulled double mutant | HH122_F7 | 3.01 | 81 |
| ZL1.10.1 | Hulled double mutant | HH122_F7 | 2.71 | 84 |
| ZL2.1.1 | SSIIa mutant | 871 | 1.87 | 77 |
| ZL2.1.1 | SSIIa mutant | 871 | 1.82 | 81 |
| ZL2.3.1 | SSIIa mutant | Himalaya292 | 1.7 | 80 |
| ZL2.3.1 | SSIIa mutant | Himalaya292 | 1.87 | 82 |
| ZL2.2.1 | SSIIa mutant | HH50_F7 | 2.15 | 86 |

TABLE 7-continued

RS content and GI level of breads produced with 30% barley flour

| Sample ID | Genotype | Line name | RS (g/100 g) | GI level |
|---|---|---|---|---|
| ZL2.2.1 | SSIIa mutant | HH50_F7 | 1.69 | 84 |
| ZL1.2.1 | Wildtype | Himalaya | 0.96 | 93 |
| ZL1.2.1 | Wildtype | Himalaya | 1.02 | 94 |
| ZL2.8.1 | Wildtype | Tantangara | 0.84 | 83 |
| ZL2.8.1 | Wildtype | Tantangara | 0.89 | 85 |

TABLE 8

Statistical analysis of the effects of genotype on RS content (mg RS per g starch) of bread produced with 100% barley flour

| Genotype | No of samples | RS content 100% (g/100 g) | SD | Total starch in breads (%) | SD | mg RS per g starch | SD |
|---|---|---|---|---|---|---|---|
| amo1 mutant | 1 | $2.2^b$ | 0.3 | $57.4^a$ | — | $41.7^c$ | |
| hulless double mutant | 3 | $5.5^a$ | 0.1 | $52.7^a$ | 1.8 | $105.1^a$ | 2.8 |
| hulled double mutant | 2 | $5.4^a$ | 0.4 | $51.8^a$ | 4.7 | $106.9^a$ | 3.3 |
| SSIIa mutant | 3 | $1.9^b$ | 0.4 | $25.1^b$ | 3.0 | $75.0^b$ | 8.1 |
| Wildtype | 2 | $0.7^c$ | 0.3 | $51.6^a$ | 2.6 | $16.3^d$ | 4.5 |
| L.S.D. (P < 0.05) | | 0.5 | | 8.9 | | 16.3 | |

TABLE 9

Statistical analysis of the effects of genotype on RS content (mg RS per g starch) of breads produced with 30% barley flour

| Genotype | No Sample | RS content 30% (g/100 g) | SD | Total starch in breads (%) | SD | mg RS per g starch | SD |
|---|---|---|---|---|---|---|---|
| amo1 mutant | 1 | $1.9^b$ | 0.3 | $61.9^a$ | — | $30.7^b$ | |
| hulless double mutant | 3 | $3.1^a$ | 0.2 | $65.3^a$ | 2.2 | $47.5^a$ | 0.8 |
| hulled double mutant | 2 | $3.0^a$ | 0.1 | $63.7^a$ | 1.1 | $47.1^a$ | 3.0 |
| SSIIa mutant | 3 | $1.8^b$ | 0.3 | $58.0^b$ | 2.3 | $31.6^b$ | 0.3 |
| Wildtype | 2 | $1.0^c$ | 0.1 | $65.1^a$ | 0.1 | $14.6^c$ | 1.1 |
| L.S.D. (P < 0.05) | | 0.3 | | 5.6 | | 4.2 | |

TABLE 10

Statistical analysis of the effects of genotype on GI level of the 10 g breads produced with 30% or 100% barley flour

| Genotype | No Sample | GI level 100% | SD | GI level 30% | SD |
|---|---|---|---|---|---|
| amo1 mutant | 2 | $68.5^a$ | 2.1 | $84.5^a$ | 3.5 |
| hulless double mutant | 6 | $63.5^b$ | 4.5 | $83.2^a$ | 2.1 |
| hulled double mutant | 4 | $60.8^b$ | 4.1 | $83.5^a$ | 0.8 |
| SSIIa mutant | 6 | $63.9^b$ | 10.3 | $82.3^a$ | 3.9 |
| Wildtype | 4 | $80.3^a$ | 2.9 | $87.8^a$ | 4.5 |
| L.S.D. (P < 0.05) | | 12.1 | | 5.8 | |

GI level 30%: GI level of the breads that contained 30% barley flour.
GI level 100%: GI level of the breads that contained 100% barley flour.
L.S.D.: it is the least significant difference; differences greater than this are significant (P < 0.05).
$^a$ and $^b$ based on LSD, mean values with the same letter are not significantly different, and with the different letter are significantly different at significant difference (P < 0.05).

TABLE 11

Summary of sequence identifiers

| SEQUENCE ID NO: | DESCRIPTION |
|---|---|
| 1 | Barley ssIIIa gene from Himalaya, genomic sequence beginning from the translation start codon |
| 2 | Barley SSIIIa cDNA from a wildtype barley cv. Himalaya, beginning at the translation initiation codon |
| 3 | Barley SSIIIa cDNA from an amo1 mutant (HAG, amo1-38 allele), beginning at translation initiation codon |
| 4 | Barley SSIIIa amino acid sequence from a wildtype barley cv. Himalaya, and from Himalaya292 |
| 5 | Barley SSIIIa amino acid sequence from an amo1 mutant (High Amylose Glacier, amo1-38 allele) |
| 6 | Wheat SSIIIa cDNA (GenBank Accession No: AF258608) |
| 7 | Wheat SSIIIb cDNA (GenBank Accession No: EU333946.2) |
| 8 | Wheat SSIIIa amino acid seqence (GenBank Accession No: AF258608) |
| 9 | Wheat SSIIIb amino acid seqence (GenBank Accession No: EU333946.2) |
| 10 | Primer SSIIaF |
| 11 | Primer SSIIaR |
| 12 | Primer HHac0501F |
| 13 | Primer HHac0501R |
| 14 | Oligonucleotide primers SSIIIaF and SSIIIa-P5F |
| 15 | Oligonucleotide primer SSIIIaR |
| 16 | Primer ZLSSIIIa-P1F and ZLwSSIII5'F |
| 17 | Primer ZLSSIIIa-P1R |
| 18 | Primer ZLSSIIIa-P2F |
| 19 | Primer ZLSSIIIa-P2R |
| 20 | Primer ZLSSIIIa-P3F |
| 21 | Primer ZLSSIIIa-P3R |
| 22 | Primes ZLSSIIIa-P1F and ZLSSIIIa-P4R |
| 23 | Primer SSIIIa-P5R |
| 24 | Primer SSIIIa-F |
| 25 | Primer SSIIIa-R |
| 26 | Primer SSIIIb-F |
| 27 | Primer SSIIIb-R |
| 28 | Primer ZLhph253 |
| 29 | Primer ZLhph915 |
| 30 | PCR primer Bx17-3' |
| 31 | PCR primer ZLSSIIIa-IR_RM |
| 32 | Wildtype Himalaya SSIIa cDNA |
| 33 | Himalaya292 SSIIa cDNA |
| 34 | SSIII conserved amino acid motif |
| 35 | SSIII conserved amino acid motif |
| 36 | SSIII conserved amino acid motif |
| 37 | SSIII conserved amino acid motif |
| 38 | SSIII conserved amino acid motif |
| 39 | SSIII conserved amino acid motif |
| 40 | SSIII conserved amino acid motif |
| 41 | SSIII conserved amino acid motif |
| 42 | Primer ZLBSSIII-2GI7R |
| 43 | Primer ZLwSSIIIN-1F |
| 44 | Primer ZLBSSIIIE3-2R |
| 45 | Primer ZLSSIII-IR-FM |
| 46 | Primer ZLBSSIIIE3-1R |
| 47 | Primer ZLBSSIII-2TLF1 |
| 48 | Primer ZLBSSIII-2R12 |
| 49 | Primer ZLBSSIII-2G19F |
| 50 | Primer ZLBSS3E3R7 |
| 51 | Primer ZLSS3P21 |
| 52 | Primer ZLwSS3P2 |
| 53 | Primer ZLBSSIII-2TLF2 |
| 54 | Primer ZLBSSIII-2TLR2 |
| 55 | Primer ZLSS3P3 |
| 56 | Primer ZLBSSIII-2R14 |
| 57 | Primer ZLBSSIII-2G17F |
| 58 | Primer ZLBSSIII-2R9 |
| 59 | Primer ZLBSSIII-2F5 |
| 60 | Primer ZLBSSIII-2SNPR4 |
| 61 | Primer ZLBSSIII-2F6 |
| 62 | Primer ZLSS3P16 |
| 63 | Primer ZLBSSIII-2F15 |
| 64 | Primer ZLBSSIII-2R15 |
| 65 | Primer ZLSS3P14 |
| 66 | Primer ZLBSSIII-2R |
| 67 | Primer ZLBSSIII-2P4F |

TABLE 11-continued

Summary of sequence identifiers

| SEQUENCE ID NO: | DESCRIPTION |
|---|---|
| 68 | Primer ZLSS3P4 |
| 69 | Primer ZLBSSIII-2F7 |
| 70 | Primer ZLSS3P11 |
| 71 | HAG Barley SSIIIa amino acid sequence |
| 72 | Glacier Barley SSIIIa amino acid sequence |

TABLE 12

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 13

Exemplary and Preferred Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Abel et al., *Plant Journal* 10: 981-991, 1996
Adams et al., *Anal. Biochem.*, 266: 77-84, 1999
Almeida and Allshire, *Trends Cell Biol.* 15: 251-258, 2005
Altschul et al., *J. Mol. Biol*, 215: 403-10, 1990
Altschul et al., *Nucleic Acids Res.* 25: 3389, 1997
An, *Methods in Enzymology*, 153: 292, 1987
Ausubel et al., *"Current Protocols in Molecular Biology"*, John Wiley & Sons Inc, 1994-1998, Chapter 15, Unit 19.3.
Ausubel et al., (eds.), *Current Protocols in Molecular Biology*, John Wiley & Sons, NY, 6.3.1-6.3.6., 1989
Banks et al., *Starch/die Stärke*, 23: 118-124, 1971
Barker et al., *Plant Mol. Biol.*, 2: 235-350, 1983
Batey et al., *J. Sci. Food Agric.* 74: 503-508, 1997
Bechtold et al., *C. R. Acad. Sci. Paris*, 316: 1194, 1993
Bell, *Journal of the Science of Food and Agriculture* 36: 815, 1985
Bernfeld, *Amylases alpha and beta*. In: Colowick S. Kaplan N (eds) *Methods in enzymology*. Academic, NY, p 149, 1955
Bevan et al., *Nucl. Acid Res.*, 11: 369, 1983
Birch, *Ann Rev Plant Physiol Plant Mol Biol.* 48: 297-326, 1997
Bourque, *Plant Sci.* 105: 125-149, 1995
Cao et al., *Plant Physiology.* 120: 205-16, 1999
Castro et al., *Biomacromolecules* 6: 2260-2270, 2005
Chamberlain et al., *Aust. J. Plant Physiol.*, 21: 95-112, 1994
Clarke and Rahman, *Threoretical and Applied Genetics* 110: 1259-1267, 2005
Clarke et al., *Functional and Integrative Genomics* 8: 211-221, 2008
Clough and Bent, (1998)
Comai et al., *Plant J.* 37: 778-786, 2004
Coutu et al., *Transgenic Res* 16: 771-781, 2007
Cuevas, *Carbohydrate Polymers* 81: 524-532, 2010
De Framond, *Biotechnology*, 1: 262, 1983
Deikman et al., *EMBO J.*, 2: 3315-3320, 1998
DellaPenna et al., *Plant Cell*, 1:53-63, 1989
Denyer et al., *Plant Journal* 10: 1135-1143, 1996
Devereaux et al., *Nucleic Acids Research* 12: 387-395, 1984
Durai et al., *Nucleic Acids Research* 33(18): 5978-5990, 2005
Fitzgerald et al., *Cereal Chem.* 86: 492-498, 2009
Fromm et al., *Proc. Natl. Acad. Sci. U.S.A.* 82: 5824, 1985
Garfinkel et al., *Cell*, 27: 143-153, 1983
Greve, *J. Mol. Appl. Genet.*, 1: 499-511, 1983
Hartmann and Endres, *Manual of Antisense Methodology*, Kluwer, 1999
Haseloff and Gerlach, *Nature* 334: 585-591, 1988
Hayashi et al., *Effects of ion beam irradiation on mutation induction in rice. Cyclotrons and Their Applications 2007*, Eighteenth international Conference 237-239, 2007
Hendrix et al., *J. Insect Physiol.*, 47: 423-432, 2001
Henikoff et al., *Plant Physiol.* 135: 630-636, 2004
Hoekema et al., *Nature*, 303: 179, 1983
Joshi, *Nucl. Acid Res.* 15: 6643, 1987
Kazama et al., *Plant Biotechnology* 25: 113-117, 2008
Klein et al., *Nature*, 327: 70, 1987
Konik-Rose et al., *Starch-Stärke*, 53:14-20, 2001
Konik-Rose et al., *Theor Appl Genet*, 115: 1053-1065, 2007
Lagudah et al., *Genome* 34: 387-395, 1991
Langridge et al., *Aust J Agric Res* 52: 1043-1077, 2001
Le Provost et al., *Trends in Biotechnology* 28(3): 134-141, 2009
Lemieux, *Current Genomics*, 1: 301-311, 2000
Li et al., *Plant Physiol*, 120: 1147-1156, 1999a
Li et al., *Plant Physiology* 123: 613-624, 2000
Libessart et al., *Plant Cell.* 7(8): 1117-1127, 1995
Liu et al., *Biotechnology and Bioengineering*, 106: 97-105, 2010
Lunn and Hatch, *Planta* 197: 385-391, 1995
Maddelein et al., *The Journal of Biological Chemistry* 269: 25150-25157, 1994
Medbery et al., *Plant Cell*, 4: 185-192, 1992
Medberry et rd., *Plant J.* 3: 619-626, 1993
Meyers and Miller, *Cabios*, 4: 11-17, 1989
Millar and Waterhouse, *Funct Integr Genomics*, 5: 129-135, 2005

Morell et al., *Plant Journal* 34: 173-185, 2003
Morrison and Laignelet, *Journal of Cereal Science I*: 9-20, 1983
Morrison et al., *J Cereal Sci,* 2: 257-271, 1984
Morrison et al., *J Cereal Sci,* 2: 257-271, 1984
Needleman and Wünsch, *J. Mol. Biol.* 48: 444-453, 1970
Nelson & Rines, *Biochem. Biophys. Res. Comm.,* 9: 297-300, 1962
Niedz et al., *Plant Cell Reports,* 14: 403, 1995
O'Shea et al., *Carbohydr Res,* 307: 1-12, 1998
Ow et al., *Science,* 234: 856, 1986
Pasquinelli et al., *Curr Opin Genet Develop* 15: 200-205, 2005
Perriman et al., *Gene,* 113: 157-163, 1992
Potrykus et al., *Mol. Gen. Genet.* 199: 183, 1985
Prasher et al., *Biochem. Biophys. Res. Comm.* 126: 1259-68, 1985
Prosky et al., *AOAC* 985: 29, 1985
Rahman et al., *Austr J Plant Physiol* 22: 793-803, 1995
Rahman et al., *Genome* 40: 465-474, 1997
Ramsay et al., *Genetics* 156: 1997-2005, 2000
Reddy and Appels, *Theor. Appl. Genet.,* 85(5): 616-624, 1992
Regina et al., *Proc Natl Acad Sci USA,* 103: 3546-3551, 2006
Remington's Pharmaceutical Sciences, 18th Ed., Mack Publishing, Company, Easton, Pa., U.S.A. 1990
Robinson, *The Organic Constituents of Higher Plants,* Cordus Press, North Amherst, USA, 1980, Example 9
Ruuska et al., *Functional Plant Biology* 33: 799-809, 2006
Salomon et al., *EMBO J.,* 3: 141-146, 1984
Sambrook et al., *Molecular Cloning: A Laboratory Manual* (2nd ed.). Cold Spring Harbour Laboratory, Cold Spring Harbour, N.Y., 1989
Schulman and Kammiovirta, *Starch,* 43: 387-389, 1991
Senior, *Biotech. Genet. Engin. Revs,* 15: 79-119, 1998
Shimamoto et al., *Nature,* 338: 274-276, 1989
Shippy et al., *Mol. Biotech.* 12: 117-129, 1999
Slade and Knauf, *Transgenic Res.* 14: 109-115, 2005
Smith et al., *Nature,* 407: 319-320, 2000
Stalker et al., *Science,* 242: 419, 1988
Theander et al., *J AOAC Int* 78: 1030-1044, 1995
Thillet et al., *J. Biol. Chem.* 263: 12500, 1988
Thompson et al., *Carbohydrate Res.,* 331: 149-161, 2001
Tingay et al., *Plant Journal* 11: 1369-1376, 1997
Topping et al., *Starch-Stärke,* 55: 539-545, 2003
Toyota et al., *Planta* 223: 248-257, 2006
Veronese et al., *Enz. Microbial Tech.,* 24: 263-269, 1999
Wan and Lemaux, *Plant Physiol.* 104: 37-48, 1994
Wang et al., *Acta Hort.* 461: 401-405, 1998
Ward et al., *Biomacromolecules* 7: 866-876, 2006
Waterhouse et al., *Proc. Natl. Acad. Sci. U.S.A.* 95: 13959-13964, 1998
Wood et al., *Plant Biotech J* 7: 914-924, 2009
Yamamori et al., *Theoretical and Applied Genetics* 101: 21-29, 2000
Zhang et al., *Plant Physiology* 138: 663-674, 2005
Zwar and Chandler, *Planta* 197: 39-48, 1995

The invention claimed is:

1. A process for producing a food ingredient or beverage ingredient, wherein the process comprises:
   (i) obtaining barley grain comprising
      (a) a starch content of which at least 40% (w/w) is amylose,
      (b) a null mutation of a gene encoding starch synthase IIa (SSIIa), wherein the barley grain is homozygous for the null mutation,
      (c) a level of activity of a starch synthase IIIa (SSIIIa) protein which is less than 25% of the level or activity relative to that of the SSIIIa protein in barley grain of variety Himalaya,
      (d) a starch content of 41-65% (w/w), and
   (ii) processing the barley grain to produce the food ingredient or beverage ingredient.

2. The process of claim 1, wherein the starch content of the barley grain comprises 50% (w/w) amylose.

3. The process of claim 1, wherein the starch content of the barley grain comprises 60% (w/w) amylose.

4. The process of claim 1, wherein the starch content of the barley grain is at least 43% by weight of the barley grain.

5. The process of claim 1, wherein a β-glucan-content of 5-9% (w/w) is present in the barley grain.

6. The process of claim 1, wherein a β-glucan content of greater than 9% (w/w) is present in the barley grain.

7. The process of claim 1, wherein a fructan content of 2-11% (w/w) is present in the barley grain.

8. The process of claim 7, wherein the fructan content has a degree of polymerization from 3 to 12.

9. The process of claim 1, wherein the food ingredient is wholemeal, flour, starch, bran, β-glucan, fructan, non-starch polysaccharides, a baking ingredient, a baking mix, a thickening agent, or cracked, ground, polished, milled, kibbled, rolled or pearled grain.

10. A process for producing a food product or beverage product, wherein the process comprises:
   (i) producing a food ingredient or beverage ingredient by the process of claim 1; and
   (ii) mixing the food ingredient or beverage ingredient so produced with another food ingredient or beverage ingredient,
   thereby producing the food product or beverage product.

11. The process of claim 10, wherein the food ingredient or beverage ingredient is used as a bulking agent, a dietary fibre, a texturizing agent, a preservative, a sweetener, a thickening agent, a probiotic agent or any combination of these, in the food or beverage product.

12. The process of claim 10, comprising a step of assessing the level or type of starch or starch synthase activity, starch content, amylose, amylopectin, β-glucan, fructan, non-starch polysaccharides, dietary fibre, or resistant starch in the barley grain, the food ingredient, the beverage ingredient, the food product or the beverage product following step (i).

13. The process of claim 10, wherein the food product is a breakfast cereal, biscuit, muffin, muesli bar, noodle, bread, cake, pancake, tortilla, bun, pastry, cracker, pizza, croissant, bagel, pretzel, pasta, soup, sauce, confectionary or other farinaceous good.

14. The process of claim 10, wherein the food ingredient or beverage ingredient is used to increase the level of starch, amylose, amylopectin, resistant starch, dietary fibre, protein, lipid, water soluble carbohydrate, β-glucan, fructan or non-starch carbohydrate in the food product or beverage product, or to decrease the glycemic index (GI) of said food product or beverage product.

15. A process for providing starch, amylose, amylopectin, β-glucan, fructan, non-starch polysaccharide, dietary fibre or resistant starch to improve one or more indicators of health in a mammal, wherein the process comprises administering to the mammal the food product or beverage product produced by the process of claim 10.

16. The process of claim 1, wherein the barley grain is non-transgenic barley grain.

17. The process of claim 1, wherein the barley grain has a germination rate of at least 90% relative to the germination rate of wild-type barley grain.

18. The process of claim 1, wherein the gene encoding the SSIIIa protein of the barley grain is an allele of SSIIIa other than an allele whose cDNA has a nucleic acid sequence set forth as SEQ ID NO:3.

19. The process of claim 1, wherein the barley grain is homozygous for an allele of a SSIIIa gene which comprises a null mutation.

20. The process of claim 10, wherein the gene encoding the SSIIIa protein of the barley grain is an allele of SSIIIa other than an allele whose cDNA has a nucleic acid sequence set forth as SEQ ID NO:3.

21. The process of claim 10, wherein the barley grain is homozygous for an allele of a SSIIIa gene which comprises a null mutation.

* * * * *

SEQUENCE LISTING

```
<160> NUMBER OF SEQ ID NOS: 72

<210> SEQ ID NO 1
<211> LENGTH: 9550
<212> TYPE: DNA
<213> ORGANISM: Hordeum vulgare

<400> SEQUENCE: 1
atggagatgt ctctctggcc acggagccct ctgtgtcctc ggggcaggca gccgctcgtc      60
gtcgtcgtct gtccggccgg cctcgcgcag gtacggacga ttaaggttct tgattcggtt     120
ggttcccgga atgttctttg atttgagaat tgaattgagt ggtatgcgtc gtacgttgat     180
catcccggtt ctgtcccggg tcgcgtctgt tgtgattttg atttgcttcg tctctgggaa     240
catttacatc ggggagccgg cgttctttcc cgggtggatt ttctcatggg ttatcgggag     300
gattttgatt tgcatgtcga agatactgcc tatttaattt gttggtctgg gattcttata     360
cattggctta aaacgacgtg attttagttt tgctggaaga gataaagaac atgatttctg     420
ttatatttgt tataaaaaaa ttccctgttt ctagtgtttc agtctgcatg atcatggaaa     480
ggtttcttgt caatgttact gcttgtaaat ttgaagtgga aatttccatg gaaagcgttt     540
caaaaaacga aacagaaatt cattgtttat ttacattatc tgctcctatg tctgtgatga     600
agttatttcc ttcagttatt tccatacata ttttctgcga tgatgttatt tctgtatgta     660
atgccagcat taccatcttt ttataagctg gtctttggct gccatatagc gagtgaatca     720
gtagtttgaa ttgtgctaat gtttatgtcg aaacggaact ccggagacga tataaaatgg     780
attacatact ctctgtctgt ttatcagaga aatttatcct tgcttagatg aggtcagaag     840
gcaatttcag ttgaatttat ctgagaggca taaataattt ggtagtgatt aagtcgattt     900
ctgttccgat tattcgtcaa tacattctgg tttgctcaag cattgttcta taagaaggtt     960
```

```
ttcttttatg ttcaaacacg ttgaactgca caacttattt cccttttgtg tgtttccagc    1020 cttttttggat gaatggcaga tttactcgaa gcaggactgt tcgatgcatg gtagcaagtt    1080
caggtttggg gaataaatttg tcaaaaggtt tagcctatca atctattaga tgttctgtta    1140
agttcatgtc tgtccaaatt acaccatgca gattctccta ataggaaatc aaggaggttg    1200
gtatcacctc aggttaaagt catttcttct agaggatata cgacaagact cattgttgaa    1260
ccaagcaccg agaatacaga acacaataat ggggatgaag aaattcttga cacatacaat    1320
gcgctattac ataccgaggc agcagaatgg acagatacta gagaagctga aactgctgaa    1380
gcagactcgt cacaaaatgc ttcaagcagt tctataatca gggaactaga tcggcggat    1440 gaagatatac ttgcggttga tctgacagtg aatgcactga gcagtgtaac gaagagggaa    1500
gtggatgcag cggacaaagc tagagttgaa gaggacgtat ttgagctgga tttgccagca    1560
actacattga gaagtgtgat agtggatgtg atcgatgata atgggactgt gcaagagaca    1620
ttgagaagtg tgatagtgga tgtgactgat gatgtggcgg acaaagctag agttgaagaa    1680
gacatatttg agctggattt ttcaggaaat gtttcaagca gtgcgacgac cgtggaacta    1740
gatgcggttg atgaagtcgg gcctgttcaa gacacatttg aggcgtcctt gtcaggaaat    1800
gtttcaaaca gtgcaacggt acaggaagtg gatgcagttg atgaagctgg gaatgatcaa    1860
gacatattta agcagatttt atcaggaaat atttttttcaa gcagtacaac agtggaggtg    1920
ggtgtggtgg atgaagctgg gtctacaaaa gataggtttg agatggattc gtcaggaaat    1980
gtttcaacaa gtgcgactat gtgggatgca attgatgaag ccgtggctga tcaagatgca    2040
gttgaggcgg atttgtcagg aaatgcttca agctgggcaa catacagaga attggatgat    2100
atggtggatg aaaatagatc agaagaggaa acatttgtaa tggatttagt gggtgaagct    2160
accgatgaag aagagaatta ccaacagcaa tatcctgtac cgtcttcatt ctctatgtgg    2220
gacaaggcta ttgctaaaac tggtgtcagt ttgaatcctg agccgcgact taccagcgtt    2280
caagaacaag ggaaagtaaa ttttagtgat aaacaagatc tgtcaattgc tgatttacca    2340
ggacaaaacc aatcaatcgt tggttcctgt aaacaagata atcaatcgc tgatgtcgcg    2400 ggaccacccc aatcaatttt tggttctagt aaacaacacc ggccaattgt tgcttttccgc    2460 aaacaaaacc attcaattgt tagtgaccct aaacaaaagc agtccatagt tggattccgt    2520
agtcaggatc tttcggctgt tgatctccct aagcaaaaca taccaattgt tggtacgtcg    2580
agcgagggtc aaacaaagca agttcctgtt gtcgatagac aggatgcgct gtacgtgaat    2640
ggactggaac ttaaggaggg agatcacaga tctgagaaaa ccgacgagga tgcgcttcat    2700
gtaaagttta atattgacaa cgtgttgcag aagcatctgg cagatagaac ccaagcagtg    2760
gaaaccacca tttggaagga agttgatgag aacatctttt acatgactga acatcagata    2820
ggttctactg aaggacatat ggtacttaac gaggatgagc tttctataac tgaaattgga    2880
atggggagtg tgataaaaat tcagcatgcg ctttctgagg aagagctttc atggtctgaa    2940
gatgaagtgc agttaaataa ggatgatgga caatatgaag ttgatgagac ttctgcgtcc    3000
tttaccgttg aacaagatat ccaggggcca ccacaggatg ttgtggatcc acaagcacta    3060
cgggcgatgc tgcaagaact tgctgacaaa aattattcga tgaggaacaa actgtttgtt    3120
tttccagagg tggtgaaagc tgattcagtt attgatcttt atttaaatcg tgacctaaca    3180
gctttggcga atgaacccga tgtcgtcatc aaaggagcat tcaatggttg gaaatggaag    3240
cttttcagtt aaagattgca caagagtgac cttgagggg tttggtggtc ttgcaaactg    3300 cacatacccca aggaggccta cagattagac tttgtgttct tcaacggtcg cacggtctat    3360
```

```
gagaacaatg gcaacaatga tttctgtata ggaatagaag gcactatgaa tgaggacctg   3420
ttcgaggatt tcttggttaa agaaaagcaa agggagcttg agaaacttgc catggaagaa   3480
gctgaaagga ggacacagac tgacgaacag cggcgaagga agaagcaag  ggctgcagat   3540 gaagctgtca gggcacaagc gaaggccgag atagagatca agaagaataa attgcacagt   3600
atgttgagtt tggccagaac atgtgatgat aatttgtggt acatagaggc tagcacagat   3660
acaagaggag atactatcag gttatattat aacagaaact caaggcccct tgcacatagt   3720
actgagattt ggatgcatgg tggttacaac aattggacag atggactctc tattgttgaa   3780
agctttgtca gtgcaatga  cgaggacggc gattggtggt atgcagatgg taagacatct   3840
caacctttgt atatgaggca acattgtttt gattcttttt tgttgaggca acattgtttt   3900
gattctggca tgatgctcct acaaatatgg catgaatttc cttgttttat taatgtcatg   3960
agaaagcatt ttattaactc gaaggccgtg gaagcttagc ctttaccttg ttttgtacat   4020
gtacagtcat tctacctgaa aaagcacttg tgttagactg ggttttgct  gatgggccag   4080 ctgggaatgc aaggaactac gacaacaata gtcgaaaaga tttccatgct attattccaa   4140
acaaaaatgt aaccaagaaa ggcttctggg tgcaagagga gcaaaacatc tatacaaggc   4200
ttctgcaaga aggagagaa  aaggaagaaa ttatgagaag aaaggtcagt tgcaacaaaa   4260
tctttgcata tagatctgta tagttctaat cagttgagtg atggcacatt tgtttccttt   4320
ttaccatttt ccaagttcaa aatgcatggt tccacgcaag tttatccaaa atcacttaat   4380
aatatactaa tcacaactaa cttatcatta agaccgttcc tacttcaaat ttgcaaggta   4440 attcccttc  gggctggttg gtttgatgag taactggcaa ttaacaaaca caagattttt   4500
ttaatttgcg gtggatatac tgatgtttga acaaaacat  atgatcagga ttatttgggt   4560
tgactcatgc tcctttttt  tacctacaca ggctgagaga agtgcaaata tgaaagctga   4620
gatgaaggca aaaactatgc gaaggtttct gctttcccag aaacacattg tttataccga   4680
accgcttgaa gtacgtgccg gaaccgcagt ggatgtgctg tacaatccct ctaacacagt   4740
gctaaatgga aagacggagg tttggttag  atgctccttt aacctctgga tgcatccaag   4800
tggggcattg ccacctcaga agatggtgaa atcgggggat ggatcgctct taaaagcaac   4860
aggtttgagc ttgcgttctt acatcactgt tattagtata tatataacca tttttatgca   4920
tcaatacagt caagtgcaac taatgatcca cagatagtat caaatatcta ctgttctgtt   4980
attggtaaga attagctagg tctttagcca tacagataag caactacagt actatataag   5040
attgaagctg ttttgagacc gagtgtttgt ttgggtggct agccgaagcg ggttgaagtg   5100
cttgcaggca ccccctccgc agggtgagca gtcaccattc ttcttaaaaa ttatggcacc   5160
aagggctagt cccggttggt cgagttctat agccattttt ttggagtgtg actgggagaa   5220
tctttctggt ataaggccta taggcctact ttgatatatg ttgtgaagtc gcttaagcct   5280
tgttataacg tagaaattta gtgccccaac tcgaccaaat ctctgttaaa ttggtttact   5340
gtgtactgta tgaatcaatg gcgcagaggc cggggggtaat aaagcttcca tttttttacaa   5400 ataagttact tatcctactt gccttgtaat taccgagtac gaaatttact gtgcccccag   5460
ccagacattt tctttgacat gacttatgtt actgttggat gtatggtgcg gttgctttat   5520
actccctccg tcccaaaata actgtctcaa ccttaatgca actttatact aaagctagta   5580
caaagttgag acacttattt tgagacagaa ggagtaatat aaagtggggg aaacccttt   5640 tcgtcaatta ccgagtacga tmcagaacac agaaaatctg tatccttcct atttcggtat   5700
```

```
gtttatctat gttccttgtc cagttaatgt tccaccggat gcctatatga tggactttgt   5760
tttctccgag tcggatgaaa atgggatcta tgacaacagg aatgggatgg actatcatat   5820
tcctgtttct gattcaattg aaacggagaa ttacatgcgt attatccata ttgccgtcga   5880
gatggcccct gttgcaaagg taatataatt ctaaggccag tttctgtgat tcgaggcgag   5940
aactcatcac cttttaccat ttttctttct ataccataat aatatgctct gtcattatca   6000
atgatctcat aggttggagg tctcggggat gttgttacaa gtctttcacg tgctgttcaa   6060
gatctagggc atactgtcga ggttattctt ccgaagtacg actgtttgaa ccaaagcagt   6120
gtaagttgaa gtactttact acatattcta ttcatttagt cttaaaaatt tcaactcaaa   6180
atgccacgaa gcttcaattg aagctaaaga gttctgaaag tatcttttcac tgcgatggag   6240
cggcagtacg gtggcacagg ccccaataaa ccatatatga ccccaacaag gggatgccaa   6300
gatcagtagg cactaatgaa tttccgttgt tttacatcga ttatacatta ttaatcaagt   6360
tacatctatt tcaatgcagg tgaaggattt acatttatat caaagttttt cttggagtgg   6420
cacagaaata aaagtatggg ttggacaagt cgaaaacctg accgtttact tcctggagcc   6480
tcaaaatggg tatgaatcag ctaatgtata gttgagtgat ataaaacata tcgctccttt   6540
tcacaaaatt attaggctag agccttgtac tggtttataa tgtgtaccct tttctcattc   6600
atgtagttac ttgtcgtaga ctataaaagc caattagtga cataaatacg ttgccacgtt   6660
ggccttggcg ttccaagctg agagctagtt ataacagtga tatgtgagat tagtggctct   6720
ataaccactt ttgagctaaa ggattttttct gctagatgtt ccaataaata caactaattt   6780
ttaaattcca tgatcactct tggactcata gcctgcatga ccaagaacac cgctaaaatc   6840
atcgcttggg cacaaaaggt tgagcatgcg tttgattggc agatttcagc ttctctagat   6900
tacagacaca cagttacaac ttccattatc tggtatggga ttaccatttc aaccaataga   6960
aatatgaaag aaagaaatgt tgtcatttga atgttagagc tttacaatca gcactattta   7020
tattaaatta aatgaattac ttgtctggtt gtctctttct ggtttctttc tgtaaatgga   7080
tgccaatatc tgctcaggtt ttgcttgtag caggcttcac aaactattta tttcgacatt   7140
ttcttttta ggatgtttgg cgtcggatgt gtatatggaa ggatgatga ccgcagattt   7200
ggcttcttct gtcattctgc tctagagttt atcctccaga atggactttc tccagtaagt   7260
attatttaga ataatatctg ttgtattggc ttttctttgt gacactacac tttgttgttt   7320
accattccag tgcaccatgt tcaaaagctt gtattcaccg tgttactttc agtttcttta   7380
ctactccttg tactaaatca gtgacaatta atatggattg gagggagtag cttatttgct   7440
gcattggtgt ttcctttcca acatactcta ctatctgaat gctacctgtg tattcgcaat   7500
aattgcttgt ttcttccctt ccatttctca gttaaaataa cttgtatctg tattcacgtg   7560
atagcatata atacattgcc atgattggtc aagtgctccg gtcgcctggc tatataagga   7620
acactattcc caatccagaa tggcaagtac tcgggttgta tttaccatcc acaatcttga   7680
atttggagca cattatattg gtaaagcaat gacatactgt gataaagcca caactgtgag   7740
tgccttactg tcttgtaatt tttaatcatt ctgtttggcg cacaaaaaat attttacatg   7800
ttcaactatt tccacccaat gcttgcaggt ttctcctaca tattcaaggg aagtggcagg   7860
ccatggtgcc atcgctcctc atcgtgagaa attctacggc attctcaatg gaattgatcc   7920
agatatctgg gatccgtaca ctgacaattt tataccggta ccaatttta tttccagagt   7980
gcaagtagat acgaaagcca cagatagtta tatgcttaac tctgcatttt atataacttc   8040
aggtccctta tacttatgag aatgttgttg aaggcaagag tgctgcaaaa agggccttgc   8100
```

```
agcagaagtt tggattacag caaactgatg tccctgttgt cggaatcatc acccgtctga    8160
cagcccagaa gggaatccac ctcatcaagc acgcaattca ccaaactctt gaaagcaacg    8220
gacaggtcca tccatccctt gcccttgtga acgataaatg cctaatgttt ctttagaaaa    8280
aaaatgcgta atgtgtttgt ttacttgaaa acaaaagact gaaaatgaag tgtttggttt    8340
ttaggtggtt ttgcttggtt cagctccaga tcatcgaata caaggcgatt tttgcagatt    8400
ggccgatgct cttcatggtg tttaccatgg tagggtgaag cttgttctaa cctacgatga    8460
gcctcttctc cacctggtga gctccaacat cctacacacc atctagtcag ccctccatta    8520
agggagctgg agactacttg tgtataattt agcttgatga tcgatcatgc tgcagatata    8580
cgctggctcc gactttattc ttgttccttc aatcttcgaa ccctgtggct aacacaact     8640 tgttgccatg cgttatggat cgatccctat tgttcggaaa actggaggtg tgtttataac    8700
tgtttatcat catcatgctg cactgctttg cgtatgttga gctgtttgac atgaaatgga    8760
aatttatcct tccgcgttgc agggcttcac gacactgtct tcgacgtaga caatgataag    8820
gaacgggctc ggtctcttgg tcttgaacca atgggttca gtttcgacgg agccgacagc     8880
aacggcgtgg attatgcgct taacaggcaa gtaccgttca tcaattagcc ctgaattcag    8940
taatggtgct aggttattca ccgtgctgtt ccatacccca tttcagagca atcgccgctt    9000
ggttcgatgc ccgtgattgg ttccactccc tgtgtaagag ggtcatggag caagactgg     9060 catggaaccg gcccgcgctg gactacattg aattgtatca tgccgctcga aaattctgac    9120
acccaactga accaaccaac ggcaagaaca aaccgttatg ggatcgacta atacagggct    9180
gtgcagatcc tcttgctcca gctagtctca tcttcagtta gttcaaagcg cgttgtggga    9240
tcgactgcag gtctacagtc atacatagct gaggatcctc ttgcctcctc cacctggggg    9300
aacaaagcag aaatggatga gtgcattggg aagacttta tgtatgtatt gttaaaattt     9360 tcctttcct tccctgcacc tggaaatggt taagcgcatc gccgagataa gaaccgcagt     9420
gacgttttgt gagtagcttt gtaaattctc tcatcttgtg aaaattaatg tgcatgttag    9480
gctctctgat catgtggaag ctttgttata tgttactgat gatatacatc aatgatattt    9540
acatttgtgg                                                           9550
```

<210> SEQ ID NO 2
<211> LENGTH: 5088
<212> TYPE: DNA
<213> ORGANISM: Hordeum vulgare

<400> SEQUENCE: 2

```
atggagatgt ctctctggcc acggagccct ctgtgtcctc ggggcaggca gccgctcgtc     60
gtcgtcgtct gtccggccgg cctcgcgcag ccttttttgga tgaatggcag atttactcga    120
agcaggactg ttcgatgcat ggtagcaagt tcagattctc ctaataggaa atcaaggagg    180
ttggtatcac ctcaggttaa agtcatttct tctagaggat atacgacaag actcattgtt    240
gaaccaagca ccgagaatac agaacacaat aatggggatg aagaaattct tgacacatac    300
aatgcgctat tacataccga ggcagcgaaa tggacagata ctagagaagc tgaaactgct    360
gaagcagact cgtcacaaaa tgcttcaagc agttctataa tcaggaact agatgcggcg     420 gatgaagata tacttgcggt tgatctgaca gtgaatgcac tgagcagtgt aacgaagagg    480
gaagtggatg cagcggacaa agctagagtt gaagaggacg tatttgagct ggatttgcca    540
gcaactacat tgagaagtgt gatagtggat gtgatcgatg ataatgggac tgtgcaagag    600
```

```
acattgagaa gtgtgatagt ggatgtgact gatgatgtgg cggacaaagc tagagttgaa      660
gaagacatat ttgagctgga tttttcagga aatgtttcaa gcagtgcgac gaccgtggaa      720
ctagatgcgg ttgatgaagt cgggcctgtt caagacacat ttgaggcgtc cttgtcagga      780
aatgtttcaa acagtgcaac ggtacaggaa gtggatgcag ttgatgaagc tgggaatgat      840
caagacatat ttaaagcaga tttatcagga aatattttt caagcagtac aacagtggag       900
gtgggtgtgg tggatgaagc tgggtctaca aagataggt ttgagatgga ttcgtcagga       960
aatgtttcaa caagtgcgac tatgtgggat gcaattgatg aagccgtggc tgatcaagat     1020
gcagttgagg cggatttgtc aggaaatgct tcaagctggg caacatacag agaattggat     1080
gatatggtgg atgaaaatag atcagaagag gaaacatttg taatggattt agtgggtgaa     1140
gctaccgatg aagaagagaa ttaccaacag caatatcctg taccgtcttc attctctatg     1200
tgggacaagg ctattgctaa aactggtgtc agtttgaatc ctgagccgcg acttaccagc     1260
gttcaagaac aagggaaagt aaattttagt gataaacaag atctgtcaat tgctgattta     1320
ccaggacaaa accaatcaat cgttggttcc tgtaaacaag ataaatcaat cgctgatgtc     1380
gcgggaccac cccaatcaat ttttggttct agtaaacaac accggccaat tgttgctttc     1440
cgcaaacaaa accattcaat tgttagtgac cctaaacaaa agcagtccat agttggattc     1500
cgtagtcagg atcttttcggc tgttgatctc cctaagcaaa acataccaat tgttggtacg     1560
tcgagcgagg gtcaaacaaa gcaagttcct gttgtcgata cacaggatgc gctgtacgtg     1620
aatggactgg aacttaagga gggagatcac agatctgaga aaccgacga ggatgcgctt      1680 catgtaaagt ttaatattga caacgtgttg cagaagcatc tggcagatag aacccaagca     1740
gtggaaacca ccatttggaa ggaagttgat gaggaacatc tttacatgac tgaacatcag     1800
ataggttcta ctgaaggaca tatggtactt aacgaggatg agctttctat aactgaaatt     1860
ggaatgggga gtggtgataa aattcagcat gcgctttctg aggaagagct ttcatggtct     1920
gaagatgaag tgcagttaaa taaggatgat ggacaatatg aagttgatga acttctgcg      1980 tcctttaccg ttgaacaaga tatccagggg ccaccacagg atgttgtgga tccacaagca     2040
ctacgggcga tgctgcaaga acttgctgac aaaaattatt cgatgaggaa caaactgttt     2100 gttttttccag aggtggtgaa agctgattca gttattgatc tttatttaaa tcgtgaccta     2160
acagctttgg cgaatgaacc cgatgtcgtc atcaaaggag cattcaatgg ttggaaatgg     2220
aagcttttca gtgaaagatt gcacaagagt gaccttggag gggtttggtg gtcttgcaaa     2280
ctgcacatac ccaaggaggc ctacagatta gactttgtgt tcttcaacgg tcgcacggtc     2340
tatgagaaca atggcaacaa tgatttctgt ataggaatag aaggcactat gaatgaggac     2400
ctgttcgagg atttcttggt taaagaaaag caaagggagc ttgagaaact tgccatggaa     2460
gaagctgaaa ggaggacaca gactgacgaa cagcggcgaa ggaaagaagc aagggctgca     2520
gatgaagctg tcagggcaca agcgaaggcc gagatagaga tcaagaagaa taaattgcac     2580
agtatgttga gtttggccag aacatgtgat gataatttgt ggtacataga ggctagcaca     2640
gatacaagag gagatactat caggttatat tataacagaa actcaaggcc ccttgcacat     2700
agtactgaga tttggatgca tgtggttac aacaattgga cagatggact ctctattgtt     2760
gaaagctttg tcaagtgcaa tgacgaggac ggcgattggt ggtatgcaga tgtcattcta     2820
cctgaaaaag cacttgtgtt agactgggtt tttgctgatg ggccagctgg gaatgcaagg     2880
aactacgaca caaatagtcg aaaagatttc catgctatta ttccaaacaa aaatgtaacc     2940
aagaaaggct tctgggtgca agaggagcaa aacatctata caaggcttct gcaagaaagg     3000
```

| | | |
|---|---|---|
| agagaaaagg aagaaattat gagaagaaag gctgagagaa gtgcaaatat gaaagctgag | 3060 |
| atgaaggcaa aaactatgcg aaggtttctg ctttcccaga aacacattgt ttataccgaa | 3120 |
| ccgcttgaag tacgtgccgg aaccgcagtg gatgtgctgt acaatccctc taacacagtg | 3180 |
| ctaaatggaa agacggaggt ttggtttaga tgctccttta acctctggat gcatccaagt | 3240 |
| ggggcattgc cacctcagaa gatggtgaaa tcggggatg gatcgctctt aaaagcaaca | 3300 |
| gttaatgttc caccggatgc ctatatgatg gactttgttt tctccgagtc ggatgaaaat | 3360 |
| gggatctatg acaacaggaa tgggatggac tatcatattc ctgtttctga ttcaattgaa | 3420 |
| acggagaatt acatgcgtat tatccatatt gccgtcgaga tggcccctgt tgcaaaggtt | 3480 |
| ggaggtctcg gggatgttgt tacaagtctt tcacgtgctg ttcaagatct agggcatact | 3540 |
| gtcgaggtta ttcttccgaa gtacgactgt ttgaaccaaa gcagtgtgaa ggatttacat | 3600 |
| ttatatcaaa gttttcttg gagtggcaca gaaataaaag tatgggttgg acaagtcgaa | 3660 |
| aacctgaccg tttacttcct ggagcctcaa aatgggatgt ttggcgtcgg atgtgtatat | 3720 |
| ggaaggaatg atgaccgcag atttggcttc ttctgtcatt ctgctctaga gtttatcctc | 3780 |
| cagaatggac tttctccaca tataatacat tgccatgatt ggtcaagtgc tccggtcgcc | 3840 |
| tggctatata aggaacacta ttcccaatcc agaatggcaa gtactcgggt tgtatttacc | 3900 |
| atccacaatc ttgaatttgg agcacattat attggtaaag caatgacata ctgtgataaa | 3960 |
| gccacaactg tttctcctac atattcaagg gaagtggcag gccatggtgc catcgctcct | 4020 |
| catcgtgaga aattctacgg cattctcaat ggaattgatc cagatatctg ggatccgtac | 4080 |
| actgacaatt ttataccggt ccttatact tatgagaatg ttgttgaagg caagagtgct | 4140 |
| gcaaaagggg ccttgcagca gaagtttgga ttacagcaaa ctgatgtccc tgttgtcgga | 4200 |
| atcatcaccc gtctgacagc ccagaaggga atccacctca tcaagcacgc aattcaccaa | 4260 |
| actcttgaaa gcaacggaca ggtggttttg cttggttcag ctccagatca tcgaatacaa | 4320 |
| ggcgattttt gcagattggc cgatgctctt catggtgttt accatggtag ggtgaagctt | 4380 |
| gttctaacct acgatgagcc tctttctcac ctgatatacg ctggctccga ctttattctt | 4440 |
| gttccttcaa tcttcgaacc ctgtggctta acacaacttg ttgccatgcg ttatggatcg | 4500 |
| atccctattg ttcggaaaac tggagggctt cacgacactg tcttcgacgt agacaatgat | 4560 |
| aaggaacggg ctcggtctct tggtcttgaa ccaaatgggt tcagtttcga cggagccgac | 4620 |
| agcaacggcg tggattatgc gcttaacaga gcaatcgccg cttggttcga tgcccgtgat | 4680 |
| tggttccact ccctgtgtaa gagggtcatg gagcaagact ggtcatggaa ccggcccgcg | 4740 |
| ctggactaca ttgaattgta tcatgccgct cgaaaattct gacacccaac tgaaccaacc | 4800 |
| aacggcaaga acaaaccgtt atgggatcga ctaatacagg gctgtgcaga tcctcttgct | 4860 |
| ccagctagtc tcatcttcag ttagttcaaa gcgcgttgtg ggatcgactg caggtctaca | 4920 |
| gtcatacata gctgaggatc ctcttgcctc ctccacctgg gggaacaaag cagaaatgga | 4980 |
| tgagtgcatt gggaagactt ttatgtatgt attgttaaaa ttttcctttt ccttccctgc | 5040 |
| acctggaaat ggttaagcgc atcgccgaga taagaaccgc agtgacgt | 5088 |

<210> SEQ ID NO 3
<211> LENGTH: 5088
<212> TYPE: DNA
<213> ORGANISM: Hordeum vulgare

<400> SEQUENCE: 3

```
atggagatgt ctctctggcc acggagccct ctgtgtcctc ggggcaggca gccgctcgtc      60
gtcgtcgtct gtccggccgg cctcgcgcag ccttttttgga tgaatggcag atttactcga    120
agcaggactg ttcgatgcat ggtagcaagt tcagattctc ctaataggaa atcaaggagg    180
ttggtatcac ctcaggttaa agtcatttct tctagaggat atacgacaag actcattgtt    240
gaaccaagca ccgagaatac agaacacaat aatggggatg aagaaattct tgacacatac    300
aatgcgctat tacataccga ggcagcgaaa tggacagata ctagagaagc tgaaactgct    360
gaagcagact cgtcacaaaa tgcttcaagc agttctataa tcagggaact agatgcggcg    420
gatgaagata tacttgcggt tgatctgaca gtgaatgcac tgagcagtgt aacgaagagg    480
gaagtggatg cagcggacaa agctagagtt gaagaggacg tatttgagct ggatttgcca    540
gcaactacat tgagaagtgt gatagtggat gtgatcgatg ataatgggac tgtgcaagag    600
acattgagaa gtgtgatagt ggatgtgact gatgatgtgg cggacaaagc tagagttgaa    660
gaagacatat ttgagctgga tttttcagga aatgtttcaa gcagtgcgac gaccgtggaa    720
ctagatgcgg ttgatgaagt cgggcctgtt caagacacat tgaggcgtc cttgtcagga    780
aatgtttcaa acagtgcaac ggtacaggaa gtggatgcag ttgatgaagc tgggaatgat    840
caagacatat ttaaagcaga tttatcagga aatattttt caagcagtac aacagtggag    900
gtgggtgtgg tggatgaagc tgggtctaca aaagataggt ttgagatgga ttcgtcagga    960
aatgtttcaa caagtgcgac tatgtgggat gcaattgatg aagccgtggc tgatcaagat   1020
gcagttgagg cggatttgtc aggaaatgct tcaagctggg caacatacag agaattggat   1080
gatgtggtgg atgaaaatag atcagaagag gaaacatttg taatggattt agtgggtgaa   1140
gctaccgatg aagaagagaa ttaccaacag caatatcctg taccgtcttc attctctatg   1200
tgggacaagg ctattgctaa aactggtgtc agtttgaatc ctgagccgcg acttaccagc   1260
gttcaagaac aagggaaagt aaatttttagt gataaacaag atctgtcaat tgctgattta   1320
ccaggacaaa accaatcaat cgttggttcc tgtaaacaag ataaatcaat cgctgatgtc   1380
gcgggaccac cccaatcaat ttttggttct agtaaacaac accggccaat tgttgctttc   1440
cgcaaacaaa accattcaat tgttagtgac cctaaacaaa agcagtccat agttggattc   1500
cgtagtcagg atctttcggc tgttgatctc cctaagcaaa acataccaat tgttggtacg   1560
tcgagcgagg gtcaaacaaa gcaagttcct gttgtcgata gacaggatgc gctgtacgtg   1620
aatggactgg aacttaagga gggagatcac agatctgaga aaaccgacga ggatgtgctt   1680
catgtaaagt ttaatattga caacgtgttg cagaagcatc tggcagatag aacccaagca   1740
gtggaaacca ccatttggaa ggaagttgat gaggaacatc tttacatgac tgaacatcag   1800
ataggttcta ctgaaggaca tatggtactt aacgaggatg agctttctat aactgaaatt   1860
ggaatgggga gtggtgataa aattcagcat gcgctttctg aggaagagct ttcatggtct   1920
gaagatgaag tgcagttaaa taaggatgat ggacaatatg aagttgatga acttctgcg    1980
tcctttaccg ttgaacaaga tatccagggg ccaccacagg atgttgtgga tccacaagca   2040
ctacgggcga tgctgcaaga acttgctgac aaaaattatt cgatgaggaa caaactgttt   2100
gttttttccag aggtggtgaa agctgattca gttattgatc tttatttaaa tcgtgaccta   2160
acagctttgg cgaatgaacc cgatgtcgtc atcaaaggag cattcaatgg ttggaaatgg   2220
aagcttttca gtgaaagatt gcacaagagt gacctcggag gggtttggtg gtcttgcaaa   2280
ctgcacatac ccaaggaggc ctacagatta gactttgtgt tcttcaacgg tcgcacggtc   2340
tatgagaaca atggcaacaa tgatttctgt ataggaatag aaggcactat gaatgaggac   2400
```

```
ctgttcgagg atttcttggt taaagaaaag caaagggagc ttgagaaact tgccatggaa    2460
gaagctgaaa ggaggacaca gactgacgaa cagcggcgaa ggaaagaagc aagggctgca    2520
gatgaagctg tcagggcaca agcgaaggcc gagatagaga tcaagaagaa taaattgcac    2580
agtatgttga gtttggccag aacatgtgat gataatttgt ggtacataga ggctagcaca    2640
gatacaagag gagatactat caggttatat tataacagaa actcaaggcc ccttgcacat    2700
agtactgaga tttggatgca tggtggttac aacaattgga cagatggact ctctattgtt    2760
gaaagctttg tcaagtgcaa tgacgaggac ggcgattggt ggtatgcaga tgtcattcta    2820
cctgaaaaag cacttgtgtt agactgggtt tttgctgatg ggccagctgg gaatgcaagg    2880
aactacgaca acaatagtcg aaaagatttc catgctatta ttccaaacaa aaatgtaacc    2940
aagaaaggct tctgggtgca agaggagcaa aacatctata caaggcttct gcaagaaagg    3000
agagaaaagg aagaaattat gagaagaaag gctgagagaa gtgcaaatat gaaagctgag    3060
atgaaggcaa aaactatgcg aaggtttctg ctttcccaga aacacattgt ttataccgaa    3120
ccgcttgaag tacgtgccgg aaccgcagtg gatgtgctgt acaatccctc taacacagtg    3180
ctaaatggaa agacggaggt ttggtttaga tgctcccttta acctctggat gcatccaagt    3240
ggggcattgc cacctcagaa gatggtgaaa tcggggatg gatcgctctt aaaagcaaca    3300
gttaatgttc caccggatgc ctatatgatg gactttgttt tctccgagtc ggatgaaaat    3360
gggatctatg acaacaggaa tgggatggac tatcatattc ctgtttctga ttcaattgaa    3420
acggagaatt acatgcgtat tatccatatt gccgtcgaga tggcccctgt tgcaaaggtt    3480
ggaggtctcg gggatgttgt tacaagtctt tcacgtgctg ttcaagatct agggcatact    3540
gtcgaggtta ttcttccgaa gtacgactgt ttgaaccaaa gcagtgtgaa ggatttacat    3600
ttatatcaaa gtttttcttg gagtggcaca gaaataaaag tatgggttgg acaagtcgaa    3660
aacctgaccg tttacttcct ggagcctcaa aatgggatgt ttggcgtcgg atgtgtatat    3720
ggaaggaatg atgaccgcag atttggcttc ttctgtcatt ctgctctaga gtttatcctc    3780
cagaatggac tttctccaca tataatacat tgccatgatt ggtcaagtgc tccggtcgcc    3840
tggctatata aggaacacta ttcccaatcc agaatggcaa gtactcgggt tgtatttacc    3900
atccacaatc ttgaatttgg agcacattat attggtaaag caatgacata ctgtgataaa    3960
gccacaactg tttctcctac atattcaagg gaagtggcag gccatggtgc catcgctcct    4020
catcgtgaga aattctacgg cattctcaat ggaattgatc cagatatctg ggatccgtac    4080
actgacaatt ttataccggt cccttatact tatgagaatg ttgttgaagg caagagtgct    4140
gcaaaaaggg ccttgcagca gaagtttgga ttacagcaaa ctgatgtccc tgttgtcgga    4200
atcatcaccc gtctgacagc ccagaaggga atccacctca tcaagcacgc aattcaccaa    4260
actcttgaaa gcaacggaca ggtggttttg cttggttcag ctccagatca tcgaatacaa    4320
ggcgattttt gcagattggc cgatgctctt catggtgttt accatggtag ggtgaagctt    4380
gttctaacct acgatgagcc tctttctcac ctgatatacg ctggctccga ctttattcgt    4440
gttccttcaa tcttcgaacc tgtggcttaa acacaacttg ttgccatgcg ttatggatcg    4500
atccctattg ttcggaaaac tggagggctt cacgacactc tcttcgacgt agacaatgat    4560
aaggaacggg ctcggtctct tggtcttgaa ccaaatgggt tcagtttcga cggagccgac    4620
agcaacggcg tggattatgc gcttaacaga gcaatcgccg cttggttcga tgcccgtgat    4680
tggttccact ccctgtgtaa gagggtcatg gagcaagact ggtcatggaa ccggcccgcg    4740
```

-continued

```
ctggactaca ttgaattgta tcatgccgct cgaaaattct gacacccaac tgaaccaacc   4800
aacggcaaga acaaaccgtt atgggatcga ctaatacagg gctgtgcaga tcctcttgct   4860
ccagctagtc tcatcttcag ttagttcaaa gcgcgttgtg ggatcgactg caggtctaca   4920
gtcatacata gctgaggatc ctcttgcctc ctccacctgg gggaacaaag cagaaatgga   4980
tgagtgcatt gggaagactt ttatgtatgt attgttaaaa ttttcctttt ccttccctgc   5040
acctggaaat ggttaagcgc atcgccgaga taagaaccgc agtgacgt                5088

<210> SEQ ID NO 4
<211> LENGTH: 1593
<212> TYPE: PRT
<213> ORGANISM: Hordeum vulgare

<400> SEQUENCE: 4
```

Met Glu Met Ser Leu Trp Pro Arg Ser Pro Leu Cys Pro Arg Gly Arg
1               5                   10                  15

Gln Pro Leu Val Val Val Val Cys Pro Ala Gly Leu Ala Gln Pro Phe
            20                  25                  30

Trp Met Asn Gly Arg Phe Thr Arg Ser Arg Thr Val Arg Cys Met Val
        35                  40                  45

Ala Ser Ser Asp Ser Pro Asn Arg Lys Ser Arg Arg Leu Val Ser Pro
    50                  55                  60

Gln Val Lys Val Ile Ser Ser Arg Gly Tyr Thr Thr Arg Leu Ile Val
65                  70                  75                  80

Glu Pro Ser Thr Glu Asn Thr Glu His Asn Asn Gly Asp Glu Ile
                85                  90                  95

Leu Asp Thr Tyr Asn Ala Leu Leu His Thr Glu Ala Ala Glu Trp Thr
            100                 105                 110

Asp Thr Arg Glu Ala Glu Thr Ala Glu Ala Asp Ser Ser Gln Asn Ala
        115                 120                 125

Ser Ser Ser Ser Ile Ile Arg Glu Leu Asp Ala Ala Asp Glu Asp Ile
    130                 135                 140

Leu Ala Val Asp Leu Thr Val Asn Ala Leu Ser Ser Val Thr Lys Arg
145                 150                 155                 160

Glu Val Asp Ala Ala Asp Lys Ala Arg Val Glu Asp Val Phe Glu
                165                 170                 175

Leu Asp Leu Pro Ala Thr Thr Leu Arg Ser Val Ile Val Asp Val Ile
            180                 185                 190

Asp Asp Asn Gly Thr Val Gln Glu Thr Leu Arg Ser Val Ile Val Asp
        195                 200                 205

Val Thr Asp Asp Val Ala Asp Lys Ala Arg Val Glu Glu Asp Ile Phe
    210                 215                 220

Glu Leu Asp Phe Ser Gly Asn Val Ser Ser Ser Ala Thr Thr Val Glu
225                 230                 235                 240

Leu Asp Ala Val Asp Glu Val Gly Pro Val Gln Asp Thr Phe Glu Ala
                245                 250                 255

Ser Leu Ser Gly Asn Val Ser Asn Ser Ala Thr Val Gln Glu Val Asp
            260                 265                 270

Ala Val Asp Glu Ala Gly Asn Asp Gln Asp Ile Phe Lys Ala Asp Leu
        275                 280                 285

Ser Gly Asn Ile Phe Ser Ser Ser Thr Thr Val Glu Val Gly Val Val
    290                 295                 300

Asp Glu Ala Gly Ser Thr Lys Asp Arg Phe Glu Met Asp Ser Ser Gly
305                 310                 315                 320

-continued

```
Asn Val Ser Thr Ser Ala Thr Met Trp Asp Ala Ile Asp Glu Ala Val
            325                 330                 335
Ala Asp Gln Asp Ala Val Glu Ala Asp Leu Ser Gly Asn Ala Ser Ser
        340                 345                 350
Trp Ala Thr Tyr Arg Glu Leu Asp Asp Met Val Asp Glu Asn Arg Ser
        355                 360                 365
Glu Glu Glu Thr Phe Val Met Asp Leu Val Gly Glu Ala Thr Asp Glu
    370                 375                 380
Glu Glu Asn Tyr Gln Gln Gln Tyr Pro Val Pro Ser Ser Phe Ser Met
385                 390                 395                 400
Trp Asp Lys Ala Ile Ala Lys Thr Gly Val Ser Leu Asn Pro Glu Pro
            405                 410                 415
Arg Leu Thr Ser Val Gln Glu Gln Gly Lys Val Asn Phe Ser Asp Lys
        420                 425                 430
Gln Asp Leu Ser Ile Ala Asp Leu Pro Gly Gln Asn Gln Ser Ile Val
        435                 440                 445
Gly Ser Cys Lys Gln Asp Lys Ser Ile Ala Asp Val Ala Gly Pro Pro
    450                 455                 460
Gln Ser Ile Phe Gly Ser Ser Lys Gln His Arg Pro Ile Val Ala Phe
465                 470                 475                 480
Arg Lys Gln Asn His Ser Ile Val Ser Asp Pro Lys Gln Lys Gln Ser
            485                 490                 495
Ile Val Gly Phe Arg Ser Gln Asp Leu Ser Ala Val Asp Leu Pro Lys
        500                 505                 510
Gln Asn Ile Pro Ile Val Gly Thr Ser Ser Glu Gly Gln Thr Lys Gln
        515                 520                 525
Val Pro Val Asp Arg Gln Asp Ala Leu Tyr Val Asn Gly Leu Glu
    530                 535                 540
Leu Lys Glu Gly Asp His Arg Ser Glu Lys Thr Asp Glu Asp Ala Leu
545                 550                 555                 560
His Val Lys Phe Asn Ile Asp Asn Val Leu Gln Lys His Leu Ala Asp
            565                 570                 575
Arg Thr Gln Ala Val Glu Thr Thr Ile Trp Lys Glu Val Asp Glu Glu
        580                 585                 590
His Leu Tyr Met Thr Glu His Gln Ile Gly Ser Thr Glu Gly His Met
        595                 600                 605
Val Leu Asn Glu Asp Glu Leu Ser Ile Thr Glu Ile Gly Met Gly Ser
    610                 615                 620
Gly Asp Lys Ile Gln His Ala Leu Ser Glu Glu Leu Ser Trp Ser
625                 630                 635                 640
Glu Asp Glu Val Gln Leu Asn Lys Asp Gly Gln Tyr Glu Val Asp
            645                 650                 655
Glu Thr Ser Ala Ser Phe Thr Val Gln Asp Ile Gln Gly Pro Pro
        660                 665                 670
Gln Asp Val Val Asp Pro Gln Ala Leu Arg Ala Met Leu Gln Glu Leu
        675                 680                 685
Ala Asp Lys Asn Tyr Ser Met Arg Asn Lys Leu Phe Val Phe Pro Glu
    690                 695                 700
Val Val Lys Ala Asp Ser Val Ile Asp Leu Tyr Leu Asn Arg Asp Leu
705                 710                 715                 720
Thr Ala Leu Ala Asn Glu Pro Asp Val Val Ile Lys Gly Ala Phe Asn
            725                 730                 735
```

-continued

```
Gly Trp Lys Trp Lys Leu Phe Ser Glu Arg Leu His Lys Ser Asp Leu
            740                 745                 750
Gly Gly Val Trp Trp Ser Cys Lys Leu His Ile Pro Lys Glu Ala Tyr
        755                 760                 765
Arg Leu Asp Phe Val Phe Phe Asn Gly Arg Thr Val Tyr Glu Asn Asn
    770                 775                 780
Gly Asn Asn Asp Phe Cys Ile Gly Ile Glu Gly Thr Met Asn Glu Asp
785                 790                 795                 800
Leu Phe Glu Asp Phe Leu Val Lys Glu Lys Gln Arg Glu Leu Glu Lys
                805                 810                 815
Leu Ala Met Glu Glu Ala Glu Arg Arg Thr Gln Thr Asp Glu Gln Arg
            820                 825                 830
Arg Arg Lys Glu Ala Arg Ala Ala Asp Glu Ala Val Arg Ala Gln Ala
        835                 840                 845
Lys Ala Glu Ile Glu Ile Lys Lys Asn Lys Leu His Ser Met Leu Ser
    850                 855                 860
Leu Ala Arg Thr Cys Asp Asp Asn Leu Trp Tyr Ile Glu Ala Ser Thr
865                 870                 875                 880
Asp Thr Arg Gly Asp Thr Ile Arg Leu Tyr Tyr Asn Arg Asn Ser Arg
                885                 890                 895
Pro Leu Ala His Ser Thr Glu Ile Trp Met His Gly Gly Tyr Asn Asn
            900                 905                 910
Trp Thr Asp Gly Leu Ser Ile Val Glu Ser Phe Val Lys Cys Asn Asp
        915                 920                 925
Glu Asp Gly Asp Trp Trp Tyr Ala Asp Val Ile Leu Pro Glu Lys Ala
    930                 935                 940
Leu Val Leu Asp Trp Val Phe Ala Asp Gly Pro Ala Gly Asn Ala Arg
945                 950                 955                 960
Asn Tyr Asp Asn Asn Ser Arg Lys Asp Phe His Ala Ile Ile Pro Asn
                965                 970                 975
Lys Asn Val Thr Lys Lys Gly Phe Trp Val Gln Glu Glu Gln Asn Ile
            980                 985                 990
Tyr Thr Arg Leu Leu Gln Glu Arg  Arg Glu Lys Glu Glu  Ile Met Arg
        995                  1000                 1005
Arg Lys  Ala Glu Arg Ser  Ala Asn Met Lys Ala Glu  Met Lys Ala
    1010                 1015                 1020
Lys Thr  Met Arg Arg Phe  Leu Leu Ser Gln Lys His  Ile Val Tyr
    1025                 1030                 1035
Thr Glu  Pro Leu Glu Val  Arg Ala Gly Thr Ala Val  Asp Val Leu
    1040                 1045                 1050
Tyr Asn  Pro Ser Asn Thr Val  Leu Asn Gly Lys Thr  Glu Val Trp
    1055                 1060                 1065
Phe Arg  Cys Ser Phe Asn Leu  Trp Met His Pro Ser  Gly Ala Leu
    1070                 1075                 1080
Pro Pro  Gln Lys Met Val Lys  Ser Gly Asp Gly Ser  Leu Leu Lys
    1085                 1090                 1095
Ala Thr  Val Asn Val Pro Pro  Asp Ala Tyr Met Met  Asp Phe Val
    1100                 1105                 1110
Phe Ser  Glu Ser Asp Glu Asn  Gly Ile Tyr Asp Asn  Arg Asn Gly
    1115                 1120                 1125
Met Asp  Tyr His Ile Pro Val  Ser Asp Ser Ile Glu  Thr Glu Asn
    1130                 1135                 1140
Tyr Met  Arg Ile Ile His Ile  Ala Val Glu Met Ala  Pro Val Ala
```

```
            1145                1150                1155

Lys Val Gly Gly Leu Gly Asp Val Val Thr Ser Leu Ser Arg Ala
    1160                1165                1170

Val Gln Asp Leu Gly His Thr Val Glu Val Ile Leu Pro Lys Tyr
    1175                1180                1185

Asp Cys Leu Asn Gln Ser Ser Val Lys Asp Leu His Leu Tyr Gln
    1190                1195                1200

Ser Phe Ser Trp Ser Gly Thr Glu Ile Lys Val Trp Val Gly Gln
    1205                1210                1215

Val Glu Asn Leu Thr Val Tyr Phe Leu Glu Pro Gln Asn Gly Met
    1220                1225                1230

Phe Gly Val Gly Cys Val Tyr Gly Arg Asn Asp Asp Arg Arg Phe
    1235                1240                1245

Gly Phe Phe Cys His Ser Ala Leu Glu Phe Ile Leu Gln Asn Gly
    1250                1255                1260

Leu Ser Pro His Ile Ile His Cys His Asp Trp Ser Ser Ala Pro
    1265                1270                1275

Val Ala Trp Leu Tyr Lys Glu His Tyr Ser Gln Ser Arg Met Ala
    1280                1285                1290

Ser Thr Arg Val Val Phe Thr Ile His Asn Leu Glu Phe Gly Ala
    1295                1300                1305

His Tyr Ile Gly Lys Ala Met Thr Tyr Cys Asp Lys Ala Thr Thr
    1310                1315                1320

Val Ser Pro Thr Tyr Ser Arg Glu Val Ala Gly His Gly Ala Ile
    1325                1330                1335

Ala Pro His Arg Glu Lys Phe Tyr Gly Ile Leu Asn Gly Ile Asp
    1340                1345                1350

Pro Asp Ile Trp Asp Pro Tyr Thr Asp Asn Phe Ile Pro Val Pro
    1355                1360                1365

Tyr Thr Tyr Glu Asn Val Val Glu Gly Lys Ser Ala Ala Lys Arg
    1370                1375                1380

Ala Leu Gln Gln Lys Phe Gly Leu Gln Gln Thr Asp Val Pro Val
    1385                1390                1395

Val Gly Ile Ile Thr Arg Leu Thr Ala Gln Lys Gly Ile His Leu
    1400                1405                1410

Ile Lys His Ala Ile His Gln Thr Leu Glu Ser Asn Gly Gln Val
    1415                1420                1425

Val Leu Leu Gly Ser Ala Pro Asp His Arg Ile Gln Gly Asp Phe
    1430                1435                1440

Cys Arg Leu Ala Asp Ala Leu His Gly Val Tyr His Gly Arg Val
    1445                1450                1455

Lys Leu Val Leu Thr Tyr Asp Glu Pro Leu Ser His Leu Ile Tyr
    1460                1465                1470

Ala Gly Ser Asp Phe Ile Leu Val Pro Ser Ile Phe Glu Pro Cys
    1475                1480                1485

Gly Leu Thr Gln Leu Val Ala Met Arg Tyr Gly Ser Ile Pro Ile
    1490                1495                1500

Val Arg Lys Thr Gly Gly Leu His Asp Thr Val Phe Asp Val Asp
    1505                1510                1515

Asn Asp Lys Glu Arg Ala Arg Ser Leu Gly Leu Glu Pro Asn Gly
    1520                1525                1530

Phe Ser Phe Asp Gly Ala Asp Ser Asn Gly Val Asp Tyr Ala Leu
    1535                1540                1545
```

Asn Arg Ala Ile Ala Ala Trp Phe Asp Ala Arg Asp Trp Phe His
        1550                1555                1560

Ser Leu Cys Lys Arg Val Met Glu Gln Asp Trp Ser Trp Asn Arg
        1565                1570                1575

Pro Ala Leu Asp Tyr Ile Glu Leu Tyr His Ala Ala Arg Lys Phe
        1580                1585                1590

<210> SEQ ID NO 5
<211> LENGTH: 1593
<212> TYPE: PRT
<213> ORGANISM: Hordeum vulgare

<400> SEQUENCE: 5

Met Glu Met Ser Leu Trp Pro Arg Ser Pro Leu Cys Pro Arg Gly Arg
1               5                   10                  15

Gln Pro Leu Val Val Val Cys Pro Ala Gly Leu Ala Gln Pro Phe
            20                  25                  30

Trp Met Asn Gly Arg Phe Thr Arg Ser Arg Thr Val Arg Cys Met Val
        35                  40                  45

Ala Ser Ser Asp Ser Pro Asn Arg Lys Ser Arg Arg Leu Val Ser Pro
    50                  55                  60

Gln Val Lys Val Ile Ser Ser Arg Gly Tyr Thr Thr Arg Leu Ile Val
65              70                  75                  80

Glu Pro Ser Thr Glu Asn Thr Glu His Asn Asn Gly Asp Glu Glu Ile
            85                  90                  95

Leu Asp Thr Tyr Asn Ala Leu Leu His Thr Glu Ala Ala Glu Trp Thr
            100                 105                 110

Asp Thr Arg Glu Ala Glu Thr Ala Glu Ala Asp Ser Ser Gln Asn Ala
        115                 120                 125

Ser Ser Ser Ser Ile Ile Arg Glu Leu Asp Ala Ala Asp Glu Asp Ile
    130                 135                 140

Leu Ala Val Asp Leu Thr Val Asn Ala Leu Ser Ser Val Thr Lys Arg
145                 150                 155                 160

Glu Val Asp Ala Ala Asp Lys Ala Arg Val Glu Glu Asp Val Phe Glu
            165                 170                 175

Leu Asp Leu Pro Ala Thr Thr Leu Arg Ser Val Ile Val Asp Val Ile
            180                 185                 190

Asp Asp Asn Gly Thr Val Gln Glu Thr Leu Arg Ser Val Ile Val Asp
        195                 200                 205

Val Thr Asp Asp Val Ala Asp Lys Ala Arg Val Glu Glu Asp Ile Phe
    210                 215                 220

Glu Leu Asp Phe Ser Gly Asn Val Ser Ser Ala Thr Thr Val Glu
225                 230                 235                 240

Leu Asp Ala Val Asp Glu Val Gly Pro Val Gln Asp Thr Phe Glu Ala
            245                 250                 255

Ser Leu Ser Gly Asn Val Ser Asn Ser Ala Thr Val Gln Glu Val Asp
        260                 265                 270

Ala Val Asp Glu Ala Gly Asn Asp Gln Asp Ile Phe Lys Ala Asp Leu
    275                 280                 285

Ser Gly Asn Ile Phe Ser Ser Thr Thr Val Glu Val Gly Val Val
        290                 295                 300

Asp Glu Ala Gly Ser Thr Lys Asp Arg Phe Glu Met Asp Ser Ser Gly
305                 310                 315                 320

Asn Val Ser Thr Ser Ala Thr Met Trp Asp Ala Ile Asp Glu Ala Val

```
                    325                 330                 335
Ala Asp Gln Asp Ala Val Glu Ala Asp Leu Ser Gly Asn Ala Ser Ser
                340                 345                 350

Trp Ala Thr Tyr Arg Glu Leu Asp Asp Val Val Asp Glu Asn Arg Ser
                355                 360                 365

Glu Glu Glu Thr Phe Val Met Asp Leu Val Gly Glu Ala Thr Asp Glu
                370                 375                 380

Glu Glu Asn Tyr Gln Gln Gln Tyr Pro Val Pro Ser Ser Phe Ser Met
385                 390                 395                 400

Trp Asp Lys Ala Ile Ala Lys Thr Gly Val Ser Leu Asn Pro Glu Pro
                405                 410                 415

Arg Leu Thr Ser Val Gln Glu Gln Gly Lys Val Asn Phe Ser Asp Lys
                420                 425                 430

Gln Asp Leu Ser Ile Ala Asp Leu Pro Gly Gln Asn Gln Ser Ile Val
                435                 440                 445

Gly Ser Cys Lys Gln Asp Lys Ser Ile Ala Asp Val Ala Gly Pro Pro
                450                 455                 460

Gln Ser Ile Phe Gly Ser Ser Lys Gln His Arg Pro Ile Val Ala Phe
465                 470                 475                 480

Arg Lys Gln Asn His Ser Ile Val Ser Asp Pro Lys Gln Lys Gln Ser
                485                 490                 495

Ile Val Gly Phe Arg Ser Gln Asp Leu Ser Ala Val Asp Leu Pro Lys
                500                 505                 510

Gln Asn Ile Pro Ile Val Gly Thr Ser Ser Glu Gly Gln Thr Lys Gln
                515                 520                 525

Val Pro Val Asp Arg Gln Asp Ala Leu Tyr Val Asn Gly Leu Glu
                530                 535                 540

Leu Lys Glu Gly Asp His Arg Ser Glu Lys Thr Asp Glu Asp Val Leu
545                 550                 555                 560

His Val Lys Phe Asn Ile Asp Asn Val Leu Gln Lys His Leu Ala Asp
                565                 570                 575

Arg Thr Gln Ala Val Glu Thr Thr Ile Trp Lys Glu Val Asp Glu Glu
                580                 585                 590

His Leu Tyr Met Thr Glu His Gln Ile Gly Ser Thr Glu Gly His Met
                595                 600                 605

Val Leu Asn Glu Asp Glu Leu Ser Ile Thr Glu Ile Gly Met Gly Ser
                610                 615                 620

Gly Asp Lys Ile Gln His Ala Leu Ser Glu Glu Glu Leu Ser Trp Ser
625                 630                 635                 640

Glu Asp Glu Val Gln Leu Asn Lys Asp Asp Gly Gln Tyr Glu Val Asp
                645                 650                 655

Glu Thr Ser Ala Ser Phe Thr Val Glu Gln Asp Ile Gln Gly Pro Pro
                660                 665                 670

Gln Asp Val Val Asp Pro Gln Ala Leu Arg Ala Met Leu Gln Glu Leu
                675                 680                 685

Ala Asp Lys Asn Tyr Ser Met Arg Asn Lys Leu Phe Val Phe Pro Glu
                690                 695                 700

Val Val Lys Ala Asp Ser Val Ile Asp Leu Tyr Leu Asn Arg Asp Leu
705                 710                 715                 720

Thr Ala Leu Ala Asn Glu Pro Asp Val Val Ile Lys Gly Ala Phe Asn
                725                 730                 735

Gly Trp Lys Trp Lys Leu Phe Ser Glu Arg Leu His Lys Ser Asp Leu
                740                 745                 750
```

```
Gly Gly Val Trp Trp Ser Cys Lys Leu His Ile Pro Lys Glu Ala Tyr
            755                 760                 765

Arg Leu Asp Phe Val Phe Phe Asn Gly Arg Thr Val Tyr Glu Asn Asn
    770                 775                 780

Gly Asn Asn Asp Phe Cys Ile Gly Ile Glu Gly Thr Met Asn Glu Asp
785                 790                 795                 800

Leu Phe Glu Asp Phe Leu Val Lys Glu Lys Gln Arg Glu Leu Glu Lys
                805                 810                 815

Leu Ala Met Glu Glu Ala Glu Arg Arg Thr Gln Thr Asp Glu Gln Arg
            820                 825                 830

Arg Arg Lys Glu Ala Arg Ala Ala Asp Glu Ala Val Arg Ala Gln Ala
            835                 840                 845

Lys Ala Glu Ile Glu Ile Lys Lys Asn Lys Leu His Ser Met Leu Ser
850                 855                 860

Leu Ala Arg Thr Cys Asp Asp Asn Leu Trp Tyr Ile Glu Ala Ser Thr
865                 870                 875                 880

Asp Thr Arg Gly Asp Thr Ile Arg Leu Tyr Tyr Asn Arg Asn Ser Arg
                885                 890                 895

Pro Leu Ala His Ser Thr Glu Ile Trp Met His Gly Tyr Asn Asn
            900                 905                 910

Trp Thr Asp Gly Leu Ser Ile Val Glu Ser Phe Val Lys Cys Asn Asp
            915                 920                 925

Glu Asp Gly Asp Trp Trp Tyr Ala Asp Val Ile Leu Pro Glu Lys Ala
            930                 935                 940

Leu Val Leu Asp Trp Val Phe Ala Asp Gly Pro Ala Gly Asn Ala Arg
945                 950                 955                 960

Asn Tyr Asp Asn Asn Ser Arg Lys Asp Phe His Ala Ile Ile Pro Asn
                965                 970                 975

Lys Asn Val Thr Lys Lys Gly Phe Trp Val Gln Glu Gln Asn Ile
            980                 985                 990

Tyr Thr Arg Leu Leu Gln Glu Arg  Arg Glu Lys Glu Glu  Ile Met Arg
            995                 1000                1005

Arg Lys  Ala Glu Arg Ser Ala  Asn Met Lys Ala Glu  Met Lys Ala
    1010                1015                1020

Lys Thr  Met Arg Arg Phe Leu  Leu Ser Gln Lys His  Ile Val Tyr
    1025                1030                1035

Thr Glu  Pro Leu Glu Val Arg  Ala Gly Thr Ala Val  Asp Val Leu
    1040                1045                1050

Tyr Asn  Pro Ser Asn Thr Val  Leu Asn Gly Lys Thr  Glu Val Trp
    1055                1060                1065

Phe Arg  Cys Ser Phe Asn Leu  Trp Met His Pro Ser  Gly Ala Leu
    1070                1075                1080

Pro Pro  Gln Lys Met Val Lys  Ser Gly Asp Gly Ser  Leu Leu Lys
    1085                1090                1095

Ala Thr  Val Asn Val Pro Pro  Asp Ala Tyr Met Met  Asp Phe Val
    1100                1105                1110

Phe Ser  Glu Ser Asp Glu Asn  Gly Ile Tyr Asp Asn  Arg Asn Gly
    1115                1120                1125

Met Asp  Tyr His Ile Pro Val  Ser Asp Ser Ile Glu  Thr Glu Asn
    1130                1135                1140

Tyr Met  Arg Ile Ile His Ile  Ala Val Glu Met Ala  Pro Val Ala
    1145                1150                1155
```

```
Lys Val Gly Gly Leu Gly Asp Val Val Thr Ser Leu Ser Arg Ala
1160                1165                1170

Val Gln Asp Leu Gly His Thr Val Glu Val Ile Leu Pro Lys Tyr
1175                1180                1185

Asp Cys Leu Asn Gln Ser Ser Val Lys Asp Leu His Leu Tyr Gln
1190                1195                1200

Ser Phe Ser Trp Ser Gly Thr Glu Ile Lys Val Trp Val Gly Gln
1205                1210                1215

Val Glu Asn Leu Thr Val Tyr Phe Leu Glu Pro Gln Asn Gly Met
1220                1225                1230

Phe Gly Val Gly Cys Val Tyr Gly Arg Asn Asp Asp Arg Arg Phe
1235                1240                1245

Gly Phe Phe Cys His Ser Ala Leu Glu Phe Ile Leu Gln Asn Gly
1250                1255                1260

Leu Ser Pro His Ile Ile His Cys His Asp Trp Ser Ser Ala Pro
1265                1270                1275

Val Ala Trp Leu Tyr Lys Glu His Tyr Ser Gln Ser Arg Met Ala
1280                1285                1290

Ser Thr Arg Val Val Phe Thr Ile His Asn Leu Glu Phe Gly Ala
1295                1300                1305

His Tyr Ile Gly Lys Ala Met Thr Tyr Cys Asp Lys Ala Thr Thr
1310                1315                1320

Val Ser Pro Thr Tyr Ser Arg Glu Val Ala Gly His Gly Ala Ile
1325                1330                1335

Ala Pro His Arg Glu Lys Phe Tyr Gly Ile Leu Asn Gly Ile Asp
1340                1345                1350

Pro Asp Ile Trp Asp Pro Tyr Thr Asp Asn Phe Ile Pro Val Pro
1355                1360                1365

Tyr Thr Tyr Glu Asn Val Val Glu Gly Lys Ser Ala Ala Lys Arg
1370                1375                1380

Ala Leu Gln Gln Lys Phe Gly Leu Gln Gln Thr Asp Val Pro Val
1385                1390                1395

Val Gly Ile Ile Thr Arg Leu Thr Ala Gln Lys Gly Ile His Leu
1400                1405                1410

Ile Lys His Ala Ile His Gln Thr Leu Glu Ser Asn Gly Gln Val
1415                1420                1425

Val Leu Leu Gly Ser Ala Pro Asp His Arg Ile Gln Gly Asp Phe
1430                1435                1440

Cys Arg Leu Ala Asp Ala Leu His Gly Val Tyr His Gly Arg Val
1445                1450                1455

Lys Leu Val Leu Thr Tyr Asp Glu Pro Leu Ser His Leu Ile Tyr
1460                1465                1470

Ala Gly Ser Asp Phe Ile Arg Val Pro Ser Ile Phe Glu Pro Cys
1475                1480                1485

Gly Leu Thr Gln Leu Val Ala Met Arg Tyr Gly Ser Ile Pro Ile
1490                1495                1500

Val Arg Lys Thr Gly Gly Leu His Asp Thr Val Phe Asp Val Asp
1505                1510                1515

Asn Asp Lys Glu Arg Ala Arg Ser Leu Gly Leu Glu Pro Asn Gly
1520                1525                1530

Phe Ser Phe Asp Gly Ala Asp Ser Asn Gly Val Asp Tyr Ala Leu
1535                1540                1545

Asn Arg Ala Ile Ala Ala Trp Phe Asp Ala Arg Asp Trp Phe His
```

Ser Leu Cys Lys Arg Val Met Glu Gln Asp Trp Ser Trp Asn Arg
1565                1570                    1575

Pro Ala Leu Asp Tyr Ile Glu Leu Tyr His Ala Ala Arg Lys Phe
1580                1585                    1590

<210> SEQ ID NO 6
<211> LENGTH: 5346
<212> TYPE: DNA
<213> ORGANISM: Triticum aestivum

<400> SEQUENCE: 6

```
cggcacgagg tttagtaggt tccgggaaat ggagatgtct ctctggccac ggagcccct     60
gtgccctcgg agcaggcagc cgctcgtcgt cgtccggccg ccggccgcg gcggcctcac    120
gcagcctttt ttgatgaatg cagatttac tcgaagcagg accttcgat gcatggtagc    180
aagttcagat cctcctaata ggaaatcaag aaggatggta ccacctcagg ttaaagtcat    240
ttcttctaga ggatatacga caagactcat tgttgaacca agcaacgaga atacagaaca    300
caataatcgg gatgaagaaa ctcttgatac atacaatgcg ctattaagta ccgagacagc    360
agaatggaca gataatagag aagccgagac tgctaaagcg gactcgtcgc aaaatgcttt    420
aagcagttct ataattgggg aagtggatgt ggcggatgaa gatatacttg cggctgatct    480
gacagtgtat tcattgagca gtgtaatgaa gaaggaagtg gatgcagcgg acaaagctag    540
agttaaagaa gacgcatttg agctggattt gccagcaact acattgagaa gtgtgatagt    600
agatgtgatg gatcataatg ggactgtaca agagacattg agaagtgtga tagtagatgt    660
gatggatcat aatgggactg tacaagagac attgagaagt gtgatagtag atgtgatgga    720
tgatgcggcg gacaaagcta gagttgaaga agacgtattt gagctggatt tgtcaggaaa    780
tatttcaagc agtgcgacga ccgtggaact agatgcggtt gacgaagtcg ggcctgttca    840
agacaaattt gaggcgacct catcaggaaa tgtttcaaac agtgcaacgg tacgggaagt    900
ggatgcaagt gatgaagctg gaatgatca aggcatattt agagcagatt tgtcaggaaa    960
tgttttttca agcagtacaa cagtggaagt gggtgcagtg gatgaagctg ggtctataaa   1020
ggacaggttt gagacggatt cgtcaggaaa tgtttcaaca agtgcgccga tgtgggatgc   1080
aattgatgaa accgtggctg atcaagacac atttgaggcg gatttgtcgg gaaatgcttc   1140
aagctgcgca acatacagag aagtggatga tgtggtggat gaaactagat cagaagagga   1200
aacatttgca atggatttgt ttgcaagtga atcaggccat gagaaacata tggcagtgga   1260
ttatgtgggt gaagctaccg atgaagaaga gacttaccaa cagcaatatc cagtaccgtc   1320
ttcattctct atgtgggaca aggctattgc taaaacaggt gtaagtttga atcctgagct   1380
gcgacttgtc agggttgaag aacaaggcaa agtaaatttt agtgataaaa aagacctgtc   1440
aattgatgat ttaccaggac aaaaccaatc gatcattggt tcctataaac aagataaatc   1500
aattgctgat gttgcgggac cgacccaatc aattttttggt tctagtaaac aacaccggtc   1560
aattgttgct ttccccaaac aaaaccagtc aattgttagt gtcactgagc aaaagcagtc   1620
catagttgga ttccgtagtc aagatctttc ggctgttagt ctccctaaac aaaacgtacc   1680
aattgttggt acgtcgagag agggtcaaac aaagcaagtt cctgttgttg atagacagga   1740
tgcattgtat gtgaatggac tggaagctaa ggagggagat cacacatccg agaaaactga   1800
tgaggatgcg cttcatgtaa agtttaatgt tgacaatgtg ttgcggaagc atcaggcaga   1860
tagaacccaa gcagtggaaa agaaaacttg gaagaaagtt gatgaggaac atctttacat   1920
```

```
gactgaacat cagaaacgtg ctgccgaagg acagatggta gttaacgagg atgagctttc    1980
tataactgaa attggaatgg ggagaggtga taaaattcag catgtgcttt ctgaggaaga    2040
gctttcatgg tctgaagatg aagtgcagtt aattgaggat gatggacaat atgaagttga    2100
cgagacctct gtgtccgtta acgttgaaca agatatccag gggtcaccac aggatgttgt    2160
ggatccgcaa gcactaaagg tgatgctgca agaactcgct gagaaaaatt attcgatgag    2220
gaacaagctg tttgtttttc cagaggtagt gaaagctgat tcagttattg atctttattt    2280
aaatcgtgac ctaacagctt tggcgaatga acccgatgtc gtcatcaaag gagcattcaa    2340
tggttggaaa tggaggcttt tcactgaaag attgcacaag agtgaccttg aggggtttg    2400
gtggtcttgc aaactgtaca tacccaagga ggcctacaga ttagactttg tgttcttcaa    2460
cggtcgcacg gtctatgaga acaatggcaa caatgatttc tgtataggaa tagaaggcac    2520
tatgaatgaa gatctgtttg aggatttctt ggttaaagaa aagcaaaggg agcttgagaa    2580
acttgccatg gaagaagctg aaaggaggac acagactgaa aacagcggc gaagaaagga    2640
agcaagggct gcagatgaag ctgtcagggc acaagcgaag gccgagatag agatcaagaa    2700
gaaaaaattg caaagtatgt tgagtttggc cagaacatgt gttgataatt tgtggtacat    2760
agaggctagc acagatacaa gaggagatac tatcaggtta tattataaca gaaactcgag    2820
gccacttgcg catagtactg agatttggat gcatggtggt tacaacaatt ggacagatgg    2880
actctctatt gttgaaagct ttgtcaagtg caatgacaaa gacggcgatt ggtggtatgc    2940
agatgttatt ccacctgaaa aggcacttgt gttggactgg gttttgctg atgggccagc    3000
tgggaatgca aggaactatg acaacaatgc tcgacaagat ttccatgcta ttcttccgaa    3060
caacaatgta accgaggaag gcttctgggc gcaagaggag caaaacatct atacaaggct    3120
tctgcaagaa aggagagaaa aggaagaaac catgaaaaga aaggctgaga gaagtgcaaa    3180
tatcaaagct gagatgaagg caaaaactat gcgaaggttt ctgctttccc agaaacacat    3240
tgtttatacc gaaccgcttg aaatacgtgc cggaaccaca gtggatgtgc tatacaatcc    3300
ctctaacaca gtgctaaatg aaagtcggag gggttggttt agatgctcct ttaacctttg    3360
gatgcattca agtggggcat tgccacccca gaagatggtg aaatcagggg atgggccgct    3420
cttaaaagca acagttgatg ttccaccgga tgcctatatg atggactttg ttttctccga    3480
gtgggaagaa gatgggatct atgacaacag gaatgggatg gactatcata ttcctgtttc    3540
tgattcaatt gaaacagaga attacatgcg tattatccac attgccgttg agatggcccc    3600
cgttgcaaag gttggaggtc ttggggatgt tgttacaagt ctttcacgtg ccattcaaga    3660
tctaggacat actgtcgagg ttattctccc gaagtacgac tgtttgaacc aaagcagtgt    3720
caaggattta catttatatc aaagttttc ttggggtggt acagaaataa agtatgggt    3780
tggacgagtc gaagacctga ccgtttactt cctggaacct caaaatggga tgtttggcgt    3840
tggatgtgta tatggaagga atgatgaccg cagatttggg ttcttctgtc attctgctct    3900
agagtttatc ctccagaatg aatttctcc acatataata cattgccatg attggtcaag    3960
tgctccggtc gcctggctat ataaggaaca ctattcccaa tccagaatgg caagcactcg    4020
ggttgtattt accatccaca atcttgaatt tggagcacat tatattggta aagcaatgac    4080
atactgtgat aaagccacaa ctgtttctcc tacatattca agggacgtgg caggccatgg    4140
cgccattgct cctcatcgtg agaaattcta cggcattctc aatggaaattg atccagatat    4200
ctgggatccg tacactgaca attttatccc ggtccccttat acttgtgaga atgttgtcga    4260
```

```
aggcaagaga gctgcaaaaa gggccttgca gcagaagttt ggattacagc aaactgatgt      4320
ccctattgtc ggaatcatca cccgtctgac agcccagaag ggaatccacc tcatcaagca      4380
cgcaattcac cgaactctcg aaagcaacgg acatgtggtt ttgcttggtt cagctccaga      4440
tcatcgaata caaggcgatt tttgcagatt ggccgatgct cttcatggtg tttaccatgg      4500
tagggtgaag cttgttctaa cctatgatga gcctctttct cacctgatat acgctggctc      4560
ggacttcata attgttcctt caatcttcga accctgtggc ttaacacaac ttgttgccat      4620
gcgttatgga tcgatcccta tagttcggaa aactggagga cttcacgaca cagtcttcga      4680
cgtagacaat gataaggacc gggctcggtc tcttggtctt gaaccaaatg ggttcagttt      4740
cgacggagcc gacagcaatg gcgtggatta tgccctcaac agagcaatcg gcgcttggtt      4800
cgatgcccgt gattggttcc actccctgtg taagagggtc atggagcaag actggtcgtg      4860
gaaccggccc gcactggact acattgaatt gtaccatgcc gctcgaaaat tctgacaccc      4920
aactgaacca atgacaagaa caagcgcatt gtgggatcga ctagtcatac agggctgtgc      4980
agatcgtctt gcttcagtta gtgccctctt cagttagttc caagcgcact acagtcgtac      5040
atagctgagg atcctcttgc ctcctaccag ggggaacaaa gcagaaatgc atgagtgcat      5100
tgggaagact tttatgtata ttgttaaaaa aatttccttt tcttttcctt ccctgcacct      5160
ggaaatggtt aagcgcatcg ccgagataag aaccgcagtg acattctgtg agtagctttg      5220
tatattctct catcttgtga aaactaatgt tcatgttagg ctgtctgatc atgtggaagc      5280
tttgttatat gttacttatg gtatacatca atgatattta catttgtgga aaaaaaaaa       5340 aaaaaa                                                                 5346
```

<210> SEQ ID NO 7
<211> LENGTH: 3863
<212> TYPE: DNA
<213> ORGANISM: Triticum aestivum

<400> SEQUENCE: 7

```
gtcgggttttt gattttctcc tgggcaatgg agatggctct ccgggcgcag agcccgctct       60
gctcccggag ccgcccggtg ctcctcgtgc ggcccgccgt ccctggcctc gcgcagtcta      120
tcgtcaagtg cagcagattt acaagaagca ggctcgttcg gtgcatggta gcaagctcat      180
atcccaagag gaatccgagg agatcatcag ctcctaagcc caaggcact gcctccagag       240 aatatgctcc aagaccttct gccgaatctt ggacctccac gaagaagact gaacatagca      300
gcgctgatga gacggtgat cttggcgcaa gcaatgggac gctcagtagt gacacagcag       360
agcagacaag taccgcagag gaagaatacg aggtggaatt cccaggaaat gtttctagca      420
gcgtggagcc gaagggtgtg aacgaggaag aggttgacca aaagcagcct cctgcattga      480
cttccacatc catggatgct gagtctgtta atgaagcaac ggagcacaca agtaccgcaa      540
atgaatcatc tgaggttgac ttctcaggaa atgtctctag cagcgtggtg ctggaggtag      600
tagatgaatc tgagactgaa gaagaggctg accagaagca gtcatcagca tcttccacct      660
ccatggatgt tgagtcaatt gacagagaac ttgaggggta ccgtgtcaga ataagtgcac      720
tggtgggtgc tagcacccaa ggacaggacc aatcaattat tggtgttcat gaacaagaca      780
aatcggtaat tacttccgat gagcaagaca tatcagctgt tgatgttcct gaacaaagcc      840
agtcagttgt tgctgtcacc agagaagata caacagacca aaccaccagc gaacaggata      900
tcactgaagc ggtagtagag gagatagcca gcaagaatct cgtggcaaga aaacattctt      960
catcagaaga tggcgttggg gcaaggaaac atgccaatga agagccattg gttgctggtg     1020
```

```
atggactgag ggtaacagag gatgaagaac aacatgaacc agagatgcaa gaacaggtaa    1080
agatggatgt tgatcctcaa gcactaaagc gaaggcttga agagcttgca gataaaaatt    1140
attcgattgg gaataagtgt tttgttttc ctgaattagt ggaagctgat tcagttattg      1200
atctttactt aaatcgtagc atgtcggcct tagcaaatga gcctgataatc cttatcaaag    1260 gggcattcaa tggttggaga tggaaccatt tcactgaaaa attgcataga agtgaattaa     1320
caggggattg gtggtgttgt aagctctacc tacccaagca ggcatacaga ttagactttg    1380
tgttctttaa tggtgacact gtctatgaaa acaacagtta taatgatttc gtcctgcata    1440
tagaaggtga cggggatgaa cactcatttg aggacttctt gcttgaagaa aagcaaaggg    1500
aacttgaaag gcttgctgca gaagaagctg aaagggaaag acaagccgag gaggagcgcc    1560
ggaaggagga agaaagggcc gcaatggagg ctgacagggc acaggcaaaa gctgaggttg    1620
agacgacgag gaataaattg cagcatgtgt tgggtttagc cagcagatat gtcgataatc    1680
tatggtatat acagcctagc acatacaaag gaggggatag ggtcagattg tactataatc    1740
gaagctcgag accactaaag cataaaaatg agatttggtt gcatgggggt tacaataact    1800
ggactgatgg gccctctatt gttgagagac tagtcaaatc tgaagaacag gatggtgatt    1860
ggtggtatgc aaatgttact ctacctgaaa gcgcattggt gtatgactgc gtattagctg    1920
atggatcacc tgggaacgca agcaagtatg ataaacatgg gaagcaagat ttcatgctg     1980 gccgttcaaa gagcatatcc gatgacttat tttgggtgga agaagaacgt aggatatttg    2040
aaaggcttca gcgagaaaga acagagaagg aggatgctgg tcggagaaag gctgagataa    2100
ctgcaaggat gaaagctgag atgaaggaga agactatgag agagtttctt ctctcacaga    2160
aacacattgt gtatactgag ccacttgaag tgcgtgcagg gaccacagtt gatgttctat    2220
acaatccttc taacacagtg ctgaatggaa gtccagaagt ttggttcaga tgttcctta     2280 atcgttggac tcatcctagt ggtcctttgc cgccccaaaa gatggtgaat gaagtaaatg    2340
gttcacactt acaagctaca gttagggttc cttttggatgc atatatgatg actttgttt    2400 tctctgagtc ggaagaaggt gggatatatg acaaccggga tgggatggac tatcatgttc    2460
ctgtgtctga ttccacggca aaggaaccac ctatgcatat tgtgcacatt gcagtggaaa    2520
tggctcctat tgcaaaggtt gggggccttg gtgatgttgt tactagtctt tcacgggcta    2580
ttcaagattc aggccacaag gttgaggtta tttttctaaa gtatgactgt ttaaatctaa    2640
gcaatgtgaa ggatttacat tgccgtcaaa gttctacttg gggtggcaca gagataaaag    2700
tatggtttgg aaaggttgaa ggcatctctg tttatttctt ggaaccgcag aatgggatgt    2760
tttgggttgg atgtgtctat ggaaagaacg atgaaagtag atttggtttc ttttgtcatt    2820
ctgccctgga gtttcttctc cagagtggct cttctccaga tatcatacac tgtcatgatt    2880
ggtcaagtgc tccagttgct tggctgtaca agcaacagta tgttcataat gggctgccaa    2940
atggtcgggt tgtatttacc atccacaatc ttgaatttgg ggtacatcac attggcaaag    3000
caatggcaca ttgtgataag gctacaactg tttcgtacac atattcgaag gaagtgtctg    3060
gacatggttc tattgctcct cattatttca aattccatgg cattcgtaat ggaattgatt    3120
ctgatatttg ggatccctat aatgacaact tcattccggt ccattatact tctgagaatg    3180
ttgttgaggg taagagttct gcaaaaaggg cattgcagga gaagcttgga ttacaccaaa    3240
ctgattcccc tctagtcgga atcatcagtc ggcttacagc ccagaaggga attcaccta    3300 tcagacatgc aatttatcga actcttgaac gcaatggaca ggtggtttta ctaggctcag    3360
```

-continued

```
ctccagatca tcgcatacaa ggtgacttta gcaacttagc agctaaactg catggtgaat    3420
ttgatggtcg cgtgaagctt tgtttaactt atgacgagcc actatcacat ttaatatatg    3480
ctggcgccga cttcattctc gtgccttcca ttttcgaacc ttgtggttta acacagctta    3540
ctgctatgcg atatggatcc atcccaattg ttcggacaac tggaggcctt tatgatacca    3600
tttttgatgt ggacgatgat aaggatcggg cccgtgaaca aggccttgag ccgaacggat    3660
tcagcttcga aggagctgac agcaatggcg tagattatgc gctcgacagg gcgatcacca    3720
catggtacga cgctcgcgac tggcatcact ccctctgcaa gcgggtcatg gagcaggatt    3780
ggtcctggaa ccggcctgct ctggactaca tggaactgta ccatcccacg cgcaagaact    3840
gagactttaa gctggcaggg aga                                            3863
```

<210> SEQ ID NO 8
<211> LENGTH: 1628
<212> TYPE: PRT
<213> ORGANISM: Triticum aestivum

<400> SEQUENCE: 8

```
Met Glu Met Ser Leu Trp Pro Arg Ser Pro Leu Cys Pro Arg Ser Arg
1               5                   10                  15

Gln Pro Leu Val Val Arg Pro Ala Gly Arg Gly Leu Thr Gln
            20                  25                  30

Pro Phe Leu Met Asn Gly Arg Phe Thr Arg Ser Arg Thr Leu Arg Cys
        35                  40                  45

Met Val Ala Ser Ser Asp Pro Pro Asn Arg Lys Ser Arg Arg Met Val
    50                  55                  60

Pro Pro Gln Val Lys Val Ile Ser Ser Arg Gly Tyr Thr Thr Arg Leu
65                  70                  75                  80

Ile Val Glu Pro Ser Asn Glu Asn Thr Glu His Asn Asn Arg Asp Glu
                85                  90                  95

Glu Thr Leu Asp Thr Tyr Asn Ala Leu Leu Ser Thr Glu Thr Ala Glu
            100                 105                 110

Trp Thr Asp Asn Arg Glu Ala Glu Thr Ala Lys Ala Asp Ser Ser Gln
        115                 120                 125

Asn Ala Leu Ser Ser Ser Ile Ile Gly Glu Val Asp Val Ala Asp Glu
    130                 135                 140

Asp Ile Leu Ala Ala Asp Leu Thr Val Tyr Ser Leu Ser Ser Val Met
145                 150                 155                 160

Lys Lys Glu Val Asp Ala Ala Asp Lys Ala Arg Val Lys Glu Asp Ala
                165                 170                 175

Phe Glu Leu Asp Leu Pro Ala Thr Thr Leu Arg Ser Val Ile Val Asp
            180                 185                 190

Val Met Asp His Asn Gly Thr Val Gln Glu Thr Leu Arg Ser Val Ile
        195                 200                 205

Val Asp Val Met Asp His Asn Gly Thr Val Gln Glu Thr Leu Arg Ser
    210                 215                 220

Val Ile Val Asp Val Met Asp Asp Ala Ala Asp Lys Ala Arg Val Glu
225                 230                 235                 240

Glu Asp Val Phe Glu Leu Asp Leu Ser Gly Asn Ile Ser Ser Ala
                245                 250                 255

Thr Thr Val Glu Leu Asp Ala Val Asp Glu Val Gly Pro Val Gln Asp
            260                 265                 270

Lys Phe Glu Ala Thr Ser Ser Gly Asn Val Ser Asn Ser Ala Thr Val
        275                 280                 285
```

```
Arg Glu Val Asp Ala Ser Asp Glu Ala Gly Asn Asp Gln Gly Ile Phe
        290                 295                 300

Arg Ala Asp Leu Ser Gly Asn Val Phe Ser Ser Thr Thr Val Glu
305                 310                 315                 320

Val Gly Ala Val Asp Glu Ala Gly Ser Ile Lys Asp Arg Phe Glu Thr
                325                 330                 335

Asp Ser Ser Gly Asn Val Ser Thr Ser Ala Pro Met Trp Asp Ala Ile
                340                 345                 350

Asp Glu Thr Val Ala Asp Gln Asp Thr Phe Glu Ala Asp Leu Ser Gly
            355                 360                 365

Asn Ala Ser Ser Cys Ala Thr Tyr Arg Glu Val Asp Val Val Asp
370                 375                 380

Glu Thr Arg Ser Glu Glu Thr Phe Ala Met Asp Leu Phe Ala Ser
385                 390                 395                 400

Glu Ser Gly His Glu Lys His Met Ala Val Asp Tyr Val Gly Glu Ala
                405                 410                 415

Thr Asp Glu Glu Glu Thr Tyr Gln Gln Gln Tyr Pro Val Pro Ser Ser
                420                 425                 430

Phe Ser Met Trp Asp Lys Ala Ile Ala Lys Thr Gly Val Ser Leu Asn
            435                 440                 445

Pro Glu Leu Arg Leu Val Arg Val Glu Gln Gly Lys Val Asn Phe
450                 455                 460

Ser Asp Lys Lys Asp Leu Ser Ile Asp Asp Leu Pro Gly Gln Asn Gln
465                 470                 475                 480

Ser Ile Ile Gly Ser Tyr Lys Gln Asp Lys Ser Ile Ala Asp Val Ala
                485                 490                 495

Gly Pro Thr Gln Ser Ile Phe Gly Ser Ser Lys Gln His Arg Ser Ile
                500                 505                 510

Val Ala Phe Pro Lys Gln Asn Gln Ser Ile Val Ser Val Thr Glu Gln
            515                 520                 525

Lys Gln Ser Ile Val Gly Phe Arg Ser Gln Asp Leu Ser Ala Val Ser
530                 535                 540

Leu Pro Lys Gln Asn Val Pro Ile Val Gly Thr Ser Arg Glu Gly Gln
545                 550                 555                 560

Thr Lys Gln Val Pro Val Val Asp Arg Gln Asp Ala Leu Tyr Val Asn
                565                 570                 575

Gly Leu Glu Ala Lys Glu Gly Asp His Thr Ser Glu Lys Thr Asp Glu
                580                 585                 590

Asp Ala Leu His Val Lys Phe Asn Val Asp Asn Val Leu Arg Lys His
            595                 600                 605

Gln Ala Asp Arg Thr Gln Ala Val Glu Lys Lys Thr Trp Lys Lys Val
610                 615                 620

Asp Glu Glu His Leu Tyr Met Thr Glu His Gln Lys Arg Ala Ala Glu
625                 630                 635                 640

Gly Gln Met Val Val Asn Glu Asp Glu Leu Ser Ile Thr Glu Ile Gly
                645                 650                 655

Met Gly Arg Gly Asp Lys Ile Gln His Val Leu Ser Glu Glu Leu
                660                 665                 670

Ser Trp Ser Glu Asp Glu Val Gln Leu Ile Glu Asp Gly Gln Tyr
            675                 680                 685

Glu Val Asp Glu Thr Ser Val Ser Val Asn Val Glu Gln Asp Ile Gln
                690                 695                 700
```

```
Gly Ser Pro Gln Asp Val Val Asp Pro Gln Ala Leu Lys Val Met Leu
705                 710                 715                 720

Gln Glu Leu Ala Glu Lys Asn Tyr Ser Met Arg Asn Lys Leu Phe Val
                725                 730                 735

Phe Pro Glu Val Val Lys Ala Asp Ser Val Ile Asp Leu Tyr Leu Asn
            740                 745                 750

Arg Asp Leu Thr Ala Leu Ala Asn Glu Pro Asp Val Val Ile Lys Gly
        755                 760                 765

Ala Phe Asn Gly Trp Lys Trp Arg Leu Phe Thr Glu Arg Leu His Lys
    770                 775                 780

Ser Asp Leu Gly Gly Val Trp Trp Ser Cys Lys Leu Tyr Ile Pro Lys
785                 790                 795                 800

Glu Ala Tyr Arg Leu Asp Phe Val Phe Phe Asn Gly Arg Thr Val Tyr
                805                 810                 815

Glu Asn Asn Gly Asn Asn Asp Phe Cys Ile Gly Ile Glu Gly Thr Met
            820                 825                 830

Asn Glu Asp Leu Phe Glu Asp Phe Leu Val Lys Glu Lys Gln Arg Glu
        835                 840                 845

Leu Glu Lys Leu Ala Met Glu Glu Ala Glu Arg Arg Thr Gln Thr Glu
    850                 855                 860

Glu Gln Arg Arg Arg Lys Glu Ala Arg Ala Ala Asp Glu Ala Val Arg
865                 870                 875                 880

Ala Gln Ala Lys Ala Glu Ile Glu Ile Lys Lys Lys Leu Gln Ser
                885                 890                 895

Met Leu Ser Leu Ala Arg Thr Cys Val Asp Asn Leu Trp Tyr Ile Glu
            900                 905                 910

Ala Ser Thr Asp Thr Arg Gly Asp Thr Ile Arg Leu Tyr Tyr Asn Arg
        915                 920                 925

Asn Ser Arg Pro Leu Ala His Ser Thr Glu Ile Trp Met His Gly Gly
    930                 935                 940

Tyr Asn Asn Trp Thr Asp Gly Leu Ser Ile Val Glu Ser Phe Val Lys
945                 950                 955                 960

Cys Asn Asp Lys Asp Gly Asp Trp Trp Tyr Ala Asp Val Ile Pro Pro
                965                 970                 975

Glu Lys Ala Leu Val Leu Asp Trp Val Phe Ala Asp Gly Pro Ala Gly
            980                 985                 990

Asn Ala Arg Asn Tyr Asp Asn Asn Ala Arg Gln Asp Phe His Ala Ile
        995                 1000                1005

Leu Pro Asn Asn Asn Val Thr Glu Glu Gly Phe Trp Ala Gln Glu
    1010                1015                1020

Glu Gln Asn Ile Tyr Thr Arg Leu Leu Gln Glu Arg Arg Glu Lys
    1025                1030                1035

Glu Glu Thr Met Lys Arg Lys Ala Glu Arg Ser Ala Asn Ile Lys
    1040                1045                1050

Ala Glu Met Lys Ala Lys Thr Met Arg Arg Phe Leu Leu Ser Gln
    1055                1060                1065

Lys His Ile Val Tyr Thr Glu Pro Leu Glu Ile Arg Ala Gly Thr
    1070                1075                1080

Thr Val Asp Val Leu Tyr Asn Pro Ser Asn Thr Val Leu Asn Gly
    1085                1090                1095

Lys Ser Glu Gly Trp Phe Arg Cys Ser Phe Asn Leu Trp Met His
    1100                1105                1110

Ser Ser Gly Ala Leu Pro Pro Gln Lys Met Val Lys Ser Gly Asp
```

-continued

```
                1115                1120                1125
Gly Pro Leu Leu Lys Ala Thr Val Asp Val Pro Asp Ala Tyr
        1130                1135                1140
Met Met Asp Phe Val Phe Ser Glu Trp Glu Glu Asp Gly Ile Tyr
        1145                1150                1155
Asp Asn Arg Asn Gly Met Asp Tyr His Ile Pro Val Ser Asp Ser
        1160                1165                1170
Ile Glu Thr Glu Asn Tyr Met Arg Ile Ile His Ile Ala Val Glu
        1175                1180                1185
Met Ala Pro Val Ala Lys Val Gly Gly Leu Gly Asp Val Val Thr
        1190                1195                1200
Ser Leu Ser Arg Ala Ile Gln Asp Leu Gly His Thr Val Glu Val
        1205                1210                1215
Ile Leu Pro Lys Tyr Asp Cys Leu Asn Gln Ser Ser Val Lys Asp
        1220                1225                1230
Leu His Leu Tyr Gln Ser Phe Ser Trp Gly Gly Thr Glu Ile Lys
        1235                1240                1245
Val Trp Val Gly Arg Val Glu Asp Leu Thr Val Tyr Phe Leu Glu
        1250                1255                1260
Pro Gln Asn Gly Met Phe Gly Val Gly Cys Val Tyr Gly Arg Asn
        1265                1270                1275
Asp Asp Arg Arg Phe Gly Phe Phe Cys His Ser Ala Leu Glu Phe
        1280                1285                1290
Ile Leu Gln Asn Glu Phe Ser Pro His Ile Ile His Cys His Asp
        1295                1300                1305
Trp Ser Ser Ala Pro Val Ala Trp Leu Tyr Lys Glu His Tyr Ser
        1310                1315                1320
Gln Ser Arg Met Ala Ser Thr Arg Val Val Phe Thr Ile His Asn
        1325                1330                1335
Leu Glu Phe Gly Ala His Tyr Ile Gly Lys Ala Met Thr Tyr Cys
        1340                1345                1350
Asp Lys Ala Thr Thr Val Ser Pro Thr Tyr Ser Arg Asp Val Ala
        1355                1360                1365
Gly His Gly Ala Ile Ala Pro His Arg Glu Lys Phe Tyr Gly Ile
        1370                1375                1380
Leu Asn Gly Ile Asp Pro Asp Ile Trp Asp Pro Tyr Thr Asp Asn
        1385                1390                1395
Phe Ile Pro Val Pro Tyr Thr Cys Glu Asn Val Val Glu Gly Lys
        1400                1405                1410
Arg Ala Ala Lys Arg Ala Leu Gln Gln Lys Phe Gly Leu Gln Gln
        1415                1420                1425
Thr Asp Val Pro Ile Val Gly Ile Ile Thr Arg Leu Thr Ala Gln
        1430                1435                1440
Lys Gly Ile His Leu Ile Lys His Ala Ile His Arg Thr Leu Glu
        1445                1450                1455
Ser Asn Gly His Val Val Leu Leu Gly Ser Ala Pro Asp His Arg
        1460                1465                1470
Ile Gln Gly Asp Phe Cys Arg Leu Ala Asp Ala Leu His Gly Val
        1475                1480                1485
Tyr His Gly Arg Val Lys Leu Val Leu Thr Tyr Asp Glu Pro Leu
        1490                1495                1500
Ser His Leu Ile Tyr Ala Gly Ser Asp Phe Ile Ile Val Pro Ser
        1505                1510                1515
```

```
Ile Phe Glu Pro Cys Gly Leu Thr Gln Leu Val Ala Met Arg Tyr
    1520                1525                1530

Gly Ser Ile Pro Ile Val Arg Lys Thr Gly Gly Leu His Asp Thr
    1535                1540                1545

Val Phe Asp Val Asp Asn Asp Lys Asp Arg Ala Arg Ser Leu Gly
    1550                1555                1560

Leu Glu Pro Asn Gly Phe Ser Phe Asp Gly Ala Asp Ser Asn Gly
    1565                1570                1575

Val Asp Tyr Ala Leu Asn Arg Ala Ile Gly Ala Trp Phe Asp Ala
    1580                1585                1590

Arg Asp Trp Phe His Ser Leu Cys Lys Arg Val Met Glu Gln Asp
    1595                1600                1605

Trp Ser Trp Asn Arg Pro Ala Leu Asp Tyr Ile Glu Leu Tyr His
    1610                1615                1620

Ala Ala Arg Lys Phe
    1625

<210> SEQ ID NO 9
<211> LENGTH: 1271
<212> TYPE: PRT
<213> ORGANISM: Triticum aestivum

<400> SEQUENCE: 9

Met Glu Met Ala Leu Arg Ala Gln Ser Pro Leu Cys Ser Arg Ser Arg
1               5                   10                  15

Pro Val Leu Leu Val Arg Pro Ala Val Pro Gly Leu Ala Gln Ser Ile
            20                  25                  30

Val Lys Cys Ser Arg Phe Thr Arg Ser Arg Leu Val Arg Cys Met Val
        35                  40                  45

Ala Ser Ser Tyr Pro Lys Arg Asn Pro Arg Arg Ser Ser Ala Pro Lys
    50                  55                  60

Pro Lys Gly Thr Ala Ser Arg Glu Tyr Ala Pro Arg Pro Ser Ala Glu
65                  70                  75                  80

Ser Trp Thr Ser Thr Lys Lys Thr Glu His Ser Ser Ala Asp Glu Asp
                85                  90                  95

Gly Asp Leu Gly Ala Ser Asn Gly Thr Leu Ser Ser Asp Thr Ala Glu
            100                 105                 110

Gln Thr Ser Thr Ala Glu Glu Tyr Glu Val Glu Phe Pro Gly Asn
        115                 120                 125

Val Ser Ser Ser Val Glu Pro Lys Gly Val Asn Glu Glu Val Asp
    130                 135                 140

Gln Lys Gln Pro Pro Ala Leu Thr Ser Thr Ser Met Asp Ala Glu Ser
145                 150                 155                 160

Val Asn Glu Ala Thr Glu His Thr Ser Thr Ala Asn Glu Ser Ser Glu
                165                 170                 175

Val Asp Phe Ser Gly Asn Val Ser Ser Val Val Leu Glu Val Val
            180                 185                 190

Asp Glu Ser Glu Thr Glu Glu Glu Ala Asp Gln Lys Gln Ser Ser Ala
        195                 200                 205

Ser Ser Thr Ser Met Asp Val Glu Ser Ile Asp Arg Glu Leu Glu Gly
    210                 215                 220

Tyr Arg Val Arg Ile Ser Ala Leu Val Gly Ala Ser Thr Gln Gly Gln
225                 230                 235                 240

Asp Gln Ser Ile Ile Gly Val His Glu Gln Asp Lys Ser Val Ile Thr
```

```
            245                 250                 255
Ser Asp Glu Gln Asp Ile Ser Ala Val Asp Val Pro Glu Gln Ser Gln
            260                 265                 270

Ser Val Val Ala Val Thr Arg Glu Asp Thr Thr Asp Gln Thr Thr Ser
            275                 280                 285

Glu Gln Asp Ile Thr Glu Ala Val Val Glu Glu Ile Ala Ser Lys Asn
            290                 295                 300

Leu Val Ala Arg Lys His Ser Ser Glu Asp Gly Val Gly Ala Arg
305                 310                 315                 320

Lys His Ala Asn Glu Glu Pro Leu Val Ala Gly Asp Gly Leu Arg Val
                325                 330                 335

Thr Glu Asp Glu Glu Gln His Glu Pro Glu Met Gln Glu Gln Val Lys
            340                 345                 350

Met Asp Val Asp Pro Gln Ala Leu Lys Arg Arg Leu Glu Glu Leu Ala
            355                 360                 365

Asp Lys Asn Tyr Ser Ile Gly Asn Lys Cys Phe Val Phe Pro Glu Leu
        370                 375                 380

Val Glu Ala Asp Ser Val Ile Asp Leu Tyr Leu Asn Arg Ser Met Ser
385                 390                 395                 400

Ala Leu Ala Asn Glu Pro Asp Ile Leu Ile Lys Gly Ala Phe Asn Gly
                405                 410                 415

Trp Arg Trp Asn His Phe Thr Glu Lys Leu His Arg Ser Glu Leu Thr
            420                 425                 430

Gly Asp Trp Trp Cys Cys Lys Leu Tyr Leu Pro Lys Gln Ala Tyr Arg
            435                 440                 445

Leu Asp Phe Val Phe Phe Asn Gly Asp Thr Val Tyr Glu Asn Asn Ser
        450                 455                 460

Tyr Asn Asp Phe Val Leu His Ile Glu Gly Asp Gly Asp Glu His Ser
465                 470                 475                 480

Phe Glu Asp Phe Leu Leu Glu Glu Lys Gln Arg Glu Leu Glu Arg Leu
                485                 490                 495

Ala Ala Glu Glu Ala Glu Arg Glu Arg Gln Ala Glu Glu Arg Arg
            500                 505                 510

Lys Glu Glu Glu Arg Ala Ala Met Glu Ala Asp Arg Ala Gln Ala Lys
        515                 520                 525

Ala Glu Val Glu Thr Thr Arg Asn Lys Leu Gln His Val Leu Gly Leu
            530                 535                 540

Ala Ser Arg Tyr Val Asp Asn Leu Trp Tyr Ile Gln Pro Ser Thr Tyr
545                 550                 555                 560

Lys Gly Gly Asp Arg Val Arg Leu Tyr Tyr Asn Arg Ser Ser Arg Pro
                565                 570                 575

Leu Lys His Lys Asn Glu Ile Trp Leu His Gly Gly Tyr Asn Asn Trp
        580                 585                 590

Thr Asp Gly Pro Ser Ile Val Glu Arg Leu Val Lys Ser Glu Glu Gln
            595                 600                 605

Asp Gly Asp Trp Trp Tyr Ala Asn Val Thr Leu Pro Glu Ser Ala Leu
        610                 615                 620

Val Tyr Asp Cys Val Leu Ala Asp Gly Ser Pro Gly Asn Ala Ser Lys
625                 630                 635                 640

Tyr Asp Lys His Gly Lys Gln Asp Phe His Ala Gly Arg Ser Lys Ser
                645                 650                 655

Ile Ser Asp Asp Leu Phe Trp Val Glu Glu Arg Arg Ile Phe Glu
            660                 665                 670
```

-continued

```
Arg Leu Gln Arg Glu Arg Thr Glu Lys Glu Asp Ala Gly Arg Lys
                675                 680                 685

Ala Glu Ile Thr Ala Arg Met Lys Ala Glu Met Lys Glu Lys Thr Met
            690                 695                 700

Arg Glu Phe Leu Leu Ser Gln Lys His Ile Val Tyr Thr Glu Pro Leu
705                 710                 715                 720

Glu Val Arg Ala Gly Thr Thr Val Asp Val Leu Tyr Asn Pro Ser Asn
                725                 730                 735

Thr Val Leu Asn Gly Ser Pro Glu Val Trp Phe Arg Cys Ser Phe Asn
                740                 745                 750

Arg Trp Thr His Pro Ser Gly Pro Leu Pro Pro Gln Lys Met Val Asn
                755                 760                 765

Glu Val Asn Gly Ser His Leu Gln Ala Thr Val Arg Val Pro Leu Asp
                770                 775                 780

Ala Tyr Met Met Asp Phe Val Phe Ser Glu Ser Glu Glu Gly Gly Ile
785                 790                 795                 800

Tyr Asp Asn Arg Asp Gly Met Asp Tyr His Val Pro Val Ser Asp Ser
                805                 810                 815

Thr Ala Lys Glu Pro Pro Met His Ile Val His Ile Ala Val Glu Met
                820                 825                 830

Ala Pro Ile Ala Lys Val Gly Gly Leu Gly Asp Val Val Thr Ser Leu
                835                 840                 845

Ser Arg Ala Ile Gln Asp Ser Gly His Lys Val Glu Val Ile Phe Leu
                850                 855                 860

Lys Tyr Asp Cys Leu Asn Leu Ser Asn Val Lys Asp Leu His Cys Arg
865                 870                 875                 880

Gln Ser Ser Thr Trp Gly Gly Thr Glu Ile Lys Val Trp Phe Gly Lys
                885                 890                 895

Val Glu Gly Ile Ser Val Tyr Phe Leu Glu Pro Gln Asn Gly Met Phe
                900                 905                 910

Trp Val Gly Cys Val Tyr Gly Lys Asn Asp Glu Ser Arg Phe Gly Phe
                915                 920                 925

Phe Cys His Ser Ala Leu Glu Phe Leu Leu Gln Ser Gly Ser Ser Pro
                930                 935                 940

Asp Ile Ile His Cys His Asp Trp Ser Ser Ala Pro Val Ala Trp Leu
945                 950                 955                 960

Tyr Lys Gln Gln Tyr Val His Asn Gly Leu Pro Asn Gly Arg Val Val
                965                 970                 975

Phe Thr Ile His Asn Leu Glu Phe Gly Val His His Ile Gly Lys Ala
                980                 985                 990

Met Ala His Cys Asp Lys Ala Thr Thr Val Ser Tyr Thr Tyr Ser Lys
                995                 1000                1005

Glu Val Ser Gly His Gly Ser Ile Ala Pro His Tyr Phe Lys Phe
        1010                1015                1020

His Gly Ile Arg Asn Gly Ile Asp Ser Asp Ile Trp Asp Pro Tyr
        1025                1030                1035

Asn Asp Asn Phe Ile Pro Val His Tyr Thr Ser Glu Asn Val Val
        1040                1045                1050

Glu Gly Lys Ser Ser Ala Lys Arg Ala Leu Gln Glu Lys Leu Gly
        1055                1060                1065

Leu His Gln Thr Asp Ser Pro Leu Val Gly Ile Ile Ser Arg Leu
        1070                1075                1080
```

-continued

```
Thr Ala Gln Lys Gly Ile His Leu Ile Arg His Ala Ile Tyr Arg
    1085            1090                1095

Thr Leu Glu Arg Asn Gly Gln Val Val Leu Leu Gly Ser Ala Pro
    1100            1105                1110

Asp His Arg Ile Gln Gly Asp Phe Ser Asn Leu Ala Ala Lys Leu
    1115            1120                1125

His Gly Glu Phe Asp Gly Arg Val Lys Leu Cys Leu Thr Tyr Asp
    1130            1135                1140

Glu Pro Leu Ser His Leu Ile Tyr Ala Gly Ala Asp Phe Ile Leu
    1145            1150                1155

Val Pro Ser Ile Phe Glu Pro Cys Gly Leu Thr Gln Leu Thr Ala
    1160            1165                1170

Met Arg Tyr Gly Ser Ile Pro Ile Val Arg Thr Gly Gly Leu
    1175            1180                1185

Tyr Asp Thr Ile Phe Asp Val Asp Asp Lys Asp Arg Ala Arg
    1190            1195                1200

Glu Gln Gly Leu Glu Pro Asn Gly Phe Ser Phe Glu Gly Ala Asp
    1205            1210                1215

Ser Asn Gly Val Asp Tyr Ala Leu Asp Arg Ala Ile Thr Thr Trp
    1220            1225                1230

Tyr Asp Ala Arg Asp Trp His His Ser Leu Cys Lys Arg Val Met
    1235            1240                1245

Glu Gln Asp Trp Ser Trp Asn Arg Pro Ala Leu Asp Tyr Met Glu
    1250            1255                1260

Leu Tyr His Pro Thr Arg Lys Asn
    1265            1270

<210> SEQ ID NO 10
<211> LENGTH: 23
<212> TYPE: DNA
<213> ORGANISM: Hordeum vulgare

<400> SEQUENCE: 10
cctggaacac ttcagactgt acg                                              23

<210> SEQ ID NO 11
<211> LENGTH: 22
<212> TYPE: DNA
<213> ORGANISM: Hordeum vulgare

<400> SEQUENCE: 11
agcatcacca gctgcacgtc ct                                               22

<210> SEQ ID NO 12
<211> LENGTH: 38
<212> TYPE: DNA
<213> ORGANISM: Hordeum vulgare

<400> SEQUENCE: 12
cacgacgttg taaaacgaca cttaagtgcc atgcaaag                              38

<210> SEQ ID NO 13
<211> LENGTH: 19
<212> TYPE: DNA
<213> ORGANISM: Hordeum vulgare

<400> SEQUENCE: 13
agggacaaaa atggctaag                                                   19
```

<210> SEQ ID NO 14
<211> LENGTH: 17
<212> TYPE: DNA
<213> ORGANISM: Hordeum vulgare

<400> SEQUENCE: 14
ggaggtctcg gggatgt                                                      17

<210> SEQ ID NO 15
<211> LENGTH: 23
<212> TYPE: DNA
<213> ORGANISM: Hordeum vulgare

<400> SEQUENCE: 15
gctccaggaa gtaaacggtc agg                                               23

<210> SEQ ID NO 16
<211> LENGTH: 21
<212> TYPE: DNA
<213> ORGANISM: Hordeum vulgare

<400> SEQUENCE: 16
atggagatgt ctctctggcc a                                                 21

<210> SEQ ID NO 17
<211> LENGTH: 22
<212> TYPE: DNA
<213> ORGANISM: Hordeum vulgare

<400> SEQUENCE: 17
tctgcatacc accaatcgcc gt                                                22

<210> SEQ ID NO 18
<211> LENGTH: 23
<212> TYPE: DNA
<213> ORGANISM: Hordeum vulgare

<400> SEQUENCE: 18
atcgtgacct aacagctttg gcg                                               23

<210> SEQ ID NO 19
<211> LENGTH: 25
<212> TYPE: DNA
<213> ORGANISM: Hordeum vulgare

<400> SEQUENCE: 19
gacagaagaa cccaaatctg cggtc                                             25

<210> SEQ ID NO 20
<211> LENGTH: 23
<212> TYPE: DNA
<213> ORGANISM: Hordeum vulgare

<400> SEQUENCE: 20
ggaggtctcg gggatgttgt tac                                               23

<210> SEQ ID NO 21
<211> LENGTH: 27
<212> TYPE: DNA
<213> ORGANISM: Hordeum vulgare

<400> SEQUENCE: 21
ccacaaatgt aaatatcatt gatgtat                                           27

```
<210> SEQ ID NO 22
<211> LENGTH: 23
<212> TYPE: DNA
<213> ORGANISM: Hordeum vulgare

<400> SEQUENCE: 22
acgtcactgc ggttcttatc tcg                                        23

<210> SEQ ID NO 23
<211> LENGTH: 24
<212> TYPE: DNA
<213> ORGANISM: Hordeum vulgare

<400> SEQUENCE: 23
ggttccagga agtaaacggt cagg                                       24

<210> SEQ ID NO 24
<211> LENGTH: 39
<212> TYPE: DNA
<213> ORGANISM: Hordeum vulgare

<400> SEQUENCE: 24
aaaaggatcc ggtaccgttc taacctatga tgagcctct                       39

<210> SEQ ID NO 25
<211> LENGTH: 38
<212> TYPE: DNA
<213> ORGANISM: Hordeum vulgare

<400> SEQUENCE: 25
aaaagaattc actagtgaat tttcgagcgg catggtac                        38

<210> SEQ ID NO 26
<211> LENGTH: 40
<212> TYPE: DNA
<213> ORGANISM: Hordeum vulgare

<400> SEQUENCE: 26
aaaaggatcc ggtaccggtg aatttgatgg tcccgtgtag                      40

<210> SEQ ID NO 27
<211> LENGTH: 39
<212> TYPE: DNA
<213> ORGANISM: Hordeum vulgare

<400> SEQUENCE: 27
aaaagaattc actagtcagt tcttgcgcgt ggatggtac                       39

<210> SEQ ID NO 28
<211> LENGTH: 23
<212> TYPE: DNA
<213> ORGANISM: Hordeum vulgare

<400> SEQUENCE: 28
cgacgtctgt cgagaagttt ctg                                        23

<210> SEQ ID NO 29
<211> LENGTH: 23
<212> TYPE: DNA
<213> ORGANISM: Hordeum vulgare

<400> SEQUENCE: 29
```
ctccagaaga agatgttggc gac    23

<210> SEQ ID NO 30
<211> LENGTH: 23
<212> TYPE: DNA
<213> ORGANISM: Hordeum vulgare

<400> SEQUENCE: 30
caaccatgtc ctgaaccttc acc    23

<210> SEQ ID NO 31
<211> LENGTH: 26
<212> TYPE: DNA
<213> ORGANISM: Hordeum vulgare

<400> SEQUENCE: 31
gcttggttca acaatgagtc ttgtcg    26

<210> SEQ ID NO 32
<211> LENGTH: 2920
<212> TYPE: DNA
<213> ORGANISM: Hordeum vulgare

<400> SEQUENCE: 32
cctcgaggtg cgtttacccc acacagagta cactccaact ccagtccaat ccagcccact    60
gccgcttctg cccgcccatc gtaccgtcgc ccgccccgat cccggccgcc gccatgtcgt    120
cggcggtcgc gtccccgcg tccttcctcg cgctcgcgtc cgcctcgccc gggagatcat    180
cacggaggag ggcgagggtg ggcgcgtcgc caacccgcgc tggggccggc aggctgcaat    240
ggcggccgtc gccgctgcag cgcacggctc gcgacggagc ggtggccgcg cgcgccgccg    300
ggatcgacga cgccgcgccc ggtaggcagc ccgcgctcg ccgctatggc gccgccacca    360
aggtcgcgga tcccgtcaag acgctcgatc gcgacgccgc ggaaggtggt gggccgtccc    420
cgccggcacc gaggcaggac gccgcccgtc tgccgagtaa gaacggcacg ctgatcaacg    480
gtgagaacaa acctaccggc ggcggtggcg cgactaaaga cagcgggctt gccacacccg    540
cacgcgcgcc ccatctgtca atccaaaaca gagtaccggt gaacggtgaa acaaacata    600
aggtcgcctc gccgccgacc agcatagtgg atgtcgcgtc tccgggttcc gcagctaaca    660
tttccatcag taacaaggtg ccgccgtccg ttgtcccagc caagaagacg ccgccgtcgt    720
ccgttttccc ggccaagaag acgctgccgt cgtccggctc aaattttgtg tcctcggcct    780
ctgctcccag gctggacact gtcagcgatg tggaacttgc acagaagaag gatgcgctga    840
ttgtcaaaga agctccaaaa ccaaaggctc tttcggcccc tgcagccccc gctgtacaag    900
aagacctttg ggatttcaag aaatacattg gtttcgagga gcccgtggag gccaaggatg    960
atggctcggc tgttgcagat gatgcgggtt cctttgaaca tcaccagaat catgattccg    1020
gacctttggc aggggagaac gtcatgaacg tggtcgtcgt tgctgctgaa tgttctccct    1080
ggtgcaaaac aggtggtctt ggagatgttg cgggtgcttt gccaaggct ttggctaaga    1140
gaggacatcg tgttatggtt gtggtaccaa ggtatgggga ctatgaggaa gcctacgatg    1200
tcggagtccg aaaatactac aaggctgctg acaggatat ggaagtgaat tatttccatg    1260
cttatatcga tggagtggat tttgtgttca ttgacgctcc tctcttccga caccgtcagc    1320
aagacattta tggggcagc agacaggaaa ttatgaagcg catgattttg ttctgcaagg    1380
ccgctgtcga ggttccttgg cacgttccat gcggcggtgt cccttacggg gatgaaaatc    1440
tggtcttcat tgcaaatgat tggcacacgg cactcctgcc tgtctatctg aaagcatatt    1500

```
acagggacca tggtttgatg caatacagtc gctccgttat ggtgatacat aacatcgctc    1560
accagggccg tggccctgta gatgaattcc cgttcaccga gttgcctgag cactacctgg    1620
aacacttcag actgtacgac cccgtcggcg gtgagcacgc caactacttc gccgccggcc    1680
tgaagatggc ggaccaggtt gtcgtcgtga gccccgggta cctgtgggag ctgaagacgg    1740
tggagggcgg ctgggggctt cacgacatca tacggcagaa cgactggaag acccgcggca    1800
tcgtgaacgg catcgacaac atggagtgga accctgaggt ggacgtccac ctgaagtcgg    1860
acggctacac caacttctcc ctgaagacgc tggactccgg caagcggcag tgcaaggagg    1920
ccctgcagcg cgagctgggg ctgcaggtcc ggcgacgt gccgctgctc gggttcatcg     1980 gcggctgga cgggcagaag ggcgtggaga tcatcgcgga cgcgatgccc tggatcgtga    2040
gccaggacgt gcagctggtg atgctgggca cggggcgcca cgacctggag agcatgctgc    2100
agcacttcga gcgggagcac cacgacaagg tgcgcgggtg ggtgggttc tccgtgcgcc     2160 tggcgcaccg gatcacggcg ggcgccgacg cgctcctcat gccctccgg ttcgagccgt     2220 gcgggctgaa ccagctctac gcgatggcct acggcaccgt ccccgtcgtg cacgccgtcg    2280
gcggcttgag ggataccgtg ccgccgttcg accccttcaa ccactccggg ctcgggtgga    2340
cgttcgaccg cgccgaggcg cacaagctga tcgaggcgct cgggcactgc tccgcacct     2400 accgggacca caaggagagc tggaggggcc tccaggagcg cggcatgtcg caggacttca    2460
gctgggaaca tgccgccaag ctctacgagg acgtcctcgt ccaggccaag taccagtggt    2520
gaacgctgct acccggtcca gccccgcatg cgtgcatgag aggatggaaa tgcgcattgc    2580
gcacttgcag atttggcgca cgcaggaacg tgccgtcctt cttgatgaga acgccggcat    2640
ccgcgaggtt gagacgctga ttccgatctg gtccgtcgca gagtagagtg aaacgctcct    2700
tgttgcaggt atatgggaat gttttttttc cttttttttt gcgagggagg tatatgggaa    2760
tgttaacttg gtattgtaat gtggtatgct gtgtgcatta ttacatcggt tgttgttgct    2820
tattcttgct agctaagtcg gaggccaaga gcgaaagcta gctcacatgt ctgatgtatg    2880
caagtgacat ggttggtttg aaaaaaaaaa aaaaaaaaa                           2920
```

<210> SEQ ID NO 33
<211> LENGTH: 2946
<212> TYPE: DNA
<213> ORGANISM: Hordeum vulgare

<400> SEQUENCE: 33

```
gtgcgtttac cccacacaga gtacactcca actccagtcc agtccagccc actgccgctt      60
ctgcccgccc atcgtaccgt cgcccgcccc gatcccggcc gccgccatgt cgtcggcggt     120
cgcgtccccc gcgtccttcc tcgcgctcgc gtccgcctcg cccggagat catcacggag      180 gagggcgagg gtgggcgcgt cgccaacccg cgctgggcc ggcaggctgc aatggcggcc     240
gtcgccgctg cagcgcacgg ctcgcgacgg agcgtggcc gcgcgcgccg ccgggatcga     300
cgacgccgcg cccggtaggc agccccgcgc tcgccgctat ggcgccgcca ccaaggtcgc     360 ggatccgtc aagacgctcg atcgcgacgc gcgcggaagt ggtgggccgt ccccgccggc      420
accgaggcag gacgccgccc gtctgccgag taagaacggc acgctgatca acggtgagaa    480
caaacctacc ggcggcggtg gcgcgactaa agacagcggg ctgcccacac ccgcacgcgc    540
gccccatctg tcaatccaga acagagtacc ggtgaacgga gaaacaaac ataaggtcgc     600 ctcgccgccg accagcatag tggatgtcgc gtctccgggt tccgcagcca acatttccat    660
```

-continued

```
cagtaacaag gtgccgccgt ccgttgtccc agccaagaag acgccgccgt cgtccgtttt    720
cccggccaag aaggcgccgc cgtcgtccgt tgtcccggcc aagaagacgc tgccgtcgtc    780
cggctcaaat tttgtgtcct cggcctctgc tcccaggctg acactgtca gcgatgtgga    840
acttgcacag aagaaggatg cgctgattgt caaagaagct ccaaaaccaa aggctctttc    900
ggcccctgca gccccgctg tacaagaaga cctttgggat ttcaagaaat acattggttt    960
cgaggagccc gtggaggcca aggatgatgg ctcggctgtt gcagatgatg cgggttcctt   1020
tgaacatcac cagaatcatg attccggacc tttggcaggg gagaacgtca tgaacgtggt   1080
cgtcgttgct gctgaatgtt ctccctggtg caaaacaggt ggtcttggag atgttgcggg   1140
tgctttgccc aaggctttgg ctaagagagg acatcgtgtt atggttgtgg taccaaggta   1200
tggggactat gaggaagcct acgatgtcgg agtccgaaaa tactacaagg ctgctggaca   1260
ggatatggaa gtgaattatt tccatgctta tatcgatgga gtggatttg tgttcattga   1320
cgctcctctc ttccgacacc gtcagcaaga catttatggg ggcagcagac aggaaattat   1380
gaagcgcatg attttgttct gcaaggccgc tgtcgaggtt ccttggcacg ttccatgcgg   1440
cggtgtccct tacggggatg gaaatctggt cttcattgca aatgattggc acacggcact   1500
cctgcctgtc tatctgaaag catattacag ggaccatggt tgatgcaat acagtcgctc   1560
cgttatggtg atacataaca tcgctcacca gggccgtggc cctgtagatg aattcccgtt   1620
caccgagttg cctgagcact acctggaaca cttcagactg tacgaccccg tcggcggtga   1680
gcacgccaac tacttcgccg ccggcctgaa gatggcggac caggttgtcg tcgtgagccc   1740
cgggtacctg tgggagctga agacggtgga gggcggctgg gggcttcacg acatcatacg   1800
gcagaacgac tggaagaccc gcggcatcgt gaacggcatc gacaacatgg agtgaaaccc   1860
tgaggtggac gtccacctga agtcggacgg ctacaccaac ttctccctga agacgctgga   1920
ctccggcaag cggcagtgca aggaggccct gcagcgcgag ctggggctgc aggtccgcgg   1980
cgacgtgccg ctgctcgggt tcatcgggcg gctggacggg cagaagggcg tggagatcat   2040
cgcggacgcg atgccctgga tcgtgagcca ggacgtgcag ctggtgatgc tgggcacggg   2100
gcgccacgac ctggagagca tgctgcagca cttcagcgg gagcaccacg acaaggtgcg   2160
cgggtgggtg gggttctccg tgcgcctggc gcaccggatc acggcgggcg ccgacgcgct   2220
cctcatgccc tccggttcg agccgtgcgg gctgaaccag ctctacgcga tggcctacgg   2280
caccatccct gtcgtgcacg ccgtcggcgg cctgagggat accgtgccgc cgttcgaccc   2340
cttcaaccac tccgggctcg ggtggacgtt cgaccgcgcc gaggcgcaca agctgatcga   2400
ggcgctcggg cactgcctcc gcacctaccg ggaccacaag gagagctgga ggggcctcca   2460
ggagcgcggc atgtcgcagg acttcagctg gaacatgcc gccaagctct acgaggacgt   2520
cctcgtccag gccaagtacc agtggtgaac gctgctaccc ggtccagccc cgcatgcgtg   2580
catgagagga tggaaatgcg cattgcgcac ttgcagattt ggcgcacgca ggaacgtgcc   2640
gtccttcttg atgagaacgc cggcatccgc gaggttgaga cgctgattcc gatctggtcc   2700
gtcgcagagt agagtgaaac gctccttgtt gcaggtatat gggaatgttt ttttccttt   2760
ttttttgcga gggaggtata tgggaatgtt aacttggtat tgtaatgtgg tatgctgtgt   2820
gcattattac atcggttgtt gttgcttatt cttgctagct aagtcggagg ccaagagcga   2880
aagctagctc acatgtctga tgtatgcaag tgacatggtt ggtttggttg tgcagtgcaa   2940
acggca                                                              2946
```

-continued

```
<210> SEQ ID NO 34
<211> LENGTH: 11
<212> TYPE: PRT
<213> ORGANISM: Triticum aestivum

<400> SEQUENCE: 34

Lys Val Gly Gly Leu Gly Asp Val Val Thr Ser
1               5                   10

<210> SEQ ID NO 35
<211> LENGTH: 11
<212> TYPE: PRT
<213> ORGANISM: Triticum aestivum

<400> SEQUENCE: 35

Gly His Thr Val Glu Val Ile Leu Pro Lys Tyr
1               5                   10

<210> SEQ ID NO 36
<211> LENGTH: 16
<212> TYPE: PRT
<213> ORGANISM: Triticum aestivum

<400> SEQUENCE: 36

His Asp Trp Ser Ser Ala Pro Val Ala Trp Leu Tyr Lys Glu His Tyr
1               5                   10                  15

<210> SEQ ID NO 37
<211> LENGTH: 16
<212> TYPE: PRT
<213> ORGANISM: Triticum aestivum

<400> SEQUENCE: 37

Gly Ile Leu Asn Gly Ile Asp Pro Asp Ile Trp Asp Pro Tyr Thr Asp
1               5                   10                  15

<210> SEQ ID NO 38
<211> LENGTH: 16
<212> TYPE: PRT
<213> ORGANISM: Triticum aestivum

<400> SEQUENCE: 38

Asp Val Pro Ile Val Gly Ile Ile Thr Arg Leu Thr Ala Gln Lys Gly
1               5                   10                  15

<210> SEQ ID NO 39
<211> LENGTH: 10
<212> TYPE: PRT
<213> ORGANISM: Triticum aestivum

<400> SEQUENCE: 39

Asn Gly Gln Val Val Leu Leu Gly Ser Ala
1               5                   10

<210> SEQ ID NO 40
<211> LENGTH: 27
<212> TYPE: PRT
<213> ORGANISM: Triticum aestivum

<400> SEQUENCE: 40

Ala Gly Ser Asp Phe Ile Ile Val Pro Ser Ile Phe Glu Pro Cys Gly
1               5                   10                  15

Leu Thr Gln Leu Val Ala Met Arg Tyr Gly Ser
            20                  25
```

```
<210> SEQ ID NO 41
<211> LENGTH: 8
<212> TYPE: PRT
<213> ORGANISM: Triticum aestivum

<400> SEQUENCE: 41

Thr Gly Gly Leu Val Asp Thr Val
1               5

<210> SEQ ID NO 42
<211> LENGTH: 23
<212> TYPE: DNA
<213> ORGANISM: Hordeum vulgare

<400> SEQUENCE: 42
cttctgacct catctaagca agg                                           23

<210> SEQ ID NO 43
<211> LENGTH: 23
<212> TYPE: DNA
<213> ORGANISM: Hordeum vulgare

<400> SEQUENCE: 43
ctggtctttg gctgccatat agc                                           23

<210> SEQ ID NO 44
<211> LENGTH: 23
<212> TYPE: DNA
<213> ORGANISM: Hordeum vulgare

<400> SEQUENCE: 44
tctcaatgtc tcttgcacag tcc                                           23

<210> SEQ ID NO 45
<211> LENGTH: 23
<212> TYPE: DNA
<213> ORGANISM: Hordeum vulgare

<400> SEQUENCE: 45
gcatttgagc tggatttgcc agc                                           23

<210> SEQ ID NO 46
<211> LENGTH: 23
<212> TYPE: DNA
<213> ORGANISM: Hordeum vulgare

<400> SEQUENCE: 46
tcctgacgaa tccatctcaa acc                                           23

<210> SEQ ID NO 47
<211> LENGTH: 25
<212> TYPE: DNA
<213> ORGANISM: Hordeum vulgare

<400> SEQUENCE: 47
gcagttgatg aagctgggaa tgatc                                         25

<210> SEQ ID NO 48
<211> LENGTH: 23
<212> TYPE: DNA
<213> ORGANISM: Hordeum vulgare

<400> SEQUENCE: 48
```
tctccctcct taagttccag tcc                                               23

<210> SEQ ID NO 49
<211> LENGTH: 23
<212> TYPE: DNA
<213> ORGANISM: Hordeum vulgare

<400> SEQUENCE: 49
ggatctttcg gctgttgatc tcc                                               23

<210> SEQ ID NO 50
<211> LENGTH: 23
<212> TYPE: DNA
<213> ORGANISM: Hordeum vulgare

<400> SEQUENCE: 50
gccattgttc tcatagaccg tgc                                               23

<210> SEQ ID NO 51
<211> LENGTH: 23
<212> TYPE: DNA
<213> ORGANISM: Hordeum vulgare

<400> SEQUENCE: 51
atcgtgacct aacagctttg gcg                                               23

<210> SEQ ID NO 52
<211> LENGTH: 22
<212> TYPE: DNA
<213> ORGANISM: Hordeum vulgare

<400> SEQUENCE: 52
tctgcatacc accaatcgcc gt                                                22

<210> SEQ ID NO 53
<211> LENGTH: 23
<212> TYPE: DNA
<213> ORGANISM: Hordeum vulgare

<400> SEQUENCE: 53
gttgagtttg gccagaacat gtg                                               23

<210> SEQ ID NO 54
<211> LENGTH: 25
<212> TYPE: DNA
<213> ORGANISM: Hordeum vulgare

<400> SEQUENCE: 54
gtgccatcac tcaactgatt agaac                                             25

<210> SEQ ID NO 55
<211> LENGTH: 23
<212> TYPE: DNA
<213> ORGANISM: Hordeum vulgare

<400> SEQUENCE: 55
aaaggcactt gtgttggact ggg                                               23

<210> SEQ ID NO 56
<211> LENGTH: 23
<212> TYPE: DNA
<213> ORGANISM: Hordeum vulgare

<400> SEQUENCE: 56
cagtgatgta agaacgcaag ctc                                        23

<210> SEQ ID NO 57
<211> LENGTH: 23
<212> TYPE: DNA
<213> ORGANISM: Hordeum vulgare

<400> SEQUENCE: 57
cttctgacct catctaagca agg                                        23

<210> SEQ ID NO 58
<211> LENGTH: 25
<212> TYPE: DNA
<213> ORGANISM: Hordeum vulgare

<400> SEQUENCE: 58
ctcgacggca atatggataa tacgc                                      25

<210> SEQ ID NO 59
<211> LENGTH: 23
<212> TYPE: DNA
<213> ORGANISM: Hordeum vulgare

<400> SEQUENCE: 59
tctccgagtc ggatgaaaat ggg                                        23

<210> SEQ ID NO 60
<211> LENGTH: 23
<212> TYPE: DNA
<213> ORGANISM: Hordeum vulgare

<400> SEQUENCE: 60
taaaccagta caaggctcta gcc                                        23

<210> SEQ ID NO 61
<211> LENGTH: 25
<212> TYPE: DNA
<213> ORGANISM: Hordeum vulgare

<400> SEQUENCE: 61
caaagttttt cttggagtgg cacag                                      25

<210> SEQ ID NO 62
<211> LENGTH: 23
<212> TYPE: DNA
<213> ORGANISM: Hordeum vulgare

<400> SEQUENCE: 62
cagaagaacc caaatctgcg gtc                                        23

<210> SEQ ID NO 63
<211> LENGTH: 23
<212> TYPE: DNA
<213> ORGANISM: Hordeum vulgare

<400> SEQUENCE: 63
taggatgttt ggcgtcggat gtg                                        23

<210> SEQ ID NO 64
<211> LENGTH: 23
<212> TYPE: DNA
<213> ORGANISM: Hordeum vulgare

```
<400> SEQUENCE: 64
gtgtacggat cccagatatc tgg                                            23

<210> SEQ ID NO 65
<211> LENGTH: 22
<212> TYPE: DNA
<213> ORGANISM: Hordeum vulgare

<400> SEQUENCE: 65
cgccattgct cctcatcgtg ac                                             22

<210> SEQ ID NO 66
<211> LENGTH: 24
<212> TYPE: DNA
<213> ORGANISM: Hordeum vulgare

<400> SEQUENCE: 66
cttcacccta ccgtggtaaa cacc                                           24

<210> SEQ ID NO 67
<211> LENGTH: 24
<212> TYPE: DNA
<213> ORGANISM: Hordeum vulgare

<400> SEQUENCE: 67
tggattttag gtggttttgc ttgg                                           24

<210> SEQ ID NO 68
<211> LENGTH: 22
<212> TYPE: DNA
<213> ORGANISM: Hordeum vulgare

<400> SEQUENCE: 68
ctccatgacc ctcttacaca gg                                             22

<210> SEQ ID NO 69
<211> LENGTH: 23
<212> TYPE: DNA
<213> ORGANISM: Hordeum vulgare

<400> SEQUENCE: 69
gctctgtctc ttggtcttga acc                                            23

<210> SEQ ID NO 70
<211> LENGTH: 27
<212> TYPE: DNA
<213> ORGANISM: Hordeum vulgare

<400> SEQUENCE: 70
ccacaaatgt aaatatcatt gatgtat                                        27

<210> SEQ ID NO 71
<211> LENGTH: 1593
<212> TYPE: PRT
<213> ORGANISM: Hordeum vulgare

<400> SEQUENCE: 71

Met Glu Met Ser Leu Trp Pro Arg Ser Pro Leu Cys Pro Arg Gly Arg
1               5                   10                  15

Gln Pro Leu Val Val Val Cys Pro Ala Gly Leu Ala Gln Pro Phe
            20                  25                  30

Trp Met Asn Gly Arg Phe Thr Arg Ser Arg Thr Val Arg Cys Met Val
```

```
                35                  40                  45
Ala Ser Ser Asp Ser Pro Asn Arg Lys Ser Arg Leu Val Ser Pro
 50                  55                  60
Gln Val Lys Val Ile Ser Arg Gly Tyr Thr Thr Arg Leu Ile Val
 65                  70                  75                  80
Glu Pro Ser Thr Glu Asn Thr Glu His Asn Asn Gly Asp Glu Ile
                 85                  90                  95
Leu Asp Thr Tyr Asn Ala Leu Leu His Thr Glu Ala Ala Glu Trp Thr
                100                 105                 110
Asp Thr Arg Glu Ala Glu Thr Ala Glu Ala Asp Ser Ser Gln Asn Ala
                115                 120                 125
Ser Ser Ser Ile Ile Arg Glu Leu Asp Ala Ala Asp Glu Asp Ile
130                 135                 140
Leu Ala Val Asp Leu Thr Val Asn Ala Leu Ser Ser Val Thr Lys Arg
145                 150                 155                 160
Glu Val Asp Ala Ala Asp Lys Ala Arg Val Glu Glu Asp Val Phe Glu
                165                 170                 175
Leu Asp Leu Pro Ala Thr Thr Leu Arg Ser Val Ile Val Asp Val Ile
                180                 185                 190
Asp Asp Asn Gly Thr Val Gln Glu Thr Leu Arg Ser Val Ile Val Asp
                195                 200                 205
Val Thr Asp Asp Val Ala Asp Lys Ala Arg Val Glu Glu Asp Ile Phe
210                 215                 220
Glu Leu Asp Phe Ser Gly Asn Val Ser Ser Ala Thr Thr Val Glu
225                 230                 235                 240
Leu Asp Ala Val Asp Glu Val Gly Pro Val Gln Asp Thr Phe Glu Ala
                245                 250                 255
Ser Leu Ser Gly Asn Val Ser Asn Ser Ala Thr Val Gln Glu Val Asp
                260                 265                 270
Ala Val Asp Glu Ala Gly Asn Asp Gln Asp Ile Phe Lys Ala Asp Leu
                275                 280                 285
Ser Gly Asn Ile Phe Ser Ser Thr Thr Val Glu Val Gly Val Val
290                 295                 300
Asp Glu Ala Gly Ser Thr Lys Asp Arg Phe Glu Met Asp Ser Ser Gly
305                 310                 315                 320
Asn Val Ser Thr Ser Ala Thr Met Trp Asp Ala Ile Asp Glu Ala Val
                325                 330                 335
Ala Asp Gln Asp Ala Val Glu Ala Asp Leu Ser Gly Asn Ala Ser Ser
                340                 345                 350
Trp Ala Thr Tyr Arg Glu Leu Asp Asp Val Val Asp Glu Asn Arg Ser
                355                 360                 365
Glu Glu Glu Thr Phe Val Met Asp Leu Val Gly Glu Ala Thr Asp Glu
                370                 375                 380
Glu Glu Asn Tyr Gln Gln Gln Tyr Pro Val Pro Ser Ser Phe Ser Met
385                 390                 395                 400
Trp Asp Lys Ala Ile Ala Lys Thr Gly Val Ser Leu Asn Pro Glu Pro
                405                 410                 415
Arg Leu Thr Ser Val Gln Glu Gln Gly Lys Val Asn Phe Ser Asp Lys
                420                 425                 430
Gln Asp Leu Ser Ile Ala Asp Leu Pro Gly Gln Asn Gln Ser Ile Val
                435                 440                 445
Gly Ser Cys Lys Gln Asp Lys Ser Ile Ala Asp Val Ala Gly Pro Pro
                450                 455                 460
```

-continued

```
Gln Ser Ile Phe Gly Ser Ser Lys Gln His Arg Pro Ile Val Ala Phe
465                 470                 475                 480

Arg Lys Gln Asn His Ser Ile Val Ser Asp Pro Lys Gln Lys Gln Ser
                485                 490                 495

Ile Val Gly Phe Arg Ser Gln Asp Leu Ser Ala Val Asp Leu Pro Lys
            500                 505                 510

Gln Asn Ile Pro Ile Val Gly Thr Ser Ser Glu Gly Gln Thr Lys Gln
        515                 520                 525

Val Pro Val Val Asp Arg Gln Asp Ala Leu Tyr Val Asn Gly Leu Glu
    530                 535                 540

Leu Lys Glu Gly Asp His Arg Ser Glu Lys Thr Asp Glu Asp Val Leu
545                 550                 555                 560

His Val Lys Phe Asn Ile Asp Asn Val Leu Gln Lys His Leu Ala Asp
                565                 570                 575

Arg Thr Gln Ala Val Glu Thr Thr Ile Trp Lys Val Asp Glu Glu
            580                 585                 590

His Leu Tyr Met Thr Glu His Gln Ile Gly Ser Thr Glu Gly His Met
            595                 600                 605

Val Leu Asn Glu Asp Glu Leu Ser Ile Thr Glu Ile Gly Met Gly Ser
        610                 615                 620

Gly Asp Lys Ile Gln His Ala Leu Ser Glu Glu Leu Ser Trp Ser
625                 630                 635                 640

Glu Asp Glu Val Gln Leu Asn Lys Asp Asp Gly Gln Tyr Glu Val Asp
                645                 650                 655

Glu Thr Ser Ala Ser Phe Thr Val Gln Asp Ile Gln Gly Pro Pro
            660                 665                 670

Gln Asp Val Val Asp Pro Gln Ala Leu Arg Ala Met Leu Gln Glu Leu
        675                 680                 685

Ala Asp Lys Asn Tyr Ser Met Arg Asn Lys Leu Phe Val Phe Pro Glu
    690                 695                 700

Val Val Lys Ala Asp Ser Val Ile Asp Leu Tyr Leu Asn Arg Asp Leu
705                 710                 715                 720

Thr Ala Leu Ala Asn Glu Pro Asp Val Val Ile Lys Gly Ala Phe Asn
                725                 730                 735

Gly Trp Lys Trp Lys Leu Phe Ser Glu Arg Leu His Lys Ser Asp Leu
            740                 745                 750

Gly Gly Val Trp Trp Ser Cys Lys Leu His Ile Pro Lys Glu Ala Tyr
        755                 760                 765

Arg Leu Asp Phe Val Phe Asn Gly Arg Thr Val Tyr Glu Asn Asn
    770                 775                 780

Gly Asn Asn Asp Phe Cys Ile Gly Ile Glu Gly Thr Met Asn Glu Asp
785                 790                 795                 800

Leu Phe Glu Asp Phe Leu Val Lys Glu Lys Gln Arg Glu Leu Glu Lys
                805                 810                 815

Leu Ala Met Glu Glu Ala Glu Arg Thr Gln Thr Asp Glu Gln Arg
            820                 825                 830

Arg Arg Lys Glu Ala Arg Ala Ala Asp Glu Ala Val Arg Ala Gln Ala
        835                 840                 845

Lys Ala Glu Ile Glu Ile Lys Lys Asn Lys Leu His Ser Met Leu Ser
    850                 855                 860

Leu Ala Arg Thr Cys Asp Asp Asn Leu Trp Tyr Ile Glu Ala Ser Thr
865                 870                 875                 880
```

```
Asp Thr Arg Gly Asp Thr Ile Arg Leu Tyr Tyr Asn Arg Asn Ser Arg
                885                 890                 895

Pro Leu Ala His Ser Thr Glu Ile Trp Met His Gly Tyr Asn Asn
        900                 905                 910

Trp Thr Asp Gly Leu Ser Ile Val Glu Ser Phe Val Lys Cys Asn Asp
        915                 920                 925

Glu Asp Gly Asp Trp Trp Tyr Ala Asp Val Ile Leu Pro Glu Lys Ala
930                 935                 940

Leu Val Leu Asp Trp Val Phe Ala Asp Gly Pro Ala Gly Asn Ala Arg
945                 950                 955                 960

Asn Tyr Asp Asn Asn Ser Arg Lys Asp Phe His Ala Ile Ile Pro Asn
                965                 970                 975

Lys Asn Val Thr Lys Lys Gly Phe Trp Val Gln Glu Glu Gln Asn Ile
        980                 985                 990

Tyr Thr Arg Leu Leu Gln Glu Arg  Arg Glu Lys Glu Glu  Ile Met Arg
        995                 1000                1005

Arg Lys  Ala Glu Arg Ser Ala  Asn Met Lys Ala Glu  Met Lys Ala
    1010                1015                1020

Lys Thr  Met Arg Arg Phe Leu  Leu Ser Gln Lys His  Ile Val Tyr
    1025                1030                1035

Thr Glu  Pro Leu Glu Val Arg  Ala Gly Thr Ala Val  Asp Val Leu
    1040                1045                1050

Tyr Asn  Pro Ser Asn Thr Val  Leu Asn Gly Lys Thr  Glu Val Trp
    1055                1060                1065

Phe Arg  Cys Ser Phe Asn Leu  Trp Met His Pro Ser  Gly Ala Leu
    1070                1075                1080

Pro Pro  Gln Lys Met Val Lys  Ser Gly Asp Gly Ser  Leu Leu Lys
    1085                1090                1095

Ala Thr  Val Asn Val Pro Pro  Asp Ala Tyr Met Met  Asp Phe Val
    1100                1105                1110

Phe Ser  Glu Ser Asp Glu Asn  Gly Ile Tyr Asp Asn  Arg Asn Gly
    1115                1120                1125

Met Asp  Tyr His Ile Pro Val  Ser Asp Ser Ile Glu  Thr Glu Asn
    1130                1135                1140

Tyr Met  Arg Ile Ile His Ile  Ala Val Glu Met Ala  Pro Val Ala
    1145                1150                1155

Lys Val  Gly Gly Leu Gly Asp  Val Val Thr Ser Leu  Ser Arg Ala
    1160                1165                1170

Val Gln  Asp Leu Gly His Thr  Val Glu Val Ile Leu  Pro Lys Tyr
    1175                1180                1185

Asp Cys  Leu Asn Gln Ser Ser  Val Lys Asp Leu His  Leu Tyr Gln
    1190                1195                1200

Ser Phe  Ser Trp Ser Gly Thr  Glu Ile Lys Val Trp  Val Gly Gln
    1205                1210                1215

Val Glu  Asn Leu Thr Val Tyr  Phe Leu Glu Pro Gln  Asn Gly Met
    1220                1225                1230

Phe Gly  Val Gly Cys Val Tyr  Gly Arg Asn Asp Asp  Arg Arg Phe
    1235                1240                1245

Gly Phe  Phe Cys His Ser Ala  Leu Glu Phe Ile Leu  Gln Asn Gly
    1250                1255                1260

Leu Ser  Pro His Ile Ile His  Cys His Asp Trp Ser  Ser Ala Pro
    1265                1270                1275

Val Ala  Trp Leu Tyr Lys Glu  His Tyr Ser Gln Ser  Arg Met Ala
```

```
                1280                1285                1290
Ser Thr Arg Val Val Phe Thr Ile His Asn Leu Glu Phe Gly Ala
    1295                1300                1305

His Tyr Ile Gly Lys Ala Met Thr Tyr Cys Asp Lys Ala Thr Thr
    1310                1315                1320

Val Ser Pro Thr Tyr Ser Arg Glu Val Ala Gly His Gly Ala Ile
    1325                1330                1335

Ala Pro His Arg Glu Lys Phe Tyr Gly Ile Leu Asn Gly Ile Asp
    1340                1345                1350

Pro Asp Ile Trp Asp Pro Tyr Thr Asp Asn Phe Ile Pro Val Pro
    1355                1360                1365

Tyr Thr Tyr Glu Asn Val Val Glu Gly Lys Ser Ala Ala Lys Arg
    1370                1375                1380

Ala Leu Gln Gln Lys Phe Gly Leu Gln Gln Thr Asp Val Pro Val
    1385                1390                1395

Val Gly Ile Ile Thr Arg Leu Thr Ala Gln Lys Gly Ile His Leu
    1400                1405                1410

Ile Lys His Ala Ile His Gln Thr Leu Glu Ser Asn Gly Gln Val
    1415                1420                1425

Val Leu Leu Gly Ser Ala Pro Asp His Arg Ile Gln Gly Asp Phe
    1430                1435                1440

Cys Arg Leu Ala Asp Ala Leu His Gly Val Tyr His Gly Arg Val
    1445                1450                1455

Lys Leu Val Leu Thr Tyr Asp Glu Pro Leu Ser His Leu Ile Tyr
    1460                1465                1470

Ala Gly Ser Asp Phe Ile Arg Val Pro Ser Ile Phe Glu Pro Cys
    1475                1480                1485

Gly Leu Thr Gln Leu Val Ala Met Arg Tyr Gly Ser Ile Pro Ile
    1490                1495                1500

Val Arg Lys Thr Gly Gly Leu His Asp Thr Val Phe Asp Val Asp
    1505                1510                1515

Asn Asp Lys Glu Arg Ala Arg Ser Leu Gly Leu Glu Pro Asn Gly
    1520                1525                1530

Phe Ser Phe Asp Gly Ala Asp Ser Asn Gly Val Asp Tyr Ala Leu
    1535                1540                1545

Asn Arg Ala Ile Ala Ala Trp Phe Asp Ala Arg Asp Trp Phe His
    1550                1555                1560

Ser Leu Cys Lys Arg Val Met Glu Gln Asp Trp Ser Trp Asn Arg
    1565                1570                1575

Pro Ala Leu Asp Tyr Ile Glu Leu Tyr His Ala Ala Arg Lys Phe
    1580                1585                1590

<210> SEQ ID NO 72
<211> LENGTH: 1593
<212> TYPE: PRT
<213> ORGANISM: Hordeum vulgare

<400> SEQUENCE: 72

Met Glu Met Ser Leu Trp Pro Arg Ser Pro Leu Cys Pro Arg Gly Arg
1               5                   10                  15

Gln Pro Leu Val Val Val Cys Pro Ala Gly Leu Ala Gln Pro Phe
                20                  25                  30

Trp Met Asn Gly Arg Phe Thr Ser Arg Thr Val Arg Cys Met Val
            35                  40                  45
```

```
Ala Ser Ser Asp Ser Pro Asn Arg Lys Ser Arg Arg Leu Val Ser Pro
    50                  55                  60
Gln Val Lys Val Ile Ser Ser Arg Gly Tyr Thr Thr Arg Leu Ile Val
 65                  70                  75                  80
Glu Pro Ser Thr Glu Asn Thr Glu His Asn Asn Gly Asp Glu Ile
                 85                  90                  95
Leu Asp Thr Tyr Asn Ala Leu Leu His Thr Glu Ala Ala Glu Trp Thr
                100                 105                 110
Asp Thr Arg Glu Ala Glu Thr Ala Glu Ala Asp Ser Ser Gln Asn Ala
            115                 120                 125
Ser Ser Ser Ser Ile Ile Arg Glu Leu Asp Ala Ala Asp Glu Asp Ile
130                 135                 140
Leu Ala Val Asp Leu Thr Val Asn Ala Leu Ser Ser Val Thr Lys Arg
145                 150                 155                 160
Glu Val Asp Ala Ala Asp Lys Ala Arg Val Glu Glu Asp Val Phe Glu
                165                 170                 175
Leu Asp Leu Pro Ala Thr Thr Leu Arg Ser Val Ile Val Asp Val Ile
                180                 185                 190
Asp Asp Asn Gly Thr Val Gln Glu Thr Leu Arg Ser Val Ile Val Asp
            195                 200                 205
Val Thr Asp Asp Val Ala Asp Lys Ala Arg Val Glu Glu Asp Ile Phe
210                 215                 220
Glu Leu Asp Phe Ser Gly Asn Val Ser Ser Ser Ala Thr Thr Val Glu
225                 230                 235                 240
Leu Asp Ala Val Asp Glu Val Gly Pro Val Gln Asp Thr Phe Glu Ala
                245                 250                 255
Ser Leu Ser Gly Asn Val Ser Asn Ser Ala Thr Val Gln Glu Val Asp
                260                 265                 270
Ala Val Asp Glu Ala Gly Asn Asp Gln Asp Ile Phe Lys Ala Asp Leu
            275                 280                 285
Ser Gly Asn Ile Phe Ser Ser Thr Thr Val Glu Val Gly Val Val
290                 295                 300
Asp Glu Ala Gly Ser Thr Lys Asp Arg Phe Glu Met Asp Ser Ser Gly
305                 310                 315                 320
Asn Val Ser Thr Ser Ala Thr Met Trp Asp Ala Ile Asp Glu Ala Val
                325                 330                 335
Ala Asp Gln Asp Ala Val Glu Ala Asp Leu Ser Gly Asn Ala Ser Ser
                340                 345                 350
Trp Ala Thr Tyr Arg Glu Leu Asp Asp Val Val Asp Glu Asn Arg Ser
            355                 360                 365
Glu Glu Glu Thr Phe Val Met Asp Leu Val Gly Glu Ala Thr Asp Glu
370                 375                 380
Glu Glu Asn Tyr Gln Gln Gln Tyr Pro Val Pro Ser Ser Phe Ser Met
385                 390                 395                 400
Trp Asp Lys Ala Ile Ala Lys Thr Gly Val Ser Leu Asn Pro Glu Pro
                405                 410                 415
Arg Leu Thr Ser Val Gln Glu Gln Gly Lys Val Asn Phe Ser Asp Lys
                420                 425                 430
Gln Asp Leu Ser Ile Ala Asp Leu Pro Gly Gln Asn Gln Ser Ile Val
            435                 440                 445
Gly Ser Cys Lys Gln Asp Lys Ser Ile Ala Asp Val Ala Gly Pro Pro
450                 455                 460
Gln Ser Ile Phe Gly Ser Ser Lys Gln His Arg Pro Ile Val Ala Phe
```

-continued

```
                465                 470                 475                 480
            Arg Lys Gln Asn His Ser Ile Val Ser Asp Pro Lys Gln Lys Gln Ser
                            485                 490                 495
            Ile Val Gly Phe Arg Ser Gln Asp Leu Ser Ala Val Asp Leu Pro Lys
                            500                 505                 510
            Gln Asn Ile Pro Ile Val Gly Thr Ser Ser Glu Gly Gln Thr Lys Gln
                            515                 520                 525
            Val Pro Val Asp Arg Gln Asp Ala Leu Tyr Val Asn Gly Leu Glu
                            530                 535                 540
            Leu Lys Glu Gly Asp His Arg Ser Glu Lys Thr Asp Glu Asp Val Leu
            545                 550                 555                 560
            His Val Lys Phe Asn Ile Asp Asn Val Leu Gln Lys His Leu Ala Asp
                            565                 570                 575
            Arg Thr Gln Ala Val Glu Thr Thr Ile Trp Lys Glu Val Asp Glu Glu
                            580                 585                 590
            His Leu Tyr Met Thr Glu His Gln Ile Gly Ser Thr Glu Gly His Met
                            595                 600                 605
            Val Leu Asn Glu Asp Glu Leu Ser Ile Thr Glu Ile Gly Met Gly Ser
                            610                 615                 620
            Gly Asp Lys Ile Gln His Ala Leu Ser Glu Glu Leu Ser Trp Ser
            625                 630                 635                 640
            Glu Asp Glu Val Gln Leu Asn Lys Asp Asp Gly Gln Tyr Glu Val Asp
                            645                 650                 655
            Glu Thr Ser Ala Ser Phe Thr Val Glu Gln Asp Ile Gln Gly Pro Pro
                            660                 665                 670
            Gln Asp Val Val Asp Pro Gln Ala Leu Arg Ala Met Leu Gln Glu Leu
                            675                 680                 685
            Ala Asp Lys Asn Tyr Ser Met Arg Asn Lys Leu Phe Val Phe Pro Glu
                            690                 695                 700
            Val Val Lys Ala Asp Ser Val Ile Asp Leu Tyr Leu Asn Arg Asp Leu
            705                 710                 715                 720
            Thr Ala Leu Ala Asn Glu Pro Asp Val Val Ile Lys Gly Ala Phe Asn
                            725                 730                 735
            Gly Trp Lys Trp Lys Leu Phe Ser Glu Arg Leu His Lys Ser Asp Leu
                            740                 745                 750
            Gly Gly Val Trp Trp Ser Cys Lys Leu His Ile Pro Lys Glu Ala Tyr
                            755                 760                 765
            Arg Leu Asp Phe Val Phe Phe Asn Gly Arg Thr Val Tyr Glu Asn Asn
                            770                 775                 780
            Gly Asn Asn Asp Phe Cys Ile Gly Ile Glu Gly Thr Met Asn Glu Asp
            785                 790                 795                 800
            Leu Phe Glu Asp Phe Leu Val Lys Glu Lys Gln Arg Glu Leu Glu Lys
                            805                 810                 815
            Leu Ala Met Glu Glu Ala Glu Arg Arg Thr Gln Thr Asp Glu Gln Arg
                            820                 825                 830
            Arg Arg Lys Glu Ala Arg Ala Ala Asp Glu Ala Val Arg Ala Gln Ala
                            835                 840                 845
            Lys Ala Glu Ile Glu Ile Lys Lys Asn Lys Leu His Ser Met Leu Ser
                            850                 855                 860
            Leu Ala Arg Thr Cys Asp Asp Asn Leu Trp Tyr Ile Glu Ala Ser Thr
            865                 870                 875                 880
            Asp Thr Arg Gly Asp Thr Ile Arg Leu Tyr Tyr Asn Arg Asn Ser Arg
                            885                 890                 895
```

```
Pro Leu Ala His Ser Thr Glu Ile Trp Met His Gly Gly Tyr Asn Asn
            900                 905                 910

Trp Thr Asp Gly Leu Ser Ile Val Glu Ser Phe Val Lys Cys Asn Asp
        915                 920                 925

Glu Asp Gly Asp Trp Trp Tyr Ala Asp Val Ile Leu Pro Glu Lys Ala
    930                 935                 940

Leu Val Leu Asp Trp Val Phe Ala Asp Gly Pro Ala Gly Asn Ala Arg
945                 950                 955                 960

Asn Tyr Asp Asn Asn Ser Arg Lys Asp Phe His Ala Ile Ile Pro Asn
            965                 970                 975

Lys Asn Val Thr Lys Lys Gly Phe Trp Val Gln Glu Glu Gln Asn Ile
        980                 985                 990

Tyr Thr Arg Leu Leu Gln Glu Arg  Arg Glu Lys Glu Glu  Ile Met Arg
            995                1000                1005

Arg Lys  Ala Glu Arg Ser Ala  Asn Met Lys Ala Glu  Met Lys Ala
    1010                1015                1020

Lys Thr  Met Arg Arg Phe Leu  Leu Ser Gln Lys His  Ile Val Tyr
    1025                1030                1035

Thr Glu  Pro Leu Glu Val Arg  Ala Gly Thr Ala Val  Asp Val Leu
    1040                1045                1050

Tyr Asn  Pro Ser Asn Thr Val  Leu Asn Gly Lys Thr  Glu Val Trp
    1055                1060                1065

Phe Arg  Cys Ser Phe Asn Leu  Trp Met His Pro Ser  Gly Ala Leu
    1070                1075                1080

Pro Pro  Gln Lys Met Val Lys  Ser Gly Asp Gly Ser  Leu Leu Lys
    1085                1090                1095

Ala Thr  Val Asn Val Pro Pro  Asp Ala Tyr Met Met  Asp Phe Val
    1100                1105                1110

Phe Ser  Glu Ser Asp Glu Asn  Gly Ile Tyr Asp Asn  Arg Asn Gly
    1115                1120                1125

Met Asp  Tyr His Ile Pro Val  Ser Asp Ser Ile Glu  Thr Glu Asn
    1130                1135                1140

Tyr Met  Arg Ile Ile His Ile  Ala Val Glu Met Ala  Pro Val Ala
    1145                1150                1155

Lys Val  Gly Gly Leu Gly Asp  Val Val Thr Ser Leu  Ser Arg Ala
    1160                1165                1170

Val Gln  Asp Leu Gly His Thr  Val Glu Val Ile Leu  Pro Lys Tyr
    1175                1180                1185

Asp Cys  Leu Asn Gln Ser Ser  Val Lys Asp Leu His  Leu Tyr Gln
    1190                1195                1200

Ser Phe  Ser Trp Ser Gly Thr  Glu Ile Lys Val Trp  Val Gly Gln
    1205                1210                1215

Val Glu  Asn Leu Thr Val Tyr  Phe Leu Glu Pro Gln  Asn Gly Met
    1220                1225                1230

Phe Gly  Val Gly Cys Val Tyr  Gly Arg Asn Asp Asp  Arg Arg Phe
    1235                1240                1245

Gly Phe  Phe Cys His Ser Ala  Leu Glu Phe Ile Leu  Gln Asn Gly
    1250                1255                1260

Leu Ser  Pro His Ile Ile His  Cys His Asp Trp Ser  Ser Ala Pro
    1265                1270                1275

Val Ala  Trp Leu Tyr Lys Glu  His Tyr Ser Gln Ser  Arg Met Ala
    1280                1285                1290
```

-continued

| | | | | | | | | | | | |
|---|---|---|---|---|---|---|---|---|---|---|---|
| Ser | Thr 1295 | Arg | Val | Val | Phe | Thr 1300 | Ile | His | Asn | Leu | Glu 1305 | Phe | Gly | Ala |
| His | Tyr 1310 | Ile | Gly | Lys | Ala | Met 1315 | Thr | Tyr | Cys | Asp | Lys 1320 | Ala | Thr | Thr |
| Val | Ser 1325 | Pro | Thr | Tyr | Ser | Arg 1330 | Glu | Val | Ala | Gly | His 1335 | Gly | Ala | Ile |
| Ala | Pro 1340 | His | Arg | Glu | Lys | Phe 1345 | Tyr | Gly | Ile | Leu | Asn 1350 | Gly | Ile | Asp |
| Pro | Asp 1355 | Ile | Trp | Asp | Pro | Tyr 1360 | Thr | Asp | Asn | Phe | Ile 1365 | Pro | Val | Pro |
| Tyr | Thr 1370 | Tyr | Glu | Asn | Val | Val 1375 | Glu | Gly | Lys | Ser | Ala 1380 | Ala | Lys | Arg |
| Ala | Leu 1385 | Gln | Gln | Lys | Phe | Gly 1390 | Leu | Gln | Gln | Thr | Asp 1395 | Val | Pro | Val |
| Val | Gly 1400 | Ile | Ile | Thr | Arg | Leu 1405 | Thr | Ala | Gln | Lys | Gly 1410 | Ile | His | Leu |
| Ile | Lys 1415 | His | Ala | Ile | His | Gln 1420 | Thr | Leu | Glu | Ser | Asn 1425 | Gly | Gln | Val |
| Val | Leu 1430 | Leu | Gly | Ser | Ala | Pro 1435 | Asp | His | Arg | Ile | Gln 1440 | Gly | Asp | Phe |
| Cys | Arg 1445 | Leu | Ala | Asp | Ala | Leu 1450 | His | Gly | Val | Tyr | His 1455 | Gly | Arg | Val |
| Lys | Leu 1460 | Val | Leu | Thr | Tyr | Asp 1465 | Glu | Pro | Leu | Ser | His 1470 | Leu | Ile | Tyr |
| Ala | Gly 1475 | Ser | Asp | Phe | Ile | Leu 1480 | Val | Pro | Ser | Ile | Phe 1485 | Glu | Pro | Cys |
| Gly | Leu 1490 | Thr | Gln | Leu | Val | Ala 1495 | Met | Arg | Tyr | Gly | Ser 1500 | Ile | Pro | Ile |
| Val | Arg 1505 | Lys | Thr | Gly | Gly | Leu 1510 | His | Asp | Thr | Val | Phe 1515 | Asp | Val | Asp |
| Asn | Asp 1520 | Lys | Glu | Arg | Ala | Arg 1525 | Ser | Leu | Gly | Leu | Glu 1530 | Pro | Asn | Gly |
| Phe | Ser 1535 | Phe | Asp | Gly | Ala | Asp 1540 | Ser | Asn | Gly | Val | Asp 1545 | Tyr | Ala | Leu |
| Asn | Arg 1550 | Ala | Ile | Ala | Ala | Trp 1555 | Phe | Asp | Ala | Arg | Asp 1560 | Trp | Phe | His |
| Ser | Leu 1565 | Cys | Lys | Arg | Val | Met 1570 | Glu | Gln | Asp | Trp | Ser 1575 | Trp | Asn | Arg |
| Pro | Ala 1580 | Leu | Asp | Tyr | Ile | Glu 1585 | Leu | Tyr | His | Ala | Ala 1590 | Arg | Lys | Phe |